(12) United States Patent
Weidemaier et al.

(10) Patent No.: US 9,874,555 B2
(45) Date of Patent: Jan. 23, 2018

(54) METHODS, SYSTEMS, AND DEVICES FOR DETECTING AND IDENTIFYING MICROORGANISMS IN MICROBIOLOGICAL CULTURE SAMPLES

(71) Applicant: BECTON DICKINSON AND COMPANY, Franklin Lakes, NJ (US)

(72) Inventors: Kristin Weidemaier, Raleigh, NC (US); Robert L. Campbell, Bullock, NC (US); Erin Gooch Carruthers, Cary, NC (US); Adam C. Curry, Raleigh, NC (US); Kevin G. Dolan, Holly Springs, NC (US); Andrea Liebmann-Vinson, Wake Forest, NC (US); Wendy Dale Woodley, Cary, NC (US); Melody M. H. Kuroda, Durham, NC (US); Eric A. Fallows, Apex, NC (US); Miroslaw Bartkowiak, Raleigh, NC (US); Scott N. Danhof, Plain City, OH (US); Gregory S. Kramer, Hilliard, OH (US); Thomas D. Haubert, Columbus, OH (US); Michael L. Marshall, Lewis Center, OH (US); James A. Prescott, Columbus, OH (US); Randy J. Somerville, Columbus, OH (US); M. Scott Ulrich, Columbus, OH (US); David S. Sebba, Cary, NC (US)

(73) Assignee: BECTON, DICKINSON AND COMPANY, Franklin Lakes, NJ (US)

(*) Notice: Subject to any disclaimer, the term of this patent is extended or adjusted under 35 U.S.C. 154(b) by 157 days.

(21) Appl. No.: 14/391,340

(22) PCT Filed: Mar. 15, 2013

(86) PCT No.: PCT/US2013/032499
§ 371 (c)(1),
(2) Date: Oct. 8, 2014

(87) PCT Pub. No.: WO2013/165615
PCT Pub. Date: Nov. 7, 2013

(65) Prior Publication Data
US 2015/0118688 A1    Apr. 30, 2015

Related U.S. Application Data

(60) Provisional application No. 61/623,522, filed on Apr. 12, 2012, provisional application No. 61/732,650, filed on Dec. 3, 2012.

(51) Int. Cl.
*C12M 1/34* (2006.01)
*G01N 33/543* (2006.01)
(Continued)

(52) U.S. Cl.
CPC ...... *G01N 33/54333* (2013.01); *B01L 3/0217* (2013.01); *B01L 3/502* (2013.01);
(Continued)

(58) Field of Classification Search
None
See application file for complete search history.

(56) References Cited

U.S. PATENT DOCUMENTS

| 5,312,009 A | 5/1994 | Ratajczak et al. |
| 5,624,814 A | 4/1997 | Waters et al. |

(Continued)

FOREIGN PATENT DOCUMENTS

| CN | 101680900 A | 3/2010 |
| CN | 101981447 A | 2/2011 |

(Continued)

OTHER PUBLICATIONS

Burcu Guven et al: "SERS-based sandwich immunoassay using antibody coated magnetic nanoparticles for *Escherichia coli* enumeration" The Analyst, vol. 136. No. 4, Jan. 1, 2011 (Jan. 1, 2011). p. 740 XP055090034, ISSN: 0003-2654. DOI: 10.1039/c0an00473a abstract; fig.1; p. 744. para. "Detection of bacteria using SERS", p. 740-748.

(Continued)

*Primary Examiner* — Erik B Crawford
(74) *Attorney, Agent, or Firm* — Botos Churchill IP Law LLP

(57) ABSTRACT

Provided herein are methods, systems, and devices for detecting and/or identifying one or more specific microorganisms in a culture sample. Indicator particles, such as surface enhanced Raman spectroscopy (SERS)-active nanoparticles, each having associated therewith one or more specific binding members having an affinity for the one or more microorganisms of interest, can form a complex with specific microorganisms in the culture sample. Further, agitating magnetic capture particles also having associated therewith one or more specific binding members having an affinity for the one or more microorganisms of interest can be used to capture the microorganism-indicator particle complex and concentrate the complex in a localized area of an assay vessel for subsequent detection and identification. The complex can be dispersed, pelleted, and redispersed so that the culture sample can be retested a number of times during incubation so as to allow for real-time monitoring of the culture sample.

11 Claims, 91 Drawing Sheets
(76 of 91 Drawing Sheet(s) Filed in Color)

(51) Int. Cl.
G01N 33/569 (2006.01)
C12M 1/00 (2006.01)
C12M 1/26 (2006.01)
C12M 1/24 (2006.01)
G01N 35/00 (2006.01)
B03C 1/01 (2006.01)
B03C 1/28 (2006.01)
B01L 3/02 (2006.01)
B01L 3/00 (2006.01)

(52) U.S. Cl.
CPC ............ *B01L 3/50825* (2013.01); *B03C 1/01* (2013.01); *B03C 1/288* (2013.01); *C12M 23/08* (2013.01); *C12M 23/22* (2013.01); *C12M 23/38* (2013.01); *C12M 33/04* (2013.01); *C12M 41/14* (2013.01); *C12M 41/36* (2013.01); *G01N 33/56911* (2013.01); *G01N 35/0098* (2013.01); *B01L 2200/026* (2013.01); *B01L 2200/0605* (2013.01); *B01L 2200/10* (2013.01); *B03C 2201/26* (2013.01)

(56) References Cited

U.S. PATENT DOCUMENTS

| | | | |
|---|---|---|---|
| 5,653,686 A | 8/1997 | Coulter et al. | |
| 6,344,272 B1 | 2/2002 | Oldenburg et al. | |
| 6,514,767 B1 | 2/2003 | Natan | |
| 6,685,986 B2 | 2/2004 | Oldenburg et al. | |
| 6,699,724 B1 | 3/2004 | West et al. | |
| 6,913,825 B2 | 7/2005 | Ostafin et al. | |
| 8,256,542 B2 | 9/2012 | Couture et al. | |
| 2003/0053938 A1* | 3/2003 | Szeles | A61B 10/007 422/400 |
| 2003/0232388 A1 | 12/2003 | Kreimer et al. | |
| 2006/0038979 A1 | 2/2006 | Natan et al. | |
| 2008/0025877 A1 | 1/2008 | Alley et al. | |
| 2008/0113404 A1* | 5/2008 | Eden | C12M 41/36 435/39 |
| 2009/0169433 A1* | 7/2009 | Kumar | G01N 21/658 422/82.09 |
| 2010/0060893 A1* | 3/2010 | Norton | G01N 1/40 356/301 |
| 2010/0317020 A1 | 12/2010 | Roscoe et al. | |
| 2011/0143968 A1* | 6/2011 | Chen | A61B 5/1427 506/39 |
| 2011/0275061 A1 | 11/2011 | Weidemaier et al. | |
| 2012/0046203 A1 | 2/2012 | Walsh et al. | |
| 2013/0236883 A1 | 9/2013 | Atrache et al. | |

FOREIGN PATENT DOCUMENTS

| | | |
|---|---|---|
| CN | 102239245 A | 11/2011 |
| JP | 2011163910 A | 8/2011 |
| WO | 2007092941 A2 | 8/2007 |
| WO | 2008116093 A2 | 9/2008 |
| WO | 2008154332 A1 | 12/2008 |
| WO | 2012004540 A1 | 1/2012 |

OTHER PUBLICATIONS

International Search Report for Application No. PCT/US2013/032499 dated Apr. 10, 2014, 6 pages.
Averitt et al., Ultrafast optical properties of gold nanoshells, J. Opt. Soc. Am. B/vol. 16, No. Oct. 10, 1999, pp . 1814-1823.
Cao, et al., DNA-Modified Core—Shell Ag/Au Nanoparticles, J. Am. Chem. Soc. 2001, 123, 7961-7962.
Clackson, Genetically Engineered Monoclonal Antibodies, First International Symposium on the Immunotherapy of the Rheumatic Diseases, British Journal of Rheumatology, 1991, pp. 36-39.
Frens, et al., Controlled Nucleation for the Regulation of the Particle Size in Monodisperse Gold Suspensions, Philips Research Laboratories, Nature Physical Science vol. 241, 1973, pp. 20-22.
Jackson, et al., Surface-enhanced Raman scattering on tunable plasmonic nanoparticle substrates, PNAS, vol. 101, No. 52, 2004, pp. 17930-17935.
Jones, et al., Replacing the complementarity-determining regions in a human antibody with those from a mounse, Nature, vol. 321, No. 6069, 1986, pp. 522-525.
Marx, Antibodies Made to Order, Science, vol. 229, No. 4712, 1985, pp. 455-456.
Mucic, et al., DNA-Directed Synthesis of Binary Nanoparticle Network Materials, J. Am. Chem. Soc., vol. 120, No. 48, pp. 12674-12675, 1998.
Nicewarner-Pena, et al., Submicrometer Metallic Barcodes, Science, vol. 294, No. 5540, 2001, pp. 137-141.
Reimer, et al., Update on Detection of Bacteremia and Fungemia, Clinical Microbiology Reviews, vol. 10, No. 3, p. 444-465, 1997.
Riechmann, et al., Reshaping human antibodies for therapy, Nature, vol. 332, No. 6162, 1988, pp. 323-327.
Rodwell, Engineering monoclonal antibodies, Nature, vol. 342, No. 6245, 1989, pp. 99-100.
Verhoeyen, et al., Reshaping Human Antibodies: Grafting an Antilysozyme Activity, Science, vol. 239, 1988, pp. 1534-1536.
Walton, et al., Particles for Multiplexed Analysis in Solution: Detection and Identification of Striped Metallic Particles Using Optical Microscopy, Analytical Chemistry, vol. 74, No. 10, 2002, pp. 2240-2247.
Blackburn, et al., "Separation and Detection of *Salmonellae* Using Immunomagnetic Particles," Biofouling, 1991, vol. 5, pp. 143-156.
Japanese Office Action for Application No. 2015-505770 dated Jan. 6, 2017.
European Search Report issued in related EP Application No. 17182180.4 dated Oct. 27, 2017.

* cited by examiner

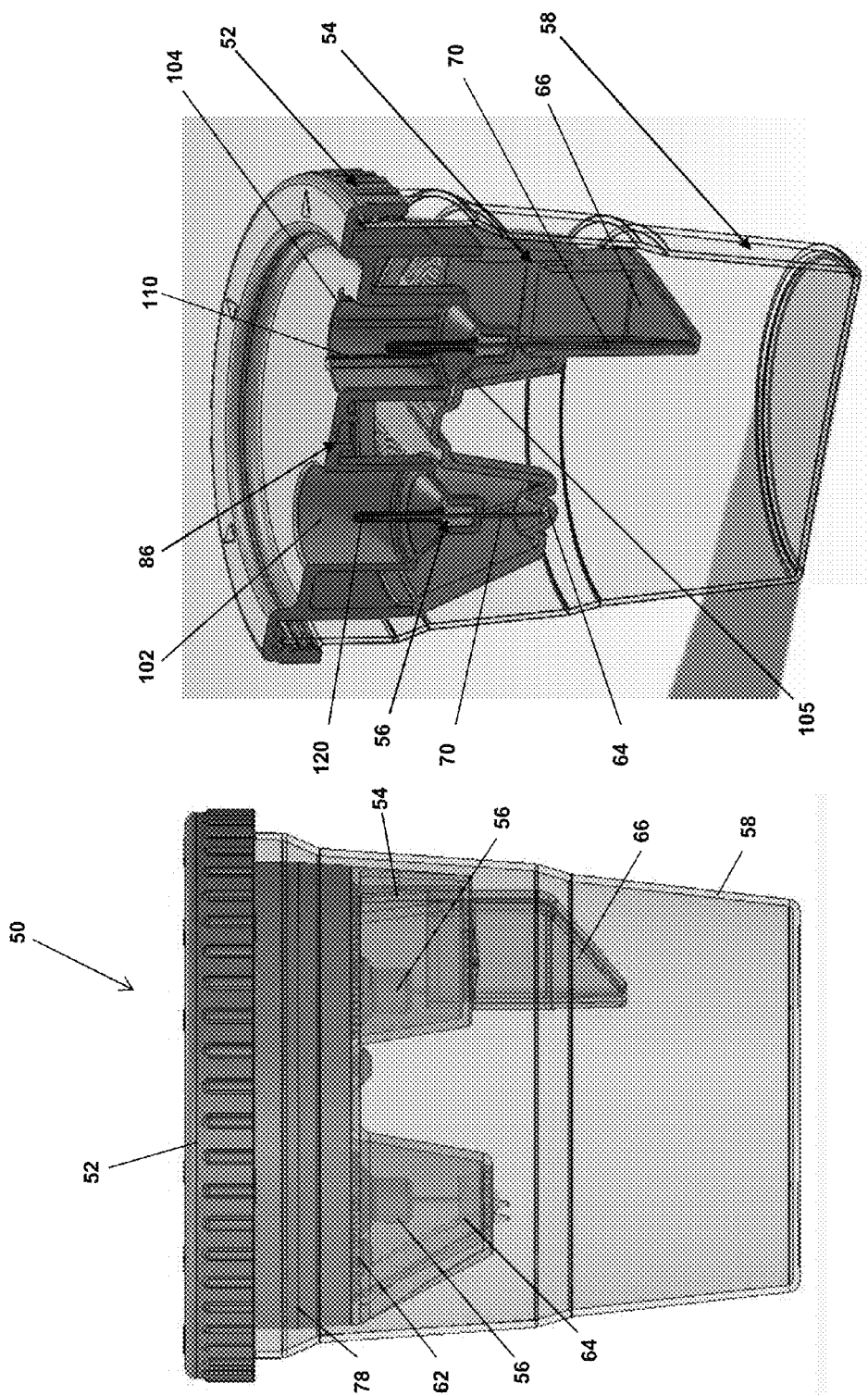

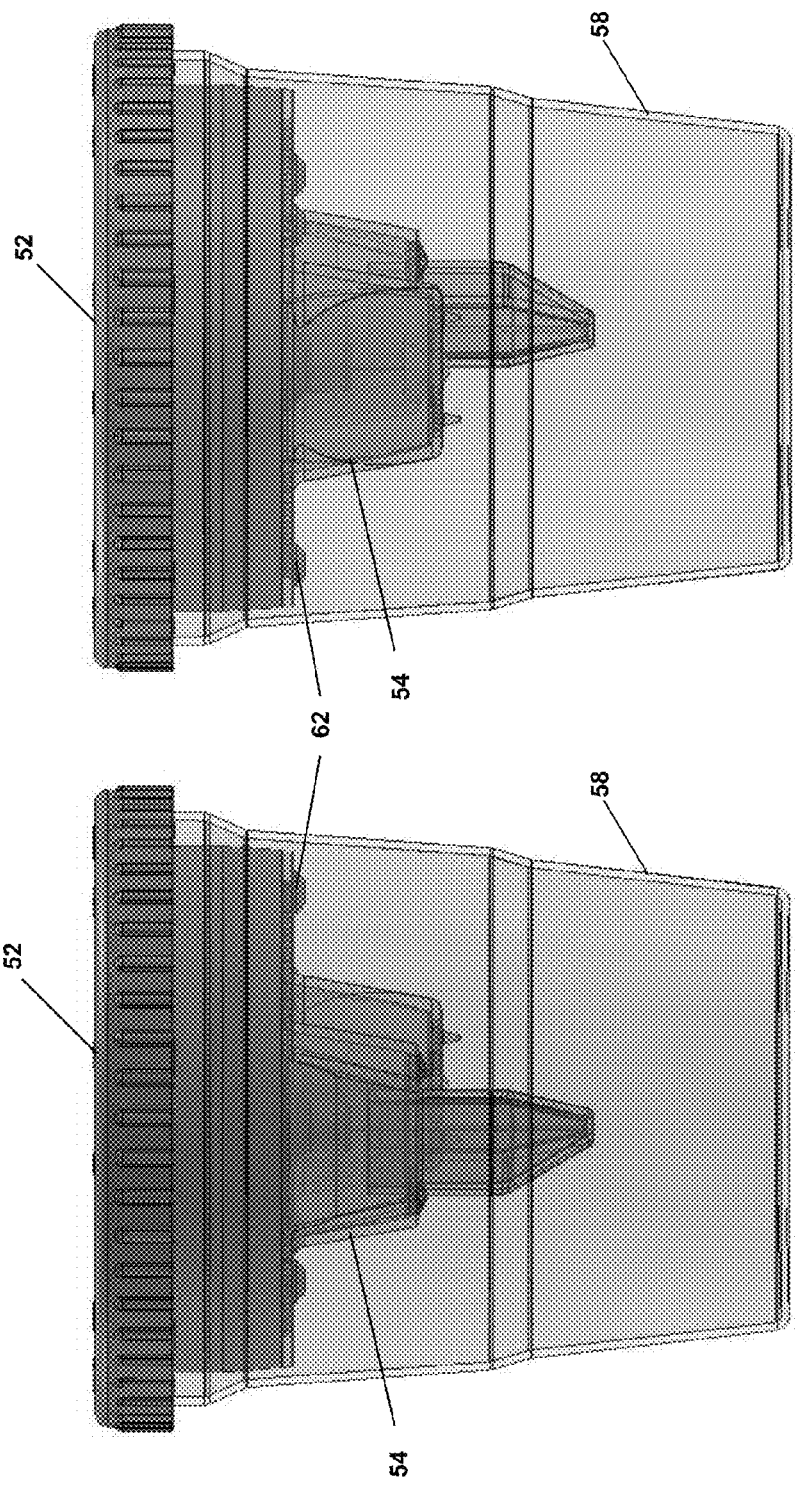

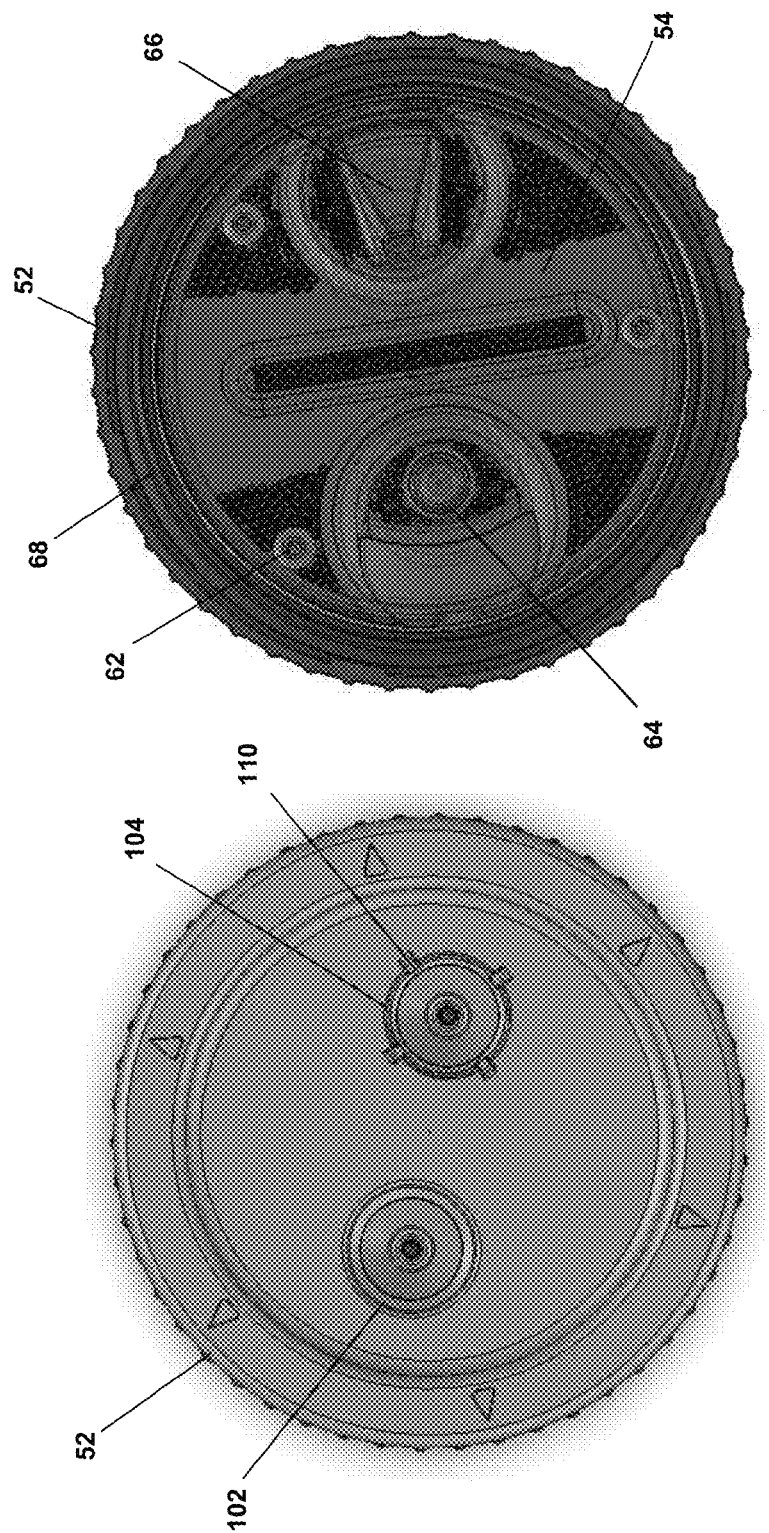

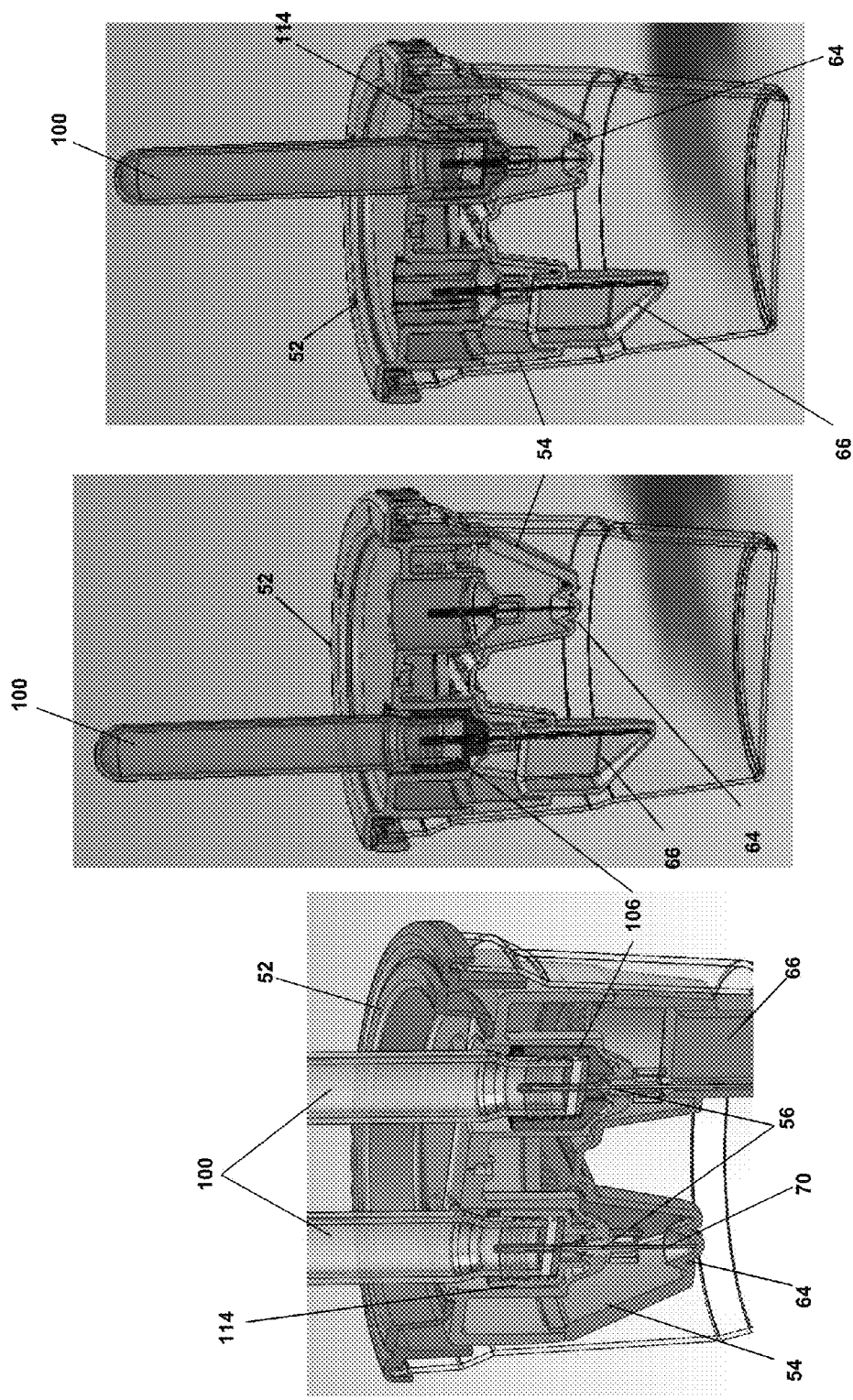

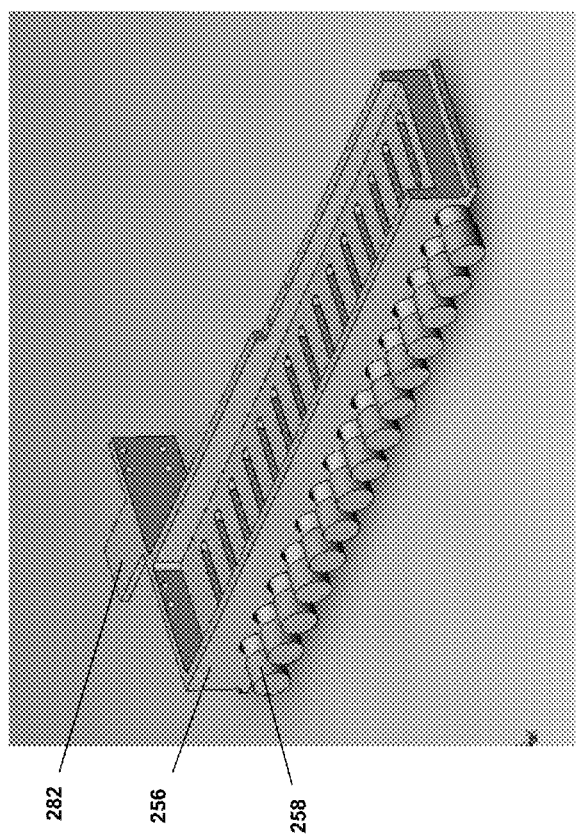
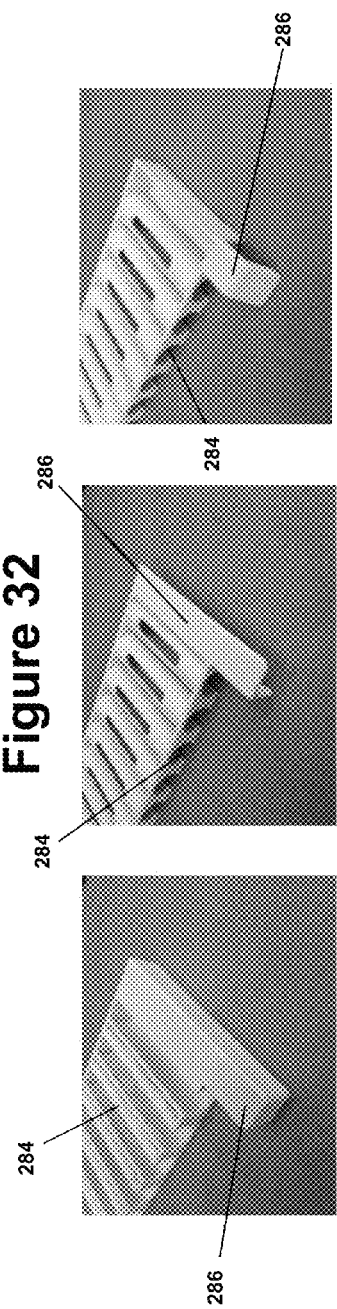
Figure 32
Figure 33A Figure 33B Figure 33C

| | Time to Detection (hours) | |
|---|---|---|
| | Bottle 1 | Bottle 2 |
| Negative control | No detection | No detection |
| Particles only (negative control) | No detection | No detection |
| E. Coli only | 11 | 10.7 |
| E. Coli + particles | 10.8 | 10.5 |

Figure 54

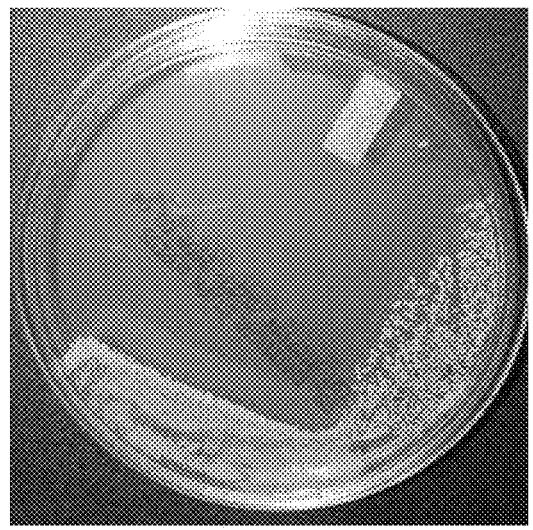
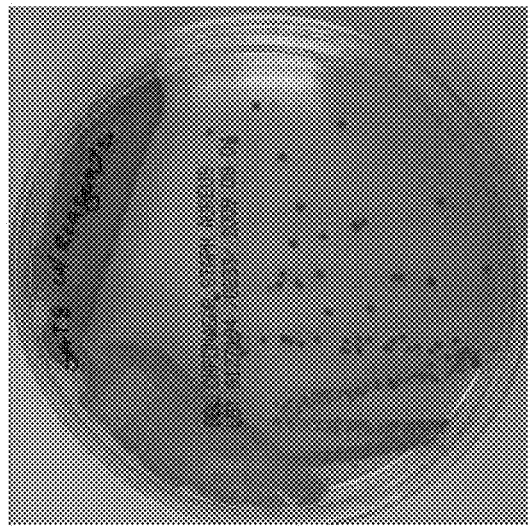
Figure 79

| Antibiotic | Resistant/Inhibitory/Sensitive | | | | E. coli | |
|---|---|---|---|---|---|---|
| | | R (mm) | I (mm) | S (mm) | No Reag. | With Reag. |
| Vancomycin | R | - | - | - | 6 | 6 |
| Clindamycin | R | - | - | - | 6 | 6 |
| Oxacillin | R | - | - | - | 6 | 6 |
| Cefoxitin | S | ≤14 | 15-17 | ≥18 | 25 | 26 |
| Meropenem | S | ≤13 | 14-15 | ≥16 | 26 | 28 |
| Ceftriaxone | S | ≤13 | 14-20 | ≥21 | 28 | 29 |
| Ampicillin | S | ≤13 | 14-16 | ≥17 | 18 | 17 |
| Erythromycin | R | - | - | - | 10 | 10 |
| Levofloxacin | S | ≤13 | 14-16 | ≥17 | 28 | 28 |
| Cefotaxime | S | ≤14 | 15-22 | ≥23 | 28 | 28 |

Figure 81

| Species | ATCC # | Results matched for +/- SERS reagents |
|---|---|---|
| E. coli | 25922 | ✓ |
| E. coli | 35218 | ✓ |
| E. coli O157 | 700728 | ✓ |
| K. pneumoniae | 700603 | ✓ |
| K. pneumoniae | 29011 | ✓ |
| S. epidermidis | 12228 | ✓ |
| S. epidermidis | 55133 | ✓ |
| S. aureus | 25923 | ✓ |
| S. aureus | 29213 | ✓ |
| C. albicans | 10231 | ✓ |

Figure 82

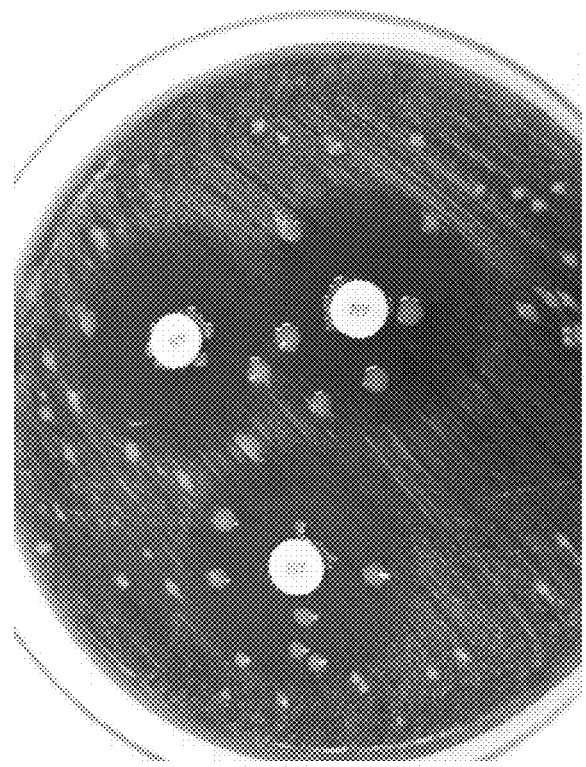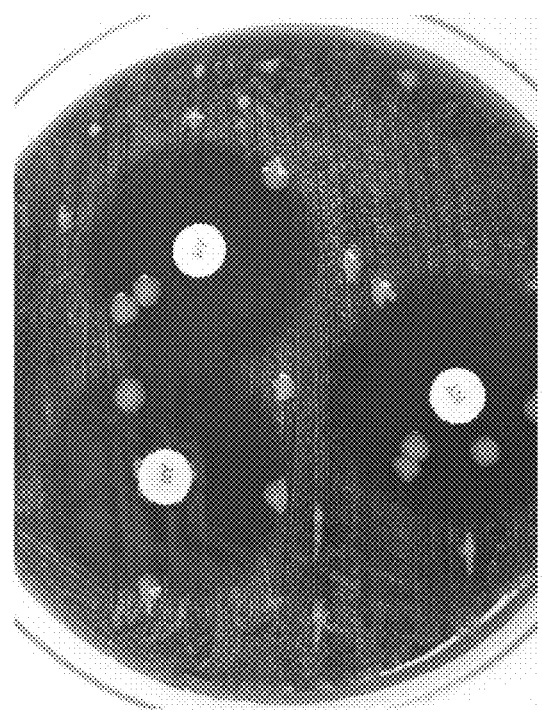
Figure 83

| Throw (mm) | Measured Frequency (Hz) | Time to Disperse (seconds) |
|---|---|---|
| 25 | 1.4 | 70 |
| 25 | 2.0 | 50 |
| 25 | 2.5* | 30 |
| 25 | 3.0* | 28 |
| 25 | 3.4* | 20 |
| 50 | 1.2 | 44 |
| 50 | 1.5* | 28 |
| 50 | 2.0* | 15 |

Figure 85

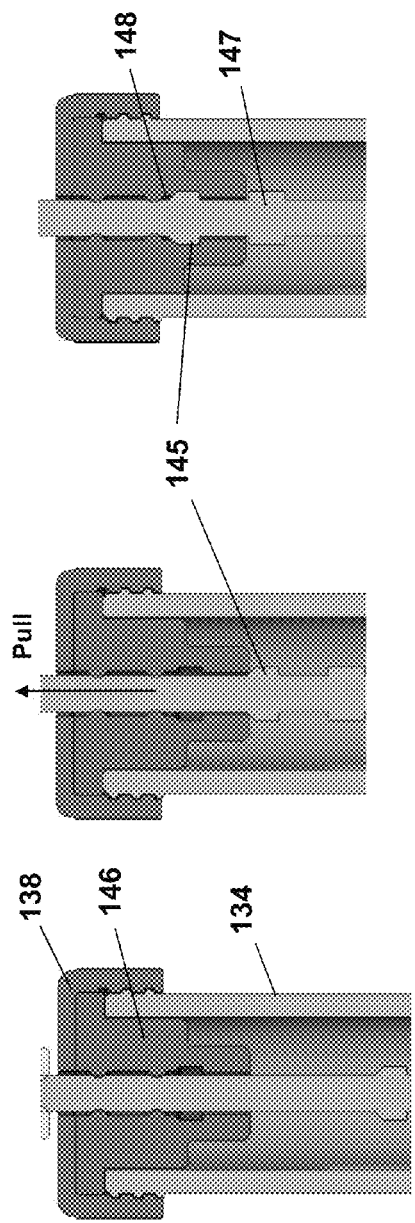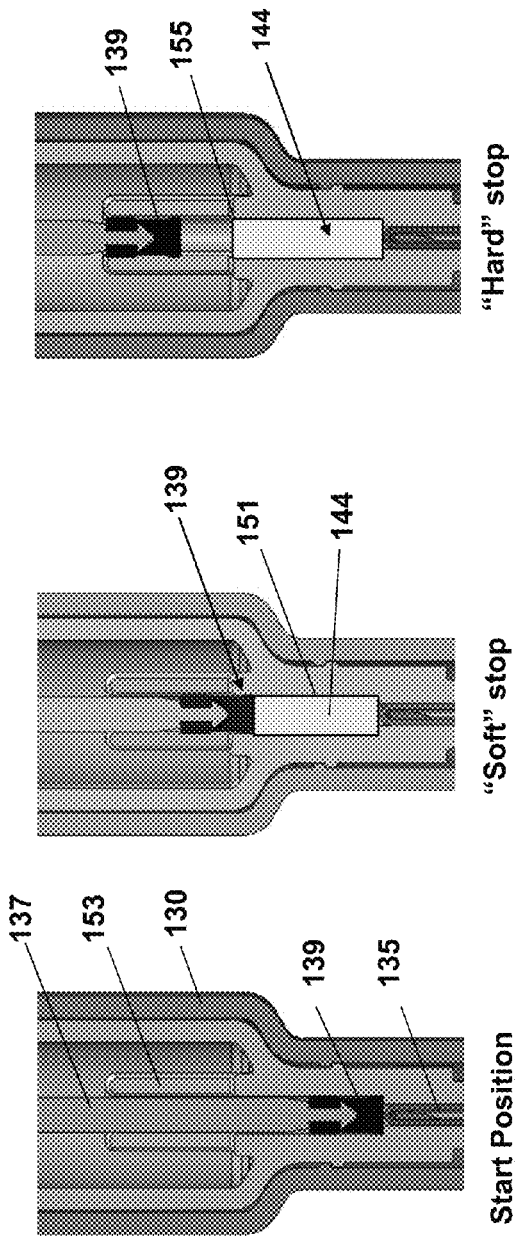
Figure 89A  Figure 89B  Figure 89C

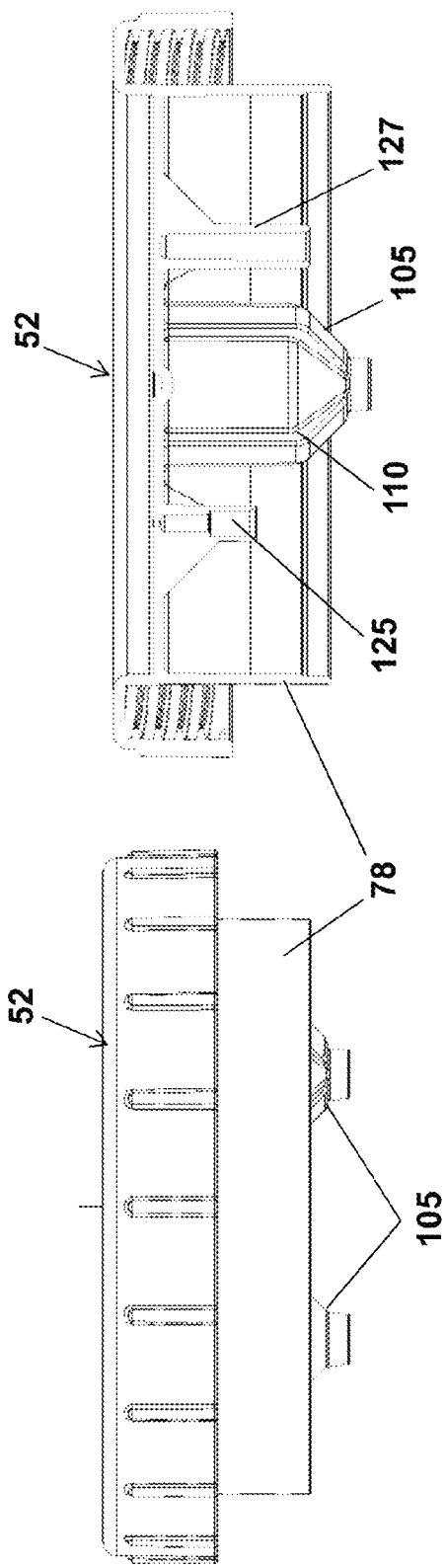

METHODS, SYSTEMS, AND DEVICES FOR DETECTING AND IDENTIFYING MICROORGANISMS IN MICROBIOLOGICAL CULTURE SAMPLES

CROSS-REFERENCE TO RELATED APPLICATIONS

This application is a U.S National Phase under 35 U.S.C §371 of International Application PCT/US2013/032499, filed Mar. 15, 2013, which claims priority to U.S. Provisional Application No. 61/623,522, filed Apr. 12, 2012, and U.S. Provisional Application No. 61/732,650, filed Dec. 3, 2012, each of which is incorporated herein in its entirety by reference.

BACKGROUND OF THE INVENTION

Field of the Invention

The presently disclosed subject matter relates to methods, systems, and devices for detecting, identifying, and quantifying microorganisms in a culture sample. More particularly, the subject matter relates to the use of indicator particles to detect and identify one or more microorganisms in a biocontained sample capable of supporting growth of microorganisms.

Background of the Invention

The ability to detect low levels of microorganisms, including pathogens, in a microbiological culture in clinical samples (e.g., blood, stool, urine, etc.) has gained significant importance in recent years. Similarly, microbiologial culture is important to public health to detect microorganisms, including pathogens, in industrial samples such as food, cosmetics, and pharmaceuticals. The ability to detect such microorganisms not only provides techniques for treating those who have already been exposed, but also to instances where exposure can be prevented, such as when testing food samples.

Foodborne illnesses significantly impact society, not only with respect to health, but also health-care costs. The CDC has estimated that each year about 1 in 6 Americans (or 48 million people) gets sick, 128,000 are hospitalized, and 3,000 die of foodborne diseases (see http://www.cdc.gov/foodsafety/facts.html). It has also been estimated that foodborne illnesses contribute to $152 billion in health-related expenses each year in the U.S., particularly for bacterial infections caused by *Campylobacter* spp., *Salmonella*, *Listeria monocytogenes* and *E. coli* (see http://www.producesafetyproject.org/admin/assets/files/Health-Related-Foodborne-Illness-Costs-Report.pdf-1.pdf).

The current level of food safety found in the U.S. is the result of Government regulations combined with industry self-monitoring influenced by market incentives, such as legal liability, brand value, reputation, and the desire to sell more food product. In the U.S., the primary agencies responsible for food safety are the U.S. Department of Agriculture (USDA) Food Safety and Inspection Services (FSIS), which is responsible for the safety of meat, poultry, and processed egg products, and the Food and Drug Administration (FDA), which is responsible for virtually all other foods. In 1996, USDA's FSIS promulgated the pathogen reduction hazard analysis critical control point (PR/HACCP) rule, which, for example, mandates generic *E. coli* testing by slaughter plants. Other FSIS regulations enforce zero limits for two deadly pathogens—*Listeria monocytogenes* in ready-to-eat meat and poultry and *E. coli* O157:H7 in ground beef (see http://www.ers.usda.gov/briefing/foodsafety/private.htm). Recently, the Food Safety Modernization Act was approved by Congress, the urgency for this legislation being underscored by continued outbreaks of foodborne illness over the last several years—from spinach to peppers to peanuts.

Food testing may occur on food samples themselves, either end product materials, intermediates, or incoming raw materials. In addition, HACCP (Hazard Analysis and Critical Control Point) plans are implemented to control the production environment so as to minimize the risk of introduction of pathogens into the food sample. As part of many HACCP plans, environmental samples are acquired from surfaces, floors, drains, and processing equipment and then analyzed for the presence and absence of pathogenic organisms. If a pathogen is detected, it may be isolated and subjected to further confirmatory testing.

Today, all food pathogen testing conducted entails a culture step to enrich the potentially low levels of microorganisms contained in a sample. Following culture of the sample, a portion is removed and tested for the presence of pathogens. Pathogen testing after culture can be done by immunoassays (e.g., bioMerieux's Vidas® automated ELISA platform or SDIX's RapidChek® lateral flow assays) or by PCR-based tests (e.g., DuPont Qualicon's BAX® system, Bio-Rad's iQ-Check™ system). If a pathogen is present in the starting sample, the culture step can increase the concentration of the pathogen as high as 1.0E8-1.0E9 cfu/mL, so that opening the sample after culture exposes both the user and the environment to a risk of contamination. This exposure inhibits many food producers from conducting pathogen testing on-site, instead choosing to send samples to external laboratories for testing. In addition, since it is unknown which samples contain pathogens and at what levels, food safety test protocols use lengthy culture times to ensure that the worst case scenario of one damaged pathogen is given sufficient time to grow to a detectable concentration. As a consequence, samples with higher pathogen loadings are cultured longer than may be strictly necessary, leading to a delay in time to results. There is thus a need in the field for pathogen test methods that minimize time to results and reduce the risk of exposure of the facility and personnel to cultured pathogens.

Similar concerns are present for clinical samples such as blood. Since the mid-1980s, along with the expanding size of the immunocompromised patient population, the incidence of septicemia caused by opportunistic pathogens, such as yeast, fungi, and mycobacteria, has risen. Bacteremia, the presence of bacteria in the blood stream, and fungemia, the presence of fungi or yeasts in the blood stream, typically are detected by collecting a venous blood sample and disposing the blood sample in a blood culture bottle containing a growth medium suitable for promoting growth of the bacteria or fungi of interest. See generally, Reimer et al., "Update on Detection of Bacteremia and Fungemia," Clinical Microbiology Reviews 10(3), 444-465 (1997). The blood culture sample can then be incubated for a period of time and checked intermittently for an indication of bacterial or fungal growth.

Instrumented methods known in the art for monitoring bacterial or fungal growth in blood culture bottles typically detect changes in the carbon dioxide and/or oxygen concentration in the blood culture bottle. These instruments detect the presence and absence of microorganisms but are not specific as to the particular type of organism present. For a nominally sterile sample such as blood, detection of a microorganism in the sample can be indicative of severe disease. However, the positive result is considered to be a partial or preliminary result and is typically not actionable. As optimum treatment of the disease relies on identification of the organism and determination of its antibiotic susceptibility, laboratory personnel must be available to advance positive cultures to full identification (ID) and antimicrobial susceptibility testing (AST). Identification of the organism requires accessing of the positive blood culture sample by laboratory personnel for further sample work-up.

Sample work-up following a positive blood culture result, i.e., a result indicating the presence but not identity of a microorganism, often includes categorization of the microorganism into one of two broad classes of organisms: Gram positive or Gram negative. Blood culture assays based on the detection of $CO_2$ or $O_2$ during the culture process cannot distinguish between pathogenic organisms, such as *S. aureus*, and contaminants, such as *S. epidermidis* since these methods are sensitive only to growth and absence of growth. Classification and identification of organisms is performed following the detection of growth in a blood culture sample. For example, kits are available for differentiating between *Staphylococcus* and *Streptococcus* species and other organisms. Kits also are available for differentiating between organisms, such as *S. aureus* and *S. epidermidis*. These kits, however, require removing at least an aliquot of a blood culture sample from the blood culture bottle and other procedures that can potentially expose the operator to the pathogen or destroy a portion of the blood culture that could be used for other analyses. They also typically require that trained laboratory staff are available to conduct the tests, potentially leading to a delay in actionable clinical results in the event that a blood culture sample goes positive when laboratory personnel are unavailable to conduct additional testing (e.g., in hospitals that operate only a single shift.)

While instruments exist today to detect the presence or absence of microorganisms in blood (e.g., by use of a carbon dioxide or oxygen sensor), these instruments are not typically useful in non-sterile samples such as stool or food samples. For samples such as, for example food, there is expected to be a significant concentration of benign microorganisms, and so detection of organisms by carbon dioxide or oxygen sensors is not inherently useful. For a food sample, it is critical to detect the presence of low levels of pathogenic organisms in a background of high benign microflora to avoid the spread of foodborne illnesses.

Therefore, there is a need for methods, systems, and devices for detecting not only the presence or absence of organisms during the culture step of nominally sterile samples, but also identification of the organisms. For non-sterile samples, such as stool and food, there is also a need for methods, systems, and devices for identifying potentially harmful organisms in a culture in a biocontained manner. Such methods, systems and devices minimize user intervention, thereby minimizing time, trained personnel, plus potential exposure of personnel and environment to the pathogen.

SUMMARY OF THE INVENTION

Embodiments of the presently disclosed subject matter provide methods, systems, and devices for detecting the presence, amount, and/or identity of specific microorganisms in a microbiological culture. According to one embodiment, the presently disclosed assays can be performed within the culture vessel, so that detection and/or identification of specific microorganisms occur in conjunction with culture, without the need for user intervention. One or more microorganisms can be identified within a single culture. The culture vessel can be fully biocontained so that the growth of the microorganism and microorganism detection and identification can occur without exposing either the user or the surrounding environment. Moreover, due to the biocontainment of the culture, the analysis of the culture may occur without the need for the user to access the culture or wash the culture.

Optically active indicator particles, such as Surface Enhanced Raman Scattering (SERS)-active nanoparticles, each having associated therewith one or more specific binding members having an affinity for the one or more microorganisms of interest, can form a complex with specific microorganisms in the microbiological culture sample. Thus, the optically active indicator particles can be any particle capable of producing an optical signal that can be detected in a culture sample without wash steps. Further, magnetic capture particles, also having associated therewith one or more specific binding members having an affinity for the one or more microorganisms of interest, which can be the same or different from the specific binding members associated with the indicator particles, can be used to capture the microorganism-indicator particle complex and concentrate the complex in a localized area of an assay vessel for subsequent detection. Importantly, embodiments of the presently disclosed methods, systems, and devices allow "real-time" detection and identification of microorganisms in a sample in which active growth of the microorganism is occurring. Samples may include microbiological cultures comprising a growth medium and a clinical sample from a human or animal (domestic or stock) such as blood, stool, urine, or cerebral spinal fluid. Samples may also include microbiological cultures comprising a growth medium and an industrial sample such as food, dairy, beverage, water, environmental, agricultural products, personal care products (including cosmetics), biotechnology, or pharmaceuticals. Importantly, the assay can be conducted in a biocontained manner without exposure of the user or environment to the sample ("closed system") and can provide automated, around the clock, detection and identification of microorganisms by monitoring the assay signal over time as the culture progresses. The combination of detection and identification with microbiological culture can lead to earlier availability of actionable results.

Detection of microorganisms by the present invention can be performed either directly or indirectly. For direct detection of micorganisms growing in culture, the specific binding members associated with the magnetic capture particles and indicator particles can have an affinity for the largely intact microorganism, e.g. by binding to the surface of bacteria or yeast. For indirect detection, the binding members associated with the magnetic capture particles and indicator particles may have an affinity for byproducts of the microorganism. Examples of byproducts could include but are not limited to secreted proteins, toxins, and cell wall components. Direct and indirect detection modes made be used alone or in combination.

According to another embodiment of the present invention, a vessel for metering a desired amount of culture sample is provided. The vessel includes a container for receiving a culture sample therein, wherein the container has an open end and a closed end. The vessel also includes a lid configured to engage the open end of the container in a fluid-tight connection. In addition, the vessel includes a basket coupled to the lid and including one or more reservoirs, wherein the basket is disposed between the open end and the closed end of the container. Where a plurality of reservoirs is used, each reservoir is configured to hold a different volume of culture sample. Moreover, the vessel includes one or more needle assemblies engaged with the lid, wherein the needle assembly includes a needle extending within a respective reservoir. Each needle is configured to selectively withdraw a sample contained in a respective reservoir, wherein each needle is further configured to engage a vial for a biocontained transfer of the sample from the reservoir to the vial. Thus, the vessel may be suitable for metering a desired amount of sample for two different assays (e.g., *Salmonella* or *Listeria*) in a single container, while facilitating transfer of the sample to a detection vial in a biocontained manner. In another embodiment of the present invention, the assay vial for receiving a sample is enclosed by a stopper or septum and cap configured to retain a vacuum. Upon connection of the assay vial cap with a compatible port containing a needle on the metering vessel, the sample is transferred in a biocontained fashion. The vial cap contains features to retain externally expressed fluid from the transfer and protect the user from contact with transfer surfaces.

Another embodiment of the present invention is directed to a system for automatically processing a plurality of tubes containing a culture sample. The system includes an incubator for receiving a plurality of sample tubes therein, wherein the incubator is configured to incubate the sample tubes at a predetermined temperature. For example, the tubes may be positioned horizontally and adjacent to each other. The incubator may be configured to incubate different assays at different temperatures according to one embodiment. The system further includes a first translational device (e.g., a "Y-stage" for movement along a Y-axis) coupled to the tray and configured to move the sample tubes within the incubator, wherein the first translational device is further configured to move the sample tubes from the incubator to a detection zone and to agitate the sample tubes within the detection zone. For instance, the first translational device may move the samples tubes along their longitudinal axes. The system also includes a magnet assembly configured to apply a magnetic field to the plurality of sample tubes within the detection zone, as well as an optical device configured to interrogate each of the plurality of sample tubes within the detection zone for detecting one or more microorganisms. The system includes a second translational device (e.g., an "X-stage" for movement along an X-axis) coupled to the optical device and configured to move the optical device within the detection zone for interrogating each of the sample tubes. The system may also include a third translational device (e.g., a "Z-stage" for movement along the Z-axis) coupled to the magnet assembly and the optical device and configured to move the magnet assembly and optical device within the detection zone to access another tray of tubes stacked vertically above the first tray. Thus, the system provides an automated and high-throughput system for processing a plurality of samples in real time during incubation of the culture tubes.

BRIEF DESCRIPTION OF THE DRAWINGS

The patent application file contains at least one drawing executed in color. Copies of this patent application with color drawing(s) will be provided by the Office upon request and payment of the necessary fee. Having thus described the presently disclosed subject matter in general terms, reference will now be made to the accompanying drawings, which are not necessarily drawn to scale, and wherein:

FIGS. 5A-5E illustrate various views of an enrichment vessel according to one embodiment of the present invention.

FIG. 6 is a cross-sectional view of an enrichment vessel according to one embodiment of the present invention.

FIG. 15 is a cross-sectional view of detection vials engaging an enrichment vessel according to an embodiment of the present invention.

FIGS. 16 and 17 are cross-sectional views of a detection vial engaging an enrichment vessel according to an embodiment of the present invention.

FIG. 32 is a perspective view of a tray for holding sample tubes according to another embodiment of the present invention.

FIGS. 33A-33C are partial views of trays for holding sample tubes according to various embodiments of the present invention.

FIG. 54 shows the results of an experiment in which time to detection of *E. coli* growth was compared for blood culture samples with and without the SERS HNW reagents suitable for use in the various embodiments of the invention.

FIG. 79 shows images of CHROMagar *S. aureus* plates streaked with a blood culture of *S. aureus* and *S. epidermdis* with SERS reagents according to embodiments of the present invention.

FIG. 81 is a table showing zone diameter measurements for *E. coli*, with and without reagents, according to an embodiment of the present invention.

FIG. 82 is a table showing a summary of the results of manual antibiotic susceptibility testing using BD Sensi-discs™ and various microorganisms with and without SERS reagents, according to one embodiment of the present invention.

FIG. 83 shows images of agar plates streaked with a blood culture of *E. coli* and *C. albicans*, with and without reagents, overlaid with anti-fungal BD Taxo™ discs, according to an embodiment of the present invention.

FIG. 85 is a table showing the effect of agitation frequency on pellet dispersion, according to an embodiment of the present invention.

FIGS. 89A-89C are enlarged cross-sectional views of a syringe engaged with an enrichment vessel according to various embodiments of the present invention.

FIG. 104 is a side view of the lid shown in FIG. 101.

FIG. 105 is a cross-sectional view of the lid shown in FIG. 101.

DETAILED DESCRIPTION OF THE INVENTION

Figure 1:
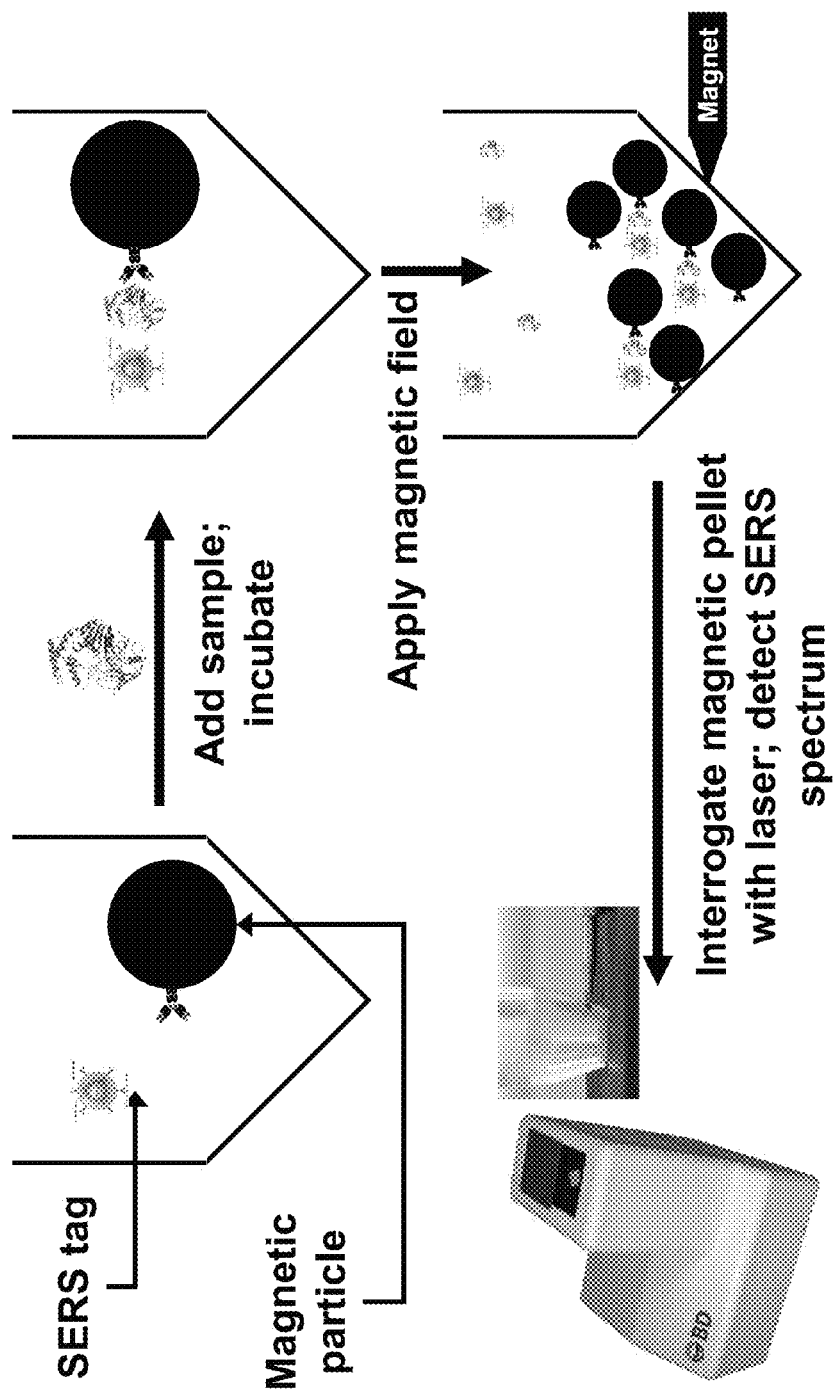
FIG. 1 is a schematic diagram showing a method of detecting and identifying a microorganism in a culture sample according to an embodiment of the invention.

The presently disclosed subject matter now will be described more fully hereinafter with reference to the accompanying Drawings, in which some, but not all embodiments of the presently disclosed subject matter are shown. Many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims. Although specific terms are employed herein, they are used in a generic and descriptive sense only and not for purposes of limitation.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass a specified value and variations thereof. Such variations may be, in some embodiments ±100%, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the presently disclosed subject matter be limited to the specific values recited when defining a range.

The embodiments of the present invention provide systems and methods which utilize indicator particles (e.g., surface enhanced Raman scattering (SERS)-active indicator particles), for detecting and/or identifying one or more microorganisms in a bacterial culture sample by a Homogeneous No Wash assay (HNW). More specifically, embodiments of the invention describe techniques for monitoring the concentration of microorganism in "real-time" as the microorganism level increases over time within a sample. The indicator particles have associated therewith one or more specific binding members having an affinity for the one or more microorganisms under test. When contacted with a microbiological culture sample containing one or more microorganisms of interest, a complex, generally referred to herein as an indicator particle-microorganism complex, between the one or more microorganisms of interest and the indicator particle with associated specific binding member can be formed. The indicator particle-microorganism complex can be captured by a magnetic capture particle and concentrated to form a pellet in a localized area (i.e., a "measurement zone") for detection by measuring the signal (e.g., SERS spectrum) and/or a visual inspection of an image of the pellet. The term "pellet", as used herein, is not meant to be limiting and in one embodiment, refers to a collection of a plurality of indicator particles and magnetic capture particles located in a localized area facilitated by application of a magnetic field, wherein the pellet is detectable using visual, optical, or other suitable means. The pellet may also include microorganisms captured therebetween, if present, and other components and/or microorganisms may be non-specifically attached to the magnetic particles. The pellet may be temporarily formed in that the pellet may be dispersed upon removal of the magnetic field as discussed in greater detail below.

Furthermore, the various embodiments of the invention pertain to the ability to conduct the HNW assay repeatedly within the same microbiological culture sample, by forming, dispersing, and reforming the pellet over time. This enables the concentration of a particular analyte to be monitored real-time within a microbiological culture sample and is particularly valuable when the microorganism concentration is changing over time, e.g. in response to bacterial growth. More particularly, embodiments of the invention pertain to the ability to conduct the HNW assay within a microbiological culture vessel, thereby simultaneously detecting and identifying a microorganism as it grows. In addition, the technique can be used in conjunction with other methods of monitoring the culture sample (such as gas sensor or image analysis).

According to an embodiment of the invention, a microbiological culture of the sample is conducted in a vessel that also contains the HNW reagents. The culture vessel is inserted into an instrument that allows incubation at a controlled temperature and contains optical devices (e.g., Raman optics, a Raman laser, and a spectrometer). At regular time intervals during the culture, a magnetic field is applied, and the SERS signal is read from the magnetic pellet. The pellet is dispersed between readings to allow continued interactions of the reagents with the sample. As the target organism concentration increases throughout the enrichment process, detection and identification of the microorganism by the SERS technology occurs as soon as the microorganism concentration reaches the detection threshold of the technology. The ability to continuously monitor the SERS signal during culture ensures that the minimal required culture time is used and that the instrument can automatically alert the user when a microorganism is detected and identified.

A further embodiment uses a camera to monitor the formation and size of a pellet during a HNW assay which contains conjugated indicator particles and magnetic beads and the targeted pathogen within a culture vessel. Images show that pellet size increases, and in some cases the pellet disappears, from the camera view as the HNW assay progresses. The growth in pellet size and/or disappearance of the pellet is an indication of the presence of the targeted pathogen. Images captured during analysis of samples that contain conjugated indicator particles and magnetic beads with no pathogen show no change in pellet size and no pellet disappearance. This method of detection can be used alone or in conjunction with another detection method.

I. General Considerations for Detection and Identification of Microorganisms in a Microbiological Culture Sample As used herein, the term "microbiological culture sample" refers to a composition comprising a "clinical" or an "industrial" sample with the potential of containing microorganisms that is disposed in, admixed, or otherwise combined with a culture medium, e.g., a blood culture broth, capable of supporting the growth of one or more microorganisms suspected of being present in the sample. More particularly, embodiments of the presently disclosed subject matter provide methods, systems, and devices for detecting microorganisms in a microbiological culture sample comprising a media capable of supporting microorganism growth in either a clinical sample, such as blood, stool, urine or cerebral spinal fluid, or in an industrial product sample, such as food, environmental swabs or sponges, water, cosmetics, hygiene products, pharmaceuticals, or other products intended for use or consumption by animals or humans.

Detecting and/or identifying microorganisms in microbiological culture samples, especially with optical or spectrometric methods, can present many challenges due to the complexity of the sample matrix. Clinical samples, particularly those such as blood or stool, are optically absorptive, making it difficult to detect optical or spectral signals without wash or lysis steps to remove optically interfering components of the original samples. Industrial samples, such as, for example food or cosmetic samples, may be optically absorptive, again requiring wash or lysis steps to remove optical interferents in the original sample. Although the application of SERS to detecting mammalian cells and microorganisms and the diagnostic application of SERS-active indicator particles to detecting a variety of analytes in the presence of blood and food samples has been reported, the application of SERS-active indicator particles to monitor bacteria and fungi concentrations in "real time" as the concentrations change due to microorganism growth has not been reported. As used herein, "real time" is not meant to be limiting and may refer to monitoring the culture sample continuously or in predetermined increments of time. For example, the culture sample may be tested repeatedly in predetermined increments of time (e.g., every 30 minutes, 1 hour, etc.) over a predetermined incubation period without opening the sample tube thereby maintaining biocontainment of the sample. "Biocontainment", as used herein, is also not meant to be limiting and may refer to the culture sample being in a closed system such that the surrounding environment outside of the container in which the culture sample is confined is not exposed to the microorganisms being cultured.

Further, the presently disclosed methods allow for the diagnostic use of indicator particles in microbiological cultures in a manner that does not inhibit the growth of the microorganism under detection.

Current methods of detecting the presence or absence of pathogens during microbiological growth, e.g. blood culture cabinets, do not specifically detect organisms, but rather a non-specific product of metabolism (e.g., carbon dioxide). Therefore, these sensors can potentially be falsely triggered by carbon dioxide produced by other processes, such as oxidation, degradation, and respiration of the blood culture cells (e.g., mammalian cells) that are normal flora in a blood sample. This significant 'blood background' signal is an important noise source that complicates positivity algorithms and decreases overall analytical sensitivity. The signal generated from a specific binding event, as described in the presently disclosed methods, will be a clear indicator that a pathogen is present and will not likely be misinterpreted.

The various embodiments of this invention allow continuous growth, detection and identification all within the geometry of a single vial. The SERS HNW technology enables a culture system capable of providing round the clock (24 hours/7 days a week) alerts on growth positive samples along with additional identifying information (e.g., gram stain information or identification). In contrast to blood culture systems currently on the market which detect the absence or presence of growth, the SERS HNW assay can provide identification of the microorganism or class of microorganisms. Antibodies conjugated to the SERS and magnetic particles can be selected to specifically identify gram positive versus gram negative bacteria. Importantly, the inherent multiplexing capabilities of the SERS technology are key for the blood culture and industrial applications.

Existing gas based sensors such as those used in blood culture cabinets are unsuitable for detecting the presence of pathogenic microorganisms in samples (e.g. stool, food, or environmental samples) wherein there is an expected high level of background benign microorganisms. There are currently no known methods for real-time pathogen detection within a food or an environmental sample, because these types of samples typically have background (benign) microorganisms that also grow during culture, so a growth based sensor cannot distinguish between growth of the background organisms and growth of the target pathogen.

In addition, existing methods for microorganism identification require a combination of sample preparation and/or wash steps to remove interfering components, minimize background signal, and/or generate a sample that is optically transparent. Because of the sample preparation and wash requirements, these methods cannot be applied within an ongoing culture.

The SERS-HNW assay overcomes the problems of the need for wash steps by generating a Raman signal that can be read in a dirty or non-isolated sample. It also enables multiplexed detection and identification in complex matrices, thereby making it suitable for the multiplexed detection of blood stream infections or food pathogens. These attributes of the HNW assay have been previously disclosed. However, in all known previous disclosures, the HNW assay was applied a single time to a single sample, i.e., one pellet was formed and read to generate the "answer" (identification+detection). There has been no indication that the conduction of the HNW assay would be compatible with the specific requirements of real-time monitoring in culture, specifically:

The need to maintain viability of the culture (complex formation with the microorganism cannot inhibit growth);

Ability to reliably and reproducibly disperse the magnetic pellet once it has been formed to enable the SERS and magnetic reagents to continue interacting with the sample;

Ability of SERS HNW assay signal to increase and decrease over time in response to continuous changes in target concentration; and Ability to conduct the HNW assay on large volumes such as are typically used in blood culture and industrial applications, as one would have initially expected that the reagent volume requirements would have been cost prohibitive and/or that one would be unable to form a pellet that was representative of the entire volume. (Any reasonable-sized magnetic field would be expected to only pull magnetic particles from the local micro-environment.)

An HNW assay according to an embodiment of the invention can be used to detect pathogens such as *E. coli, Listeria, Salmonella*, etc. growing in food or environmental samples. Since the presence of even a single damaged organism is significant, samples are typically cultured in order to recover and selectively grow the pathogen to a detectable level. Because the initial sample may have a range of pathogen concentrations, varying levels of damage to the pathogen, and/or highly variable competing background microorganisms, the required culture time to reach the limit of detection for any given analytical method can vary wildly. For this reason, detection protocols are typically formulated for "worst case" scenarios i.e. the length of culture time is chosen to ensure that the single damaged pathogen is grown to a detectable level. Detection and identification of the pathogen (e.g., by immunoassay or PCR) is then performed at the completion of culture. Since the initial load of pathogen in any given sample cannot be known a priori, all samples are subjected to this long culture protocol to ensure that no pathogens are missed. However, it is likely that many samples would have yielded positive detection and identification after shorter culture protocols, providing earlier notification to the tester that there is a problem with the sample. The combination of the SERS-based HNW assay with culture allows real-time monitoring of the pathogen load in the sample throughout the culture, providing the significant advantage that samples with higher pathogen loads are detected as early as possible in the culture protocol.

II. Systems, Methods, and Devices for the Identification of Microorganisms in a Microbiological Culture Sample Embodiments of the present invention are directed to methods, systems, and devices for detecting and identifying microorganisms in a culture sample. With reference to FIG. 1, the process generally includes providing a plurality of indicator particles, binding members, and magnetic capture particles in a vessel and adding a sample that potentially includes one or more microorganisms. The vessel may also include culture or growth media to aid in selectivity or additional growth of microorganisms. The sample is then incubated and agitated for a predetermined period of time. At selected time points or on a predetermined schedule over the course of incubation, a magnetic field is applied to the vessel so as to form a pellet. The pellet is then interrogated with a light source to produce a detectable signal (e.g., a SERS spectrum) that is detected and analyzed. The pellet may then be dispersed and the process repeated at the next determined time point.

Figure 2:
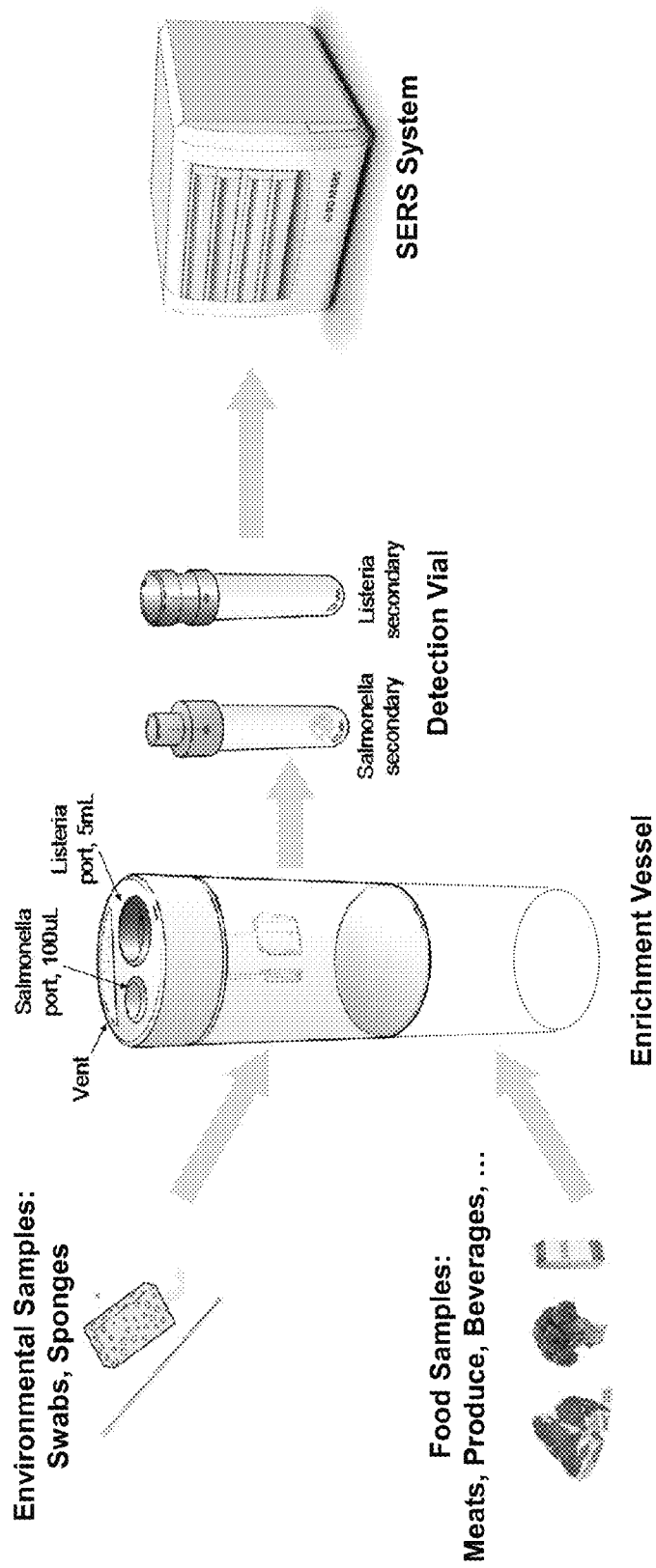
FIG. 2 is a schematic diagram showing an enrichment vessel and a detection vial for containing and transferring a culture sample according to one embodiment of the present invention.

FIG. 2 shows one embodiment of the methodology and devices that may be used to detect and identify microorganisms in a culture sample. In this regard, FIG. 2 illustrates that a desired volume of an environmental sample (e.g., about 1 L or less), a food sample (e.g., about 25 g to 375 g resulting in a volume of about 250 mL to 3 L), or a clinical sample (e.g., about 100 mL or less) is obtained and placed in an enrichment vessel. In this instance, the enrichment vessel is configured to facilitate analysis of Salmonella or Listeria assays. The enrichment vessel is incubated for a predetermined period of time, after which a predetermined amount of sample is transferred to a detection vial in a biocontained manner, which will be explained in further detail below. The detection vial is then placed in a real-time SERS system for further incubation and automated analysis using SERS technology, which is also discussed in further detail below.

According to one embodiment, the SERS system is configured to accommodate a plurality of detection vials and thereby provide a high throughput system. The SERS system may also be configured to facilitate an automated analysis of a plurality of different assays. For example, the SERS system may include dedicated zones for handling and analysis of each assay.

Figure 3:
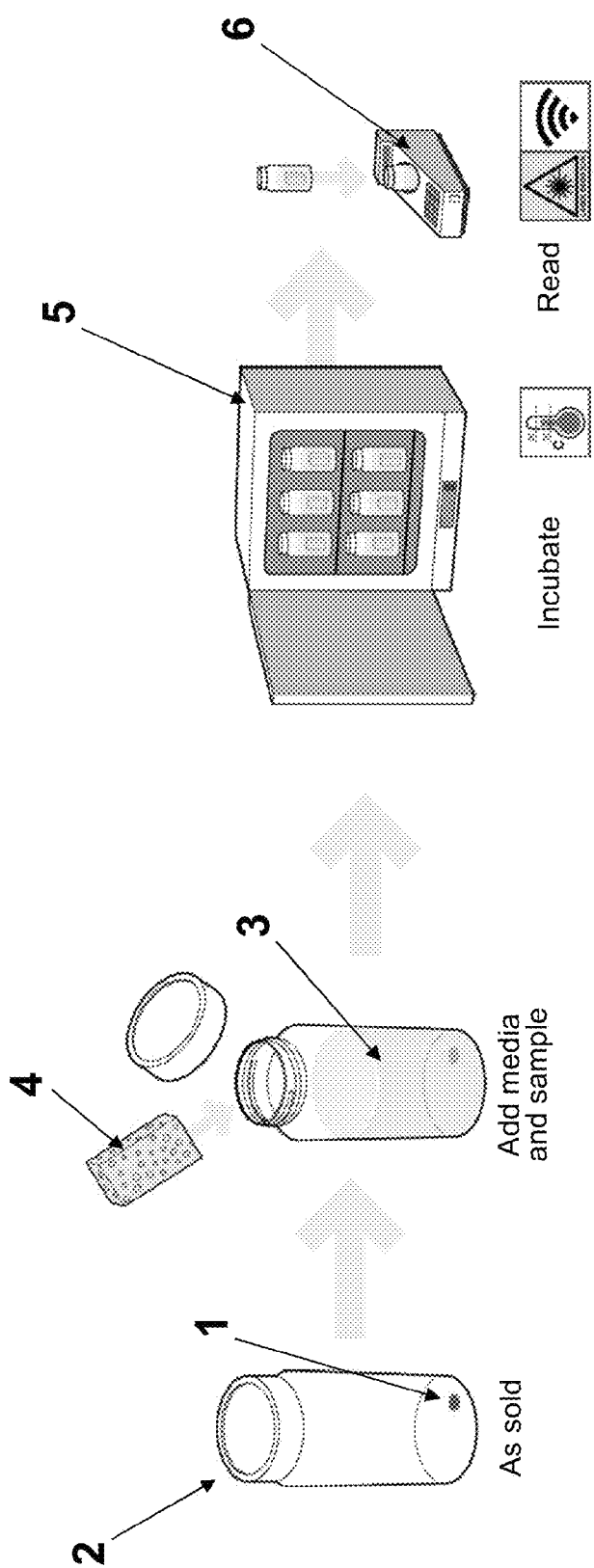
FIG. 3 is a schematic diagram showing a method of intermittent detecting and identifying of a microorganism in a culture sample according to an embodiment of the invention.

The systems and methods according to the embodiments of the invention provide real-time monitoring of microorganism growth in microbiological culture samples. FIG. 3 shows an embodiment of intermittent monitoring of microorganism growth or an endpoint embodiment. In this embodiment, SERS HNW reagents 1 are added to the vessel 2 where the culture occurs. The media 3 and sample 4 are added to the vessel 2, and the vessel 2 is placed into an incubator 5 so that the microorganism (e.g. bacteria, yeast, or cells) is allowed to grow. At user selected time points (either during the culture or at the end of a culture period) the vessel is removed from the incubator 5 and placed in a SERS reader 6, which (after appropriate mixing of the sample) forms a magnetic pellet and reads the Raman signal. The vessel can then be reinserted into the incubator 5 to allow further growth time, if no Raman signal is detected.

Figure 4:
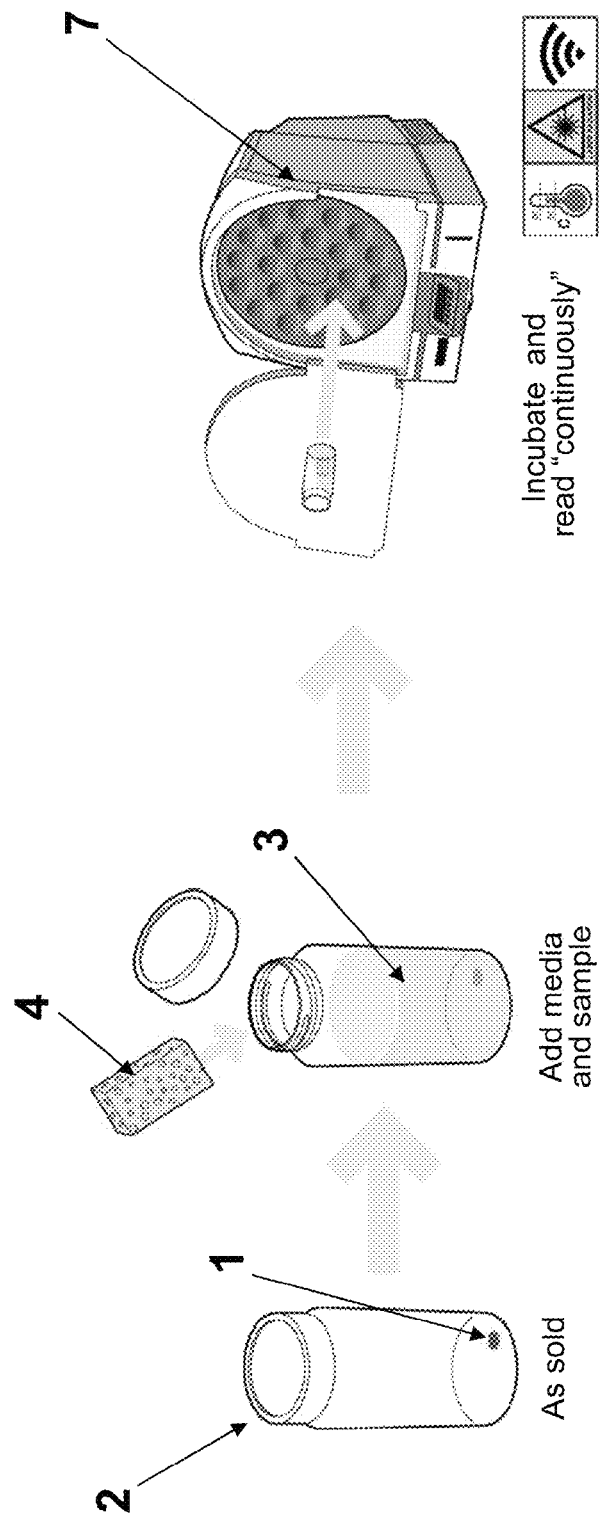
FIG. 4 is a schematic diagram showing a method of real-time detecting and identifying of a microorganism in a culture sample according to an embodiment of the invention.

FIG. 4 shows an alternate embodiment in which the SERS signal is continuously monitored during bacterial growth. In this embodiment, the incubator and SERS reader are integrated into a single instrument 7 which, at prescribed time points, forms the magnetic pellet, reads the SERS signal, and disperses the reagents without need for user intervention.

A. Enrichment Vessel and Detection Vial

Microbiological culture bottles, tubes, syringes, vials, vessels, and the like (e.g., enrichment vessels and, detection vials) suitable for use with the presently disclosed methods, systems, and devices can, in some embodiments, be made of glass or plastic. In some applications, a multilayered plastic is desirable to control gas permeability. In those embodiments wherein the microbiological culture vessel is made of multilayered plastic, the bottle may be injection or blow molded and have inner and outer layers of polyester, polypropylene, polyethylene, polyvinyl chloride, polycarbonate, polyethylene terephthalate (PET), cyclic olefin copolymer (COC), or any copolymer or mixture thereof separated by an intermediate layer of nylon, ethylene vinyl alcohol (EVOH), polyethylene vinyl alcohol, or copolymers or mixtures thereof. However, it is understood that the vessel may not be multilayered in other embodiments and formed using similar techniques (e.g., injection or blow molding). In some applications, the vessel components may be treated with surface coating or chemical methods to control vessel/sample interactions or physical properties. In some embodiments, the vessel can be transparent to visible radiation, although, in particular embodiments, such transparency is not required. Additionally, in some embodiments, the presently disclosed vessels can be adaptable to sterilization. Further, in some embodiments, the vessel is suitable for aerobic or anaerobic culture. In one embodiment, the vessel is gas permeable. In addition, the vessel may include a constant wall thickness along its length which may enhance pelleting and optical analysis.

Figure 8:
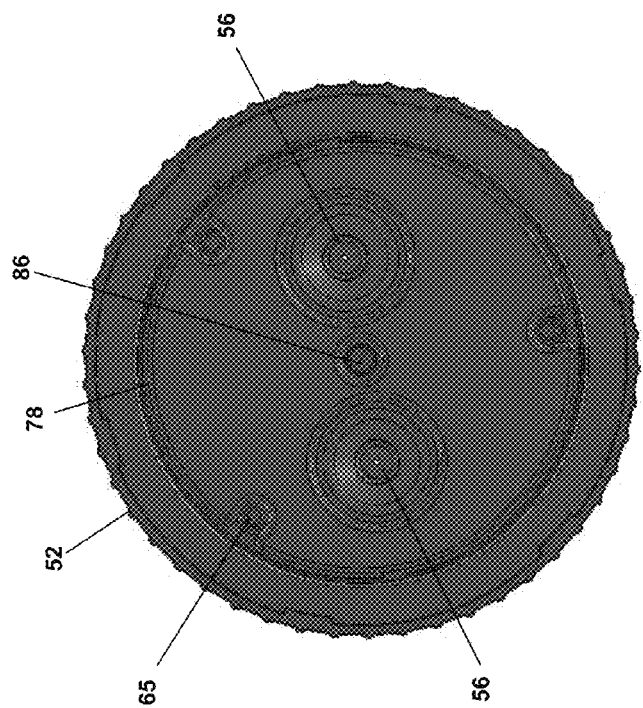
FIG. 8 is a bottom view of lid for an enrichment vessel according to one embodiment of the present invention.
Figure 7:
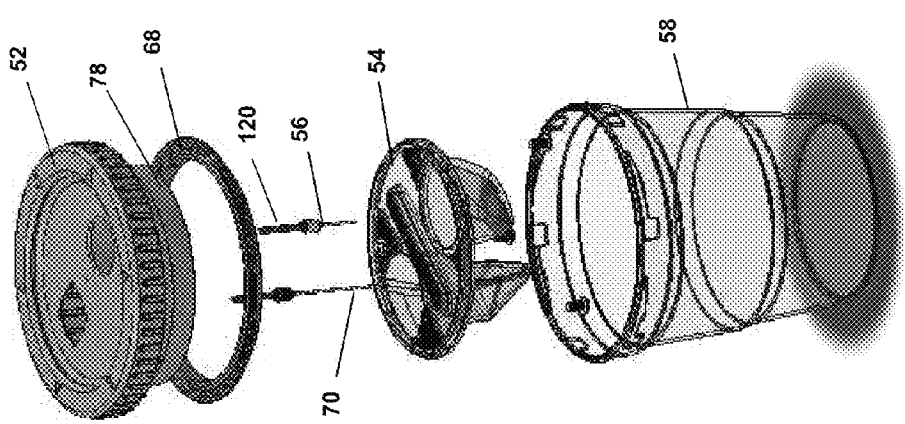
FIG. 7 is an exploded view of an enrichment vessel according to one embodiment of the present invention.
Figure 100:
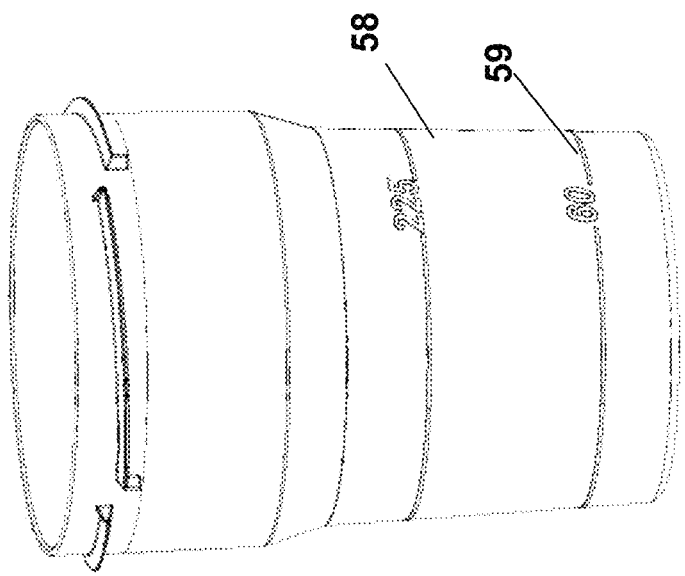
FIG. 100 is a perspective view of a container for an enrichment vessel according to one embodiment of the present invention.

FIGS. 5A-5E and 7 depict an enrichment vessel 50 according to one embodiment of the present invention. Optionally, the enrichment vessel 50 may hold dried or liquid culture media. The enrichment vessel generally includes a lid 52, a basket 54, needle assemblies 56, and a container 58. The lid 52 is engaged with the basket 54 and is configured to engage and seal the container 58 in a fluid-tight connection, such as using a threaded or snap-fit attachment. In one example, the lid 52 may be threaded onto the container 58 but would include one or more back-off features to prevent unscrewing of the lid without the additional disengagement of the back-off feature (e.g., press down and rotate the lid for removal). Thus, the lid 52, needle assemblies 56, and basket 54 may be coupled together so as to be able to engage and disengage the container 58 as a unit. For example, the lid 52 and basket 54 may be coupled together in a snap fit or using other suitable techniques such as adhesives, heat staking, or fasteners. In this regard, FIG. 9C illustrates that the basket 54 may include fastener holes 60 for engagement with fasteners 62 to secure the lid and basket together (see also FIG. 5A). FIG. 8 shows the bottom of the lid including a plurality of holes 65 that align with respective holes 60 on the basket (see FIG. 9C) for receiving the fasteners 62 therethrough. Likewise, the needle assemblies 56 may be attached to the lid 52 using similar securement techniques, such as a force fit, threaded engagement, or adhesives. The container 58 is configured to hold a desired amount of sample therein and thus, may be various sizes and shapes as needed. For example, FIGS. 5A-5C, 7, and 100 illustrate exemplary shapes of a container 58. In one embodiment, the basket 54 and container 58 may be transparent or translucent to facilitate visibility within the container and in particular, visibility of the sample within the reservoirs 64, 66. In addition, FIG. 100 illustrates that the container 58 may include one or more volume lines 59 for visualizing the amount of sample contained in the container. FIG. 7 also illustrates that the vessel 50 may include a gasket 68 or other sealing member used to ensure a fluid-tight connection between the lid 52 and the container 58.

The enrichment vessel 50 includes a pair of needle assemblies 56 and reservoirs 64, 66. However, it is understood that there may one or more needle assemblies 56 and reservoirs 64, 66 in alternative embodiments. In the illustrated embodiment, one needle assembly 56 and reservoir 64 or 66 is configured for use with a particular type of assay (e.g., *Salmonella* or *Listeria*). Because different microorganisms are cultured using different media and sample sizes, the enrichment vessel facilitates use of a single basket for different assays.

Figure 9A:
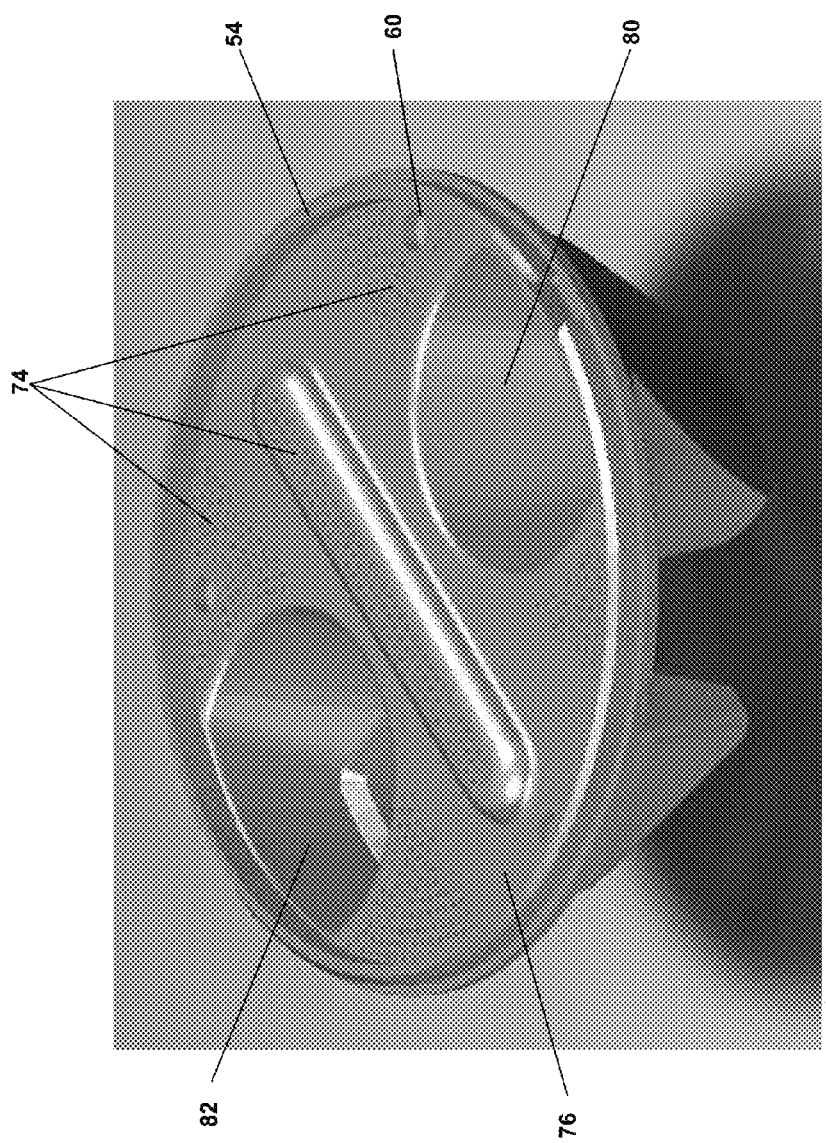
FIGS. 9A-9C are various views of a basket for an enrichment vessel according to one embodiment of the present invention.
Figure 9B:
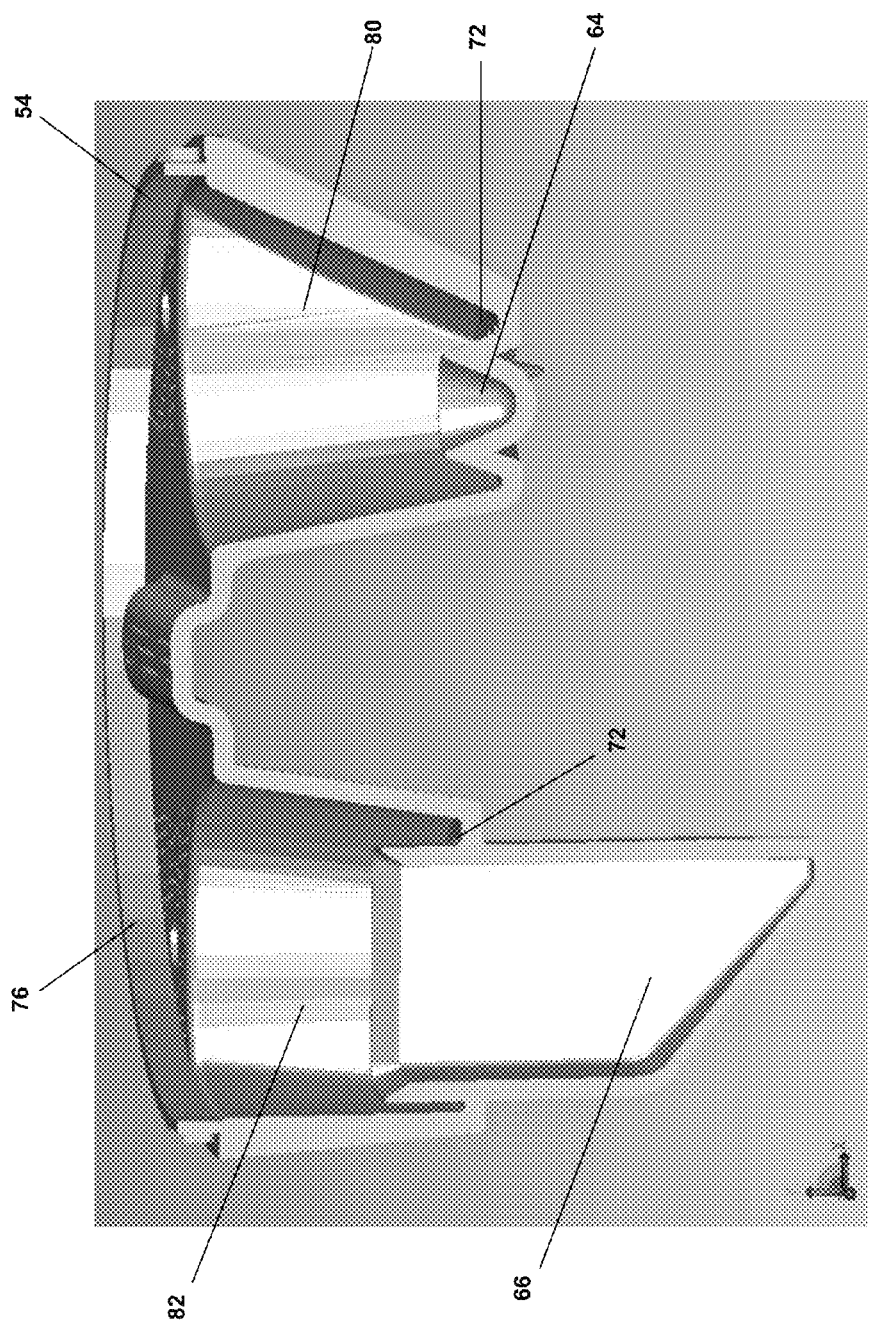
Figure 9C:
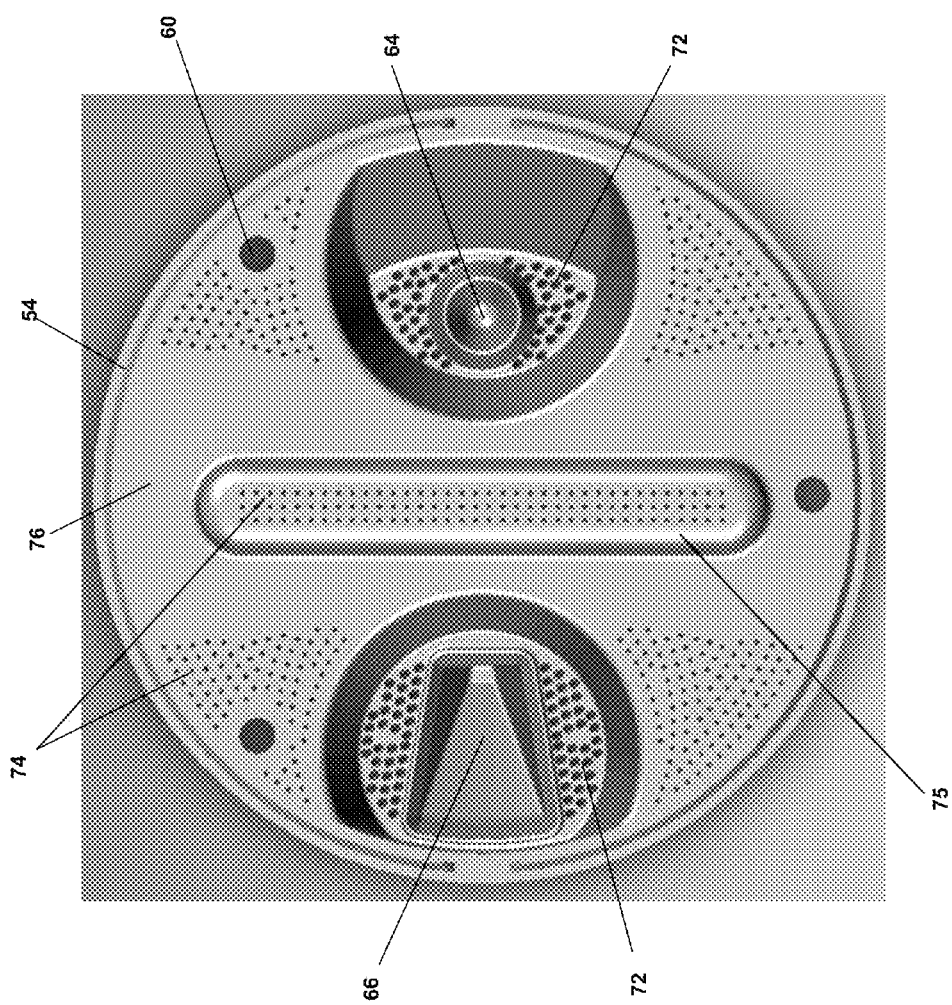

The basket 54 is shown in more detail in FIGS. 9A-9C. The basket 54 includes a pair of reservoirs 64, 66, with each reservoir configured to hold a predetermined sample volume. As shown, the reservoirs 64, 66 are spaced away from the bottom of the container 58, wherein this space is configured to hold a desired sample. In this regard, the first reservoir 66 is configured to hold a larger volume than the second reservoir 64. In one specific embodiment, the first reservoir 66 is configured to hold about 5 mL and the second reservoir 64 is configured to hold about 100 µL. As shown, the reservoirs 64, 66 may be shaped to facilitate metering of the sample as well as alignment with a respective needle assembly 56. For example, FIGS. 5A-5C and 6 illustrate that each needle 70 is inserted within a reservoir 64, 66 and to the lowest position therein to ensure that substantially all of the metered sample is removed. Thus, the length of the needle 70 may be adjusted depending on the size of the reservoir, as the needle extending within the first reservoir 66 is longer than the needle extending within the second reservoir 64. The shape of the reservoir 64, 66 may be any shape that is suitable to retain the desired amount of sample. For example, FIGS. 5A, 5B, 5C, 5E, and 9B show that the second reservoir 64 has a generally conical shape, while the first reservoir 66 has surfaces that extend along the needle and taper towards the base of the needle.

Figure 107:
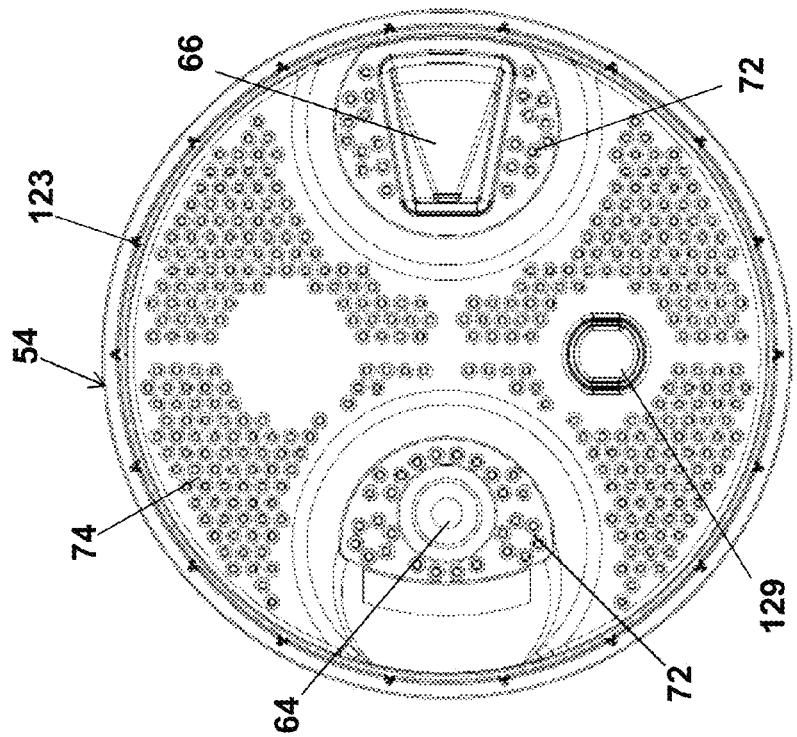
FIG. 107 is a top view of the basket shown in FIG. 106.
Figure 106:
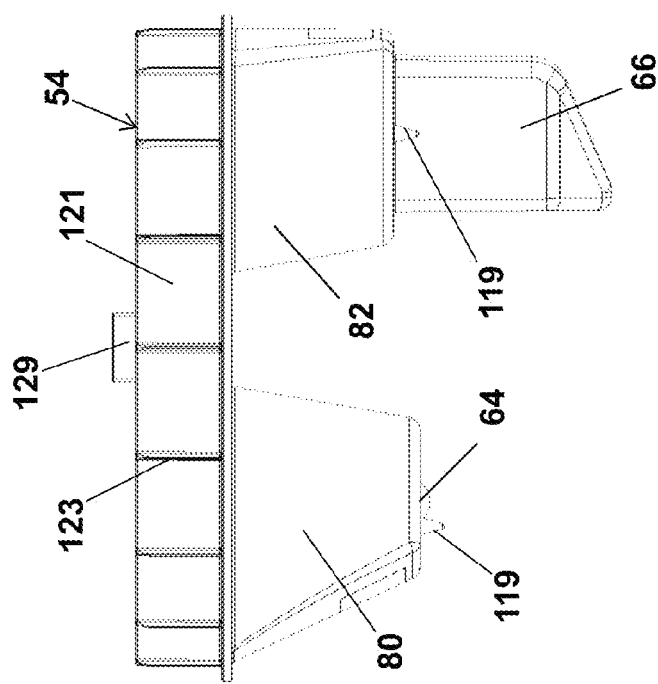
FIG. 106 is a side view of a basket for an enrichment vessel according to one embodiment of the present invention.
Figure 108:
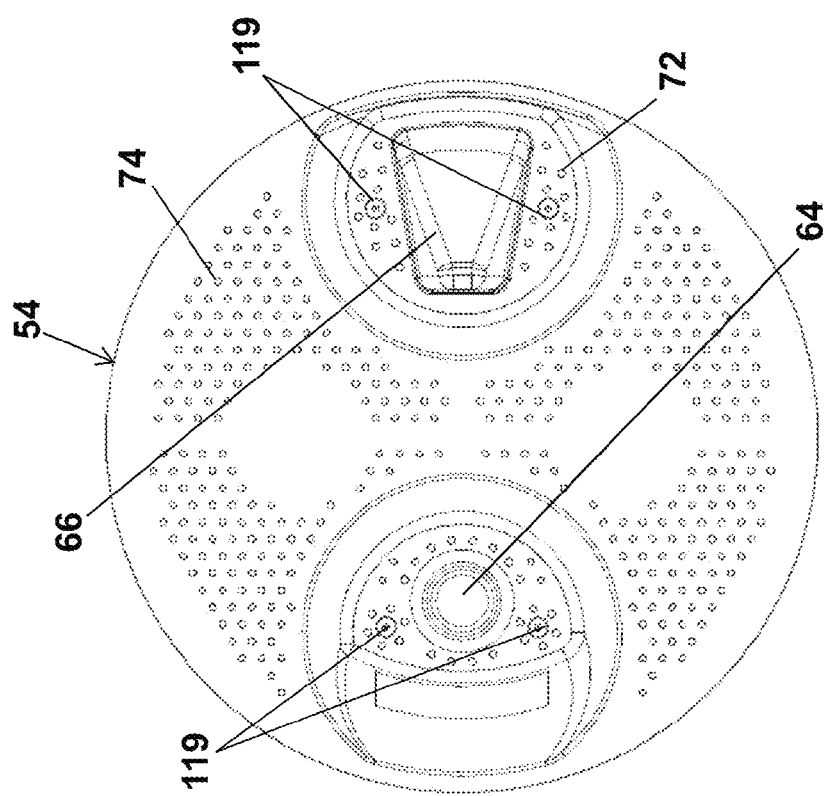
FIG. 108 is a bottom view of the basket shown in FIG. 106.

FIG. 9C particularly illustrates that the basket 54 includes a number of holes 72, 74 defined therethrough. Typically, the amount of sample in the container 58 would be below the holes 72 when the container is in an upright position, but would be at least below the entrance to each reservoir 64, 66 so that a desired volume can be metered. Holes 72 may be defined within the basket adjacent the reservoirs, while holes 74 may be defined through an upper surface 76 of the basket adjacent a lid-engaging portion 78. The holes 72 located adjacent the reservoirs 64, 66 are configured to drain excess sample within a respective reservoir. Namely, when the enrichment vessel 50 is tilted from an upright horizontal position to fill one of the reservoirs 64, 66, returning the vessel to the upright position results in the reservoir being over-filled with sample and excess sample will subsequently drain through the holes 72. As such, a desired volume is metered in a repeatable manner within each reservoir 64, 66. The holes 74 defined in the upper surface 76 of the basket 54 may be used to allow sample to enter the reservoirs 64, 66 while also preventing unwanted particulates in the sample from being transferred into the reservoirs. It is understood that the basket 54 may be modified depending on the amount of sample to be metered and the type of sample, such as by modifying the size and depth of the reservoir 64, 66, as well as the size and depth of the holes. In this regard, FIG. 9C illustrates that the holes 72, 74 may be tapered in different directions from one another for aiding in draining, with the entrance to the holes 72 adjacent the reservoir being larger than the entrance to the holes 74 in the upper surface 76 of the basket. The smaller hole entrance may be used to filter any undesirable particles from entering the reservoirs. In addition, FIGS. 106-109 illustrate an embodiment where the basket 54 includes holes 72, 74 that are approximately the same size. Moreover, the basket 54 may also include a rib 75 or other raised surface that is configured to aid in draining of fluid through the basket. In particular, the rib 75 may be at the center of the basket 54 to facilitate venting during filtering and draining by offering a surface capable of draining excess fluid above the basket with different draining characteristics than the remainder of holes in the upper surface 76 of the basket. FIGS. 106 and 108 illustrate an embodiment wherein a bottom surface of the reservoirs 64, 66 may include one or more protrusions 119 which aid draining by wicking fluid from the reservoir and allowing fluid from multiple drain holes 72 to coalesce.

As shown in FIG. 9B, each reservoir 64, 66 is separated from an upper surface 76 of the basket with a respective head space 80, 82. The head spaces 80, 82 allow the sample to readily enter a respective reservoir 64, 66 when the container is tilted. Thus, when the container 58 is tilted, sample enters through the holes 74 defined in the upper surface 76 of the basket 54, into the head space 80 or 82, and enter the reservoir 64 or 66. When the container 58 is returned to an upright position, the reservoir 64 or 66 is overfilled due to excess sample located in the head space 80 or 82, wherein the excess sample then drains through the holes 72 defined adjacent the reservoir and back into the container. As shown in FIG. 9B, the holes 72 defined adjacent the reservoirs 64, 66 are located below the opening leading into the reservoir to facilitate draining and metering the desired amount of sample.

Figure 103:
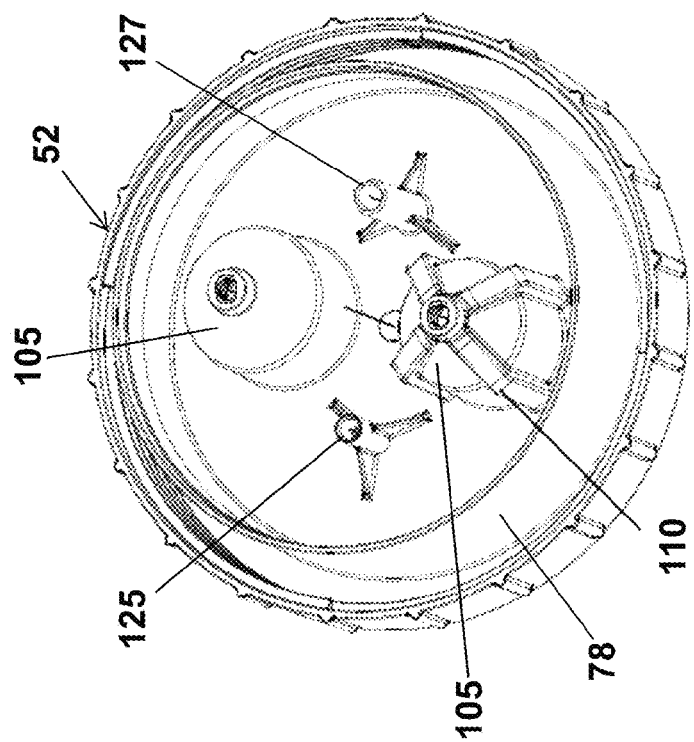
FIG. 103 is a bottom perspective view of the lid shown in FIG. 101.
Figure 102:
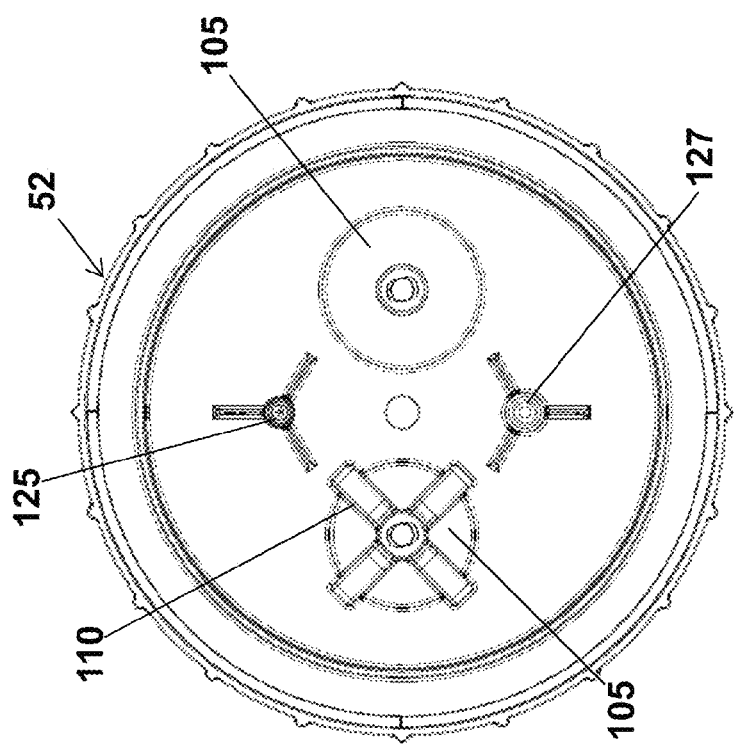
FIG. 102 is a bottom view of the lid shown in FIG. 101.

Each reservoir 64, 66 is aligned with a respective needle assembly 56 as shown in FIGS. 5A-5C and 6. In one embodiment the lid 52 includes a lid-engaging portion 78, wherein the lid engaging portion is configured to couple the basket 54 and lid together as discussed above. The lid-engaging portion 78 and basket 54 have a smaller outer diameter than the inner diameter of the opening of the container 58 so as to be configured to be inserted within the container. The lid-engaging portion 78 may also include openings for receiving respective needle assemblies 56 that extend into the reservoirs 64, 66. The needles 70 are located within the lid-engaging portion 78 so that the needles are configured to engage a detection vial as discussed in further detail below. In this regard, the lid-engaging portion 78 includes a conical or tapered surface 105 opposite a respective opening 102, 104 that is configured to receive and engage with a needle assembly 56. The needles 70 further extend through respective openings defined in the bottom of the conical surface 105 into the head space 80, 82 and within a respective reservoir 64, 66 (see FIGS. 5A-5C and 6). FIG. 6 illustrates that each needle assembly 56 may be engaged with the lid engaging portion 78 such that the needles 70 extend proximate the reservoirs 64, 66. FIG. 6 illustrates that the lid 52 may also include a vent 86 defined therein for allowing any nonhazardous, gaseous byproducts to escape from the container to prevent pressure build up during culture. FIGS. 102-103 and 105 illustrate an alternative embodiment where a vent post 125 extends from a bottom surface of the lid 52. The vent post 125 defines an opening therethrough for receiving and engaging a filter for filtering any gaseous byproducts exiting the container 58. The vent post 125 aligns with vent 86. In this regard, the vent post 125 is configured to direct nonhazardous, gaseous byproducts through the opening in the vent post and through the vent 86 defined in an upper surface of the lid 52.

Figure 109:
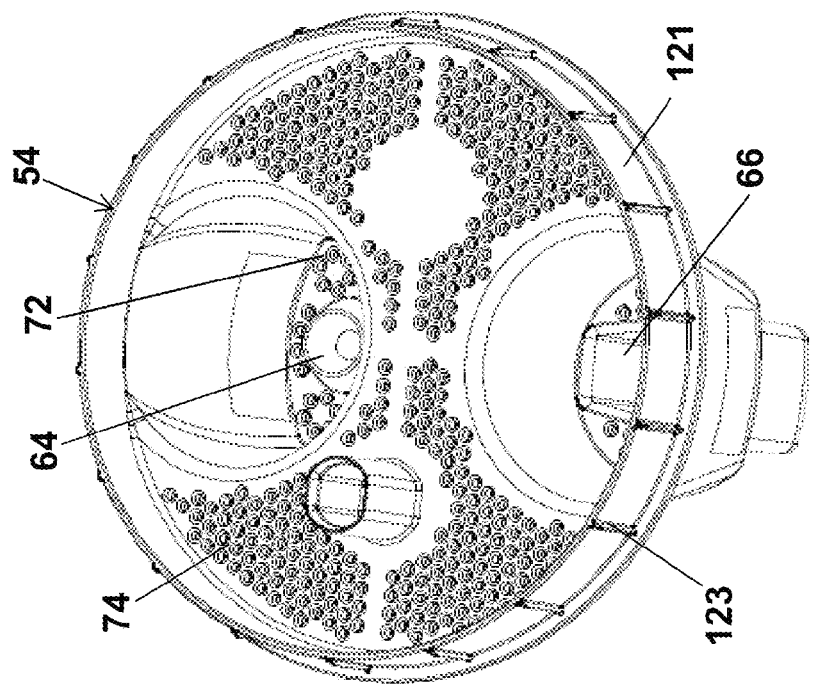
FIG. 109 is a perspective view of the basket shown in FIG. 106.

FIGS. 102-103 and 105 also illustrate that the lid 52 may further include an engagement post 127 extending outwardly from a bottom surface of the lid. The engagement post 127 is configured to align with and engage a corresponding engagement post 129 extending outwardly from an upper surface of the basket 54, as shown in FIGS. 106, 107, and 109. As illustrated, the engagement post 127 has a smaller diameter than engagement post 129, although the relative sizes of the posts may be reversed if desired. In addition, the engagement portion 78 shown in FIGS. 103-105 is configured to engage a corresponding engagement portion 121 defined on an upper surface of the basket 54 (see FIGS. 106, 107, and 109). In particular, the engagement portion 78 may be sized and configured to overlie and encircle the engagement portion 121. The outer periphery of the engagement 121 surface may define a plurality of ribs 123. When the engagement surfaces 78 and 121 are brought into engagement with one another (e.g., by sliding and/or rotating with respect to one another), the ribs may be configured to compress the ribs 123. The compression may be sufficient to create a friction fit between the lid 52 and the basket 54. In one embodiment, the ribs 123 may be crushed or otherwise deformed to create a friction fit.

Figure 101:
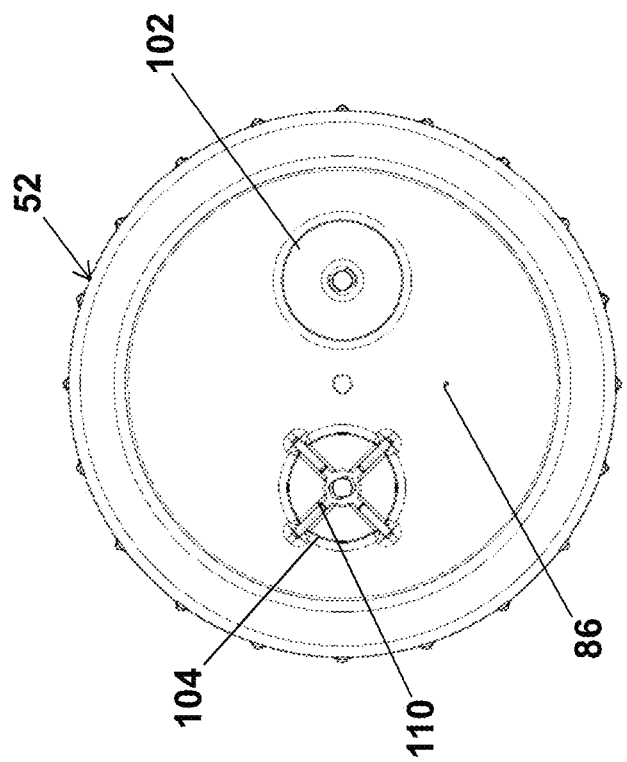
FIG. 101 is a top view of lid for an enrichment vessel according to one embodiment of the present invention.

Each needle assembly 56 is configured to engage a respective detection vial 100. The detection vial 100 may include a particular cap configuration for mating with a respective opening 102, 104 defined in the lid 52. Thus, each cap may be associated with a specific type of sample so that the risk of using the wrong media for a microorganism is minimized. For example, the lid 52 may include a keyed opening 104 that only allows mating with the cap of the detection vial when the cap is oriented to engage the keyways 110 (see FIG. 6). FIG. 101 shows an alternative embodiment of a lid 52 where keyways 110 are defined along the length of the opening 104, including along conical surface 105. The keyways 110 may be defined on the inner surface of the opening, as shown in FIG. 6, or on both the inner and outer surfaces of the opening as shown in FIGS. 101-103.

Figure 10A:
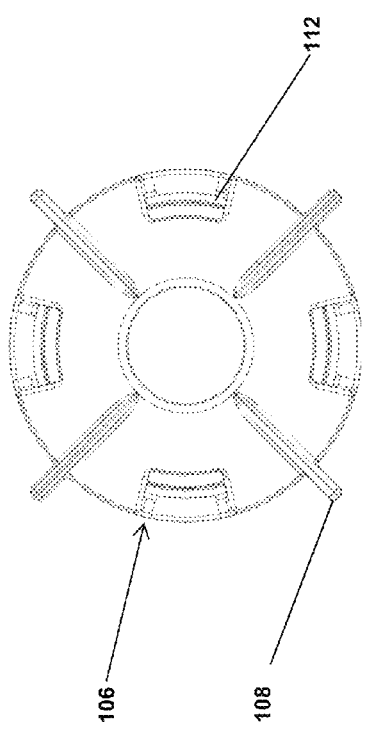
FIGS. 10A and 10B illustrate a cap for a detection vial according to one embodiment of the present invention.
Figure 10B:
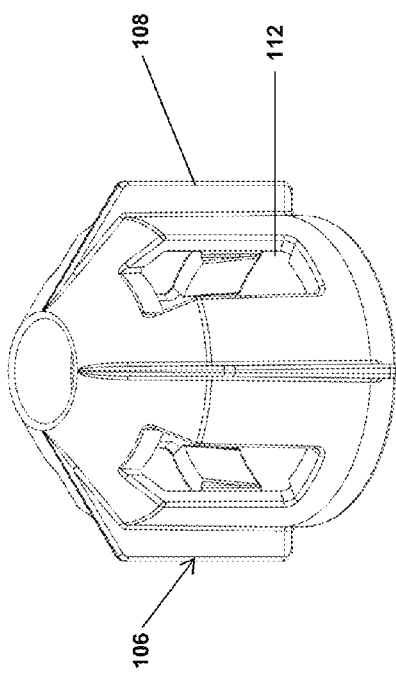

FIGS. 10A and 10B illustrate an exemplary embodiment of a cap 106 suitable for use with a detection vial. In this regard, the cap 106 includes a plurality of ribs 108 that are configured to engage respective keyways 110 defined in the opening 104 of the lid 52 (see FIG. 5D). Thus, in order for the cap 106 to be inserted within opening 104, ribs 108 would need to be radially aligned within the keyways 110. In addition, the cap 106 includes a plurality of engagement features 112 that are configured to engage the detection vial 100 in a snap fit. The snap connection may minimize ovalization of the detection vial 100, as well as dislodgement of the cap 106 during handling. It is understood that the cap 106 and detection vial 100 may be secured together using other suitable techniques, such as a threaded or crimped sleeve/cap engagement, adhesives, ultrasonic welding, and/or heat staking. FIG. 13A illustrates the cap 106 engaged with a detection vial 100, according to one embodiment of the present invention.

Figure 11A:
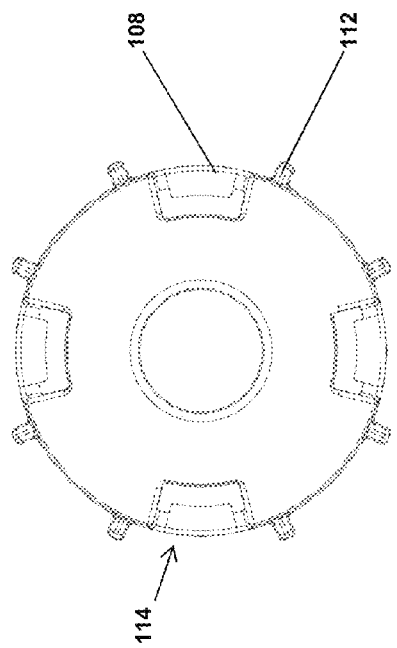
FIGS. 11A and 11B illustrate a cap for a detection vial according to one embodiment of the present invention.
Figure 11B:
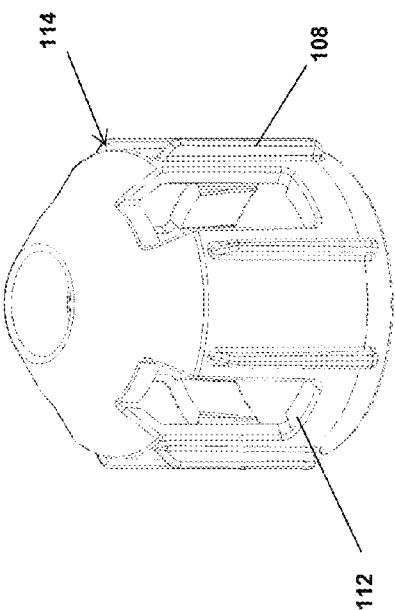

As mentioned above, the cap 106 may have different configurations for different assays so that the risk of using the incorrect detection vial 100 is eliminated. For instance, FIGS. 11A and 11B illustrate an alternative cap 114 configuration, while FIG. 14A shows the cap 114 engaged with a detection vial 100. As illustrated, each cap 106, 114 may include a plurality of ribs 108 and engagement features 112.

The cap 114 may be configured to be received within a respective opening 102, although the opening need not include corresponding keyways. Thus, the cap 114 may be received within the opening 102 regardless of its radial orientation, but the cap 114 would be incapable of being inserted within opening 104. Thus, the ribs 108 of cap 106 may prevent access to the opening 102 in the lid 52 just as the outer diameter of cap 114 may prevent access to opening 104.

Figure 12:
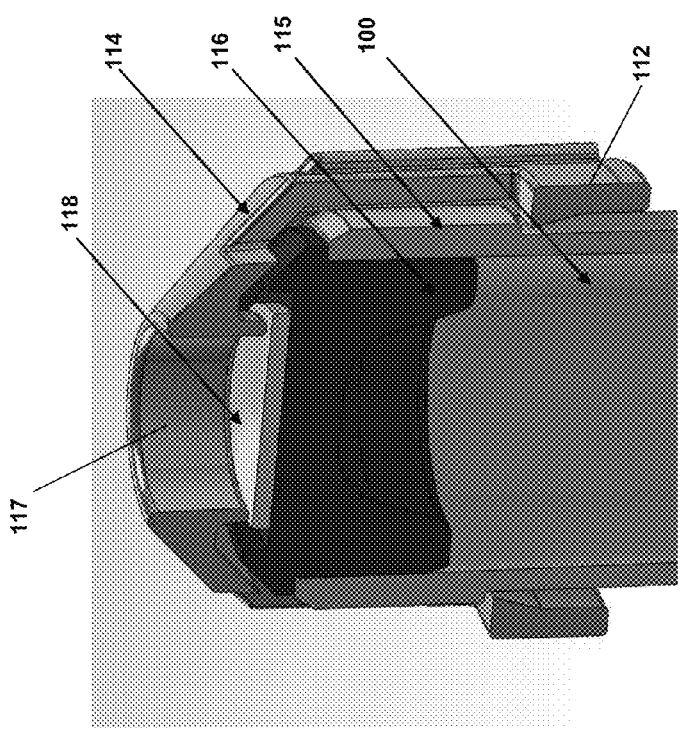
FIG. 12 is a cross-sectional view of a cap engaging a detection vial according to one embodiment of the present invention.
Figure 13B:
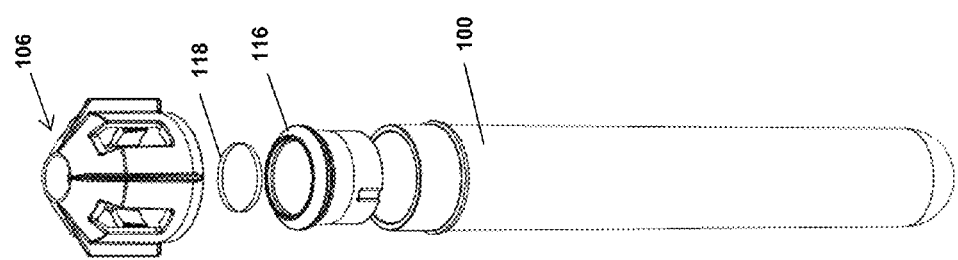
FIGS. 13A and 13B are a perspective view and an exploded view of a cap engaging a detection vial according to an embodiment of the present invention.
Figure 13A:
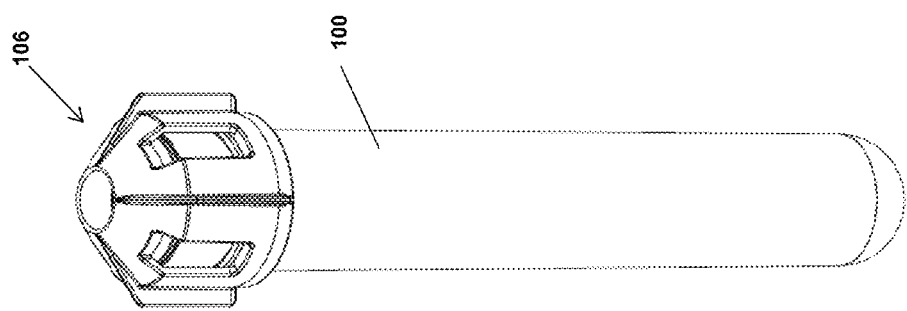
Figure 14B:
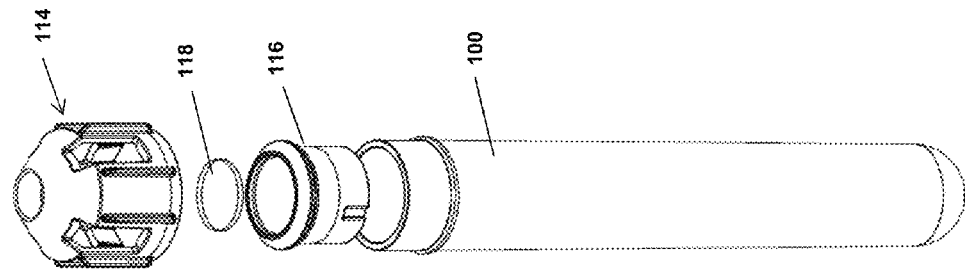
FIGS. 14A and 14B are a perspective view and an exploded view of a cap engaging a detection vial according an embodiment of the present invention.
Figure 14A:
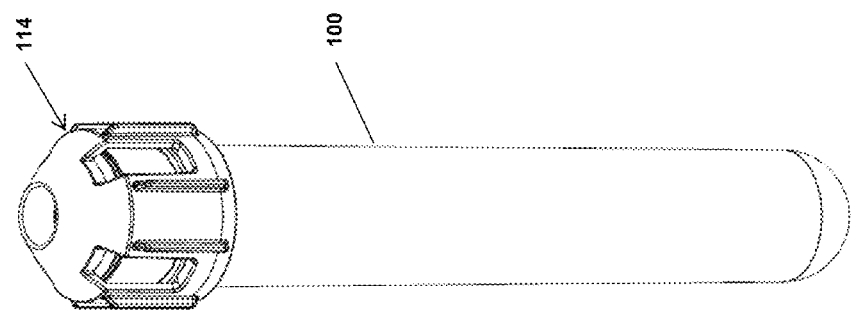

FIGS. 12, 13B, and 14B illustrate additional features of the detection vial 100 and cap 114 according to one embodiment of the present invention. Namely, the cap 114 includes a stopper 116 and an absorbent pad 118 disposed between the cap and the stopper. The absorbent pad 118 may be used to absorb any sample that exits the detection vial 100 after transferring the sample from the enrichment vessel 50 into the detection vial thereby minimizing exposure to the technician or environment. The cap 114 may also have a finger stand-off 117 to prevent accidental contact of a potentially wetted pad. Moreover, the stopper 116 may be any suitable material that is configured to create a fluid-tight connection with the detection vial 100 (i.e., liquid and gas), as well as to be pierced by a needle to reseal to a fluid tight connection after being pierced by a needle and to engage the detection vial. For instance, the stopper 116 may be a suitable rubber or elastomeric material. FIG. 12 also illustrates the engagement between the engagement features 112 and the protrusion 115 of the detection vial 100. Thus, the caps 106, 114 may engage with the detection vial 100 in a snap-fit, which would prevent unintentional removal or dislodgement of the cap. The shape of the protrusion 115 can be any shape that would allow for a retentive snap fit with the engagement features 112.

The detection vials 100 may include the reagents and optionally a media, such as for example a specific growth media, depending on the microorganism that is being tested in the sample. The reagents and media may be present in the detection vial in a dried (e.g., dehydrated) format or in a wet (e.g., hydrated) format. For example, the media and reagent may be dried. The detection vials 100 may also hold a vacuum when the stopper 116 is engaged therewith. Thus, when the detection vial 100 is inserted within a respective opening 102, 104 in the lid 52, the stopper 116 and absorbent pad 118 are pierced by the needle 70, and the sample within the reservoir 64 or 66 is pulled through the needle and into the detection vial (see FIGS. 15-17). In one example, the portion of the needle 70 extending into the opening 102 or 104 may include a protective sleeve 120 that is configured to be compressed as the detection vial 100 is pushed downwardly and into engagement with the needle. When the protective sleeve 120 is compressed, the needle 70 is exposed and penetrates the stopper 116, allowing the vacuum to pull the portion of the sample contained within the reservoir 64 or 66. After completion of the fluid transfer and removal of the detection vial 100, the protective sleeve 120 returns to its original shape covering the needle 70. As such, the transfer of sample between the enrichment vessel 50 and the detection vial 100 occurs in a biocontained manner. The vacuum within each detection vial 100 may be any amount sufficient to pull a desired amount of sample from the reservoir (e.g., 8-10 mL draw capacity for 5 mL sample). Any further excess vacuum in the detection vial 100 is exhausted by air following the fluid from the reservoir 64 or 66.

The detection vial 100 may be provided with reagents, with or without culture or growth media, stopper 116, pad 118, and cap 106 or 114 with vacuum or without vacuum, depending on the end-user (e.g., outsourced use versus in-house use). In this vein, the detection vial 100 may be assembled only to the stopper 116 for retention of reagents only, while the cap 106 or 114 is supplied separately for users who need to access the interior of the detection vial. Alternatively, the detection vial 100 can be pre-assembled with a stopper 116, pad 118, and cap 106, 114 combination as shown in FIG. 12. Furthermore, the media and reagent amount is determined by the detection vial 100, not the initial enrichment volume, according to one embodiment.

As such, the configuration of the enrichment vessel 50 and detection vial 100 enable the sample to be contained and transferred in a biocontained manner, thereby limiting exposure to the technician or facility. The enrichment vessel 50 also facilitates accurate metering of a desired volume of sample, while also being configured to accommodate a plurality of types of samples. For example, this may be particularly useful for *Salmonella* and *Listeria*, where different assays, media, and amount of sample are utilized. The enrichment vessel 50 and detection vial 100 are also configured to reduce the risk that the incorrect vial will be used for testing by incorporating mating features between the enrichment vessel and the detection vial.

Figure 86:
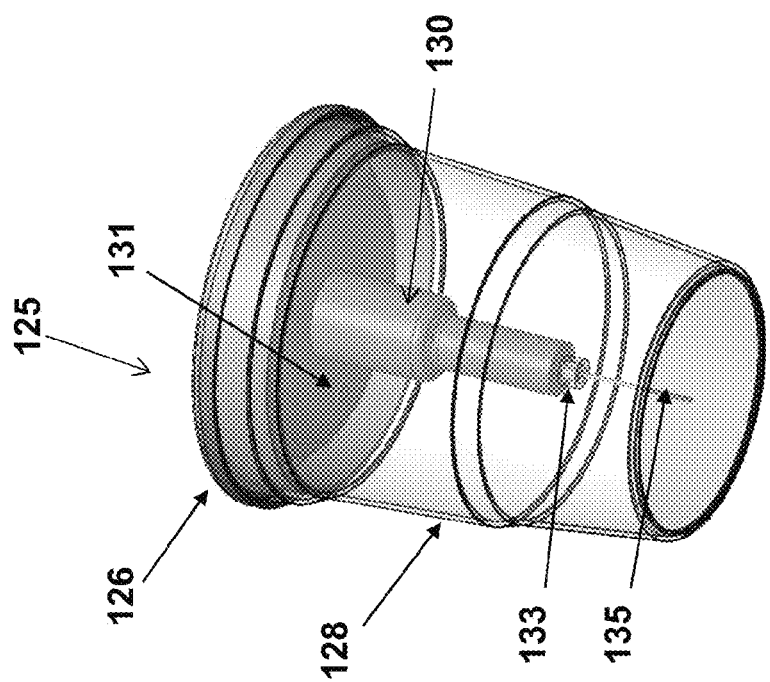
FIG. 86 illustrates an enrichment vessel according to another embodiment of the present invention.
Figure 88:
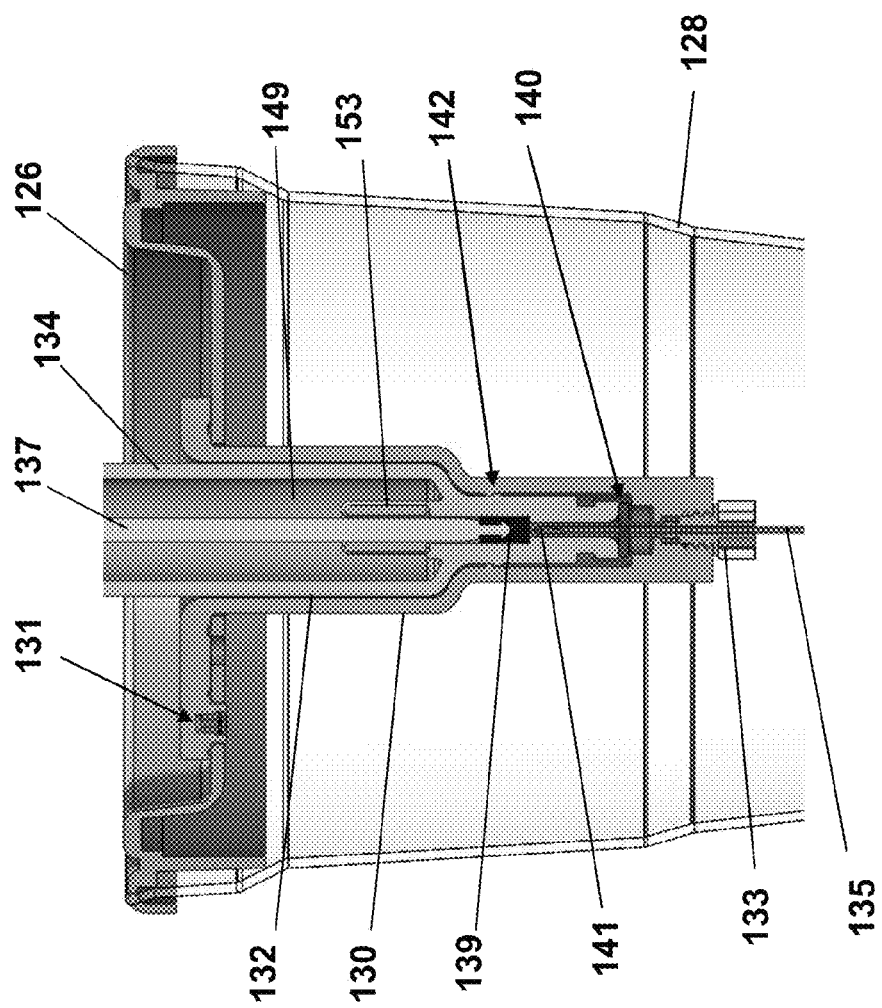
FIG. 88 is a cross-sectional view of a syringe engaged with an enrichment vessel according to one embodiment of the present invention.

FIGS. 86 and 88 illustrate another embodiment of an enrichment vessel 125. As before, the vessel 125 includes a lid 126 engaged with a container 128 in a fluid-tight manner. As shown, the enrichment vessel 125 includes a longitudinal syringe support 130 extending from the lid 126 and into the container 128. The syringe support 130 may be attached to the lid 126 or may be integrally formed therewith. The syringe support 130 includes an opening 132 configured to receive a syringe 134 therein, and is generally shaped in a mating relationship with the syringe 134. Engaged at the base of the syringe support 130 is a needle assembly including a hub 133 and a needle 135, wherein the hub is engaged with the syringe support, and the needle extends within the container 128 and is configured to draw sample therethrough. The needle 135 may include a compressible cover 141 that extends over the portion of the needle within the syringe 134. As also discussed above, the lid 126 may include a vent 131 for allowing nonhazardous, gaseous byproducts to escape from the container.

Figure 87:
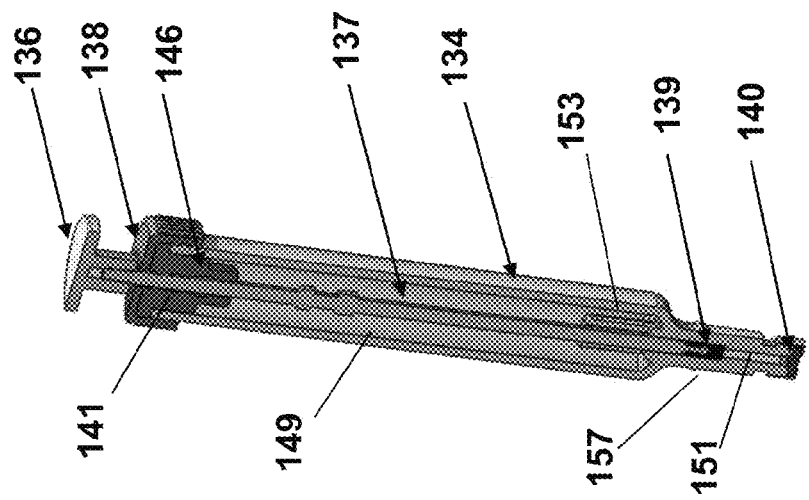
FIG. 87 is a cross-sectional view of a syringe according to one embodiment of the present invention.

FIG. 87 illustrates one embodiment of a syringe 134 that generally includes a handle 136, a plunger rod 137 coupled to the handle, a cap 138, a plunger 139 coupled to the end of the plunger rod, a septum 140, and a seal 146. FIG. 87 further illustrates that the syringe 134 is configured to engage the opening 132, such as with a twist-lock interface 142, for supporting the pull force applied while drawing the sample out of the container 128. Thus, the plunger 137 is longitudinally displaceable within the syringe 134. The septum 140 is configured to be pierced by a needle and reseal upon removal of the needle. In other embodiments, the septum 140 also includes an absorbent pad and a stand-off feature to prevent contamination to the user due to any fluid that may escape through the septum. The seal 146 is engaged with the syringe 134 and cap 138 to create a fluid-tight connection. The syringe 134 may also include a first larger bore 149 disposed within the opening 132 and a neck region 157 including a second smaller bore 151. As shown in FIGS. 87 and 88, an extension 153 extends from the neck region 157 and into the larger bore 149 such that a portion of the smaller bore 151 extends within the larger bore 149. There may be one or more slots or openings 155 defined between the extension 153 and the base of the neck region 157, as discussed in greater detail below.

FIGS. 89A-89C illustrate the progression of a start position, a "soft" stop, and a "hard" stop when removing sample from the container 128 and into the syringe 134. As shown in FIG. 89A, when the syringe 134 is engaged with the syringe support 130, the plunger 139 is positioned adjacent to the needle 135 in the start position and is configured to compress the cover 141 in order to allow fluid communication between the container 128 and the syringe 134 via the needle. FIG. 88 further illustrates that the needle 135 is configured to penetrate the septum 140 when the syringe 134 is engaged with the syringe support 130. As the plunger rod 137 is pulled outwardly from the syringe 134, a portion 144 of the sample is pulled through the needle 135 and into the bore 151, and a first engagement feature 145 on the plunger rod engages the seal 146 to stop further withdrawal thereof. In this manner, the sample is withdrawn at a desired rate whereby the fluid is able to catch up with the vacuum so that underdrawing the sample is prevented.

In FIG. 89C, the plunger rod 137 is withdrawn further from the syringe 134 whereby a second engagement feature 147 on the plunger rod 137 engages the seal 146 to prevent further withdrawal of the plunger rod. In addition, the first engagement feature 145 is engaged within a pocket 148 defined in the seal 146 that prevents the plunger rod 137 from being displaced further out of the syringe 134. As shown in FIG. 89C, the plunger 139 may be disposed within the extension 153 of the syringe 134 such that no further vacuum may be pulled due to the plunger rod 137 and plunger 139 being positioned so that the bore 151 is no longer closed. That is, when the plunger 139 is no longer covering the openings 155, the bores 149 and 151 are in fluid communication with one another such that a vacuum is no longer being pulled. Moreover, the engagement of the plunger rod 137 and the seal 146 prevents the plunger rod from being pulled back into the syringe 134, while also preventing a user from further withdrawing the plunger and risking exposure to the sample.

Figure 90B:
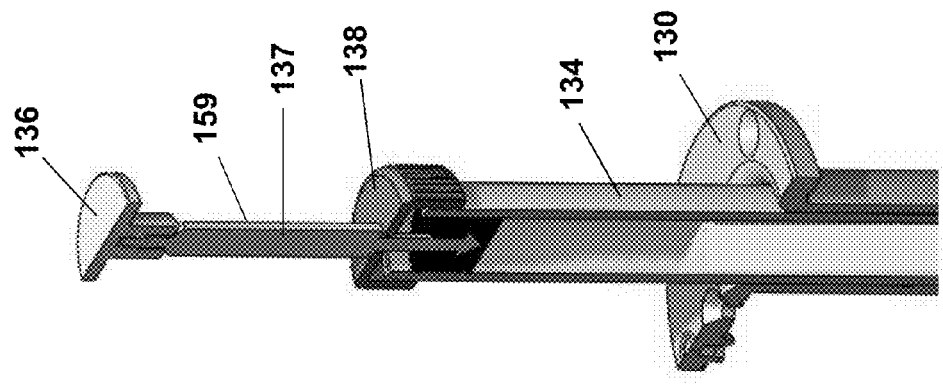
FIGS. 90A and 90B are enlarged cross-sectional views of a syringe according to one embodiment of the present invention.
Figure 90A:
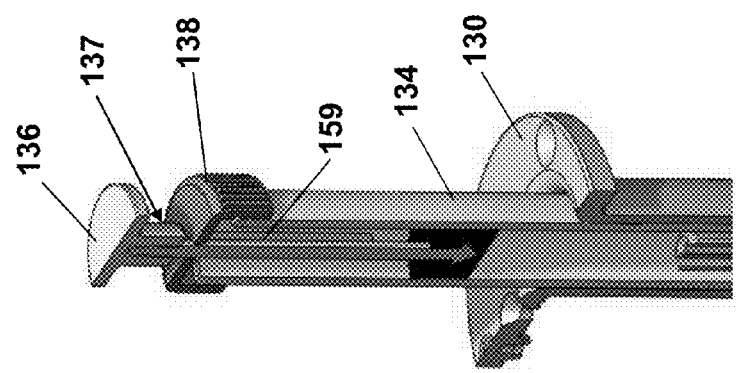

FIGS. 90A and 90B illustrate another embodiment of a plunger rod 137. The plunger rod 137 includes longitudinal ribs 159 that are configured to slide within slots defined within the cap 138. Moreover, FIG. 90B shows that the plunger 137 is able to be twisted to disengage the ribs 159 from the slots and engage the cap 138 to prevent the plunger from returning into the syringe 134.

Figure 92:
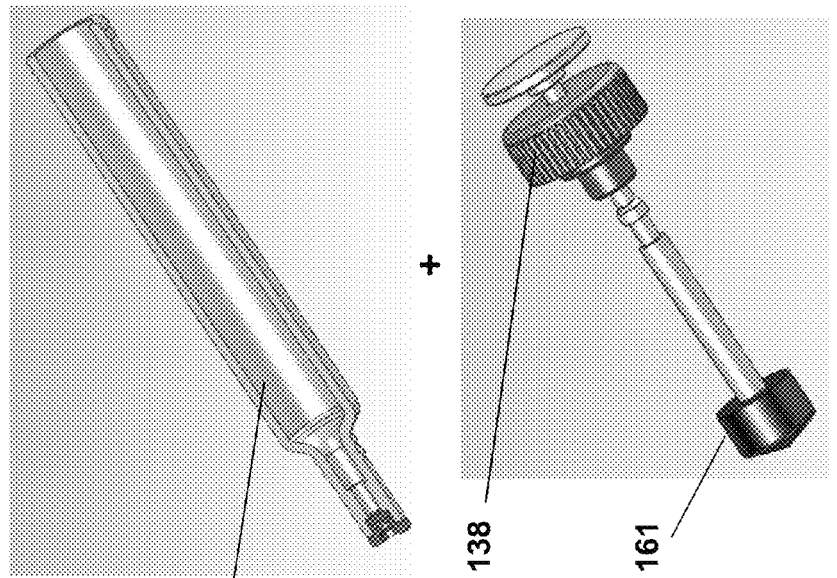
FIG. 92 is a cross-sectional view of a syringe and a perspective view of a plunger according to another embodiment of the present invention.
Figure 91:
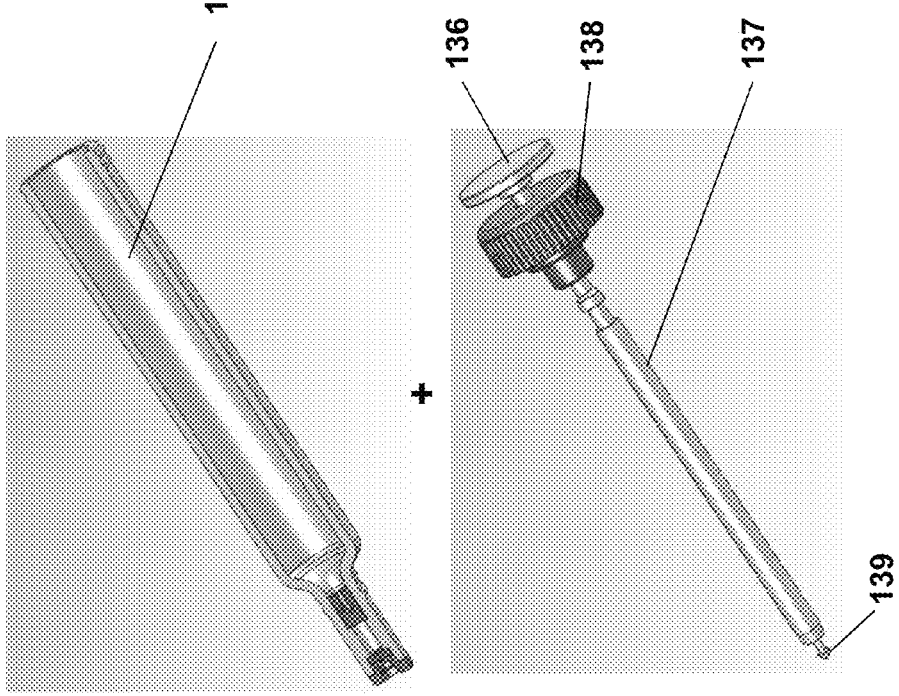
FIG. 91 is a cross-sectional view of a syringe and a perspective view of a plunger according to one embodiment of the present invention.

FIGS. 91 and 92 illustrate alternative plunger rods and plungers that may be used for withdrawing different volumes from the container 128. In this regard, FIG. 91 corresponds to that described in connection with FIGS. 87, 88, and 89A-C. Thus, the plunger 139 is suitable for withdrawing smaller volumes into the smaller bore 151 (e.g., about 125 µL). Accordingly, the size of the plunger and length of the plunger rod may be varied as needed. In another embodiment, FIG. 92 shows a plunger 161 suitable for withdrawing sample into the larger bore 149 (e.g., about 5 mL). Thus, the syringe 134 is suitable for use with different plungers for withdrawing different volumes of sample, which is useful when testing for different microorganisms (e.g., *Listeria* and *Salmonella*). Moreover, the user may receive the syringe 134 and plunger/plunger rod pre-assembled, or the user may be able to add in reagents, reconstitution fluid, etc. and then assemble the plunger/plunger rod to the syringe.

Figure 18:
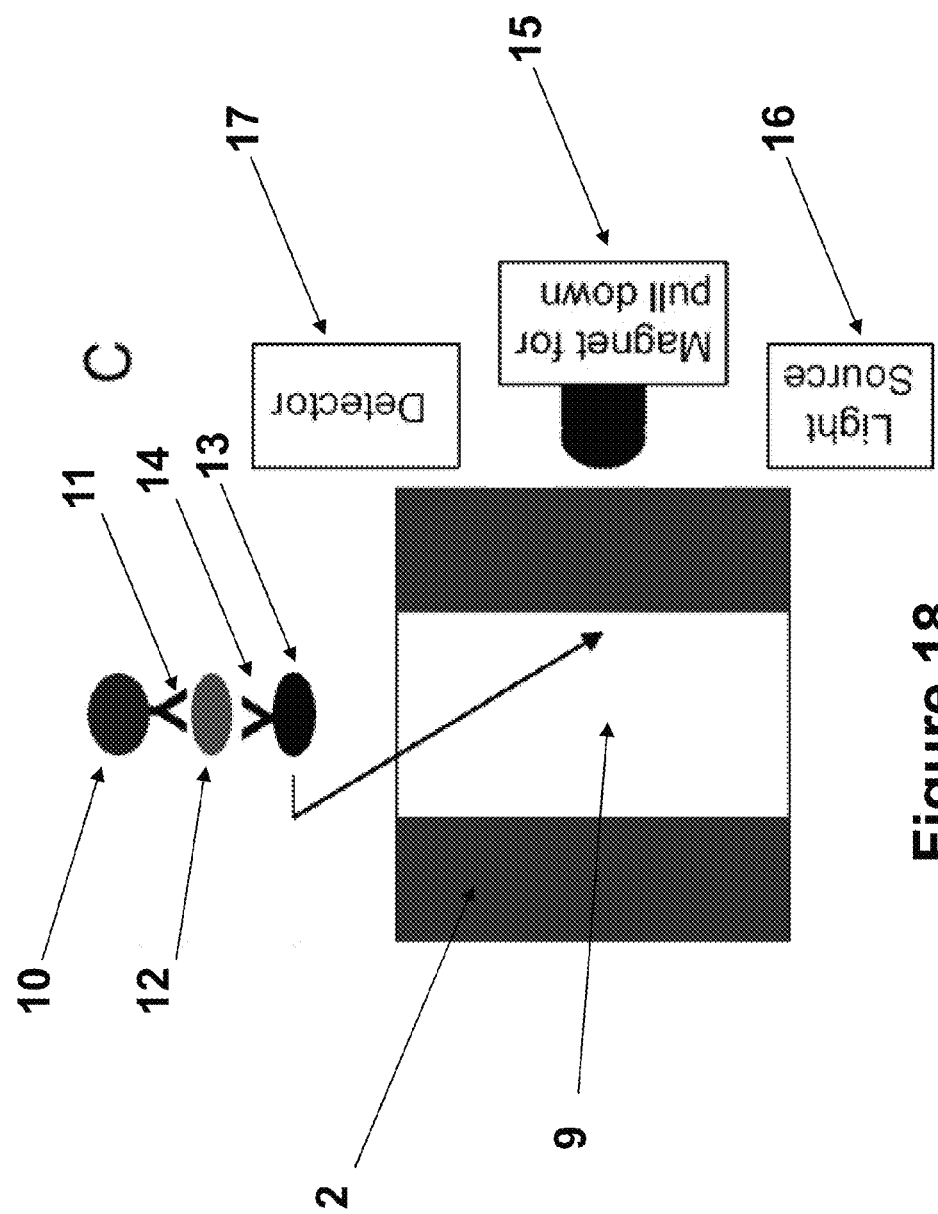
FIG. 18 is a schematic diagram showing a magnetic capture particle-microorganism-SERS-active indicator particle complex within a culture bottle according to an embodiment the invention.

A method for the detection and identification of one or more microorganisms in a microbiological culture sample according to an embodiment of the invention can be performed in a microbiological culture vessel. A microbiological culture vessel can have disposed therein one or more indicator particles and one or more magnetic capture particles each having associated therewith one or more binding members, e.g., an antibody, having an affinity for the one or more microorganisms under test. The indicator particles and magnetic capture particles can be disposed in the microbiological culture vessel prior to, concurrent with, or subsequent to disposing therein a clinical or industrial sample suspected of containing the one or more microorganisms under test. The culture growth media can be disposed in the microbiological culture vessel prior to, concurrent with, or subsequent to addition of the clinical or industrial sample. Once the indicator particles, magnetic capture particles, culture media, and clinical or industrial sample have been introduced into the culture vessel, the culture vessel is then agitated either continuously or intermittently in order to mix the indicator particles and magnetic capture particles with the combined sample and culture medium. In preferred embodiments described herein the agitation profile (e.g., speed and/or displacement) may be varied at different stages of the culture or read cycle. When present in the clinical or industrial sample, the one or more microorganisms under test can bind with the one or more binding members associated with the indicator particles and magnetic capture particles to form a magnetic capture particle-microorganism-indicator particle complex.

Where the indicator particle is SERS-active, FIG. 18 shows an example of a magnetic capture particle-microorganism-SERS-active indicator particle complex within a culture vessel 2. The SERS-active indicator particle 10, has associated therewith one or more specific binding members 11 having an affinity for one or more microorganisms 12 under test. A magnetic capture particle 13 also has associated therewith one or more specific binding members 14 having an affinity for the one or more microorganisms 12 under test. Magnetic capture particles 13 can bind to one or more microorganisms 12, which also can be bound to SERS-active particle 10, to form the magnetic capture particle-microorganism-SERS-active particle complex, which is also referred to herein as a sandwich complex, wherein the microorganism is bound simultaneously by more than one specific binding member. In this particular sandwich complex, at least one specific binding member 14 is attached to a magnetic capture particle 13 and at least one other specific binding member 11 is attached to a SERS-active indicator particle 10. Thus, the microorganism 12 is "sandwiched" between the magnetic capture particle 13 and the SERS-active indicator particle 10.

A magnetic field is applied to the sample via a magnet 15 to attract the magnetic capture particles 13 in order to localize the magnetic capture particle-microorganism-SERS-active indicator particle complexes into a pellet within the measurement zone 9 inside of the culture vessel 2 for detecting the SERS signal. Radiation from light source 16 can then be directed at the pellet and the SERS signal can be detected by Raman detector 17. Light source 16 and detector 17 are used to induce and measure, respectively, the Raman signature produced by SERS-active indicator particle 10. The localization of the magnetic capture particle-microorganism-SERS-active indicator particle complexes provides a SERS signal, the intensity of which is reflective of microorganism concentration, by localizing the SERS-active indicator particles that are bound to magnetic particles in the detection zone, thereby segregating them from the unbound SERS-active indicator particles remaining in solution.

In some embodiments, the measurement zone can be located along an inner surface of a microbiological culture bottle or vessel. For example, with respect to a bottle, the measurement zone can be located along an inner surface within or adjacent to the bottle neck; an inner surface comprising the bottle mid-section; or an inner surface along the base of the bottle adjacent to, for example, a separate sensor, e.g., a fluorescence-based sensor or a colorimetric-based sensor, or in embodiments in which a separate sensor is not present, along an inner surface of the base, i.e., the bottom, of the microbiological culture bottle. In one preferred embodiment, the measurement zone is located along an inner surface generally at the mid-section of the culture bottle or vessel. Thus, the measurement zone may be located at or closer to the center of the bottle or vessel than the ends of the bottle or vessel (e.g., within the middle 50% of the vessel).

The detection and/or identification of the one or more microorganisms of interest is accomplished only when the microorganism(s) is/are bound in the pellet as part of a binding member-microorganism-indicator particle complex. That is, no signal is generated when the one or more microorganisms are not present in the microbiological culture sample or, if present, the microorganism does not have an epitope recognized by the binding member associated with the indicator particle. Under such circumstances, the indicator particles are not substantially present in the measurement zone.

If no significant SERS signal is observed upon application of a magnetic field and optical interrogation of the pellet, the magnetic particles pulled into the pellet may be dispersed back into solution in order to continue interacting with the sample. If a microorganism is present below the limit of detection of the technology, then the microorganism concentration can increase over time as the microorganism grows in the culture media so that the SERS signal is ultimately detected in the measurement zone upon future application of the magnetic field. In essence, a magnetic pellet is formed, optically interrogated, dispersed, allowed to interact with the sample, and then reformed at a specified frequency until either a signal is observed from the binding member-microorganism-indicator particle complex or the sample is determined to be negative for the microorganism of interest. Agitation of the culture vessel at various stages throughout this process may play a critical role. Agitation serves a variety of purposes. First, it ensures mixing of the SERS and magnetic particles with the sample and culture media allowing the formation of binding member-microorganism-indicator particle complexes. Second, it enables the dispersion of the magnetic particles back into solution once the pellet is formed. Third, in a preferred embodiment, agitation can occur while the magnetic field is applied. Agitation during application of the magnetic field brings fluid from various spatial points within the culture vessel into the region of the localized magnetic field, ensuring that magnetic particles are collected from regions of the sample outside of the localized magnetic field. Finally, in samples containing particulates (e.g. resins, charcoal, or calcium carbonate), agitation prior to and during pelleting can limit the number of these particulates from settling into the detection region and interfering with the optical signal. Different agitation rates and profiles may be optimum for each of these different functions.

For example, different agitation rates (i.e., frequency) and "throw" (i.e., vial displacement along an axis) may be used in different phases of a measurement cycle. In one exemplary embodiment, a measurement cycle may include mixing, pre-pellet dispersion, pelleting, reading, and dispersion, with each phase having a particular agitation rate and throw.

In this regard, mixing includes the phase where agitation occurs during incubation, while pre-pellet dispersion occurs after mixing and prior to pelleting. Pelleting proceeds after pre-pellet dispersion and is followed by the reading phase. The reading phase corresponds to the interrogation of the vials by the read head, while the dispersion phase is provided for the pellet to be redispersed within the vial. There may or may not be delays between phases. In one embodiment, the agitation rate and throw for the phases may range from about 0 to 3 Hz and about 0 to 100 mm, respectively. For instance, the following agitation rates and throws may be used according to embodiments of the present invention: mixing—about 0.5 to 1.5 Hz and 25 to 75 mm; pre-pellet dispersion—about 1 to 2 Hz and 25 to 75 mm; pelleting—about 0.5 to 2 Hz and 25 to 75 mm; reading—0 Hz and 0 mm; and dispersion—about 1 to 2 Hz and about 25 to 75 mm. Moreover, the particular time period for each phase may also be varied. For example, the mixing phase may be significantly longer (e.g., about 5 to 60 min) than the pre-pellet dispersion, pelleting, reading, and dispersion phases (e.g., about 5 to 120 seconds per phase).

Figure 23:
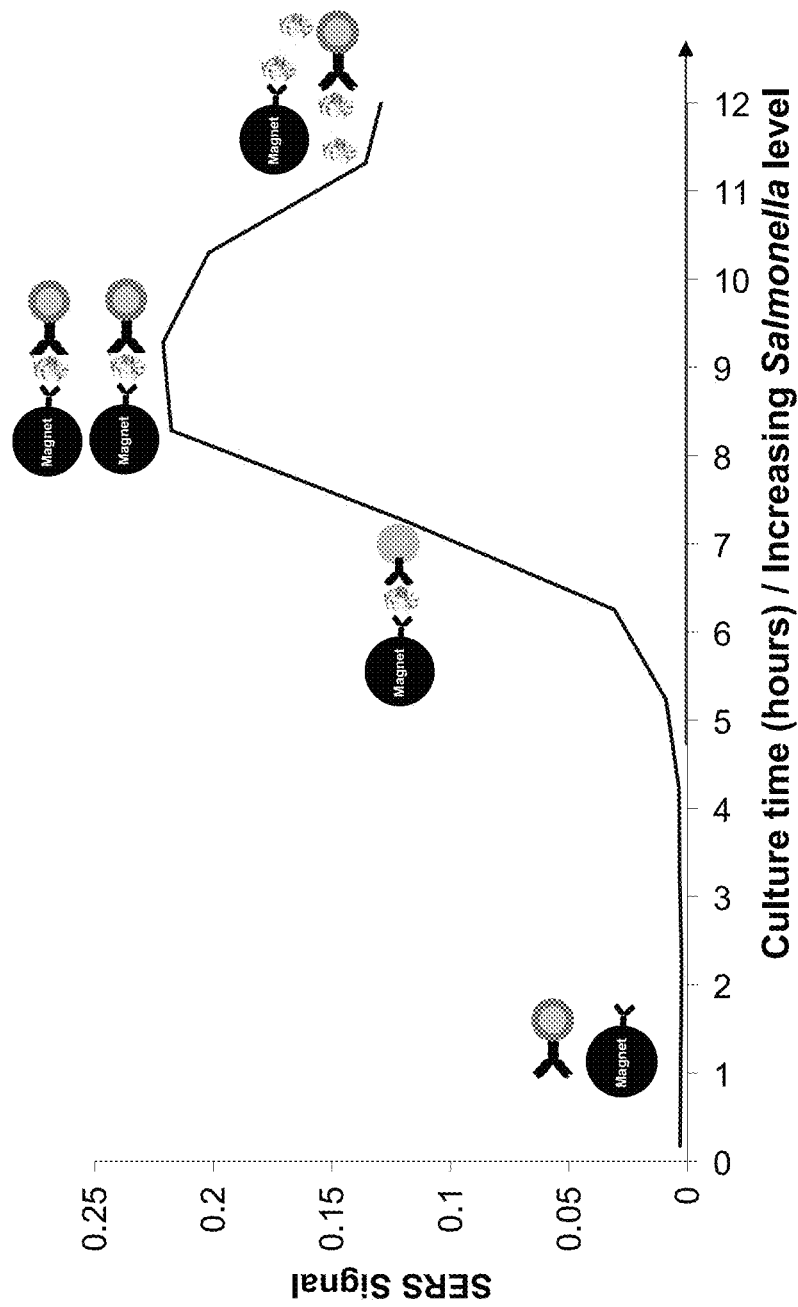
FIG. 23 shows a representative SERS signal plotted over culture time for *Salmonella* according to an embodiment of the invention.

FIG. 23 shows one example of the time-dependent SERS signal intensity of binding member-microorganism-indicator particle complexes captured by magnetic capture particles for *Salmonella*. Generally, the beginning of the upslope of the SERS signal may be indicative of the presence of the microorganism. In this regard, after about 6 hours of culture time, the presence of microorganism may be indicated, while the peak at about 9 hours indicates a higher concentration of microorganisms. However, as also shown in FIG. 23, on the downslope of the SERS signal, microorganisms may continue to be present, such as at about 12 hours. In this instance, the downslope may also signify the presence of a microorganism, which may provide a useful means of identifying positivity in certain cases, such as when a large number of microorganisms are present at the beginning of incubation. As such, either an upslope or downslope in the SERS signal may be indicative of the presence of a microorganism in the culture sample. In this regard, readings may be taken periodically over time during the incubation period in order to identify such changes in the SERS signal.

B. Indicator Particles

"Indicator particles", as used herein, may be any particle that is capable of producing a signal that can be detected directly in the culture sample without removing the sample, such as for performing wash steps. For example, the indicator particles may produce any optical signal (e.g., fluorescence or Raman or an optical image) when interrogated (e.g., with a light source). Examples of indicator particles include SERS-active particles, quantum dots, near-infrared fluorophores, or near-infrared fluorescent particles.

"Surface-enhanced Raman scattering" or "SERS" refers to the phenomenon that occurs when the Raman scattering signal, or intensity, is enhanced when a Raman-active molecule is adsorbed on or in close proximity to, e.g., within about 50 Å of, the surface of certain metals (e.g., gold or silver). Under such circumstances, the intensity of the Raman signal arising from the Raman-active molecule can be enhanced. "Surface-enhanced resonance Raman scattering" or "SERRS" refers to an increased SERS signal that occurs when the reporter molecule is in close proximity to a SERS-active nanoparticle surface is in resonance with the excitation wavelength. "Raman scattering" generally refers to the inelastic scattering of a photon incident on a molecule.

Photons that are inelastically scattered have an optical frequency (vi), which is different than the frequency of the incident light (v0). The difference in energy ($\Delta E$) between the incident light and the inelastically scattered light can be represented as ($\Delta E$)=h|v0−vi|, wherein h is Planck's constant, and corresponds to energies that are absorbed by the molecule. The incident radiation can be of any frequency v0, but typically is monochromatic radiation in the visible or near-infrared spectral region. The absolute difference |v0−vi| is an infrared, e.g., vibrational, frequency. The frequency v1 of the "Raman scattered" radiation can be greater than or less than v0, but the amount of light with frequency v1<v0 (Stokes radiation) is greater than that with frequency v1>v0 (anti-Stokes radiation).

As used herein, the term "radiation" refers to energy in the form of electromagnetic radiation that can induce surface-enhanced Raman scattering in a sample under test, e.g., a sample comprising a SERS-active nanoparticle having one or more SERS-active reporter molecules associated therewith. More particularly, the term "radiation" refers to energy in the form of electromagnetic radiation that causes the surface of a nanoparticle to induce, emit, support, or otherwise cause light scattering, e.g., Raman scattering, in a reporter molecule proximate to the nanoparticle surface.

As used herein, a "reporter molecule" refers to any molecule or chemical compound that is capable of producing a Raman spectrum when it is illuminated with radiation of a proper wavelength. A "reporter molecule" also can be referred herein as a "label," a "dye," a "Raman-active molecule," or "SERS-active molecule," each of which can be used interchangeably.

One of ordinary skill in the art would appreciate that a variety of molecules can act as SERS reporter molecules. For example, some fluorescent dye molecules also can be used as SERS reporter molecules. See, e.g., U.S. patent application Ser. No. 12/134,594 to Thomas et al., filed Jun. 6, 2008, and PCT International Patent Application No. PCT/US2008/066023 to Thomas et al., filed Jun. 6, 2008, each of which is incorporated by reference in its entirety. Generally, molecules suitable for use as SERS reporter molecules can be a small molecule, a large molecule, or a complex molecule, although the molecule does not need to be complex to act as a SERS reporter molecule. SERS reporter molecules, in some embodiments, can have at least one aromatic ring. Further, without wishing to be bound to any one particular theory, a change in polarizability of a bond is required for Raman activity. Also, symmetric molecules tend to exhibit specific and strong Raman signals. Advantageously, a reporter molecule exhibits a high Raman scattering cross section and a well-characterized spectral signature.

A SERS-active nanoparticle, as referred to herein, includes a nanoparticle having a surface that induces, causes, or otherwise supports surface-enhanced Raman light scattering (SERS) or surface-enhanced resonance Raman light scattering (SERRS). A number of surfaces are capable of producing a SERS signal, including roughened surfaces, textured surfaces, and other surfaces, including smooth surfaces.

A SERS-active indicator particle suitable for use with the presently disclosed assays includes a core, which induces the Raman effect, and can further include one or more layers and types of SERS-active materials located on the outer surface of the core, and optionally an encapsulant which partially or fully encapsulates the core or the SERS active materials.

Figure 19:
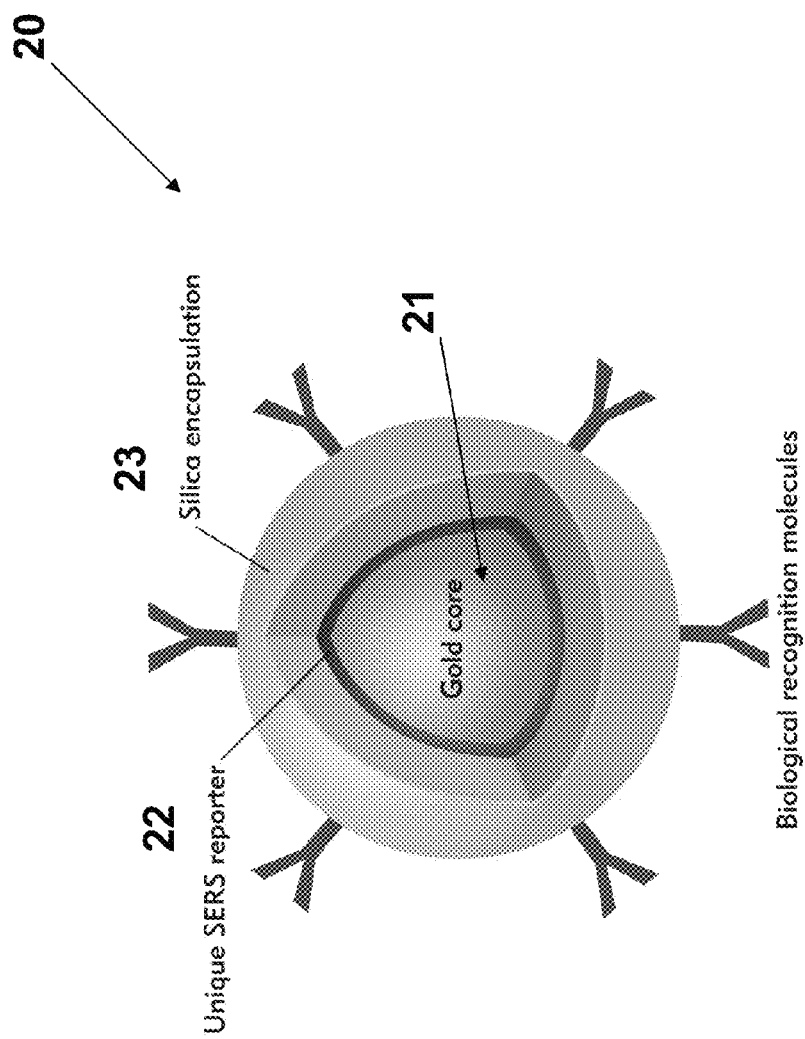
FIG. 19 depicts a SERS-active indicator particle according to one embodiment of the present invention.
Figure 20:
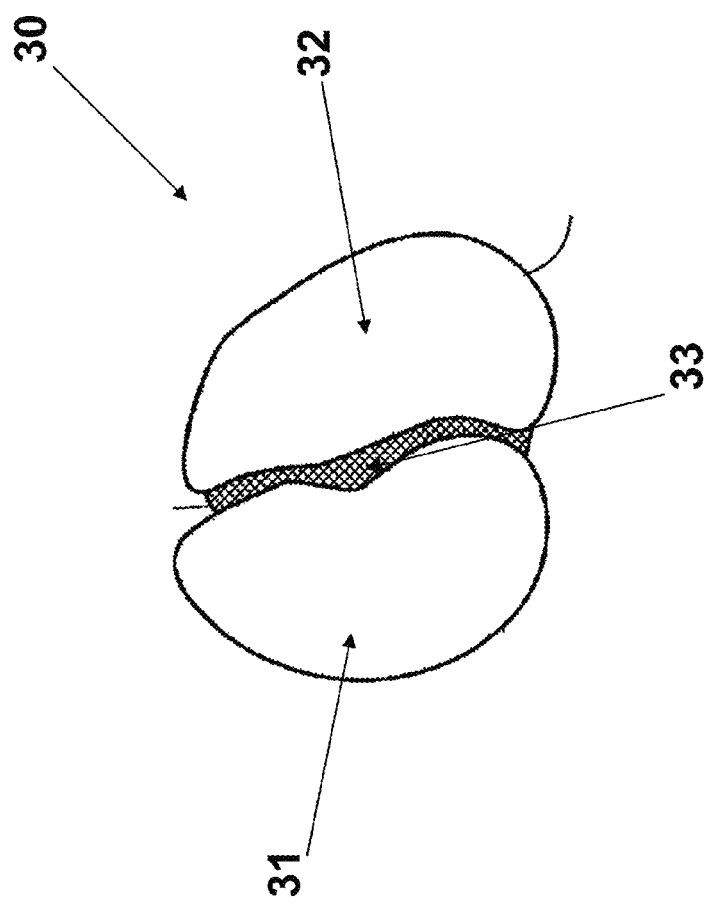
FIG. 20 depicts a SERS-active indicator particle according to one embodiment of the present invention.
Figure 21:
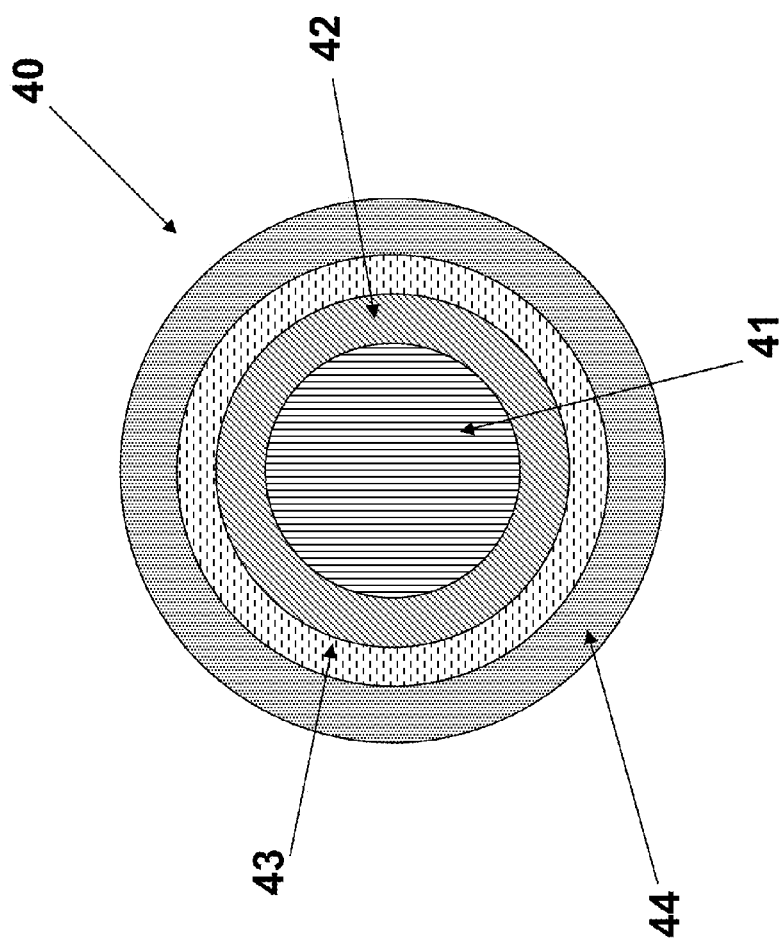
FIG. 21 depicts a SERS-active indicator particle according to one embodiment of the present invention.

FIGS. 19-21 show various examples of SERS-active indicator particles. FIG. 19 shows a SERS-active indicator particle 20 with a single SERS-active nanoparticle 21 as a core, having a reporter molecule 22 located on the outer surface of the nanoparticle core and a layer of silica 23 fully encapsulating the core and reporter molecule. Such SERS-active indicator particles are described in U.S. Pat. No. 6,514,767 to Natan, which is incorporated herein by reference in its entirety.

As used herein, the term "nanoparticle," refers to a particle having at least one dimension in the range of about 1 nm to about 1000 nm, including any integer value between 1 nm and 1000 nm (including about 1, 2, 5, 10, 20, 50, 60, 70, 80, 90, 100, 200, 500, and 1000 nm). In some embodiments, the core of the SERS-active indicator particle is a metallic nanoparticle. In some embodiments, the SERS-active indicator particle is a spherical particle, or substantially spherical particle having a diameter between about 2 nm and about 200 nm (including about 2, 5, 10, 20, 50, 60, 70, 80, 90, 100, and 200 nm). In some embodiments, the SERS-active indicator particle has a diameter between about 2 nm and about 100 nm (including about 2, 5, 10, 20, 30, 40, 50, 60, 70, 80, 90, and 100 nm) and in some embodiments, between about 20 nm and 100 nm (including about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 nm).

SERS-active indicator particles suitable for use with the presently disclosed assays also can include a core comprising two or more nanoparticles. FIG. 20 shows a SERS-active indicator particle 30 with a first SERS-active nanoparticle 31 and a second SERS-active nanoparticle 32 in the core, having a reporter molecule 33 located in between the first 31 and second 32 SERS-active nanoparticles. Such SERS-active indicator particles are described in U.S. Pat. No. 6,861,263 to Natan, which is incorporated herein by reference in its entirety. See also, for another example, U.S. Patent Application Publication No. 2003/0232388 to Kreimer et al., published Dec. 18, 2003, which is incorporated herein by reference in its entirety. Thus, the core a SERS-active indicator particle can include a single nanoparticle or can include multiple nanoparticles aggregated together. Such aggregates also can be encapsulated as further disclosed herein.

The core of a SERS-active indicator particle suitable for use with the presently disclosed methods typically comprises at least one metal, i.e., at least one element selected from the Periodic Table of the Elements that is commonly known as a metal. Suitable metals include Group 11 metals, such as Cu, Ag, and Au, or any other metals known by those skilled in the art to support SERS, such as alkali metals. In some embodiments, the core nanoparticle substantially comprises a single metal element. For example, the preparation of gold nanoparticles is described by Frens, G., Nat. Phys. Sci., 241, 20 (1972). In other embodiments, the core nanoparticle comprises a combination of at least two elements, such as an alloy, for example, a binary alloy. In some embodiments, the core nanoparticle is magnetic.

In other embodiments, the core of a SERS-active indicator particle includes two components in which a first material forms an inner core which surrounded by a shell formed from a second material, such as in an $Au_2S/Au$ core-shell particle. FIG. 21 shows such a SERS-active indicator particle 40 with an inner core 41 of $Au_2S$ surrounded by an outer shell 42 formed from Au as a core, having a reporter molecule layer 43 located on the outer surface of the core and a layer of silica 44 fully encapsulating the core and reporter molecule layer. $Au_2S/Au$ core-shell particles have been reported to have widely tunable near-IR optical resonance. See Averitt, R. D., et al., "Ultrafast optical properties of gold nanoshells," JOSA B, 16(10), 1824-1832 (1999). Further, Ag core/Au shell particles, such as those described by Cao, Y. W., et al., "DNA-modified core-shell Ag/Au nanoparticles," J. Am. Chem. Soc., 123(32), 7961-7962 (2001), or Au core/Ag shell particles, or any core-shell combination involving SERS-active metals, can be used. Other combinations suitable for use in core-shell particles also are suitable for use with the presently disclosed subject matter, including Au- or Ag-functionalized silica/alumina colloids, Au- or Ag-functionalized $TiO_2$ colloids, Au nanoparticle capped-Au nanoparticles (see, e.g., Mucic, et al., "DNA-directed synthesis of binary nanoparticle network materials," J. Am. Chem. Soc., 120(48), 12674 (1998)); Au nanoparticle-capped $TiO_2$ colloids; and particles having a Si core with a metal shell (i.e., "nanoshells"), such as silver-capped $SiO_2$ colloids or gold-capped $SiO_2$ colloids. See, e.g., Jackson, et al., Proc. Natl. Acad. Sci. U.S.A. 101(52): 17930-5 (2004); see also U.S. Pat. Nos. 6,344,272 and 6,685,986 to Oldenburg et al., each of which is incorporated herein by reference in its entirety. The use of such nanoshells in biosensing applications has been described. See U.S. Pat. No. 6,699,724 to West et al., which is incorporated herein by reference in its entirety.

Another class of nanoparticles suitable for use as a core of a SERS-active indicator particle includes nanoparticles having an internal surface. Such nanoparticles include hollow particles and hollow nanocrystals or porous or semi-porous nanoparticles. See, e.g., U.S. Pat. No. 6,913,825 to Ostafin et al., which is incorporated herein by reference in its entirety. In some embodiments, core/shell and nanoparticles having an internal surface can exhibit an improved SERS signal.

While it is recognized that particle shape and aspect ratio can affect the physical, optical, and electronic characteristics of nanoparticles, the specific shape, aspect ratio, or presence/absence of internal surface area does not bear on the qualification of a particle as a nanoparticle. Accordingly, nanoparticles suitable for use as a core of a SERS-active indicator particle can have a variety of shapes, sizes, and compositions. Further, the nanoparticle core can be solid, or in some embodiments, as described immediately hereinabove, hollow. Non-limiting examples of suitable nanoparticles for use as a core include colloidal metal hollow or filled nanobars, magnetic, paramagnetic, conductive or insulating nanoparticles, synthetic particles, hydrogels (colloids or bars), and the like. It will be appreciated by one of ordinary skill in the art that nanoparticles can exist in a variety of shapes, including but not limited to spheroids, rods, disks, pyramids, cubes, cylinders, nanohelixes, nanosprings, nanorings, rod-shaped nanoparticles, arrow-shaped nanoparticles, teardrop-shaped nanoparticles, tetrapod-shaped nanoparticles, prism-shaped nanoparticles, and a plurality of other geometric and non-geometric shapes.

Further, nanoparticles suitable for use as a core of a SERS-active indicator particle can be isotropic or anisotropic. As referred to herein, anisotropic nanoparticles have a length and a width. In some embodiments, the length of an anisotropic nanoparticle core is the dimension parallel to the aperture in which the nanoparticle was produced. In some embodiments, the anisotropic nanoparticle core has a diameter (width) of about 350 nm or less. In other embodiments, the anisotropic nanoparticle core has a diameter (width) of about 250 nm or less and in some embodiments, a diameter (width) of about 100 nm or less. In some embodiments, the width of the anisotropic nanoparticle core is between about 15 nm to about 300 nm. Further, in some embodiments, the anisotropic nanoparticle core has a length, wherein the length is between about 10 nm and 350 nm.

Much of the SERS literature (both experimental and theoretical) suggests that anisotropic particles (rods, triangles, prisms) can provide an increased enhancement of the Raman signal as compared to spheres. For example, the so-called "antenna effect" predicts that Raman enhancement is expected to be larger at areas of higher curvature. Many reports of anisotropic particles have been recently described, including silver (Ag) prisms and "branched" gold (Au) particles.

Anisotropic Au and Ag nanorods can be produced by electrodeposition into preformed alumina templates, in a manner similar to the production of Nanobarcodes® particles (Oxonica Inc., Mountain View, Calif.). See, e.g., Nicewarner-Pena, S. R., et al., "Submicrometer metallic barcodes," Science, 294, 137-141 (2001); Walton, I. D., et al., "Particles for multiplexed analysis in solution: detection and identification of striped metallic particles using optical microscopy," Anal. Chem. 74, 2240-2247 (2002). These particles can be prepared by the deposition of alternating layers of materials, typically Au and Ag, into preformed alumina templates, and can have a diameter of about 250 nm and a length of about 6 microns.

SERS-active indicator particles also suitable for use in the presently disclosed methods include composite nanostructures, e.g., satellite structures and core-shell structures, as disclosed in PCT International Patent Application No. PCT/US2008/057700 to Weidemaier et al., filed Mar. 20, 2008, which is incorporated herein by reference in its entirety.

An advantage of the embodiments of SERS assays and devices for detecting microorganisms in culture samples is the variety of SERS-active nanoparticles that can be prepared, each having a unique SERS signature. Representative SERS-active indicator particles useful for the presently disclosed methods include, but are not limited to, SERS-active indicator particles from Oxonica Inc. (Mountain View, Calif.). Such SERS-active indicator particles include a nanoparticle core labeled with SERS reporter molecules and encapsulated in a glass shell.

Figure 22:
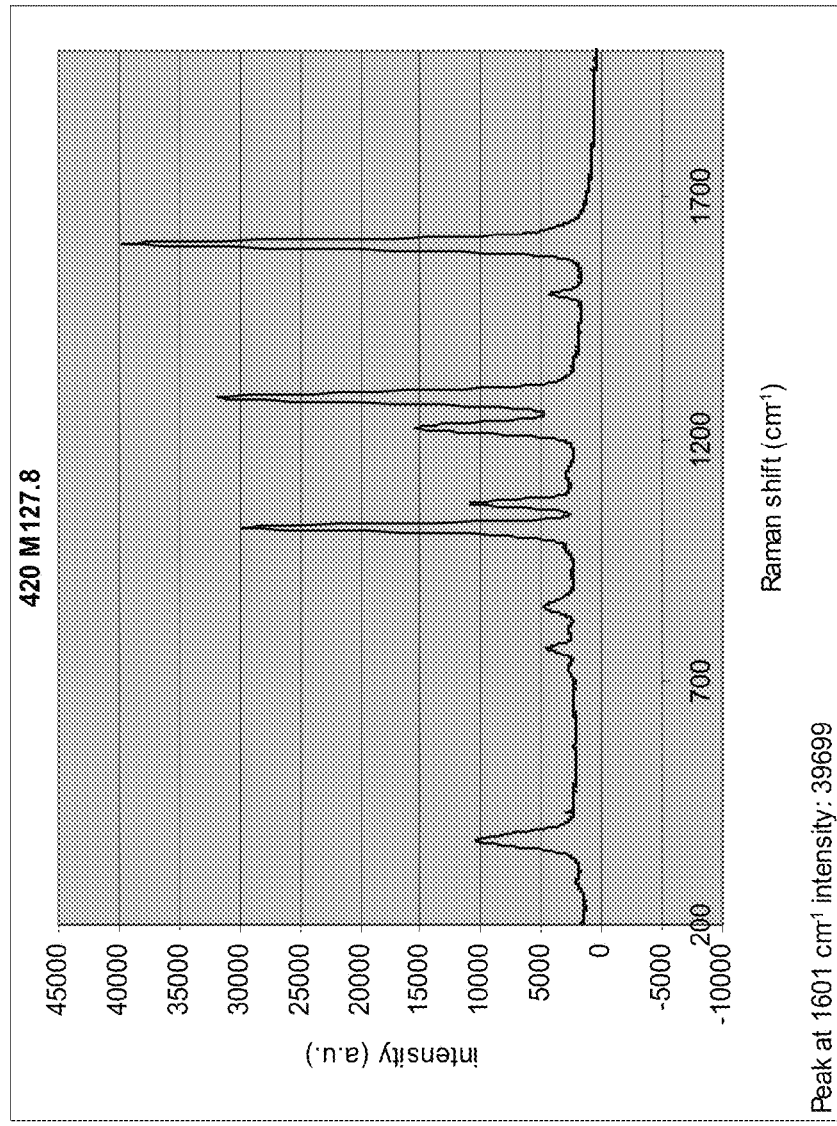
FIG. 22 shows a representative SERS spectrum of a SERS-active indicator particle having associated therewith a 4,4'-dipyridyl (DIPY) Raman-active dye according to an embodiment of the invention.

Representative, non-limiting reporter molecules include 4,4'-dipyridyl (DIPY), D8-4,4'-dipyridyl (d8DIPY), trans-1,2-bis(4-pyridyl)-ethylene (BPE), and 2-quinolinethiol (QSH), each of which have been disclosed as useful Raman-active reporter dyes in U.S. Patent Publication No. 2006/0038979 to Natan et al., published Feb. 23, 2006, which is herein incorporated by reference in its entirety. Additional non-limiting examples of suitable reporter molecules for the presently disclosed methods include 1,2-dil(4-pyridyl)acetylene (BPA), 4-azobis(pyridine) (4-AZP), GM19, 1-(4-pyridyl)-1-cyano-2-(2-fluoro-4-pyridyl)-ethylene (CN-FBPE), 1-cyano-1-(4-quinolinyl)-2-(4-pyridyl)-ethylene (CQPE), dye 10, and 4-(4-hydroxyphenylazo)pyridine (136-7). A representative SERS spectrum of SERS-active nanoparticles labeled with 4,4'-dipyridyl (DIPY) is provided in FIG. 22. As shown in FIG. 22, the DIPY dye molecule has a dominant peak at about 1601 cm-1.

SERS-active indicator particles suitable for use with the presently disclosed methods include, but are not limited to, nanoparticle cores comprising a surface enhanced Raman scattering (SERS)-active reporter molecule disclosed in U.S. patent application Ser. No. 12/134,594 to Thomas et al., filed Jun. 6, 2008, and PCT International Patent Application No. PCT/US2008/066023 to Thomas et al., filed Jun. 6, 2008, each of which is incorporated by reference in its entirety, and the variety of SERS-active indicator particles disclosed in PCT International Patent Application No. PCT/US2008/057700 to Weidemaier et al., filed Mar. 20, 2008, which is incorporated herein by reference in its entirety.

In some embodiments, the SERS-active indicator particle comprises an encapsulant. SERS-active nanoparticles have a tendency to aggregate in aqueous solution and once aggregated are difficult to re-disperse. Further, the chemical composition of some Raman-active molecules is incompatible with chemistries used to attach other molecules, such as proteins, to metal nanoparticles. These characteristics can limit the choice of Raman-active molecule, attachment chemistries, and other molecules to be attached to the metal nanoparticle. Accordingly, in some embodiments, the presently disclosed methods comprise SERS-active indicator particles in which the reporter molecule when affixed, e.g., either adsorbed or covalently attached to a nanoparticle core, can be coated or encapsulated, for example, in a shell, of a different material, including a dielectric material, such as a polymer, glass, metal, metal oxides, such as $TiO_2$ and $SnO_2$, metal sulfides or a ceramic material. Methods for preparing such SERS-active indicator particles are described in U.S. Pat. No. 6,514,767 to Natan, which is incorporated herein by reference in its entirety.

The thickness of the encapsulant can be varied depending on the physical properties required of the SERS-active indicator particle. Depending on the particular combination of nanoparticle core, encapsulant, and dye, thick coatings of encapsulant, e.g., coatings on the order of one micron or more, could potentially attenuate the Raman signal. Further, a thin coating might lead to interference in the Raman spectrum of the associated microorganism by the molecules on the encapsulant surface. At the same time, physical properties, such as the sedimentation coefficient can be affected by the thickness of the encapsulant. In general, the thicker the encapsulant, the more effective the sequestration of the SERS-active dyes on the metal nanoparticle core from the surrounding solvent.

In embodiments wherein the encapsulant is glass, the thickness of the glass typically can range from about 1 nm to about 70 nm. In exemplary, non-limiting embodiments, the SERS-active indicator particles comprise gold nanoparticles having a diameter ranging from about 50 nm to about 100 nm encapsulated in a sphere of glass having a thickness ranging from about 5 nm to about 65 nm, in some embodiments, from about 10 nm to about 50 nm; in some embodiments, from about 15 nm to about 40 nm; and, in some embodiments, about 35 nm. The optimization of the dimensions of the presently disclosed SERS-active indicator particles can be accomplished by one of ordinary skill in the art.

Further, SERS-active indicator particles comprising SERS-active dyes can be functionalized with a molecule, such as a specific binding member of a binding pair, which can bind to a target microorganism. Upon binding the target microorganism, the SERS signal of the SERS-active reporter molecule changes in such a way that the presence or amount of the target microorganism can be determined. The use of a functionalized SERS-active indicator particle has several advantages over non-functionalized indicator particle. First, the functional group provides a degree of specificity to the indicator particle by providing a specific interaction with a target microorganism. Second, the target microorganism does not have to be Raman active itself; its presence can be determined by observing changes in the SERS signal of the Raman-active dye attached to the nanoparticle core. Such measurements are referred to herein as "indirect detection," in which the presence or absence of a target microorganism in a culture sample is determined by detecting a SERS signal that does not directly emanate from the microorganism of interest.

In other embodiments, the SERS-active indicator particle comprises a SERS-active nanoparticle as a core, with no reporter molecule or encapsulant present. The surface of the core can be functionalized with a molecule, such as a specific binding member of a binding pair, which can bind to a target microorganism. Upon binding the target microorganism, the SERS spectrum of the target microorganism itself is detected to confirm the presence or amount of the target microorganism. Such measurements are referred to herein as "direct detection," in which the presence or absence of a target microorganism in a blood culture sample is determined by detecting a SERS signal that emanates directly from the microorganism of interest.

The SERS-active indicator particles can be functionalized to bind to a target analyte in at least two different ways. In some embodiments, the SERS-active reporter molecule, i.e., the SERS-active dye, can be conjugated with a specific binding member of a binding pair, whereas in other embodiments, a specific binding member of a binding pair can be attached directly to the nanoparticle core. In embodiments in which the nanoparticle core is at least partially surrounded by an encapsulating shell, the binding member can be attached to an outer surface of the encapsulating shell.

C. Specific Binding Members

As used herein, the term "specific binding member," and grammatical derivations thereof, refers to a molecule for which there exists at least one separate, complementary binding molecule. A specific binding member is a molecule that binds, attaches, or otherwise associates with a specific molecule, e.g., a microorganism of interest. When a specific binding member of a particular type binds a particular type of molecule, the specific binding members are referred to as a "specific binding pair." For example, an antibody will specifically bind an antigen. Accordingly, "specific binding pair" refers to two different molecules, where one of the molecules through chemical or physical means specifically binds the second molecule. In this sense, a microorganism under test is a reciprocal member of a specific binding pair. Representative binding members suitable for use with particular microorganisms under test are provided herein below.

Further, specific binding pairs can include members that are analogs of the original specific binding partners, for example, an analyte-analog having a similar structure to the analyte. By "similar" it is intended that, for example, an analyte-analog has an amino acid sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater amino acid sequence identity compared to an analyte amino acid sequence using alignment programs and standard parameters well known in the art. An analog of an analyte also can have the same function as an analyte.

A specific binding member, when conjugated, for example, with a SERS-active indicator particle, interacts with a specific microorganism under test in a manner capable of producing a detectable Raman signal differentiable from when a particular microorganism is present or absent, or when a particular microorganism is present in varying concentrations over time.

The term "producing a detectable signal" refers to the ability to recognize the presence of a reported group or a change in a property of a reporter group, e.g., SERS-active reporter molecule, in a manner that enables the detection of the binding member-microorganism complex. Further, the producing of a detectable signal can be reversible or non-reversible. The signal-producing event includes continuous, programmed, and episodic means, including one-time or reusable applications. The reversible signal-producing event can be instantaneous or can be time-dependent, so long as a correlation with the presence or concentration of the analyte is established.

The binding, attachment, or association between the specific binding member and, for example, a microorganism, can be chemical or physical. The term "affinity" refers to the strength of the attraction between one binding member to another member of a binding pair at a particular binding site. The term "specificity" and derivations thereof, refer to the likelihood that a binding member will preferentially bind to the other intended member of a binding pair (the target as opposed to the other components in the sample). Such binding between one binding member, e.g., a binding protein, to another binding member of a binding pair, e.g., a ligand or analyte, can be reversible.

Further, as disclosed in U.S. patent application Ser. No. 12/134,594 to Thomas et al., filed Jun. 6, 2008, and PCT International Patent Application No. PCT/US2008/066023 to Thomas et al., filed Jun. 6, 2008, each of which is incorporated by reference in its entirety, in some embodiments, a polyethylene glycol (PEG) linker can be used to attach a specific binding member to a SERS-active indicator particle, a magnetic capture particle, or to a solid support. In the presently disclosed methods, a linker molecule, e.g., PEG, also can be used to attach a specific binding member to a SERS-active indicator particle, or a magnetic capture particle. The use of a PEG linker can reduce non-specific binding in the presently disclosed assays. Eliminating non-specific adsorption can be a significant challenge to assay performance. For example, in magnetic capture assays, non-specific binding can include the process in which proteins or other biomolecules from solution adhere to the surfaces of the magnetic capture particle or SERS-active indicator particle presenting binding members for the target analyte or the process by which the surfaces of the magnetic capture particle and SERS-active nanoparticle adhere to one another via non-specific interactions. In some embodiments, the PEG linker comprises a bifunctional PEG molecule having a functional group on either terminal end of the linear molecule, separated by two or more ethylene glycol subunits. In some embodiments, the PEG molecule comprises between 2 and about 1000 ethylene glycol subunits. In particular embodiments, the PEG linker comprises at least 12 ethylene glycol subunits. Further, the PEG linker can be characterized by having a molecular weight of about 200 Da to about 100,000 Da.

Depending on the binding member, one of ordinary skill in the art would recognize upon review of the presently disclosed subject matter that linkers other than PEG can be used. For example, alkanethiols can be used as linkers for antibodies and peptides. Short chain alkanethiols, including, but not limited to, N-succinimidyl-5-acetylthioacetate (SATA) and N-succinimidyl-5-acetylthiopropionate (SATP) can be used as linkers after sulfhydryl deprotection. Other properties also can determine the choice of linker, such as the length of the linker chain. For example, PEG can be desirable in that it also acts to protect the surface of the reagent and is flexible, which can enhance the ability of the reagent to bind to the analyte of interest.

In some embodiments, the specific binding member is an immunoglobulin, also referred to herein as an antibody, which comprises an antigen binding region that binds to antigens on the target microorganism or secreted thereby.

Antibodies and fragments thereof suitable for use in the presently disclosed methods and devices may be naturally occurring or recombinantly derived and can include, but are not limited to polyclonal, monoclonal, multispecific, human, humanized, primatized, or chimeric antibodies, single-chain antibodies, epitope-binding fragments, e.g., Fab, Fab' and F(ab')2, Fd, Fvs, single-chain Fvs (scFv), disulfide-linked Fvs (sdFv), fragments comprising either a variable light (VL) or variable heavy (VH) domain, fragments produced by a Fab expression library, and anti-idiotypic (anti-Id) antibodies. In all cases, the antibody or fragment thereof will have one or more complementarity determining regions (CDRs) specific for the target antigen. For purposes of the invention, a "complementarity determining region of an antibody" is that portion of an antibody which binds to an epitope, including any framework regions necessary for such binding, and which can be comprised of a subset of amino acid residues encoded by the human heavy chain V, D and J regions, the human light chain V and J regions, and/or combinations thereof.

Those skilled in the art are enabled to make any such antibody derivatives using standard art-recognized techniques. For example, Jones et al. (1986) Nature 321: 522-525 discloses replacing the CDRs of a human antibody with those from a mouse antibody. Marx (1985) Science 229: 455-456 discusses chimeric antibodies having mouse variable regions and human constant regions. Rodwell (1989) Nature 342: 99-100 discusses lower molecular weight recognition elements derived from antibody CDR information. Clackson (1991) Br. J. Rheumatol. 3052: 36-39 discusses genetically engineered monoclonal antibodies, including Fv fragment derivatives, single chain antibodies, fusion proteins chimeric antibodies and humanized rodent antibodies. Reichman et al. (1988) Nature 332: 323-327 discloses a human antibody on which rat hypervariable regions have been grafted. Verhoeyen et al. (1988) Science 239: 1534-1536 teaches grafting of a mouse antigen binding site onto a human antibody.

D. Magnetic Capture Particles

Magnetic capture particles suitable for use with the presently disclosed embodiments can comprise from about 15% to about 100% magnetic material such as, for example, magnetite, including about 15% magnetite, about 20% magnetite, about 25% magnetite, about 30% magnetite, about 35% magnetite, about 40% magnetite, about 45% magnetite, about 50% magnetite, about 55% magnetite, about 60% magnetite, about 65% magnetite, about 70% magnetite, about 75% magnetite, about 80% magnetite, about 85% magnetite, about 90% magnetite, about 95% magnetite, and any integer between about 15% and about 100%. Further, the magnetic capture particles can have a diameter ranging from about 100 nm to about 12 microns. In some embodiments, the magnetic capture particles have a diameter ranging from about 400 nm to about 8 microns. In other embodiments, the magnetic capture particles have a diameter ranging from about 800 nm to about 4 microns. In yet other embodiments, the magnetic capture particles have a diameter ranging from about 1.6 microns to about 3.5 microns, including but not limited to, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, and about 3.3, about 3.4, about 3.5, and about 4.5 microns. Representative particles suitable for use as magnetic capture particles can be obtained from Bangs Laboratories, Inc. (Fishers, Ind.), Life Technologies (Carlsbad, Calif.), or Polyscience Laboratories (Warrington, Pa.).

Magnetic capture of the particles can be accomplished using any method known in the art, including, but not limited to, placing a strong magnet or inducing a magnetic field at a localized area of the assay vessel. The localized magnetic field can be induced, for example, by one or more permanent magnets, electromagnets, and/or materials (e.g., ferrous metals) to conduct, constrain, or focus a magnetic field. As depicted in FIG. 18, which represents one embodiment, the magnet 15 is used to localize the magnetic capture particle-microorganism-SERS-active indicator particle complexes within the measurement zone 9. Incident radiation of a desired wavelength, e.g., a laser beam, can then be focused on the pellet of concentrated magnetic capture particle-microorganism-SERS-active indicator particle complexes and the SERS signal is obtained from the complexes.

Figure 24:
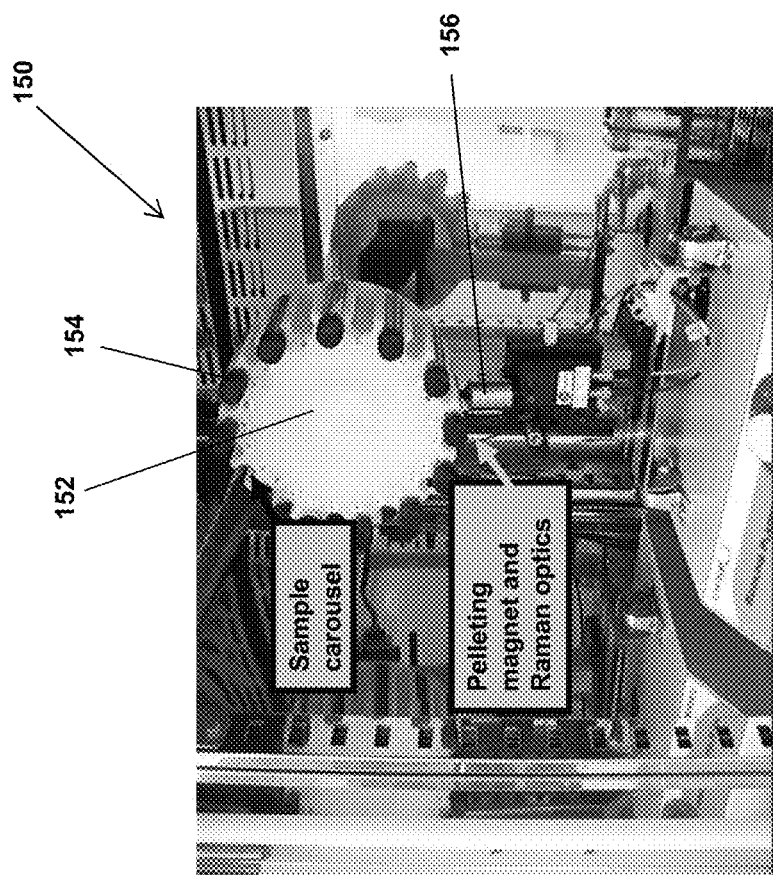
FIG. 24 depicts a system for real-time monitoring of microorganism growth according to an embodiment of the invention.

E. Real Time System for Monitoring Growth in a Microbiological Culture Sample FIG. 24 depicts an embodiment of a real-time system 150 which provides real-time monitoring of microorganism growth in microbiological culture samples for the automated detection of pathogens in clinical and industrial samples. The system 150 includes a carousel 152 that holds a plurality of culture vessels 154 within a temperature controlled enclosure. For example, up to 25 microbiological culture vessels may be used. In this embodiment, the vessels 154 are placed around the periphery of a carousel 152, which rotates to present each vessel to a pelleting and read station 156 in sequence at a programmable frequency (e.g., one reading every 10-60 minutes). The pelleting and read station 156 includes a magnet assembly to form a pellet along with an optical read head containing appropriate filters and lenses for epi-illumination and signal collection. For example, illumination may be provided by a 785 nm wavelength-stabilized laser, and collected signal is detected on a spectrometer appropriate to Raman spectroscopy. After pelleting and reading a given sample, the carousel 152 rotates to present the next sample in the carousel to the pelleting and read station 156. The sequence continues until all samples in the carousel 152 are read, at which point the carousel enters a spinning mode wherein the carousel rotates continuously until the next measurement cycle. The carousel and pelleting and read station are mounted to an arm which extends from a rocking platform. The resulting "offset rocking" motion provides agitation through both linear and rocking motion. The rocking platform operates at a selected frequency for all phases of a measurements cycle, for the duration of the experiment. The agitation serves multiple purposes. First, from the end of one measurement cycle to the start of the next, it ensures mixing of the SERS and magnetic particles with the sample and culture media, allowing the formation of binding member-microorganism-indicator particle complexes. Second, after the pellet has been read, it enables the dispersion of the magnetic particles back into solution. Third, during pelleting, agitation carries magnetic particles in the fluid from various spatial points within the sample vessel into the region of the localized magnetic field, ensuring that magnetic particles are collected from regions of the sample outside of the localized magnetic field. Finally, in samples containing particulates (e.g. resins, charcoal, or calcium carbonate), agitation prior to and during pelleting can prevent these particulates from settling into the detection region and interfering with the optical signal. As the target organism concentration increases throughout the enrichment process, detection and identification of the microorganism by optics, such as SERS technology, occurs as soon as the microorganism concentration reaches the detection threshold of the technology. The ability to continuously monitor the SERS signal during culture ensures that the minimal required culture time is used and that the instrument can automatically alert the user when a pathogen or microorganism is detected and identified.

Figure 25:
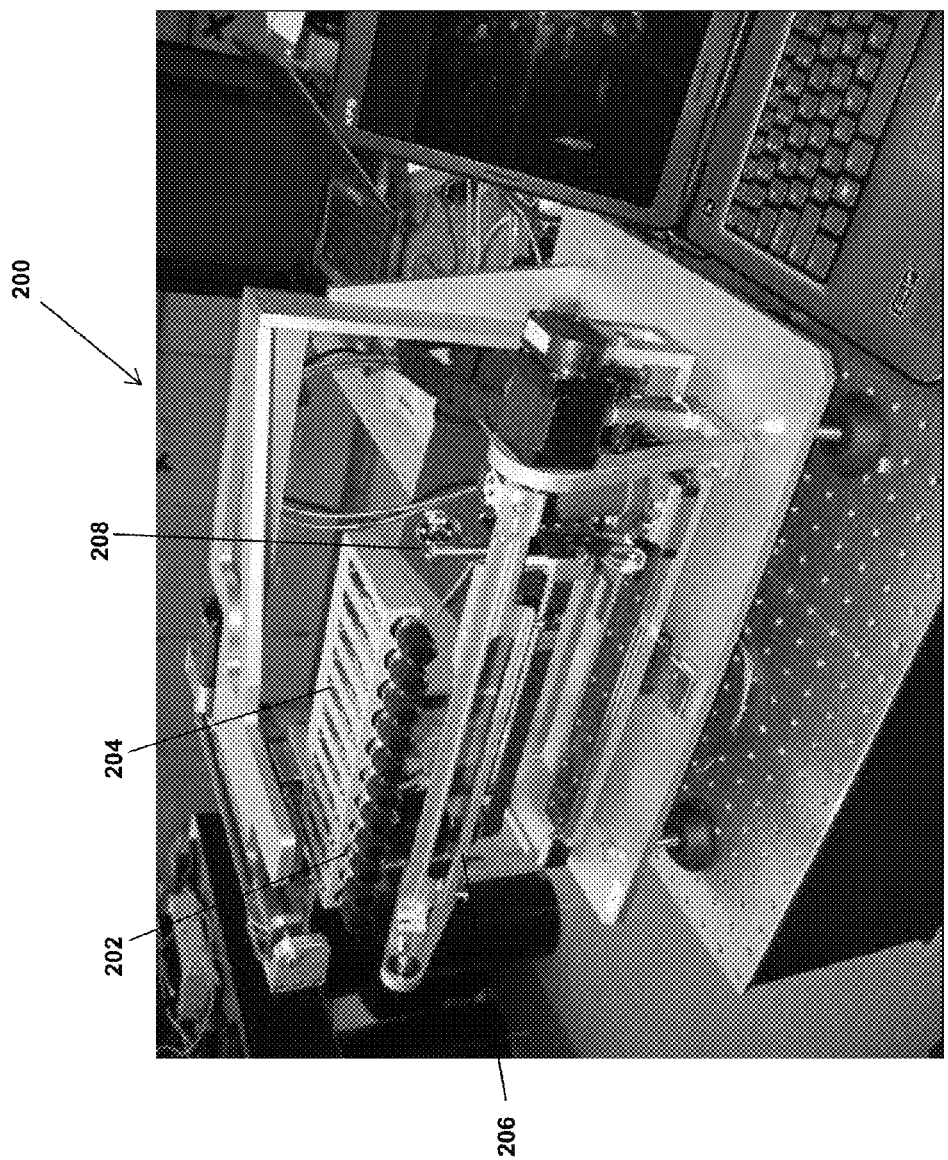
FIG. 25 depicts a system for real-time monitoring of microorganism growth according to another embodiment of the invention.

FIG. 25 shows another embodiment of a system 200 configured to process a plurality of samples. In this particular embodiment, each of the microbiological culture samples is processed in parallel and incubated within the same thermal zone. In this embodiment, the sample tubes are aligned in the same horizontal plane. The system 200 may be placed within an enclosure that forms the thermal zone.

All samples agitate together for the reagent binding, pelleting, and pellet dispersal phases. In one embodiment, after pelleting, agitation stops for all samples, and they are read in succession. The parallel processing requires a different sample arrangement than the carousel used in the first system 150 configuration. Here, the sample tubes 202 are positioned adjacent to each other in a flat tray 204. In this embodiment, agitation is by linear reciprocation along the longitudinal axis of the tubes 202, which may be programmed for different frequencies and profiles throughout the assay. This allows different types and levels agitation for the pellet formation, pellet dispersal, and reagent binding phases. It also permits the agitation to be stopped for reading. The programming of different agitation at each phase is made possible by the parallel sample processing approach.

The system 200 shown in FIG. 25 includes a magnet assembly 206 that is configured to pivot into a position adjacent to the tubes 202 for pelleting and then pivot away from the sample tubes for interrogation. For the system 200 embodiment shown in FIG. 25, the optical interrogation can occur with the magnet assembly 206 pivoted away from the sample tubes 202 after pellet formation to allow access of the optical read head 208 to the measurement zone of the sample tubes. Withdrawing the magnet assembly 206 is possible in this configuration because the samples are not agitating during reading. Alternately, a pair of magnets may be arranged in such a way as to provide a slot through which the readings are taken by the read head 208, with the magnets maintained in position after pelleting. Thus, the read head 208 is configured to move along the slot between the magnets to interrogate each tube. This offers advantages by removing the need for moving the magnets between pelleting and reading of the tubes.

FIGS. 26-29 illustrate another embodiment of a system 250 for automated and real-time monitoring of microorganism growth in culture samples. The system 250 is configured to automatically process one or more different assays simultaneously. In general, the system 250 includes a plurality of incubators 252 serviced by a single pelleting/read assembly 254 that moves behind the incubators to service (pellet and read) each tray 256 one at a time in a detection zone. Each incubator 252 is configured to receive a tray 256 holding a plurality of sample tubes 258. Each tray 256 of tubes is configured to move from the incubator 252 to the pelleting/read assembly 254 where pellets are formed and data collected in the detection zone. The pelleting/read assembly 254 comprises a magnet assembly 260 to form pellets and the optical components (e.g., Raman optics, laser, and spectrometer) to collect the optical signals.

Figure 26:
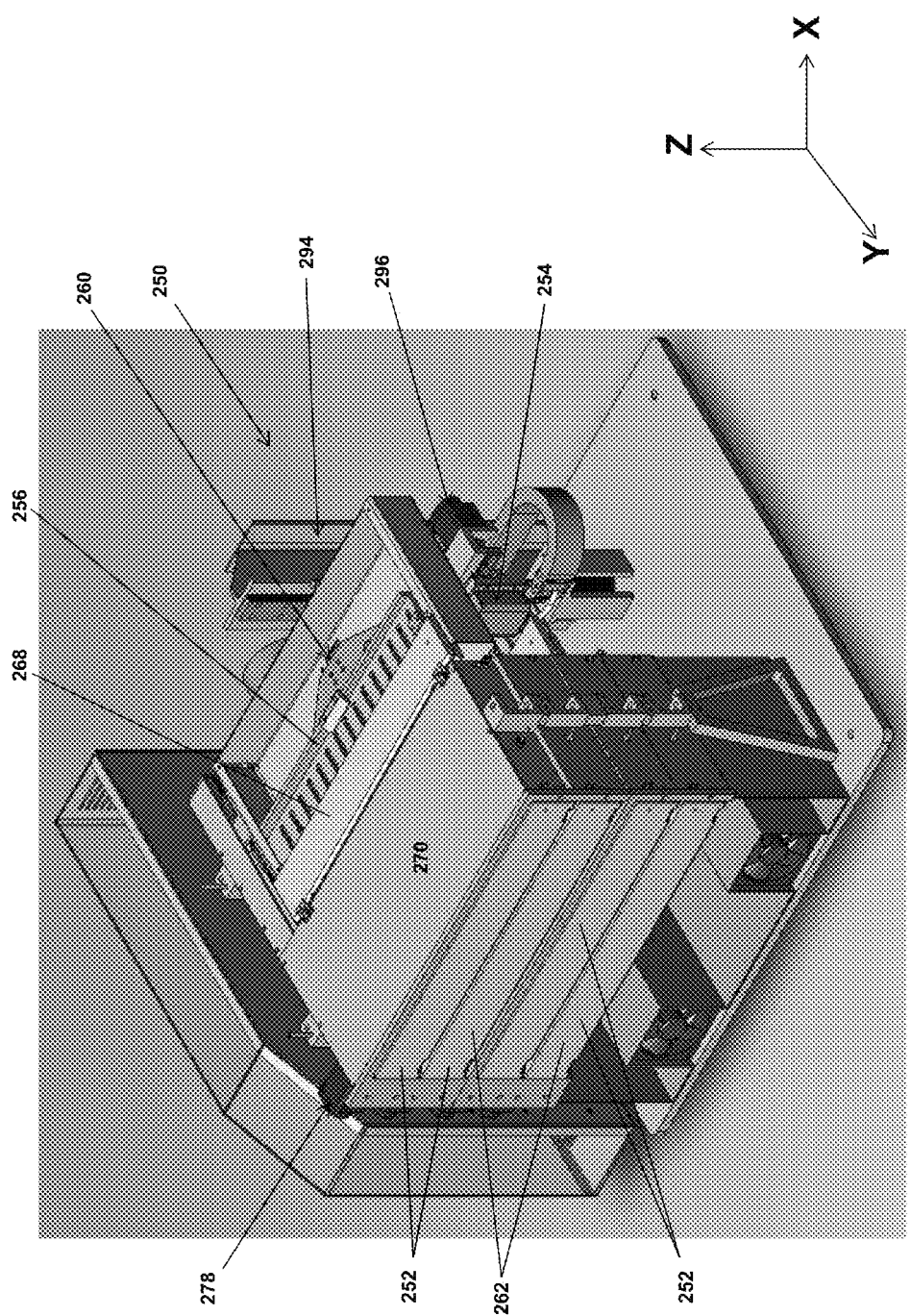
FIGS. 26-29 illustrate various views of a system for real-time monitoring of microorganism growth according to an additional embodiment of the invention.
Figure 27:
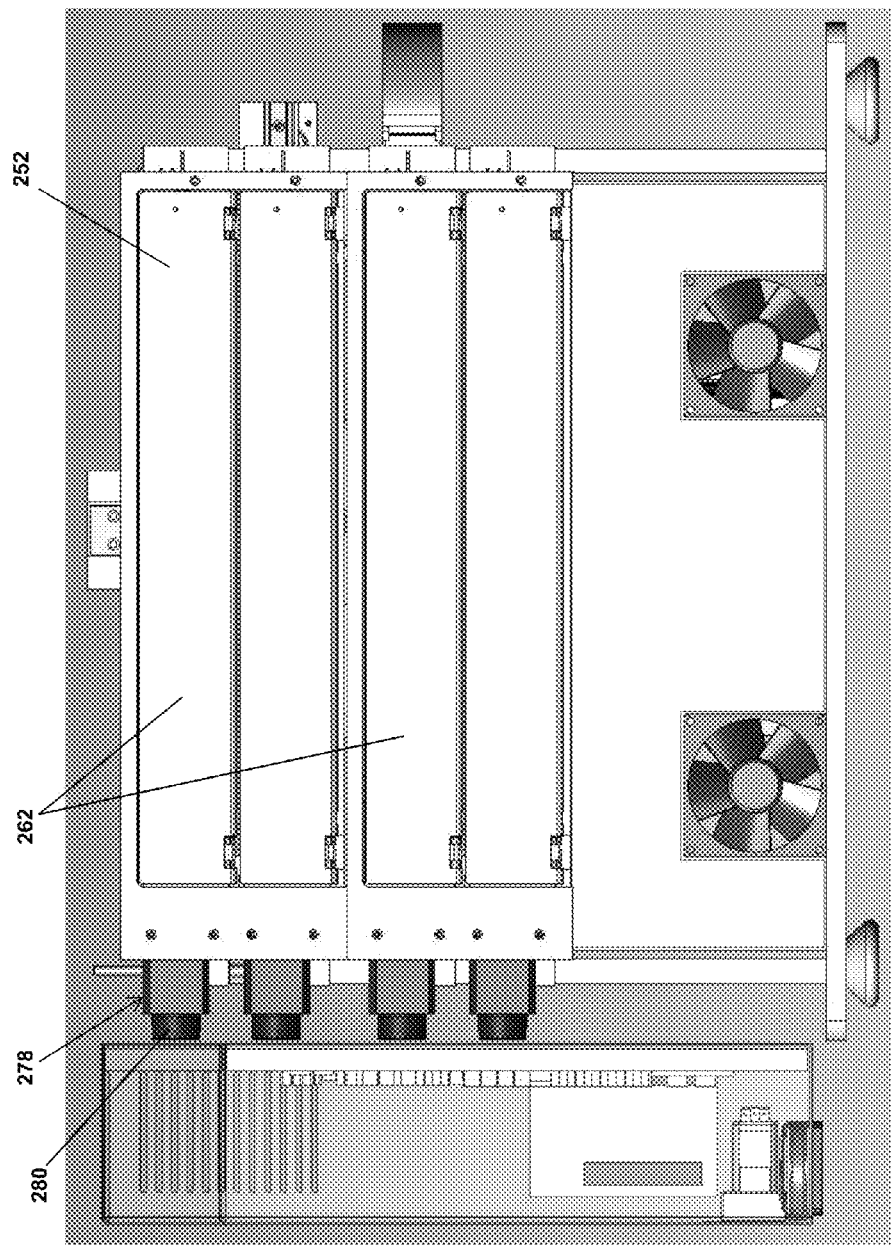
Figure 28:
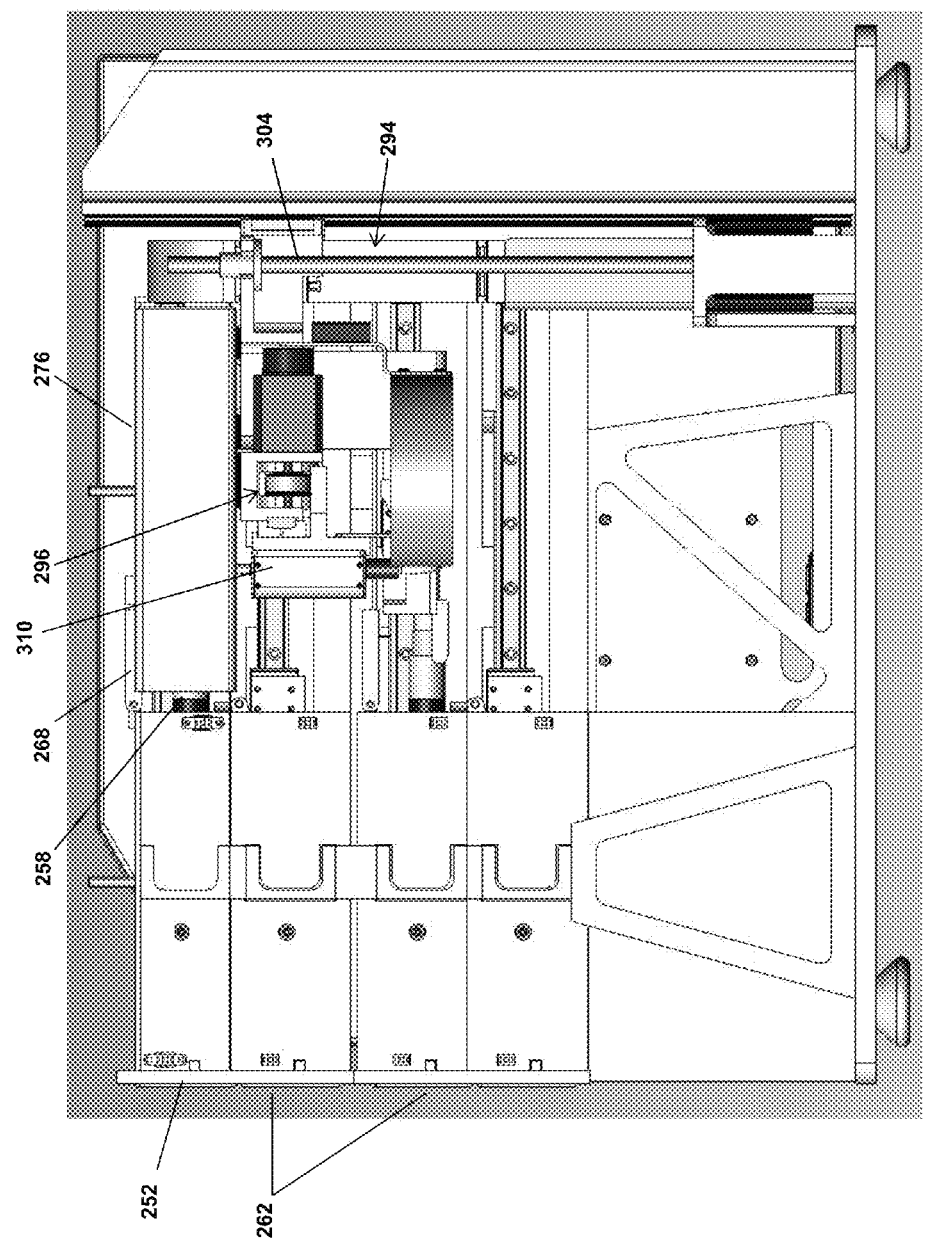
Figure 29:
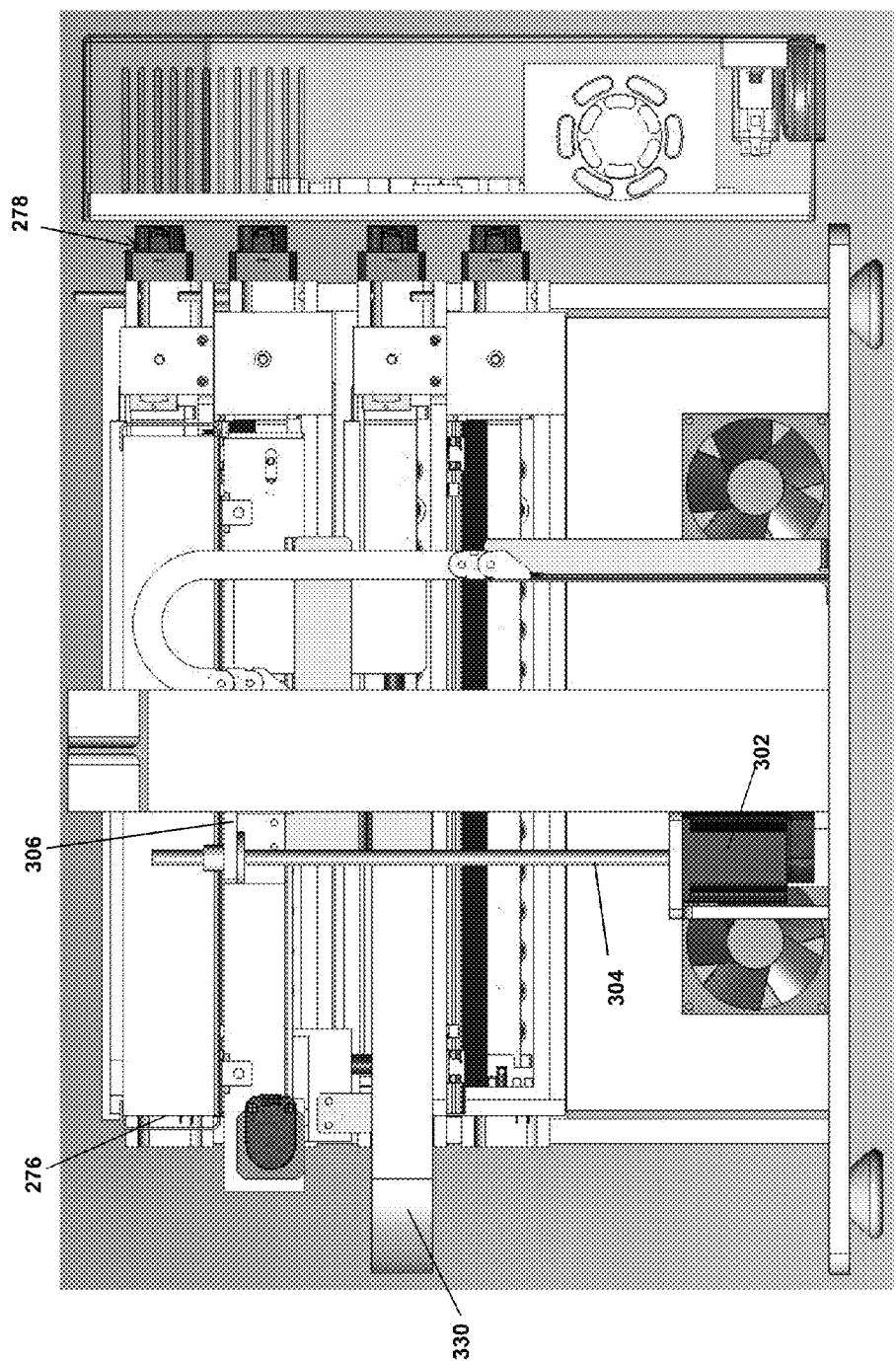

In one embodiment, the system 250 includes a plurality of incubators 252. Various assays may incubate culture samples at different temperatures. Thus, the system 250 may include a plurality of thermal zones 262 (incubation zones) that can operate at different temperatures, wherein each zone includes one or more incubators. The assays in each incubator 252 are processed simultaneously, wherein each incubator may include one or more trays 256 holding one or more sample tubes 258. However, the sample tubes 258 may not necessarily be processed in a batch. In this regard, each sample tube 258 can be placed in the incubator 252 at a different time, thereby having a different starting time for its test period. The sample tubes 258 may all be exposed to the same repeating test cycle during their test periods. The majority of sample tubes 258 may be introduced together in batches. As shown in FIGS. 26 and 27, the system includes four incubators 252 that are divided into two thermal zones 262. The thermal zones 262 may be arranged vertically such that two incubators 252 are associated with a respective thermal zone. Identical thermal zones 262 are stacked vertically as shown in FIG. 27. However, it is understood that the thermal zones 262 may be arranged horizontally, or side-by-side, if desired. Each zone 262 may include one or more incubators 252 maintained at identical incubator levels that operate at a common temperature. In one exemplary embodiment, the zones 262 are configured for processing *Salmonella* and *Listeria* assays, which are maintained at different temperatures (e.g., about 42° C. and 30° C., respectively). Thus, the system 250 is configured to process different sample tubes 258 (e.g., detection vials) regardless of the type of assay.

Figure 34:
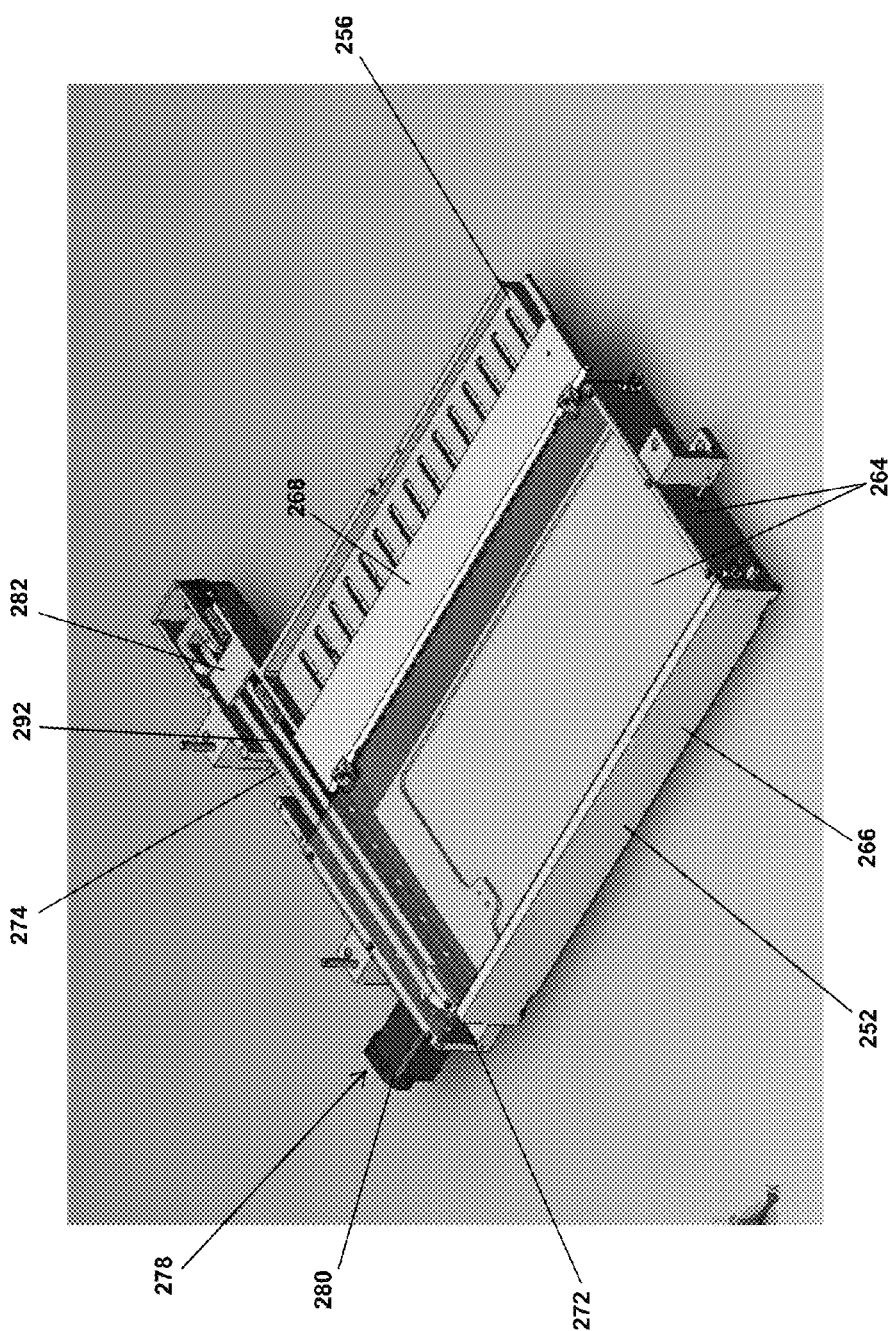
FIG. 34 is a perspective view of an incubator according to an embodiment of the present invention.
Figure 36:
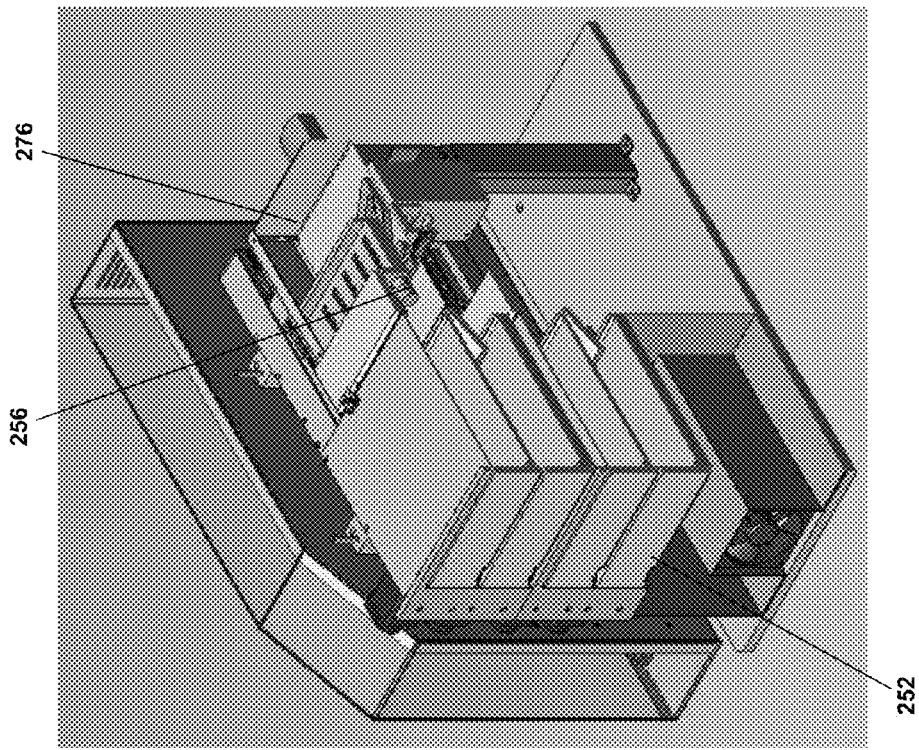
FIGS. 35-39 are various cross-sectional views of the system shown in FIGS. 26-29.
Figure 35:
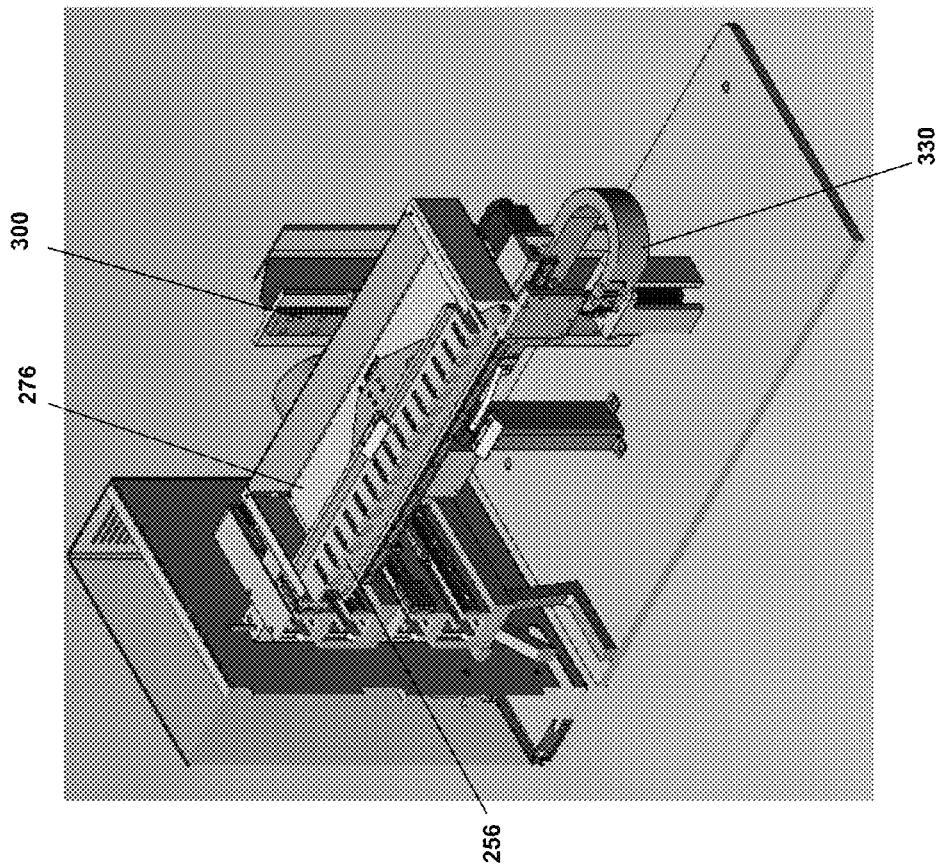
Figure 37:
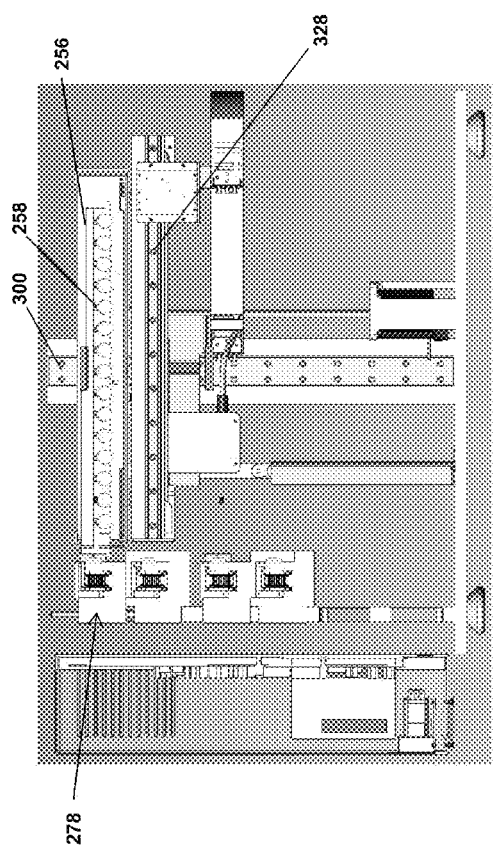
Figure 38:
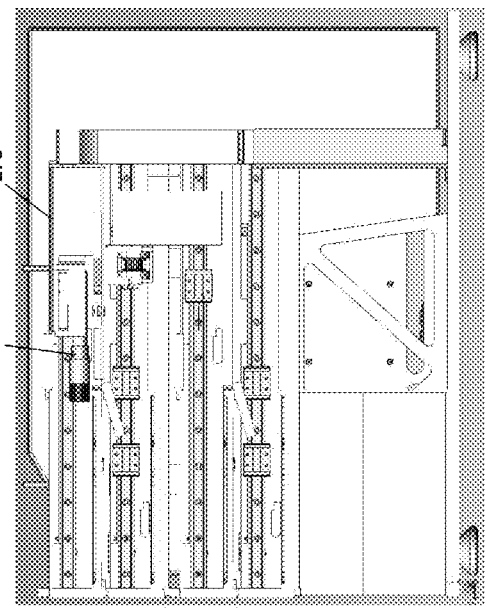

In one embodiment, each incubator 252 forms an enclosure suitable for receiving a tray 256 therein and maintaining a predetermined temperature necessary for culturing a particular sample. One example of an incubator 252 is shown in FIG. 34. The incubator 252 may include a base block 264, including the bottom and side surfaces, front and rear doors 266, 268, and a top surface 270. The incubator 252 may be formed of a variety of materials suitable for providing a temperature controlled enclosure. For example, the incubators 252 may be constructed from a single machined metal base block 264 (e.g., aluminum) that forms the bottom and sides of the temperature controlled region, while a metal plate (e.g., aluminum) forms the top surface 270. The incubator 252 may also include a channel 272 on the left side of the base block that is configured to support a belt drive 274 for oscillating the tray 256 in a Y-direction under control of a Y-stage 278. The range of motion of the tray 256 extends beyond the heated zone depth to provide tray stroke into the pellet/read area behind the incubator 252. Thus, the range of motion of each tray 256 will be based on the amount of travel needed to properly agitate the tubes 258 as well as reposition the tubes outside of the incubator 252 for pelleting and image analysis by the pelleting/read assembly 254.

In one embodiment, the incubator 252 includes a front door 266 and a rear door 268, wherein the doors cooperate with the top surface 270 and the base block 264 to form an enclosure. The front door 266 is configured to be selectively opened and closed by an operator (see e.g., FIG. 31). For example, the front door 266 may be configured to swing down so that the tray 256 can extend from the front of the incubator 252 a minimum distance and the door will not obstruct tube access or visibility. The front door 266 may be mounted using a variety of techniques to facilitate opening and closing. For instance, the front door 266 may be mounted on torsion spring loaded hinges that close the door upon tray withdrawal into the incubator 252. A pusher mechanism may extend from one or both sides of the front of the tray to aid in opening the door. According to one aspect, a flag is located inside of the front door 266 that is configured to interrupt an optical sensor mounted on the interior side wall of the incubator 252 to sense when the front door is closed.

Figure 40:
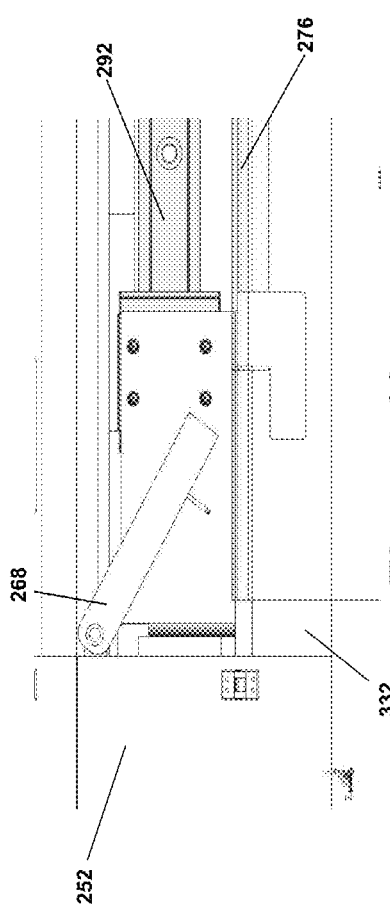
FIG. 40 is an enlarged view of a rear door of an incubator according to an embodiment of the present invention.

Similarly, the rear door 268 may be configured to open and close upon the tray 256 exiting and reentering the rear of the incubator 252 (see FIG. 40). Thus, as the tray 256 exits the incubator 252, the tray is configured to push the rear door 268 at least partially open. Like the front door 266, the rear door 268 may be mounted on torsion spring loaded hinges, and a feature on the rear of the tray 256 may be configured to push the rear door open as the tray emerges from the rear of the incubator 252. A sheath 276 is configured to receive the tray 256 upon exiting the incubator 252, and is configured for motion along a Z-axis as explained in further detail below. Once the rear door 268 is partially open, the sheath 276 may be configured to fully open the rear door as the sheath rises along the Z-axis to align with the incubator 252. With the sheath 276 holding the door open, the tray 256 is free to move in the pellet/read area without interference from the rear door 268. The rear door 268 is configured to close when the tray 256 is retracted into the incubator 252 and the sheath 276 lowers. The incubator 252 may include a sensor for indicating that the tray 256 is properly positioned therein. For instance, a flag on the inside of the rear door 268 may be configured to interrupt an optical sensor mounted on the interior side wall of the incubator to sense when the rear door is closed. This sensor may also be used as a home indicator for the tray 256. Thus, the rear door sensor may establish the tray 256 position as in or out of the rear of the incubator 252. A second home sensor may locate home for each tray 256 relative to the pelleting and optical hardware during each excursion into the pelleting/read region.

Because each incubator 252 is temperature controlled, the incubator may be wrapped by an insulating material (e.g., a closed cell foam insulation). Each of the thermal zones 262 may also be separated by an insulating material, which is useful when the zones are maintained at different temperatures. There may also be gaps between zones to limit cross talk between zones. In addition, the insulating material may be used to prevent thermal interaction when one incubator door 266 or 268 is open to the front or rear and the other is closed. Insulating spacers may separate incubators in a zone 262. Similarly, zones 262 may also be separated using spacers and insulating material.

Each incubator 252 is heated using a heating element. For example, the heating element may be configured to conduct heat through the base block 264 or provide heated air within the incubator. According to one embodiment, the heating element is a flat heating element adhered to or otherwise integrated with the bottom surface of the base block 264. The power distribution of the heating element may be tailored to minimize thermal gradients across the tubes 258 in the tray 256 to compensate for thermal loss through the Y drive 278 components on the left side of the incubator 252. Each incubator 252 may be provided with one or more sensors for monitoring temperature therein, such as the temperature of the base block 264 and/or the air within the incubator.

Figure 30:
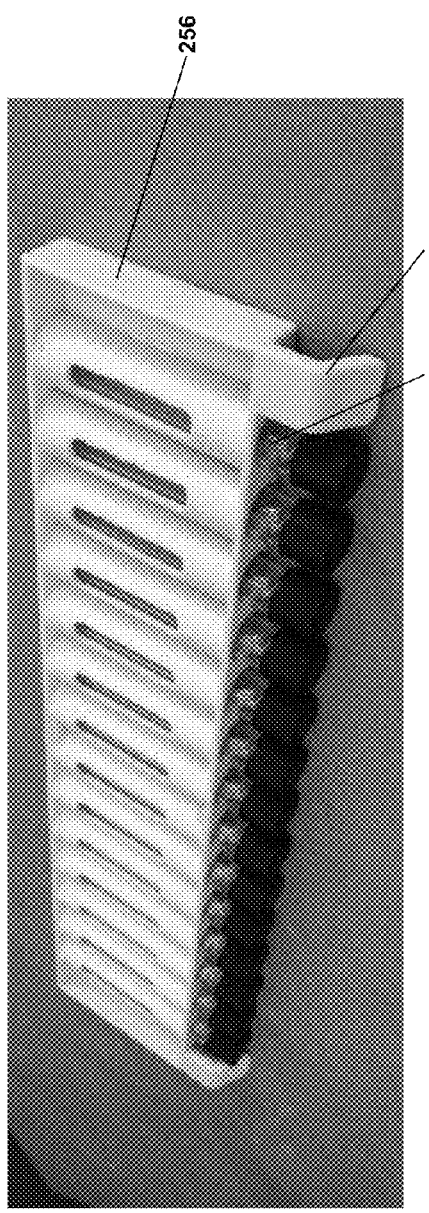
FIG. 30 is a perspective view of a tray for holding sample tubes according to an embodiment of the present invention.
Figure 31:
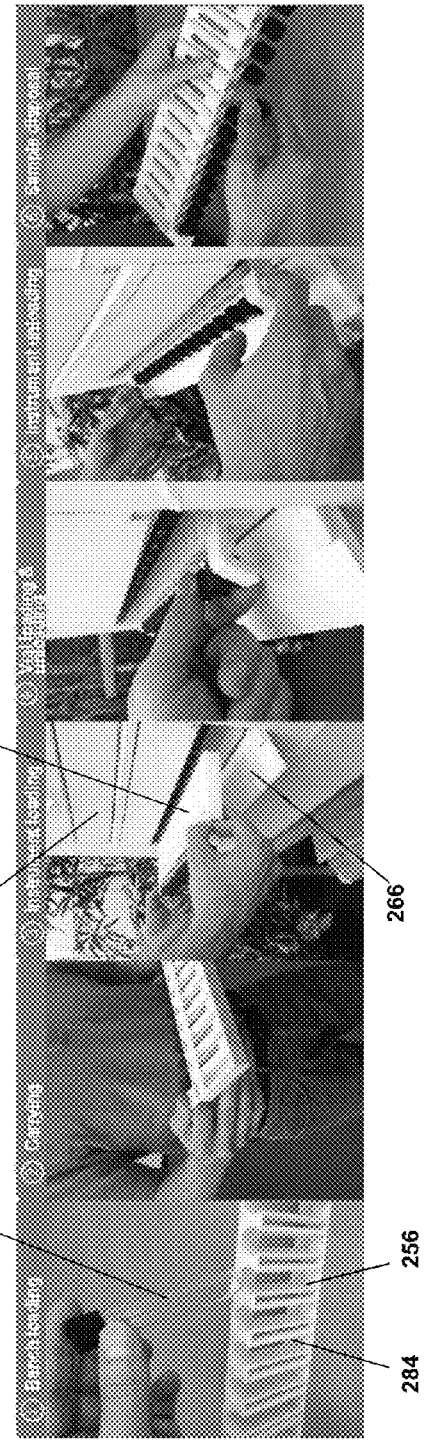
FIG. 31 illustrates sequential steps for loading sample tubes into a tray, loading the tray into an incubator, and removing the trays from the incubator, according to an embodiment of the present invention.

As discussed above, each incubator 252 is configured to receive a respective tray 256 therein. FIGS. 30-32 illustrate exemplary embodiments of trays 256 suitable for positioning within a respective incubator. A tray 256 in each incubator 252 is configured to accommodate a plurality of tubes 258. In the illustrated embodiment, the tray 256 holds 15 tubes 258 such that each thermal zone 262 holds 30 tubes, although any number of tubes may be used. The tubes 258 may be arranged horizontally in a planar array in each of the trays 256. In one embodiment shown in FIG. 31, a technician manually places sample tubes 258 into removable sample trays 256. The technician then places the trays 256 into the incubators 252. An assay is complete when a positive result is determined or when the result remains negative for a predetermined period of time. When the assay is completed, the technician removes the trays 256 to be refilled with new tubes 258. Alternatively, the technician may remove and/or add tubes to the tray individually as needed without stopping assays already in progress within other tubes in the tray or adjacent incubators. Positive samples may be segregated for further analysis. In another embodiment, the trays 256 are not removable. Thus, the tubes 258 can be placed individually into a non-removable tray 256 in each incubator 252. In yet another embodiment, the tray 256 may be unnecessary where the incubator 252 includes suitable means for holding the tubes 258 therein.

The arrangement of the tubes 258 horizontally and side-by-side in the trays 256 facilitates loading individual sample tubes or trays from the front of the incubator 252. Front loading avoids using bench space or isle space in front of the system, as a top-loaded tray would need to extend out the front of the system nearly the length of a tube to facilitate top loading. Further, the tray and sliding support would need to withstand high loads when a user exerts excessive pressure on the cantilevered extended tray.

Each tray 256 may be a variety of sizes and configurations for holding tubes 258 and facilitating placement within the incubator 252. For instance, FIG. 31 illustrates that the tubes 258 are inserted within respective slots 284 defined in the tray 256. The tubes 258 may be held in place using a force or an interference fit or biasing elements disposed within the tray 256. Where the trays 256 are removable from the incubator 252, the trays may include one or more gripping features 286 that allow a technician to hold the trays and manipulate the trays within the incubator, as shown in FIGS. 33A-33C.

In one embodiment, the tray 256 includes longitudinal slots 284 such that a portion of the tubes 258 is visible through the tray. Longitudinal slots 284 also allow the tubes 258 to protrude below the bottom surface of the tray 256 to provide a contact area with the pelleting magnets 288. To ensure sufficient contact with the magnets across the tray 256, each tube 258 may have vertical compliance in the tray. For example, a spring may hold the tube 258 down against the magnets as they rise to meet the tube. The spring may also retain the tubes 258 in the tray 256 by friction against the oscillatory tray motion.

According to one embodiment, the trays 256 are configured to oscillate horizontally along a Y axis in each incubator 252 under the control of a Y-stage 278 to agitate tubes containing a sample, culture medium, and reagent. This horizontal motion may fulfill several functions:
  a) Agitation for kinetic mixing in the incubator 252;
  b) Extending the tubes out the front of the incubator 252 for operator loading and unloading;
  c) Extending the tubes out the rear of the incubators 252 to the pelleting/read assembly 254;

d) Agitating the tubes 258 to disperse settled materials—e.g., solid components of media or samples;
e) Agitating the tubes 258 and magnets 288 in the pellet/read assembly 254 to form pellets;
f) Positioning the tubes 258 over the read head 290 for data collection;
g) Positioning tube labels over a bar code reader for sample ID;
h) Positioning the pellets over a camera to visualize pellets for internal controls, image-based detection methods, or remote diagnostics;
i) Agitating the tubes 258 to disperse pellets after reading;
j) Operating the incubator front door 266;
k) Operating the incubator rear door 268;
l) Circulating air in the incubator 252 to reduce temperature gradients.

As shown in FIG. 34, the system includes a Y-stage 278 for moving the trays 256 along a Y-axis, including for oscillating or agitating the trays and moving the trays in and out of the rear of the incubator 252. As shown in FIG. 27, each incubator 252 may include a respective Y-stage 278 disposed along the Z-axis so as to be spaced vertically from one another. The tray 256 may be coupled to the Y-stage 278 using one or more carriages 282. For example, the tray 256 may be cantilevered from a carriage 282 mounted on a linear rail 292, wherein the linear rail is mounted to the incubator base block 264. The Y-stage 278 includes a motor 280 for driving a belt 274 around timing pulleys at both ends of the rail 292. It is understood that the Y-stage 278 is configured to agitate that trays 256 at a variety of frequencies and amplitudes depending on the particular assay and application. For example, the trays 256 may be oscillated more slowly while in the incubators 252 than when positioned in the pelleting/read assembly 254.

The Y-stage 278 components may also be enclosed by an insulating material, while the motor 280 driving the Y-stage is outside the insulated area. The trays 256 and carriage 282 may move through an opening in the insulating material.

Figure 39:
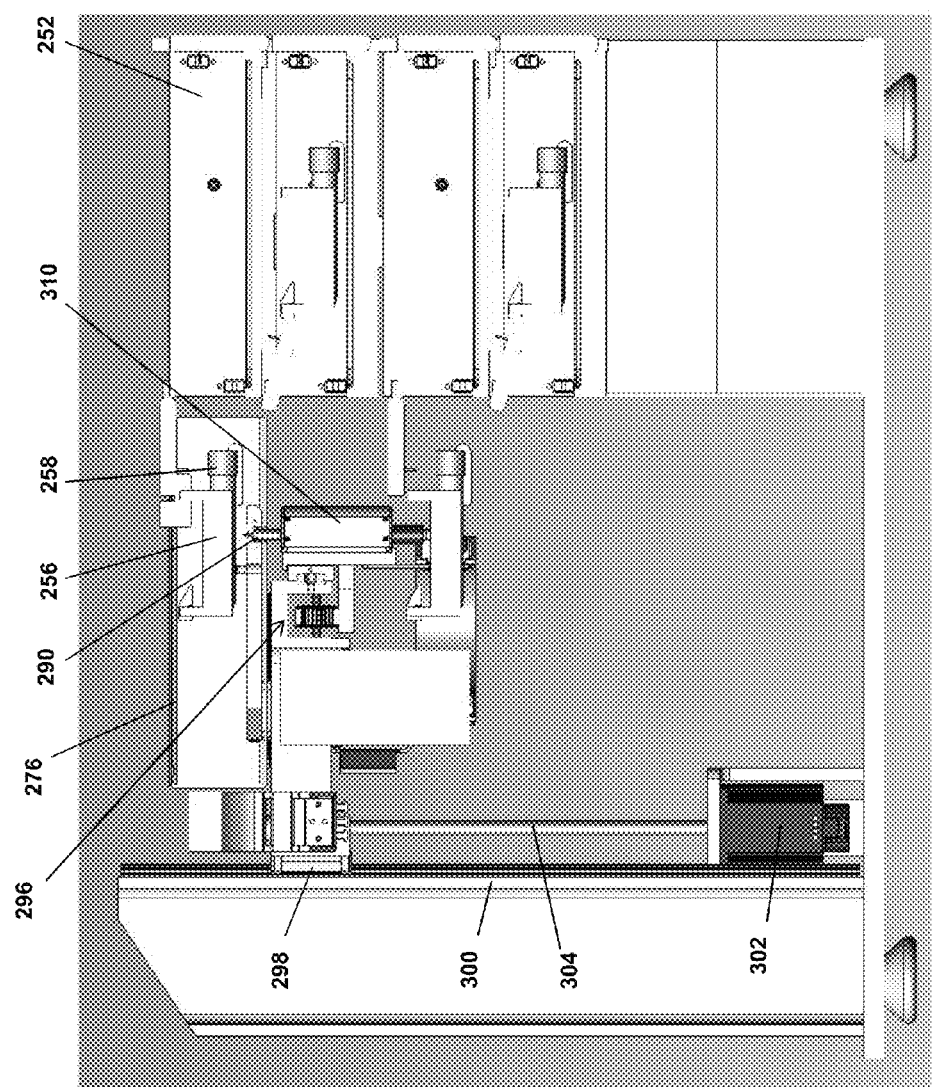
Figure 42:
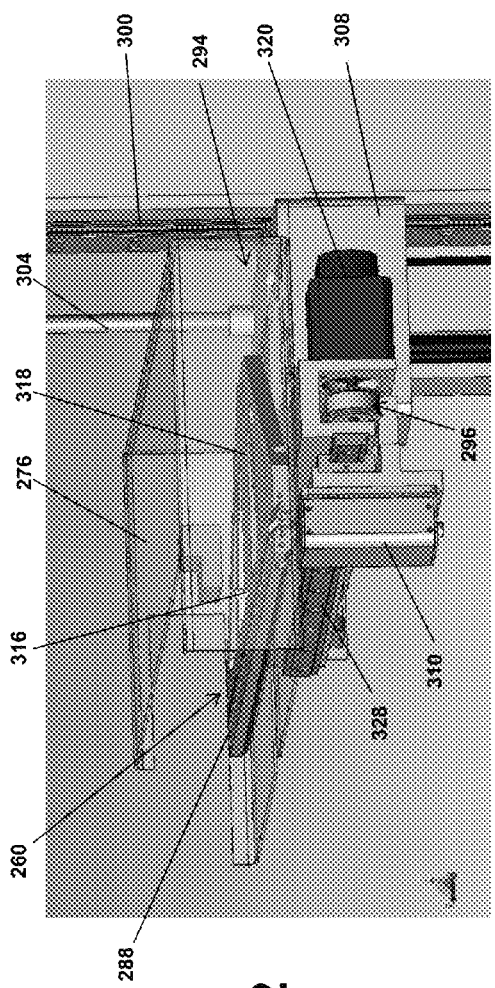
FIG. 42 is a perspective view of a magnet assembly, an X-stage, and a Z-stage according to an embodiment of the present invention.
Figure 43:
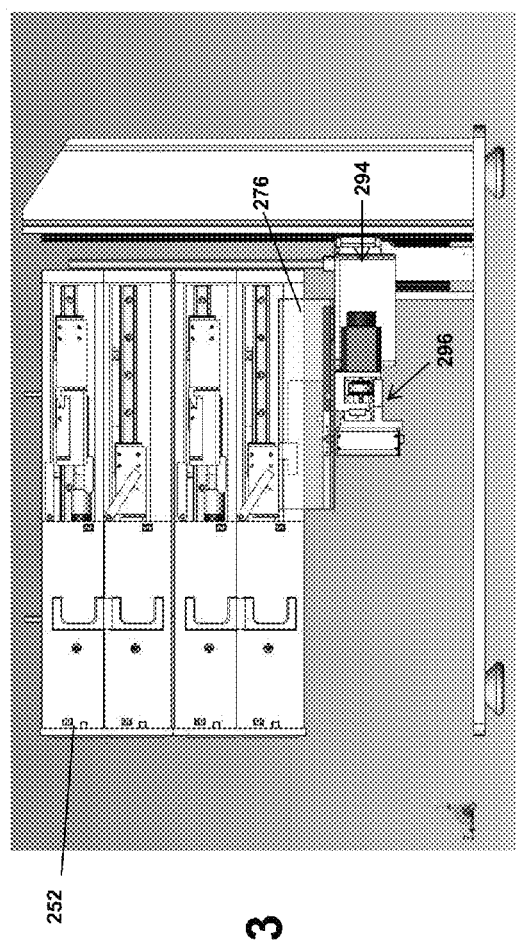
FIG. 43 is a side view of a magnet assembly, a pelleting/read assembly, an X-stage, a Y-stage, and a Z-stage in a lowered position according to an embodiment of the present invention.

The system 250 also includes a Z-stage 294 located behind the incubators 252 (see FIGS. 39, 42, and 43). The Z-stage 294 is configured to carry the sheath 276, magnet assembly 260, optical components (e.g., spectrometer 308, Raman probe 310, etc.), and X-stage 296 along a Z-axis. The Z-stage 294 may include a carriage 298 configured to ride on a vertical linear rail 300. A motor 302 is configured to raise and lower the Z-stage in a Z direction (e.g., using a linear screw and nut disposed within shaft 304 coupled to a Z-stage bracket 306). A sensor may be used to indicate when the Z-stage 294 is at the bottom of its travel in the Z-direction. The spectrometer 308, magnet assembly 260, sheath 276, and X-stage 296 are mounted to the Z-stage bracket 306 and all travel together in the Z-direction as a unit. The Z-stage 294 is configured to move in the Z-direction to accommodate each tray 256 that exits the incubator 252. The Z-stage 294 is also configured to travel below the bottom incubator 252 sufficiently to permit the bottom incubator rear door 268 to close.

Figure 45:
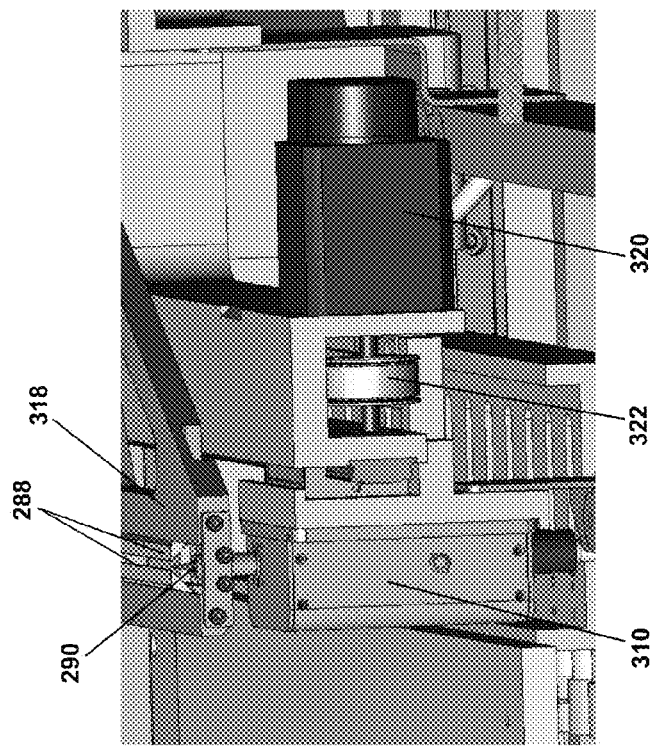
FIGS. 45 and 46 are partial perspective views of a magnet assembly, a pelleting/read assembly, and an X-stage according to one embodiment of the present invention.
Figure 44:
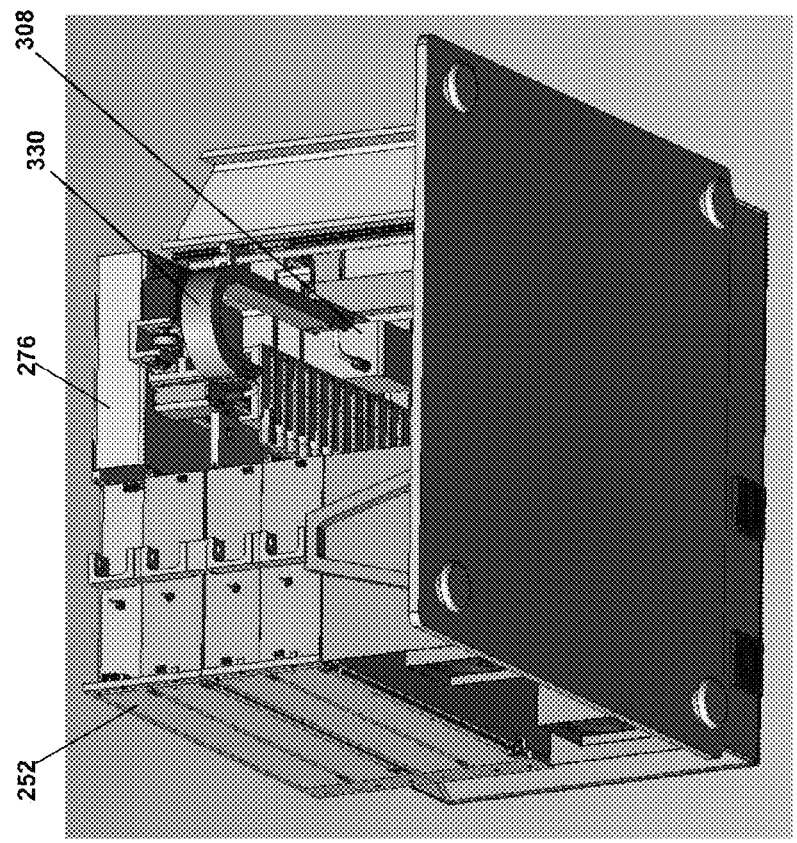
FIG. 44 is another perspective view of the system shown in FIGS. 26-29.
Figure 46:
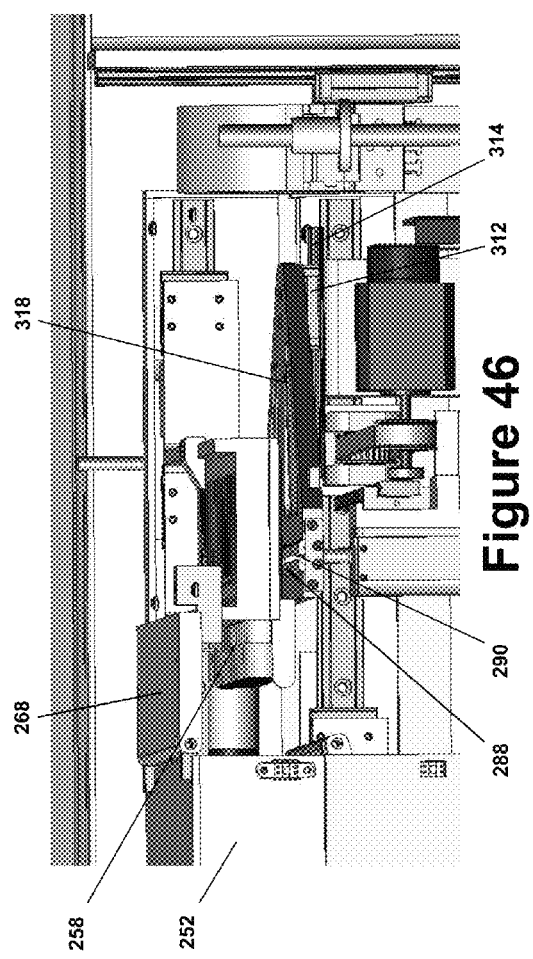

The system 250 also includes a magnet assembly 260, as shown in FIGS. 42, 45, and 46. The magnet assembly 260 may include one or more magnets 288 mounted to a magnet frame 318 configured to apply a magnetic field to the tubes 258, thereby facilitating the formation of a pellet within each tube. For example, FIGS. 45 and 46 illustrate a pair of longitudinal magnets 288 spaced apart a sufficient distance to permit the read head 290 to extend therethrough to obtain a reading. Thus, the magnets 288 may remain in position following pelleting and while the tubes 258 are being read by the read head 290. Each longitudinal magnet 288 may be a single magnet or a collection of a plurality of magnets arranged end to end.

Pellets may be formed when magnets 288 are brought into contact with, or within close proximity to, the bottom of the horizontally oriented tubes 258. The tubes 258 and magnets 288 gently oscillate during pellet formation to ensure the magnetic particles in suspension pass through the magnetic field and are attracted to a magnetic field focal point. According to one embodiment, the magnet assembly 260 is mounted to a carriage 312 that rides in the Y-direction on a rail 314 affixed to the Z-stage bracket 306 (see FIG. 46). The rail 314 may be parallel to the Y-stage rail 292.

Figure 47:
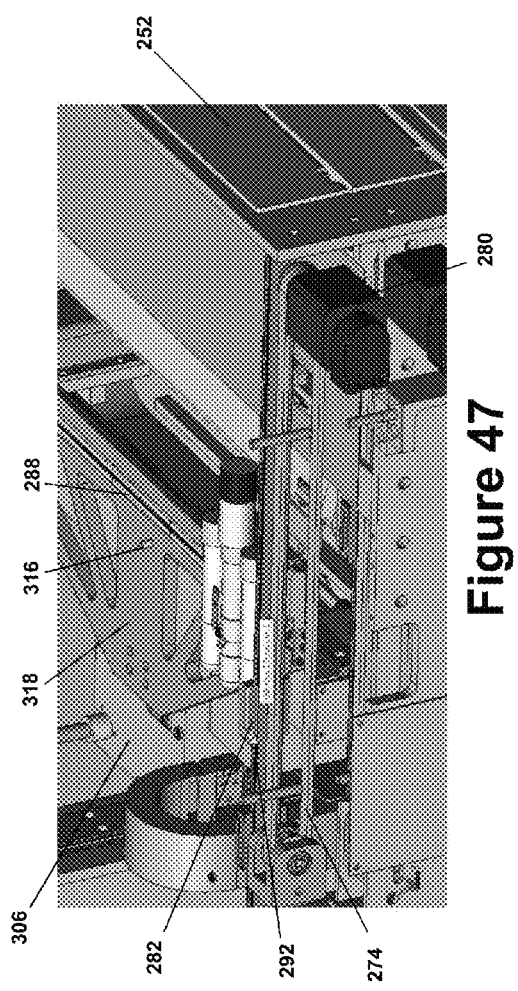
FIG. 47 is partial perspective view of a magnet assembly and a Y-stage according to one embodiment of the present invention.

When the tray 256 extends out of the rear of the incubator 252 and into the pelleting/read assembly 254, the Z-stage 294 may be raised from below along a Z-axis. As shown in FIGS. 42 and 47, a pin 316 extending outwardly from the magnet frame 318 is configured to engage with a hole in the underside of the tray 256. Once engaged, the magnet frame 318 is coupled with the tray 256, and the magnet frame and tray are able to move together in the Y-direction along rail 314. Therefore, in one embodiment, the pelleting/read assembly 254 is configured to process one tray 256 at a time. The pelleting oscillation amplitude may vary depending on a number of factors specific to a particular assay. In one example, the oscillating amplitude may be up to about 50 mm. The magnet frame 318 and tray 256 may be coupled at a position of full travel of the Y-stage in the Y-direction, while the center of the pelleting oscillations may be located forward from the coupling location to accommodate ½ the amplitude in the Y-direction.

In one embodiment, a small amount of relative motion between the oscillating tubes 258 and the magnets 288 allows the magnetic field to gather the magnetic particles into a tighter pellet. Thus, a loose coupling between the tray 256 and magnet frame 318 may be desirable. Such a coupling may be implemented, for instance, by mounting the frame 318 on a block held in a slot in the frame 318 between two springs. As the tray 256 oscillates fore and aft in the Y-direction, the frame 318 moves in relation to the tray as the springs alternately compress in a second oscillatory motion. The loose coupling stroke may be, for example, about 5 mm. The spring constants will be selected to provide the optimal oscillation frequency.

The magnet assembly 260 is configured to pellet each of the tubes 258 in the tray 256 simultaneously, according to one embodiment of the present invention. The magnets 288 may be configured to remain in place while the tubes 258 are being read by the read head 290. Alternatively, the pellets may be adequately persistent to permit the magnet 288 or tubes 258 to be moved away from one another for reading.

Figure 41:
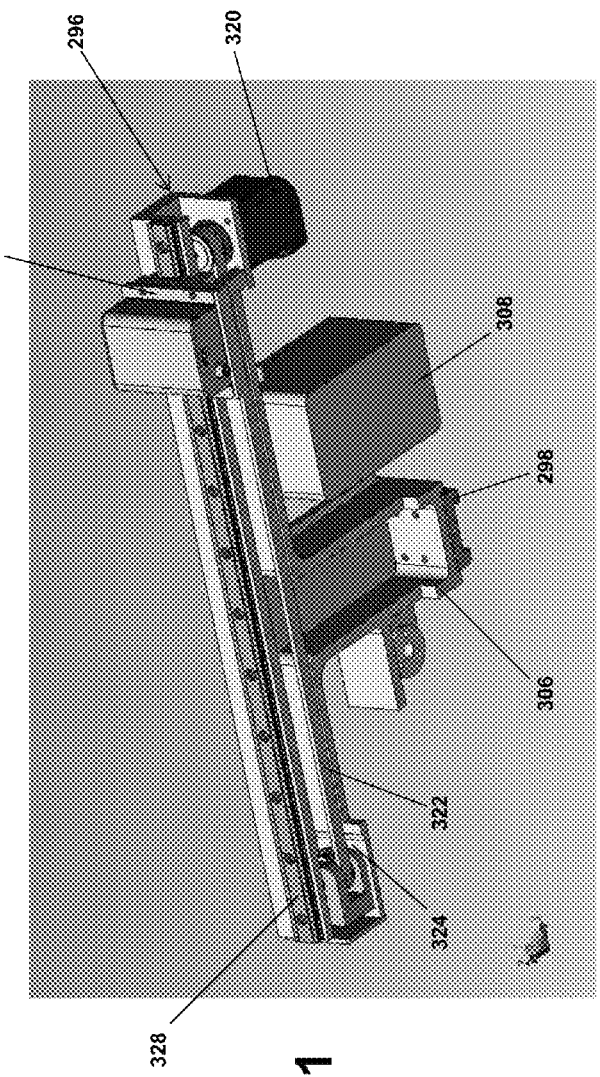
FIG. 41 is a perspective view of an X-stage according to an embodiment of the present invention.

FIG. 41 shows one example of an X-stage 296 that is coupled to the Z-stage 294. Thus, the X-stage 296 is configured to be moved in the Z direction by the Z-stage. The X-stage 296 also facilitates motion of the read head 290 in the X-direction for reading each of the tubes 258. The X-stage 296 scans the read head 290 under the array of tubes 258 to collect assay data after pellets have been formed. During pelleting, the X-stage 296 is moved to an X-position that allows a coupled tray 256 to be moved without interference with the read head 290 and the magnet assembly 260. After pelleting, with the tray 256 held stationary, the X-stage 296 translates to each tube 258, pausing to collect data until all tubes are read. The X-stage 296 is then repositioned to its start position before the tray 256 is moved. In one exemplary embodiment, the X-stage drive (e.g., motor 320 and belt 322) is mounted in a channel 324 in the Z-stage bracket 306 and utilizes a similar design as that of the Y-stage 278. The read head 290 is mounted to a carriage 326 that is configured to move along a rail 328 of the X-stage 296. A flexible sleeve 330 may be used to route the read head 290 electrical cables and flexible fiber optic cable from the Z-stage 294 to the moving read head. The flexible sleeve 330 is configured to not only protect the fiber optic bundle but also allow the fiber to flex in the X-direction and provide a desired bend radius.

According to another embodiment, the X-stage 296 is configured to carry a bar code reader (not shown) for reading a bar code or other identifier on each of the tubes 258. For example, the bar code reader may be used to confirm that the tube 258 is in the correct thermal zone 262, thereby preventing false negatives. The bar code could include other data, such as identification and assay information. As discussed above, the tubes 258 may include longitudinal slots 284 that facilitate such reading by a bar code reader. Additionally, the bar code reader may provide imaging data on pellets for internal controls, image-based detection methods, and/or remote diagnostics.

As discussed above, a sheath 276 is configured to receive each tray 256 as the tray exits the rear of the incubator 252. In particular, the insulated sheath 276 is carried on the Z-stage 294 and is configured to align with each incubator 252 to surround the tray 256 when it extends out the rear of the incubator into the pelleting/read region 254. The insulated sheath 276 minimizes the tray temperature change while the tray 256 is extended out of the incubator 252. The sheath 276 both provides an insulated sleeve and blocks air flow from cooling the tray 256 and tubes 258 contained therein. Also, the sheath 276 is constructed from materials that minimize its thermal mass and thus the heat energy exchange with a tray 256 at a different temperature from than that of the preceding zone. For example, the sheath 276 may comprise a thin aluminum structure surrounding by an insulating material. In one specific embodiment, a tray at about 30° C. entering a sheath at about 42° C. will not increase in temperature by more than about 0.5° C.

There may be a gap 332 defined between the incubator 252 and the aligned sheath 276 such that the incubator cannot fully regulate the temperature in the sheath. In those instances where the temperature in the incubator 252 is higher than ambient temperature, the air surrounding the sheath 276 may be cooler than the tray 256, so any thermal transfer from the sheath will be toward a lower tray temperature. However, some assays have an acceptable temperature tolerance should there be variations resulting from movement of the tray 256 from the incubator 252 into the sheath 276. For example, assays are more tolerant of brief negative temperature dips, e.g., about −2° C., than temperature rises, e.g., about +0.5° C. for *Salmonella* at 42° C. and *Listeria* at 30° C. Thus, it may be unnecessary to form a good thermal seal with the incubator 252 as long as negative excursions are within acceptable tolerances.

In addition to surrounding the extended tray 256, the sheath 276 may also enclose the magnet assembly 260 as shown in FIG. 42. Thus, the sheath 276 may be sized to enable the Z-stage 294 to move vertically with the magnet assembly 260 for coupling and uncoupling the tray 256, as discussed above. Moreover, the sheath 276 may include cutouts to provide clearance for the read head 290 along the bottom of the sheath and for the carriages 282 moving along the side via the Y-stage 278. The top of the sheath 276 may also include cutout for the rear incubator door 268.

Figure 48B:
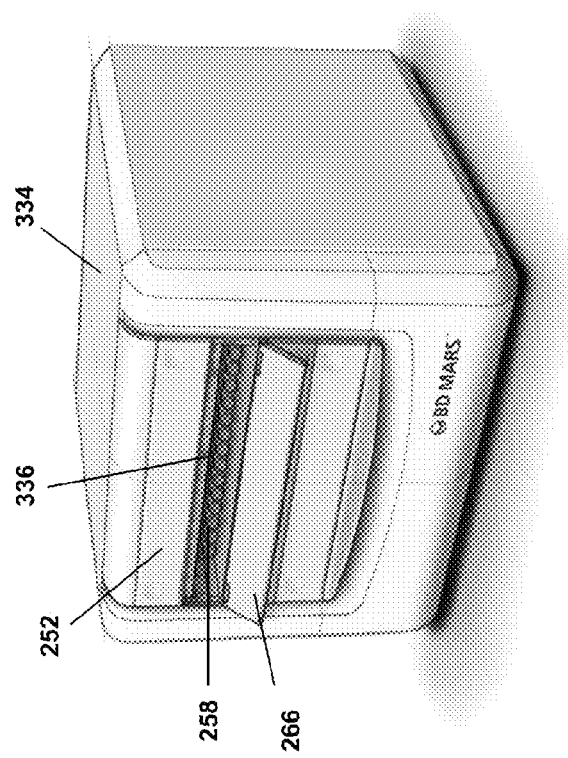
FIGS. 48A-48B are perspective views of a system for real-time monitoring of microorganism growth enclosed in a cabinet according to embodiments of the present invention.
Figure 48A:
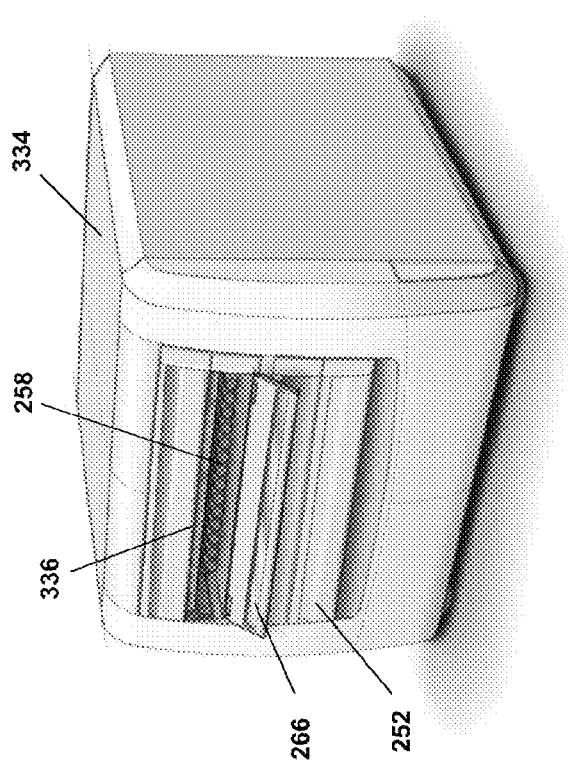

The aforementioned components of the system 250 may be enclosed in a cabinet 334, as shown in FIGS. 48A and 48B. A skin forms a cabinet 334 around the incubator 252 and pelleting/read region 254 to control air flow and add thermal control. The cabinet 334 also may also provide a safe enclosure in which the optical components operate (e.g., laser). The system 250 may further include one or more visible or audible signals for indicating the status of the assays. For example, one or more LED's 336 may be used to indicate that the assay is in progress and when a positive result occurs. Each tube 258 and/or tray 256 may include an associated LED 336 for such a purpose. Different LED colors may be used for different indications, wherein the colors may be visible when the front door 266 of the incubator 252 is open or closed.

The incubators 252 typically are maintained at a temperature that is higher than ambient. To aid in achieving this temperature difference and ensure excess heat is not delivered to trays 256 extending into the sheath 276, an air flow path may be employed. Fans with filters may also be used to pressurize the cabinet 334 to reduce dust infiltration, and other heat dissipation techniques may be used for components such as the motors. Other techniques, such as a thermal electric cooler may be used to further cool the cabinet 334.

Various electrical components may be used for interfacing with and controlling the system 250 as known to those of ordinary skill in the art. For example, various motor driver boards may be used to control the motors and provide the interface to the other devices such as sensors and encoders. Other boards may be used to provide additional functionality such as providing power and interface signals for the read head 290 and the spectrometer 308 as well as driving heaters and reading the associated thermistors. Additionally, the system 250 may employ various other components such as a microcontroller for controlling the system in an automated manner as known to those of ordinary skill in the art.

E. Agitation and Pelleting Techniques

Figure 49:
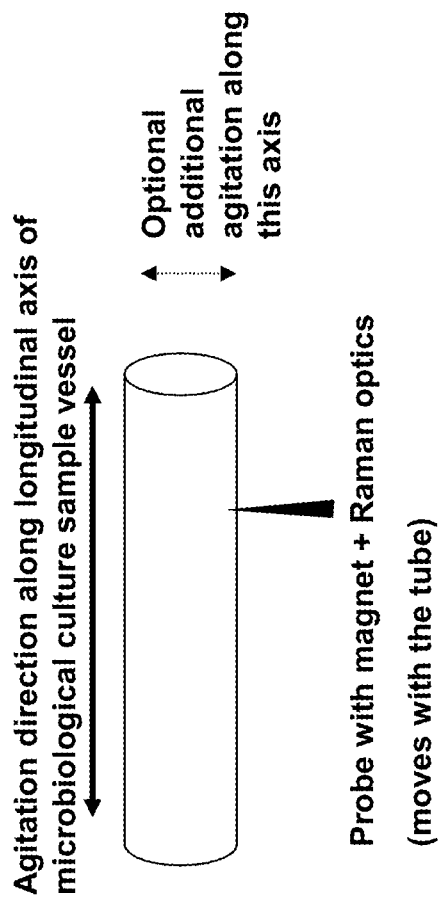
FIG. 49 illustrates a method for agitating and pelleting a culture sample according to an embodiment of the present invention.

FIG. 49 depicts methods of agitation and pelleting according to an embodiment of the invention which have been developed that minimize the reagent volume and obtain a reading that is representative of a large volume (e.g., up to 250 mL). This is accomplished primarily by agitating the culture vessel along its longitudinal axis during the application of the magnetic field. The pellet is formed on the side of the tube, along the direction of the longitudinal axis. A combination of sample-to-tube volume (e.g. 1:2), tube length/width aspect ratio (e.g., 7:1), and agitation parameters results may be selected to optimize performance. Agitation promotes more efficient pellet formation by ensuring that particles from the larger volume are brought into close proximity with the magnet. In addition, agitation helps keep non-complexed cells, microorganisms, and loose solids (e.g. resin in blood culture samples) out of the pellet by applying a force away from the magnetic field direction.

Figure 50:
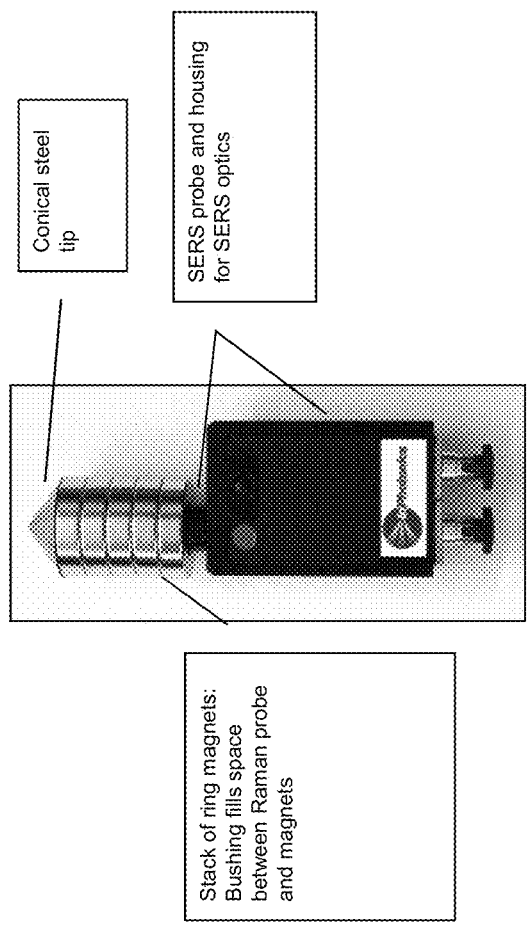
FIG. 50 depicts a pelleting and optical system according to an embodiment of the invention.

FIG. 50 depicts one embodiment of a device for forming and interrogating the magnetic pellet. This device may be used in the carousel system 150 embodiment shown in FIG. 24. In the embodiment illustrated in FIG. 50, the magnet assembly consists of a stack of ring magnets surrounding and collinear with the portion of the optical read head containing the objective lens. A hollow conical steel tip focuses the magnetic field at the tip of the cone, causing the pellet to be formed at the focus of the read head. This arrangement automatically aligns the pellet with the focus of the read head and relaxes the constraints on the alignment of tube, magnet, and read head. Consistent alignment of pellet, magnet, and read head are important for consistent measurements across all samples over the course of the assay, and this design provides reliable and repeatable pellet formation across sample tubes, over multiple reads during the course of an assay, and across instruments.

Figure 51:
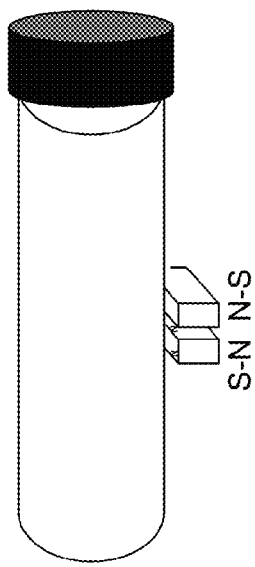
FIGS. 51 and 52 illustrate alternative magnet arrangements for pelleting a culture sample according to embodiments of the present invention.
Figure 52:
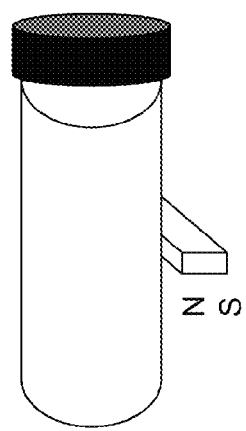

FIGS. 51 and 52 show alternate methods of forming the pellet that have been used in accordance with the systems described above. The alignment of the tubes in a horizontal plane allows the optical signal to be read with the magnets either withdrawn after pelleting or maintained in the pelleting position. This allows various magnet geometries to be tested. Two have proven to be especially effective. One, termed "North-up" uses a bar magnet with magnetization directed normal to the tube (FIG. 52). This forms a symmetric circular pellet ideal for reading with the read head. The other geometry is termed "North-facing-North pair" (FIG. 51), in which two bar magnets are positioned adjacent and parallel to each other. The magnetization is directed along the line normal to the magnets through the thickness of each magnet, such that the North poles face each other. With proper spacing between the magnets, the region of highest field gradient is in the region between the magnets, resulting in a pellet focused in the region between the magnets, which is easily accessible for reading with the magnets in place.

In another embodiment of the invention a camera is also added to the testing station to monitor the formation and size of the pellet during SERS-HNW assay which contains conjugated SERS indicator particles and magnetic beads and the targeted pathogen within a culture vessel. The pellet size increases, and in some cases the pellet disappears, from the camera view as the HNW assay progresses. The growth in pellet size and/or disappearance of the pellet is an indication of the presence of the targeted pathogen. Images captured during analysis of samples that contain conjugated SERS indicator particles and magnetic beads with no pathogen show no change in pellet size and no pellet disappearance. This method of pathogen detection can be used alone or in conjunction with another detection method such as the previously described SERS analysis as a means of validation.

Embodiments of the presently disclosed methods can be conducted with any suitable spectrometers or Raman spectrometer systems known in the art, including, for example, a Multimode Multiple Spectrometer Raman Spectrometer (Centice, Morrisville, N.C., United States of America), such as the Raman spectrometer system disclosed in U.S. Pat. No. 7,002,679 to Brady et al., which is incorporated herein by reference in its entirety. Other non-limiting examples of suitable spectrometers or Raman spectrometer systems include the Hamamatsu C9405CA and the Intevac ReporteR, and include both fiber-coupled and free-space optical configurations. Additional instrumentation suitable for use with the presently disclosed SERS-active indicator particles is disclosed in PCT International Patent Application No. PCT/US2008/057700 to Weidemaier et al., filed Mar. 20, 2008, which is incorporated herein by reference in its entirety.

Representative methods for conducting magnetic capture liquid-based SERS assays are disclosed in PCT International Patent Application No. PCT/US2008/057700 to Weidemaier et al., filed Mar. 20, 2008, which is incorporated herein by reference in its entirety. Such methods can include referencing and control methods for compensating for variations in magnetic pellet size, shape, or positioning, and methods for generating improved Raman reference spectra and spectral analysis in magnetic pull-down liquid-based assays, as also disclosed in PCT/US2008/057700. Further, multiple reporter molecules can be used to create an internal reference signal that can be used to distinguish background noise from signal detection, particularly in samples that exhibit or are expected to exhibit a relatively weak signal.

Further, as disclosed in U.S. patent application Ser. No. 12/134,594 to Thomas et al., filed Jun. 6, 2008, and PCT International Patent Application No. PCT/US2008/066023 to Thomas et al., filed Jun. 6, 2008, each of which is incorporated by reference in its entirety, dyes suitable for use as reporter molecules in SERS-active indicator particles typically exhibit relatively simple Raman spectra with narrow line widths. This characteristic allows for the detection of several different Raman-active species in the same sample volume. Accordingly, this feature allows multiple SERS-active indicator particles, each including different dyes, to be fabricated such that the Raman spectrum of each dye can be distinguished in a mixture of different types of indicator particles. This feature allows for the multiplex detection of several different target species in a small sample volume, referred to herein as multiplex assays.

Accordingly, in some embodiments, more than one type of binding member can be attached to the SERS-active indicator particle. For example, the type of binding member attached to the SERS-active indicator particle can be varied to provide multiple reagents having different affinities for different target microorganisms. In this way, the assay can detect more than one microorganism of interest or exhibit different selectivity's or sensitivities for more than one microorganism. The SERS-active indicator particle can be tailored for culture samples in which the presence of one or more microorganisms, or the concentrations of the one or more microorganisms, can vary.

A SERS assay reagent can include more than one type of label, e.g., more than one type of SERS-active reporter molecule, depending on the requirements of the assay. For example, SERS-active reporter molecules exhibiting a Raman signal at different wavelengths can be used to create a unique Raman "fingerprint" for a specific microorganism of interest, thereby enhancing the specificity of the assay. Different reporter molecules can be attached to nanoparticle cores which have attached thereto different specific binding members to provide a reagent capable of detecting more than one microorganism of interest, e.g., a plurality of microorganisms of interest.

In an embodiment of the invention, the multiplexing capabilities of the SERS HNW technology are used to identify six of the most common organisms causing blood stream infections. Six different types or "flavors" of SERS-active indicator particles are present in a blood culture bottle, each conjugated with antibodies specific to one of the six organisms to be detected. Also in the vessel are magnetic capture particles capable of forming sandwiches with the SERS-active indicator particles. The magnetic capture particles can be configured so that there is a common capture antibody or set of antibodies that sandwich multiple SERS-active indicator particles or alternatively, there could be six separate magnetic conjugates present in the vessel, with each magnetic conjugate uniquely capable of forming a sandwich with each of the six SERS-active indicator particles. When a magnetic pellet is formed and the SERS signal from the pellet is read, the measured Raman spectrum will be a contribution from each flavor of SERS-active indicator particle present in the pellet; the presence of a SERS-active indicator particle indicates the presence of the microorganism for which the SERS-active indicator particles is specific. Deconvolution algorithms can efficiently distinguish the spectra of the six individual SERS-active indicator particles from the measured aggregate spectrum.

Figure 53:
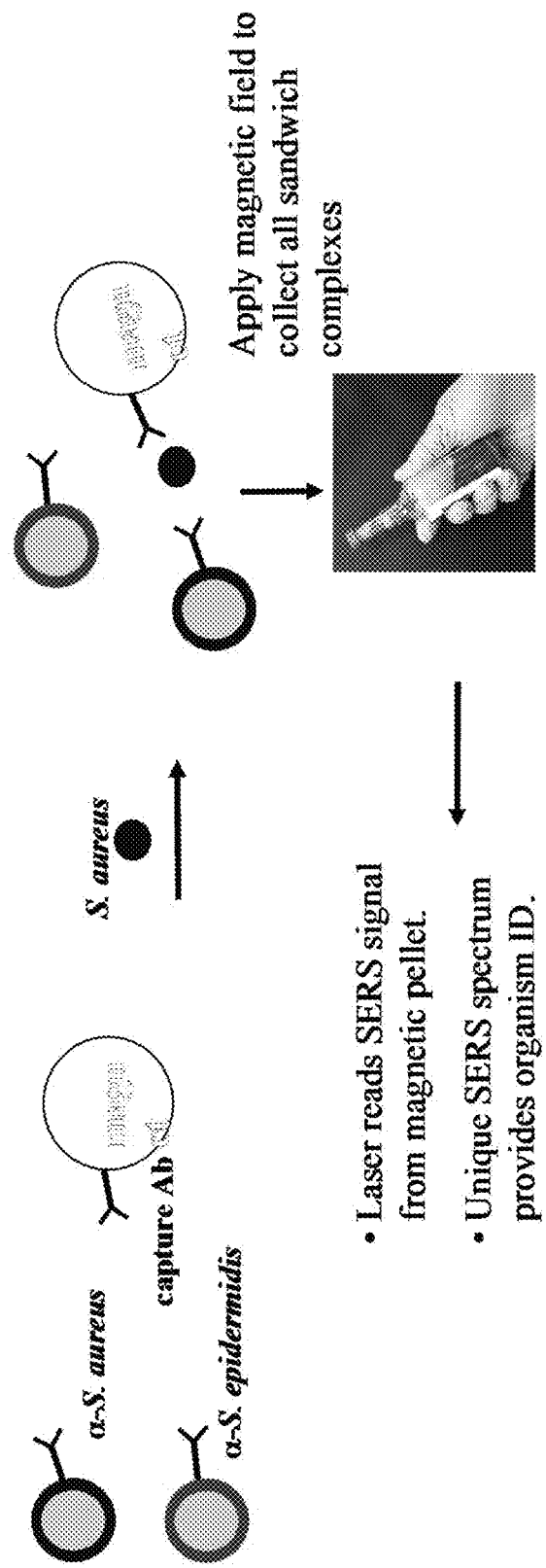
FIG. 53 depicts a multiplexed detection of *S. aureus* and *S. epidermidis* according to an embodiment of the invention.

FIG. 53 shows a schematic of a multiplexed embodiment using only two SERS-active indicator particles. In a preferred embodiment, a standard gas sensor (e.g. BACTEC™) is retained, so that both the SERS signal and the pH sensor signals are simultaneously monitored. This enables efficient detection of any microorganism that is not recognized by the SERS HNW antibodies.

As further disclosed in PCT International Patent Application No. PCT/US2008/057700 to Weidemaier et al., filed Mar. 20, 2008, in the presently disclosed assays involving SERS-active indicator particles, the SERS spectra can be amplified through the addition of a second aliquot of reporter molecules capable of generating a detectable signal and having associated therewith at least one specific binding member having an affinity for the at least one SERS-active reporter molecule associated with the one or more SERS-active indicator particles prior to, concurrent with, or subsequent to disposing the sample and/or the at least one SERS-active reporter molecules therein, wherein the second aliquot of reporter molecules is the same as the at least one SERS-active reporter molecules associated with the SERS-active indicator particles. In some embodiments, the second aliquot of reporter molecules comprises a SERS-active reporter molecule associated with a SERS-active indicator particle capable of producing a SERS signal. In those embodiments wherein a second aliquot of reporter molecules is disposed into the assay vessel, the specific binding member of the second aliquot of reporter molecules does not recognize the one or more specific binding members comprising the capture zone or attached to the magnetic capture particles.

F. Workflow Examples

According to one exemplary embodiment, a culture sample for detecting and identifying *Salmonella* may be provided in conjunction with the aforementioned embodiments. In one embodiment, *Salmonella* is first cultured in a non-selective media within the enrichment vessel, followed by a biocontained transfer into a detection vial containing the detection reagents and a second, selective media. Generally, the *Salmonella* testing includes adding media with optional supplement into a media preparation vessel. The media is then dispensed into the enrichment vessel and a sample is added into the enrichment vessel. Optionally, the sample is homogenized (e.g., by stomaching or blending) prior to addition to the enrichment vessel. In this case, the media from the media preparation vessel is added along with the sample to the homogenizer. Following homogenization, the sample is transferred into the enrichment vessel, and a lid is attached to the vessel. Once media and sample have been added to the enrichment vessel and the enrichment vessel lid has been attached, a bar code on the vessel may be read for chain of custody identification purposes. The enrichment vessel is then incubated for a predetermined period of time. Following incubation, the enrichment vessel and a detection vial may be scanned with a bar code reader. The detection vial includes a selective media and detection reagents that are particular to detecting *Salmonella*. In the case where the media in the detection vial is dehydrated, reconstitution fluid is added to the detection vial, and the vial is inverted for mixing. The enrichment container is then tilted to fill a respective reservoir with a desired amount of sample (e.g., 100 µL). The detection vial is inserted into the enrichment vessel to engage a needle within the opening for a biocontained transfer of the sample into the detection vial. The detection vial is then inserted within a real-time automated system for incubation and automated testing of the sample, including pelleting and optical analysis of the sample. Upon detection of a positive sample, the detection vial may be removed, scanned by a bar code scanner, and routed for further processing.

In an alternate exemplary embodiment, a culture sample for detecting and identifying *Listeria* may be provided in conjunction with the aforementioned embodiments. In a preferred embodiment, culture of *Listeria* within the detection vial occurs in the same media that is used in the enrichment vessel, so that a single media is used throughout the workflow. Generally, the *Listeria* testing includes adding media with optional supplement into a media preparation vessel. The media is then dispensed into the enrichment vessel and a sample is added into the enrichment vessel. Optionally, the sample is homogenized (e.g., by stomaching or blending) prior to addition to the enrichment vessel. In this case, the media from the media preparation vessel is added along with the sample to the homogenizer. Following homogenization, the sample is transferred into the enrichment vessel, and a lid is attached to the vessel. Once media and sample have been added to the enrichment vessel and the enrichment vessel lid has been attached, a bar code on the vessel may also be read for chain of custody identification purposes. The enrichment vessel is then incubated for a predetermined period of time. Following incubation, the enrichment vessel and a detection vial may be scanned with a bar code reader. The detection vial includes detection reagents that are particular to detecting *Listeria*. The enrichment container is then tilted to fill a respective reservoir with a desired amount of sample (e.g., 5 mL). The detection vial is inserted into the enrichment vessel to engage a needle within the port for a biocontained transfer of the sample into the detection vial. The detection vial is then inserted within a real-time automated system for incubation and automated testing of the sample, including pelleting and optical analysis of the sample. Upon detection of a positive sample, the detection vial may be removed, scanned by a bar code scanner, and routed for further processing.

G. Reconstitution Station

Figure 93:
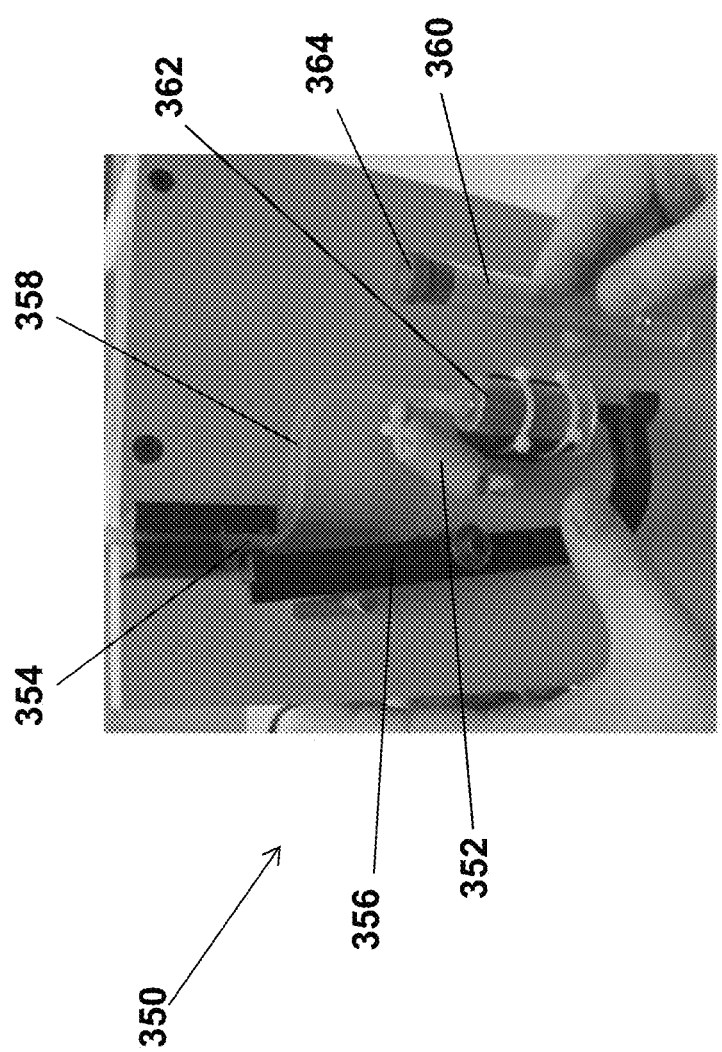
FIGS. 93-95 illustrate reconstitution stations according to various embodiments of the present invention.
Figure 95:
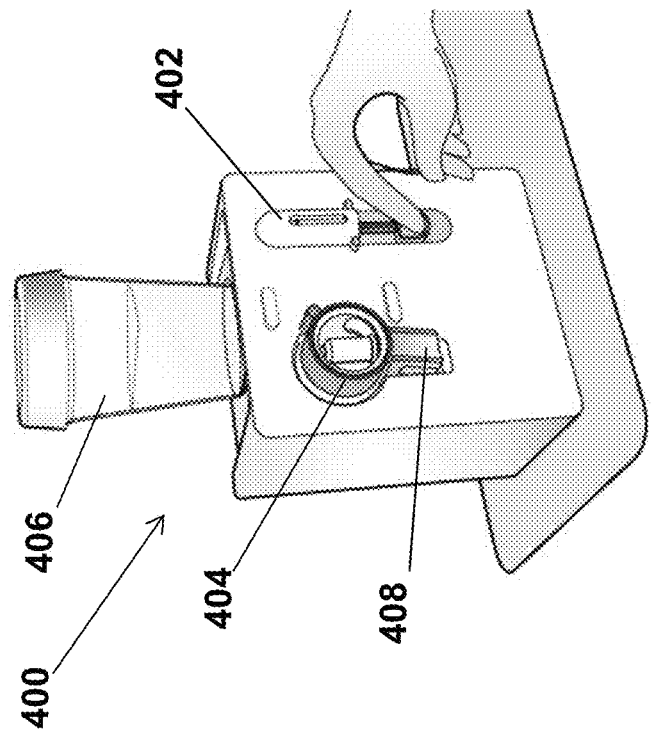
Figure 94:
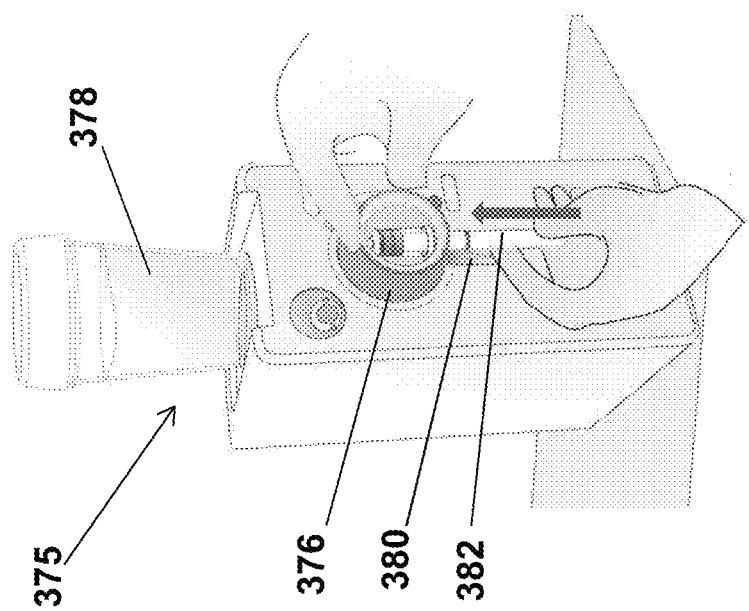

FIGS. 93-95 illustrate reconstitution stations that may be used in a conjunction with embodiments of the present invention. As discussed above, reconstitution fluid may be added to the detection vial where the media in the detection vial is dehydrated. The reconstitution stations facilitate metering of a desired volume and enable the addition of the reconstitution fluid without exhausting a vacuum retained within the detection vial. FIG. 93 illustrates an embodiment where the reconstitution station 350 includes a bladder 352 or similar secondary reservoir with a pinch valve 354. The reconstitution station 350 is gravity fed such that fluid is configured to travel from the main reservoir, through tubing 358, and into the bladder 352 when the valve 354 is open. For example, a lever 356 may be rotated clockwise to engage or pinch the tubing 358 to close off the tubing at the valve 354. A user is then able to insert the detection vial 360 into the access port 362 so that a needle disposed within the access port engages the stopper 364 to withdraw the reconstitution fluid into the tube. After the detection vial 360 is removed from the access port 362, the stopper 364 is configured to seal the detection vial to maintain the vacuum therein. Moreover, the bladder 352 is configured to automatically refill such that the reconstitution station 350 is always primed.

Alternatively, FIG. 94 illustrates a reconstitution station 375 that includes a rotary valve 376, according to another embodiment. In this regard, the reconstitution fluid is stored in reservoir 378 and is gravity fed into a second reservoir or bladder. When the rotary valve 376 is in a "closed" position, no fluid can escape from the access port 380 due to leakage from the bladder. To transfer fluid, the rotary valve 376 may be rotated to an "open" position. A detection vial 382 is inserted within the access port 380 whereby fluid can then be removed from the bladder when the stopper engages a needle disposed within the access port. Rotating the valve 376 to the open position also closes off the gravity line feeding into the bladder. When the valve 376 is rotated back to the closed position, the bladder is able to be automatically refilled. The rotary valve 376 may be operated by a knob or other suitable mechanism for opening and closing the valve, although a rotary action is not required in order for effecting such opening and closing of the valve (e.g., a valve actuated through linear motion).

FIG. 95 depicts a reconstitution station 400 that includes a syringe 402 in fluid communication with a rotary valve 404, according to another embodiment of the present invention. Unlike the prior embodiments, the reconstitution station 400 is not gravity fed, such that the reconstitution fluid is withdrawn from the reservoir 406 and into the syringe 402 through actuation of the syringe. In this regard, the syringe 402 may be configured to withdraw a desired amount of reconstitution fluid into the syringe or a bladder disposed therein when the rotary valve 404 is in a closed position. Once the syringe is filled, rotating the valve 404 to an open position allows access to the fluid contained within the syringe by inserting a detection vial within the access port 408 and engaging the needle disposed in the access port 408. Rotating the valve 404 to the open position closes off the line feeding the bladder from the reservoir 406. Again, it is understood that the rotary valve 404 may be any suitable mechanism to facilitate opening and closing of the valve. Likewise, the syringe 402 may be any suitable device configured to withdraw a desired amount of reconstitution fluid from the reservoir 406.

The portrayed examples demonstrate reconstitution stations requiring no external power sources. One skilled in the art can also envision fluid metering systems which are powered.

III. Representative Microorganisms

Embodiments of the present invention can be used to detect suspected blood stream infections arising from bacteremia and fungemia. Multiple blood samples typically are collected from separate veins of a subject, e.g., a patient, at different time intervals depending on the symptoms of the subject, e.g., the observation of a fever, or some other initial diagnosis. A volume of the blood sample, e.g., about 3 mL to about 10 mL for adults and about 1 mL for pediatric samples, can be disposed into a blood culture growth bottle after collection. Typically for each collection cycle, one sample is disposed in a blood culture growth bottle suitable for aerobic organisms and one sample is disposed in a blood culture growth bottle suitable for anaerobic organisms.

Unlike methods known in the art that detect an increase in gas production as a measure of microbial growth in blood culture samples, the presently disclosed methods advantageously allow for the detection of intracellular pathogens (e.g., bacterial, viral). Intracellular microorganisms or pathogens grow and reproduce within other cells (e.g., eukaryotic cells) and therefore, cannot be detected using gas sensors known in the art. Representative intracellular microorganisms that can be detected with the presently disclosed methods include, but are not limited to, *Chlamydia trachomatis* and *Mycobacterium tuberculosis*.

The microorganisms presented in Table 1 are commonly found in subjects as the cause of bacteremia or septicemia and are ranked in the order in which they are found in subjects. Also annotated in Table 2 are those microorganisms which collectively represent 80% of all positive results in blood culture samples and those microorganisms which are considered to be under treated.

TABLE 1

Organisms by Occurrence of Bacterial Species or Group in 2002[1]

| Ranking | Bacterial Species or Group | % | Represents 80% of all BC positives | Under Treated |
|---|---|---|---|---|
| 1 | Coagulase-negative *Staphylococcus* (including *S. epidermidis*) | 42 | X | X |
| 2 | *S. aureus* | 16.5 | X | X |
| 3 | *E. faecalis* | 8.3 | X | |
| 4 | *E. coli* | 7.2 | X | X |
| 5 | *K. pneumoniae* | 3.6 | X | X |
| 6 | *E. faecium* | 3.5 | X | |
| 7 | *Streptococci viridans* group | 3.4 | | |
| 8 | *Psuedomanas aeruginosa* | 2.5 | | X |
| 9 | *S. pneumoniae* | 2.3 | | |
| 10 | *Enterobacter cloacae* | 1.9 | | |
| 11 | *serratia marcescens* | 1.0 | | |
| 12 | *Acinetobacter baumannii* | 0.9 | | X |
| 13 | *Proteus mirabilis* | 0.9 | | |
| 14 | *Streptococcus agalactiae* | 0.8 | | |
| 15 | *Klebsiella oxytoca* | 0/6 | | |
| 16 | *Enterobacter aerogenes* | 0.5 | | |
| 17 | *Stenotrophomonas maltophilia* | 0.3 | | |
| 18 | *Citrobacter freundii* | 0.3 | | |
| 19 | *Streptocuuocus pyogenes* | 0.3 | | |
| 20 | *Enterococcus avium* | 0.2 | | |
| 21 | Others | 3.4 | | |
| | Fungi > Yeast *C. albicans* | | | X |

[1]Karlowsky, J. A. et al., "Prevalence and antimicrobial susceptibilities of bacteria isolated from blood cultures of hospitalized patients in the United States in 2002," *Annals of Clinical Microbiology and Antimicrobials* 3: 7 (2004).

Food, water, cosmetic, pharmaceutical and environmental samples are commonly screened for microorganisms including, but not limited to, enterotoxigenic *Escherichia coli* (ETEC), enteropathogenic *Escherichia coli* (EPEC), enterohemorrhagic *Escherichia coli* (EHEC), enteroinvasive *Escherichia coli* (EIEC), enteroaggregative *Escherichia coli* (EAEC), diffusely adherent *Escherichia coli* (DAEC), shiga toxin-producing *Escherichia coli* (STEC), *E. coli* O157, *E. coli* O157:H7, *E. coli* O104, *E. coli* O26, *E. coli* O45, *E. coli* O103, *E. coli* O111, *E. coli* O121 and *E. coli* O145, *Shigella* species, *Salmonella* species, *Salmonella bongori*, *Salmonella enterica*, *Campylobacter* species, *Yersinia enterocolitica*, *Yersinia* pseudotuberculosis, *Vibrio* species, *Vibrio cholera*, *Listeria* species, *Listeria monocytogenes*, *Listeria grayii*, *Listeria innocua*, *Listeria ivanovii*, *Listeria seeligeri*, *Listeria welshmeri*, *Staphylococcus* species, Coagulase negative *Staphylococcus* species, *Staphylococcus aureus*, *Bacillus cereus*, *Bacillus subtilis*, *Clostridium perfringens*, *Clostridium botulinum*, *Clostridium tetani*, *Clostridium sporogenes*, *Cronobacter* species, *Cronobacter sakazakii* (formally *Enterobacter sakazakii*), *Streptococcus* species, *S. pyogenes*, *Micrococcus* species, *Psuedomonas* species, *P.* aeruginosa, P. fluorescens, P. putida, Legionella species, Serratia species, K. pneumoniae, Enterobacter species, Alcaligenes species, Achromobacter species, yeast and molds such as Aspergillus species, Penicillium species, Acremonium species, Cladosporium species, Fusarium species, Mucor species, Rhizopus species, Stachybotrys species, Trichoderma species, Alternaria species, Geotrichum species, Neurospora species, Rhizomucor species, Rhizopus species, Ustilago species, Tolypocladium species, Mizukabi species, Spinellus species, Cladosporium species, Alternaria species, Botrytis species, Monilia species, Manoscus species, Mortierella species, Oidium species, Oosproa species, Thamnidium species, Candida species, Saccharomyces species, Trichophyton species.

In addition, these samples are often screened for indicator organisms including, but not limited to, coliforms, fecal coliforms, E. coli, Enterobacteriaceae, Enterococcus species, coliphage or bacteriophage.

Additionally, some samples are screened for clinically significant antibiotic resistant strains of microorganisms, including, but not limited to, Methicillin-resistant S. aureus and Vancomycin-resistant Enterococcus species.

Microorganisms that can be detected according to embodiments of the present invention include, but are not limited to, Gram negative bacteria, Gram positive bacteria, acid-fast Gram positive bacteria, and fungi, including yeasts. Representative bacterial and fungal microorganisms, i.e., antigens, that are targets for the presently disclosed blood culture assays are provided immediately herein below, according to one embodiment of the present invention. As noted elsewhere herein, antibodies having specificity for the antigens presented immediately herein below can include but are not limited to, polyclonal, monoclonal, Fab', Fab", recombinant antibodies, single chain antibodies (SCA), humanized antibodies, or chimeric antibodies. In all cases, the antibody will have one or more CDRs specific for the antigen listed immediately herein below. Antibodies are known in the art and are readily available for selected antigens. In some instances, the antigens are present on the cell surface. In other instances, the antigens are secreted from the cell and are present in the blood culture media as "free antigen." In yet other instances, both free and bound antigen can be measured simultaneously to confirm a bacteremia or fungemia.

Regardless of the diagnostic information sought in the culture vessel, a specific binding member will often have broad specificity. The specific binding members may be pan-strain, pan-serogroup, pan-species or pan-genera.

The bacterial cell wall is a complex, semi-rigid structure, which defines the shape of the organism, surrounds the underlying fragile cytoplasmic membrane, and protects the bacterial cell from the external environment. The bacterial cell wall is composed of a macromolecular network known as peptidoglycan, comprising carbohydrates and polypeptides that form a lattice around the bacterial cell. The bacterial cell wall provides the mechanical stability for the bacterial cell and prevents osmotic lysis. Most relevant to the present invention, it is the chemical composition of the cell wall that is used to differentiate the major species of bacteria.

The cell walls of different species of bacteria may differ greatly in thickness, structure and composition. However, there are two predominant types of bacterial cell wall, and whether a given species of bacteria has one or the other type of cell wall can generally be determined by the cell's reaction to certain dyes. Perhaps the most widely-used dye for staining bacteria is the Gram stain. When stained with this crystal violet and iodine stain, bacteria which retain the stain are called Gram positive, and those that do not are called Gram negative.

As used herein, by "Gram positive bacteria" is meant a strain, type, species, or genera of bacteria that, when exposed to Gram stain, retains the dye and is, thus, stained blue-purple.

As used herein, by "Gram negative bacteria" is meant a strain, type, species, or genera of bacteria that, when exposed to Gram stain does not retain the dye and is, thus, is not stained blue-purple. The ordinarily skilled practitioner will recognize, of course, that depending on the concentration of the dye and on the length of exposure, a Gram negative bacteria may pick up a slight amount of Gram stain and become stained light blue-purple. However, in comparison to a Gram positive bacteria stained with the same formulation of Gram stain for the same amount of time, a Gram negative bacteria will be much lighter blue-purple in comparison to a Gram positive bacteria.

Representative Gram negative bacteria include, but are not limited to, bacteria in the Enterobacteriaceae family. Representative Gram negative bacteria in the Enterobacteriaceae family include, but are not limited to bacteria in the Escherichia genus, such as E. coli species (model). Suitable binding members, e.g., antibodies, having an affinity for Gram negative bacteria in the Enterobacteriaceae family include, but are not limited to, those antibodies that specifically bind the lipopolysaccharide (LPS) or outer membrane protein (OMP). The LPS Lipid-A component, the LPS O-Region, and the LPS core having inner and outer core regions can serve as suitable antigens for specific binding members that have an affinity for Gram negative bacteria in the Escherichia genus.

Representative members of the Escherichia genus include: E. adecarboxylata, E. albertii, E. blattae, E. coli, E. fergusonfi, E. hermannii, and E. vulneris.

Another representative genus within the Enterobacteriaceae family is the Klebsiella genus, including but not limited to, Klebsiella pneumoniae (model). Suitable binding members, e.g., antibodies, having an affinity for Gram negative bacteria in the Klebsiella genus include, but are not limited to, those that specifically bind LPS, capsular polysaccharide (CPS) or K antigens (high molecular weight capsular polysaccharide with a molecular weight of about 50 to about 70 kDa), or OMP.

Representative members of the Klebsiella genus include K. granulomatis, K. mobilis, K. ornithinolytica, K. oxytoca, K. ozaenae, K. planticola, K. pneumoniae, K. rhinoscleromatis, K. singaporensis, K. terrigena, K. trevisanfi, and K. varricola.

Gram negative bacteria also include bacteria belonging to the Chlamydiaceae family. Representative Gram negative bacteria in the Chlamydiaceae family include, but are not limited to, bacteria in the Chlamydia genus, such as C. trachomatis species (model). Suitable binding members, e.g., antibodies, having an affinity for Gram negative bacteria in the Chlamydiaceae family include, but are not limited to, those that specifically bind lipopolysaccharide (LPS) or outer membrane protein (OMP), including major outer membrane protein (MOMP).

Representative members of the Chlamydia genus include: C. muridarum, C. suis, and C. trachomatis.

Suitable Gram negative bacteria can also include those within the Pseudomonas genus, including but not limited to P. aeruginosa (model), the Stenotrophomonas genus, including but not limited to, S. maftophilia (model), and the Acinetobacter genus, including but not limited to A. bau-

*mannii* (model). Suitable antigens that are recognized by specific binding members with affinity for Gram negative bacteria within the *Pseudomonas* genus include, but are not limited to, LPS, OMP, iron-regulated membrane proteins (IRMP), flagella, mucoid exopolysaccharide (MEP), and outer membrane protein F (OprF). Suitable antigens that are recognized by specific binding members with affinity for Gram negative bacteria within the *Stenotrophomonas* genus include, but are not limited to, LPS, flagella, major extracellular protease, OMP, the 30 kDa exposed protein that binds to the IgG Fc, and the 48.5 kDa membrane protein. Suitable antigens that are recognized by specific binding members with affinity for Gram negative bacteria within the *Acinetobacter* genus include, but are not limited to, LPS, LPS with D-rhamos, Bap (biofilm associated factor), capsular polysaccharide (CPS), and OMP.

Representative Gram positive bacteria include, but are not limited to, bacteria in the Micrococcaceae family. Gram positive bacteria in the Micrococcaceae family include, but are not limited to, bacteria in the *Staphylococcus* genus, including *S. epidermidis* species (model). Suitable binding members, e.g., antibodies, having an affinity for Gram positive bacteria include, but are not limited to, those that specifically bind to Lipoteichoic Acid (LTA), peptidoglycan, biofilm antigens, including 140/200-kDa biofilm antigens and 20-kDa polysaccharide (PS), or Lipid S (glycerophospho-glycolipid). Other suitable binding members that have an affinity for Gram positive bacteria in the *Staphylococcus* genus, including but not limited to *S. aureus*, include those that specifically bind teichoic acid, microbial surface components recognizing adhesion matrix molecules (MSCRAMMS), iron-responsive surface determinant A (IsdA), the 110 kDa, 98 kDa, and 67 kDa proteins, RNAIII activating protein (RAP), target of RNAIII-activating protein (TRAP), alpha toxin, poly-n-succinyl beta-1-6-glucosamine (PNSG), lipase, staphylolysin, FnBPA, FnBPB, immunodominant staphylococcal antigen, capsular polysaccharide, or the cell surface antigen associated with methycillin resistance.

Representative members of the *Staphylococcus* genus include: *S. aureus, S. auricularis, S. capitis, S. caprae, S. cohnii, S. epidermidis, S. felis, S. haemolyticus, S. hominis, S. intermedius, S. lugdunensis, S. pettenkoferi, S. saprophyticus, S. schleiferi, S. simulans, S. vitulus, S. warneri*, and *S. xylosus*.

Other representative Gram positive bacteria include bacteria in the *Enterococcus* genus, including but not limited to, *E. faecalis* (also known as Group D *Streptococcus*) and *E. faecium*. Suitable binding members, e.g., antibodies, having an affinity for *E. faecalis* include, but are not limited to, those that specifically bind to lipoteichoic acid (LTA), collagen binding surface antigen (CNA), aggregation substance (AS), capsular polysaccharide, teichoic acid-like capsular polysaccharide, Esp gene product, Gls24, Epa gene product, Ace (ECM binder), or peptidoglycan. Suitable binding members, e.g., antibodies, having an affinity for *E. faecalis* include, but are not limited to, those that specifically bind to ACM protein (collagen binder) or SagA protein.

Representative acid-fast Gram positive bacteria include, but are not limited to, bacteria in the Mycobacteriaceae family. Acid-fast Gram positive bacteria in the Mycobacteriaceae family include, but are not limited to, bacteria in the *Mycobacterium* genus, such as *M. bovis* (model) species and *M. tuberculosis* species (model). Suitable binding members, e.g., antibodies, having an affinity for acid-fast Gram positive bacteria include but are not limited to, those that specifically bind to arabinomannon (AM), lipoarabinomannon (LAM) or the 38 kDa antigen.

Representative members of the *Mycobacterium* genus include: *M. abscessus, M. africanum, M. agri, M. aichiense, M. alvei, M. arupense, M. asiaticum, M. aubagnense, M. aurum, M. austroafricanum, Mycobacterium avium* complex (MAC), including, *M. avium, M. avium paratuberculosis, M. avium silvaticum, M. avium "hominissuis," M. boenickei, M. bohemicum, M. bolletii, M. botniense, M. bovis, M. branded. M. brisbanense, M. brumae, M. canariasense, M. caprae, M. celatum, M. chelonae, M. chimaera, M. chitae, M. chlorophenolicum, M. chubuense, M. colombiense, M. conceptionense, M. confluentis, M. conspicuum, M. cookii, M. cosmeticum, M. diernhoferi, M. doricum, M. duvalii, M. elephantis, M. fallax, M. farcinogenes, M. flavescens, M. florentinum, M. fluoroanthenivorans, M. fortuitum, M. fortuitum* subsp. *acetamidolyticum, M. frederiksbergense, M. gadium, M. gastri, M. genavense, M. gilvum, M. goodii, M. gordonae, M. haemophilum, M. hassiacum, M. heckeshornense, M. heidelbergense, M. hiberniae, M. hodleri, M. holsaticum, M. houstonense, M. immunogenum, M. interjectum, M. intermedium, M. intracellulare, M. kansasii, M. komossense, M. kubicae, M. kumamotonense, M. lacus, M. lentiflavum, M. leprae, M. lepraemurium, M. madagascariense, M. mageritense, M. malmoense, M. marinum, M. massiliense, M. microti, M. monacense, M. montefiorense, M. moriokaense, M. mucogenicum, M. murale, M. nebraskense, M. neoaurum, M. neworleansense, M. nonchromogenicum, M. novocastrense, M. obuense, M. palustre, M. parafortuitum, M. parascrofulaceum, M. parmense, M. peregrinum, M. phlei, M. phocaicum, M. pinnipedii, M. porcinum, M. poriferae, M. pseudoshottsii, M. pulveris, M. psychrotolerans, M. pyrenivorans, M. rhodesiae, M. saskatchewanense, M. scrofulaceum, M. senegalense, M. seoulense, M. septicum, M. shimoidei, M. shottsii, M. simiae, M. smegmatis, M. sphagni, M. szulgai, M. terrae, M. thermoresistibile, M. tokaiense, M. triplex, M. triviale, Mycobacterium tuberculosis* complex (MTBC), including *M. tuberculosis, M. bovis, M. bovis* BCG, *M. africanum, M. canetti, M. caprae, M. pinnipedii, M. tusciae, M. ulcerans, M. vaccae, M. vanbaalenii, M. wolinskyi*, and *M. xenopi*.

Representative fungi, including yeasts, include, but are not limited to, the Saccharomycetaceae family, including, the *Candida* genus, such as with *C. albicans* (model). Suitable binding members, e.g., antibodies, having an affinity for fungi belonging to the *Candida* genus include, but are not limited to, those that specifically bind to mannan, phosphomannan, annoprotein 58 (mp58), galactomannan, Beta-D-Glucan, metalloabinitol, Cell Wall-associated glyceraldehyde-3-phosphate dehydrogenase, Enolase-(47/48 kDa), Secreted-Aspartyl-Proteinase (SAP), or heat shock protein 90 (HSP-90).

Representative members of the *Candida* genus include: *C. aaseri, C. albicans, C. amapae, C. anatomiae, C. ancudensis, C. antillancae, C. apicola, C. apis, C. atlantica, C. atmosphaerica, C. auringiensis, C. austromarina, C. azyma, C. beechii, C. bertae, C. berthetii, C. blankii, C. boidinii, C. boleticola, C. bombi, C. bombicola, C. buinensis, C. butyri, C. cantarellii, C. caseinolytica. C. casteffii, C. castrensis, C. catenulata, C. chilensis, C. chiropterorum, C. chodatii, C. ciferrii, C. coipomoensis, C. conglobata, C. cylindracea, C. dendrica, C. dendronema, C. deserticola, C. diddensiae, C. diversa, C. drimydis, C. dubliniensis, C. edax, C. entomophila, C. ergastensis, C. emobii, C. ethanolica, C. euphorbiae, C. euphorbiiphila, C. fabianii, C. famata, C. famata* var. *famata, C. famata* var. *flareri, C. fennica, C. fermenticarens, C. firmetaria, C. floricola, C. fluviatilis, C.* freyschussii, C. friedrichii, C. fructus, C. galacta, C. geochares, C. glabrata, C. glaebosa, C. glucosophila, C. gropengiesseri, C. guilliermondii, C. guilliermondii var. guilliermondii, C. guilliermondii var. membranaefaciens, C. haemulonii, C. homilentoma, C. humilis, C. incommunis, C. inconspicua, C. insectalens, C. insectamans, C. insectorum, C. intermedia, C. ishiwadae, C. karawaiewii, C. kefyr, C. krissii, C. kruisii, C. krusei, C. lactis-condensi, C. laureliae, C. lipolytica, C. llanquihuensis, C. lodderae, C. lusitaniae, C. lyxosophila, C. magnoliae, C. maltosa, C. maris, C. maritima, C. melibiosica, C. membranifaciens, C. mesenterica, C. methanosorbosa, C. milleri, C. mogii, C. montana, C. multigemmis, C. musae, C. naeodendra, C. natalensis, C. nemodendra, C. norvegensis, C. norvegica, C. odintsovae, C. oleophila, C. oregonensis, C. ovalis, C. palmioleophila. C. paludigena, C. parapsilosis, C. pararugosa, C. pelliculosa, C. peltata, C. petrohuensis, C. pignaliae, C. pini, C. populi, C. pseudointermedia, C. pseudolambica, C. psychrophila, C. pulcherrima, C. quercitrusa, C. quercuum, C. railenensis, C. reukaufii, C. rhagii, C. robusta, C. rugopelliculosa, C. rugosa, C. saitoana, C. sake, C. salida, C. salmanticensis, C. santamariae, C. santjacobensis, C. savonica, C. schatavii, C. sequanensis, C. shehatae, C. shehatae var. Insectosa, C. shehatae var. lignosa, C. shehatae var. shehatae, C. silvae, C. silvanorum, C. silvatica, C. silvicultrix, C. solani, C. sonorensis, C. sophiae-reginae, C. sorbophila, C. sorbosa, C. sorboxylosa, C. spandovensis, C. stellata, C. succiphila, C. suecica, C. tanzawaensis, C. tapae, C. techellsii, C. tenuis, C. torresii, C. tropicalis, C. tsuchiyae, C. utilis, C. vaccinii, C. valdiviana, C. valida, C. vanderwaltii, C. vartiovaarae, C. versatilis, C. vini, C. viswanathii, C. wickerhamii, C. xestobii, and C. zeylanoides.

Therapeutic antibodies such as Aurograb™ with specificity for the Methicillin-resistant *S. aureus* (MRSA) strains also can be used on capture or indicator surfaces. Likewise the therapeutic monoclonal antibody (mab) Myograb™ (Efungumab) with a specificity for the Heat shock Protein HSP90 can be used for detection of *C. albicans*.

The presently disclosed SERS-active indicator particles can be distinguished from the many other optically active materials that can be present in a culture environment, such as components of culture media used to support growth, whole blood, SPS anticoagulant, food particulates, and additives. Further, the specific SERS-active indicator particles exhibit the necessary signal intensity to allow detection of small quantities of bacterial cells. Additionally, a variety of SERS-active indicator particles, each having a unique SERS signature, allow blood culture samples to be interrogated for any one of a plurality of microorganisms (e.g., twenty) that can typically be found in mammalian, e.g., human, blood. In such embodiments, the detection of each particular microorganism can occur simultaneously, which is referred to herein as a "multiplex assay."

According to one embodiment, for example, blood culture, the primary targets for the presently disclosed multiplex assays include: Coagulase-negative Staphylococci, *S. aureus*, *E. faecalis*, *E. coli*, *K. pneumoniae*, *E. faecium*, Viridans group Streptococci, *Pseudomonas aeruginosa*, *S. pneumoniae*, *Enterobacter cloacae*, *Serratia marcescens*, *Acinetobacter baumannii*, *Proteus mirabilis*, *Streptococcus agalactie*, *Klebsiella oxytoca*, *Enterobacter aerogenes*, *Stenotrophomonas maltophilia*, *Citrobacter freundii*, *Streptococcus pyogenes*, and *Enterococcus avium*. Such multiple targets can be, in some embodiments, be simultaneously detected by a presently disclosed multiplex assay.

IV. Representative Culture Media

Representative culture media suitable for use with embodiments of the present invention are provided immediately herein below. One of ordinary skill in the art would recognize that the presently disclosed formulations can be modified to meet specific performance requirements. Additionally, these formulations, depending on the particular application, can have disposed therein, $CO_2$, $O_2$, $N_2$, and combinations thereof, to create an environment suitable for aerobic, anaerobic, or microaerophilic growth. Optionally, some culture media contain adsorbents to isolate, i.e., remove, from the culture medium, interferents, such as antibiotics or immune elements that can be present in a subject's blood sample or metabolites produced during culture. See, e.g., U.S. Pat. No. 5,624,814, which is incorporated herein by reference in its entirety. For example, the BD BACTEC™ Media Plus Anaerobic/F, BD BACTEC™ Plus Aerobic/F, and BD BACTEC™ PEDS Plus/F, each of which is available from Becton, Dickinson, and Company, Franklin Lakes, N.J., all contain resins for isolating antibiotics that otherwise can inhibit microbial growth in the blood culture medium. The resins are substantially larger in diameter than any component of blood and are more rigid than the mammalian cells found in blood. Another example of a culture absorbent is the precipitated calcium carbonate (1%-2.5% w/v) found in various Tetrathionate Broth formulations used for selectively culturing *Salmonella* in food and environmental samples. The calcium carbonate particulates neutralize the sulfuric acid produced by the reduction of tetrathionate by growing *Salmonella*.

A. BD BACTEC™ Myco/F Lytic Culture Vials

BD BACTEC™ Myco/F Lytic Culture Vials support the growth and detection of aerobic microorganisms. More particularly, BD BACTEC™ Myco/F Lytic Culture Vials are non-selective culture media to be used as an adjunct to aerobic blood culture media for the recovery of mycobacteria from blood specimens and yeast and fungi from blood and sterile body fluids.

*Mycobacterium tuberculosis* (MTB) and mycobacteria other than tuberculosis (MOTT), especially *Mycobacterium avium* complex (MAC), have become resurgent. From 1985 to 1992, the number of MTB cases reported increased 18%. Between 1981 and 1987, AIDS case surveillances indicated that 5.5% of the patients with AIDS had disseminated nontuberculous mycobacterial infections, e.g., MAC. By 1990, the increased cases of disseminated nontuberculous mycobacterial infections had resulted in a cumulative incidence of 7.6%. The incidence of fungemia also has steadily increased since the early 1980s. These increases have heightened the need for effective diagnostic procedures for fungemia and mycobacteremia.

Components of the presently disclosed formulations can include, but are not limited to, ferric ammonium citrate or an equivalent that provides an iron source for specific strains of mycobacteria and fungi, saponin or an equivalent blood lysing agent, and specific proteins and sugars to provide nutritional supplements.

B. BD BACTEC™ 12B Mycobacteria Culture Vials Middlebrook 7H12

The qualitative BACTEC™ 12B Mycobacteria Medium can be used for the culture and recovery of mycobacteria from clinical specimens, sputum, gastric, urine, tissue, mucopurulent specimens, other body fluids and other respiratory secretions, differentiation of the *Mycobacterium*

*tuberculosis* complex from other mycobacteria, and drug susceptibility testing of *M. tuberculosis*.

C. BACTEC™ LYTIC/10 Anaerobic/F Culture Vials

The BACTEC™ LYTIC/10 Anaerobic/F The BACTEC™ LYTIC/10 Anaerobic/F medium is also suitable for embodiments of the present invention.

D. BACTEC™ Plus Aerobic/F* and Plus Anaerobic/F* Culture Vials Soybean-Casein Digest Broth BACTEC™ Plus Aerobic/F and Plus Anaerobic/F media provide a qualitative procedure for the culture and recovery of microorganisms (bacteria and yeast) from blood and have been formulated to allow the addition of up to 10 mL of blood. The addition of these larger sample volumes results in overall higher detection rates and earlier times to detection.

E. BD BACTEC™ Standard Anaerobic/F Culture Vials Soybean-Casein Digest

BD BACTEC™ Standard Anaerobic/F Culture Vials Soybean-Casein Digest broth provides a qualitative procedure for the culture and recovery of anaerobic microorganisms from blood.

F. BD BACTEC™ PEDS PLUS™/F Culture Vials

BACTEC™ culture vials type PEDS PLUS™/F (enriched Soybean-Casein Digest broth with $CO_2$) are intended for use with aerobic cultures and provide for the culture and recovery of aerobic microorganisms (mainly bacteria and yeast) from pediatric and other blood specimens which are generally less than 3 mL in volume.

G. Standard/10 Aerobic/F Culture Vials

BACTEC™ Standard/10 Aerobic/F culture vials (enriched Soybean-Casein Digest broth with $CO_2$) are intended for use in aerobic blood cultures and provide for the culture and recovery of aerobic microorganisms (bacteria and yeast) from blood.

H. BacT/ALERT™ Culture Vials

BacT/ALERT™ FAN, BacT/ALERT™ FN, and BacT/ALERT™ SN culture vials (bioMérieux, Durham, N.C.) are intended for use in anaerobic blood cultures and provide for the culture and recovery of anaerobic microorganisms (bacteria and yeast) from blood.

I. Selective *E. coli* Culture Media

Modified Buffered Peptone water with pyruvate (mB-PWp) and Acriflavin-Cefsulodin-Vancomycin (ACV) Supplement is a media prescribed by the FDA Bacteriological Analytical Manual (BAM) for enriching samples for the detection of diarrheagenic *Escherichia coli*.

J. Selective *Listeria* Culture Media

Frasier Broth Base and Fraser Broth Supplement are used to selectively enrich and detect *Listeria* species. The USDA Microbiological Laboratory Guidebook (MLG) recommends the use of Fraser Broth when testing for *L. monocytogenes* in red meat, poultry, egg and environmental samples (USDA MLG Chapter 8.07, revised Aug. 3, 2009).

K. Selective *Salmonella* Culture Media

Tetrathionate Base Broth, Hajna is a media designed for the selective enrichment of *Salmonella*. Tetrathionate is generated by the addition of iodine and potassium iodide just prior to enrichment. The USDA Microbiological Laboratory Manual stipulates this broth for the selective enrichment of *Salmonella* in meat, poultry, pasteurized egg and catfish products (USDA MLG Chapter 4.05, revised Jan. 20, 2011).

L. *Salmonella* Culture Media

In addition to the culture media listed above, there are several broths commonly known in the art to culture or sustain *Salmonella*, including, but not limited to, Brain Heart Infusion Broth, Brilliant Green Sulfa Enrichment (BD Difco™), modified Brilliant Green Broth (BD Difco™), Buffered Peptone Water (BD Difco™), Buffered Peptone Casein Water (BD Difco™), Dey-Engly Broth (BD Difco™), EE Broth Mossel Enrichment (BD Difco™), Gram Negative Broth (BD Difco™), Gram Negative Broth Hajna (BD Difco™), Lactose Broth (BD Difco™), Letheen Broth (BD Difco™), Lysine Decarboxylase Broth, M Broth (BD Difco™), Malonate Broth (BD Difco™), MR-VP Broth, Nutrient Broth, One Broth-*Salmonella* (Oxoid), Phenol Red Carbohydrate Broth (BD BBL™), Potassium Cyanide Broth, Purple Carbohydrate Broth (BD BBL™), RapidChek® *Salmonella* primary media (SDIX), RapidChek® SELECT™ *Salmonella* primary with supplement (SDIX), RapidChek® SELECT™ *Salmonella* secondary media (SDIX), Rappaport-Vassiliadis Medium, modified Rappaport-Vassiliadis Medium, Rappaport-Vassiliadis R10 Broth (BD Difco™), Rappaport-Vassiliadis *Salmonella* (RVS) Soy Broth (BD Difco™), Rappaport-Vassiliadis Soya Peptone Broth, Selenite Broth (BD Difco™), Selenite-F Broth (BD BBL™), Selenite Cystine Broth (BD Difco™), Tetrathionate Broth, Tetrathionate (Hajna) Broth, Tryptone Broth, Tripticase Soy Broth, Tripticase Soy Broth with ferrous sulfate, Universal Preenrichment Broth, Universal Preenrichment Broth without ferric ammonium citrate, and Urea Broth.

M. *Listeria* Culture Media

In addition to the culture media listed above, there are several broths commonly known in the art to culture or sustain *Listeria*, including, but not limited to, Brain Heart Infusion (BHI) Broth, Buffered *Listeria* Enrichment Broth (BLEB), Nutrient Broth, Purple carbohydrate fermentation broth base (M130[15]), containing 0.5% solutions of dextrose, esculin, maltose, rhamnose, mannitol, and xylose, SIM medium, Trypticase soy broth with 0.6% yeast extract, Tryptose Broth, Modified University of Vermont (UVM) Broth, Morpholinepropanesulfonic acid-buffered *Listeria* enrichment broth (MOPS-BLEB), Demi-Frasier, Fraser broth, *Listeria* enrichment broth (BD Difco™, Oxoid), One Broth-Listeria (Oxoid), RapidChek® *Listeria* media with supplement (SDIX) and RapidChek® *Listeria* F.A.S.T.™ media (SDIX).

V. Representative Samples

The amount of one or more microorganisms present in a sample under test can be represented as a concentration. The concentration can be expressed as a qualitative value, for example, as a negative- or positive-type result, e.g., a "YES" or "NO" response, indicating the presence or absence of a microorganism, or as a quantitative value. Further, the concentration of a given microorganism in a culture sample can be reported as a relative quantity or an absolute quantity, e.g., as a "quantitative value."

The quantity (i.e., concentration) of a microorganism can be equal to zero, indicating the absence of the particular analyte sought or that the concentration of the particular analyte is below the detection limits of the assay. The quantity measured can be the signal, e.g., a SERS signal, without any additional measurements or manipulations. Alternatively, the quantity measured can be expressed as a difference, percentage or ratio of the measured value of the particular microorganism to a measured value of another compound including, but not limited to, a standard or another microorganism. The difference can be negative, indicating a decrease in the amount of measured microorganism(s). The quantities also can be expressed as a difference or ratio of the microorganism(s) to itself, measured at a different point in time. The quantities of microorganism can be determined directly from a generated signal, or the generated signal can be used in an algorithm, with the algorithm designed to correlate the value of the generated signals to the quantity of microorganism(s) in the sample. As discussed above, embodiments of the present invention are amenable for use with devices capable of measuring the concentrations of one or more microorganisms in real time.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Effect of SERS HNW Reagents on Time to Detection for *E. Coli*

FIG. 54 shows the result of an experiment in which time to detection of *E. coli* growth was compared for blood culture samples with and without the SERS HNW reagents suitable for use in the various embodiments of the invention.

In this example, unconjugated SERS-active indicator particles (SERS 440 tags) and unconjugated magnetic capture particles (Dynal® beads) were sterilized by washing with 70% ethanol. The sterilized SERS-active indicator particles and magnetic capture particles were then added to BACTEC™ Standard/10 Aerobic/F Medium bottles inoculated with *E. coli*. The time to detection for *E. coli* growth by a BACTEC™ 9050 sensor was compared for bottles with and without the HNW assay reagents. BACTEC™ bottles without *E. coli* but with and without the HNW assay reagents were included as negative controls. As can be seen, the BACTEC™ time-to-detection was unaffected by the presence of the SERS-active indicator particles and magnetic particles in this experiment. Thus the SERS HNW assay reagents do not significantly impact the ability of a microorganism to grow.

Example 2

Repeated Pelleting is Compatible with Microorganism Growth

Figure 55:
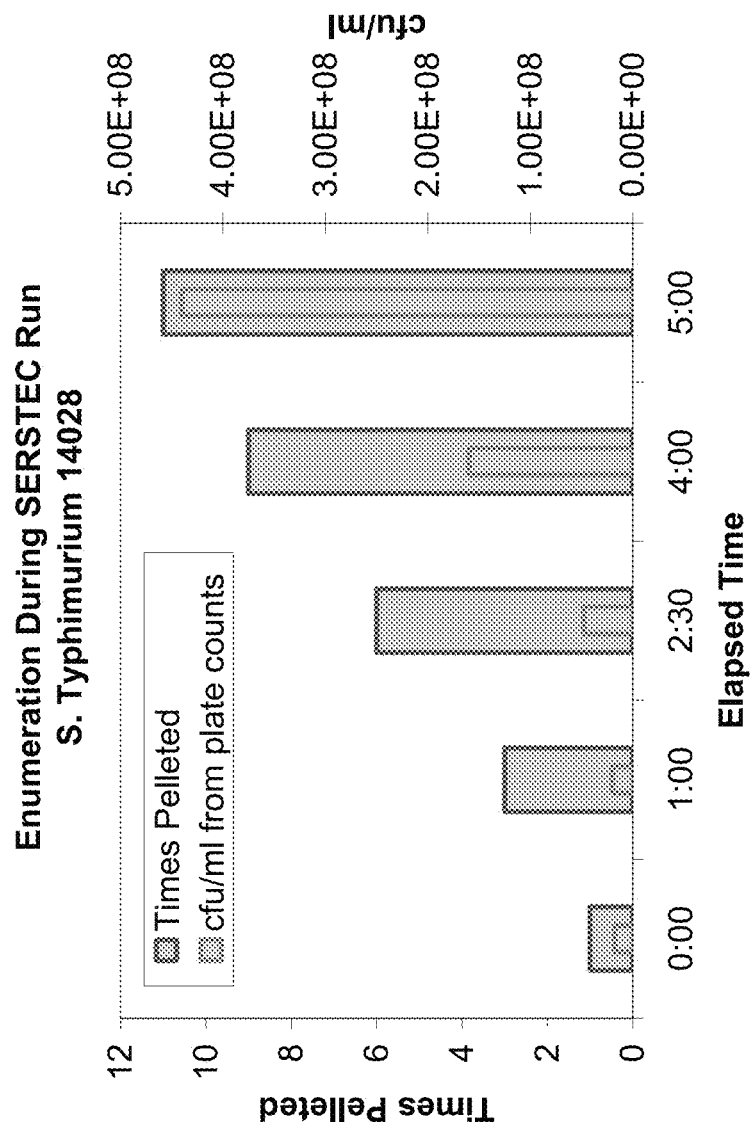
FIG. 55 shows a graph in which the growth of *Salmonella enterica* subspecies *enterica* serovar Typhimurium, henceforth referred to as *Salmonella* Typhimurium (or other *Salmonella* serovar name), was monitored in relation to the effect of pelleting thereon according to an embodiment of the invention.

FIG. 55 shows the result of an experiment in which *Salmonella* Typhimurium growth was monitored during the course of an experiment to determine if pelleting negatively affects organism growth.

In this example, S. Typhimurium (ATCC 14028) was grown in an overnight culture in SDIX *Salmonella* Select Primary Media with supplement at 42° C. A 1:100 dilution was made into SDIX *Salmonella* Secondary Media. The starting inoculation in secondary media was determined to be $1.8 \times 10^7$ cfu/ml by plate count on Nutrient agar plates. The inoculated secondary media was then put into multiple tubes, all containing SERS tags and magnetic particles conjugated to SDIX *Salmonella* antibodies. The tubes were placed in the system 150 (see FIG. 24) for monitoring during growth at 42° C. The tubes were pelleted and interrogated every 0.5 hour during growth. In this experiment, tubes were removed from the instrument after 1, 3, 6, 9 and 11 pelleting and reading cycles. These tubes were enumerated by plating dilutions onto Nutrient agar plates. As can be seen, the growth of S. Typhimurium is not compromised by the presence of SERS tags and magnetic particles, nor is it compromised by repeated pelleting and interrogation of the pellet by the laser.

Example 3

Effect of Adjusting Pelleting Frequency

In an experiment examining the effect of repeated pelleting on micro-organism growth and assay performance, a single colony of *Salmonella* Kentucky (ATCC 9263) was picked from a BD BBL™ Nutrient Agar streak plate and cultured overnight at 42° C. in 6 mL SDIX RapidChek® *Salmonella* SELECT™ primary culture media with 60 µL phage supplement. Following the primary culture, 5 mL of a secondary culture medium was prepared, consisting of 90% secondary and 10% primary SDIX RapidChek® *Salmonella* SELECT™ media. In parallel, a 1:100 dilution of primary culture into the primary medium was prepared, and 125 µL of that dilution was inoculated into a BD MGIT™ tube containing the 5 mL of secondary medium, 16 µL of SERS tags, and 20 µL of magnetic beads. The resulting dilution of 1:4000 from the final concentration of the primary culture yielded an approximate inoculation concentration of $2.5 \times 10^5$ CFU/mL. The tubes were then put into one of two carousel-based systems (see e.g., FIG. 24) for 24 hours at 42° C. at a linear agitation speed of ~1 Hz. All experimental parameters except read frequency were kept the same between the two instruments. The read frequency for each instrument was set to either 5 or 2 reads/hour.

Figure 56:
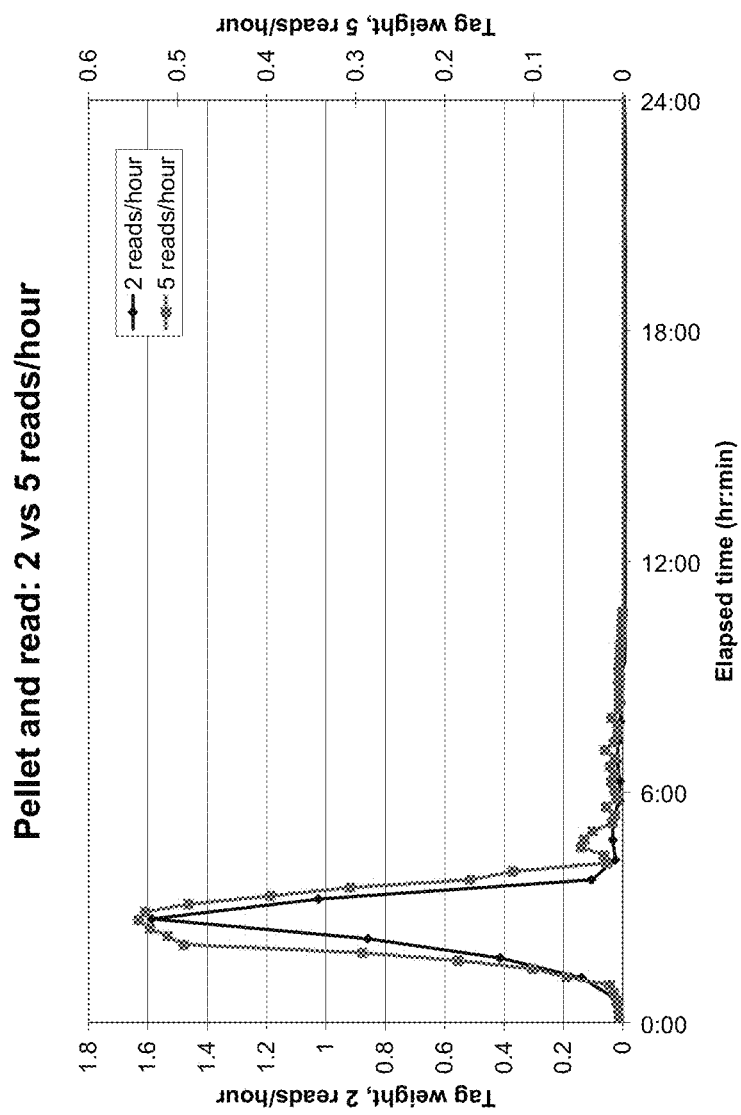
FIG. 56 shows a graph illustrating the effect of pelleting on microorganism growth according to an embodiment of the invention.

FIG. 56 shows a representative set of data from the experiment. The data from the two systems are shown, with intensity axes scaled for comparison. (Note that the absolute intensities of tag weights between instruments should not be compared due to differences in optical efficiencies.) The shapes of the growth curves are nearly identical, indicating that the increased number of cycles of pellet formation, measurement, and dispersal did not impede growth or detection. The only significant difference is that the curve with more frequent readings provides better resolution on the growth kinetics.

Example 4

Effect of Relative Motion of Sample Tube and Magnets

Reproducible pellet formation is a critical step to achieve reproducible assay signal. This example pertains to two distinct ways to form a pellet. In the first (fixed magnet), the magnet is held fixed in place, while the tube is moved over the magnet for the full extent of the agitation throw. In the second preferred configuration (coupled), shown in FIG. 49, the magnet moves along with the tube. In a series of experiments, SERS tags were covalently linked to tosyl-activated magnetic particles to form a SERS-magnetic bead pre-complex (PC). Pre-complexed beads are prepared by covalent linkage of SERS particles to Dynabeads® M-280 Tosyl-activated magnetic particles through reaction of thiol (-SH) groups on the SERS surface with tosyl (Tos) groups on the surface of the magnetic particles PC acts as a model system for pellet formation testing where the pellet can be interrogated for SERS signal. Pellet formation of PC in water as well as in a commercial secondary media for Salmonella (SDIX RapidChek® Salmonella SELECT™) was compared for the fixed magnet and coupled geometries. These tests were performed using a flat-bed system configuration (see e.g., FIG. 25).

Figure 57:
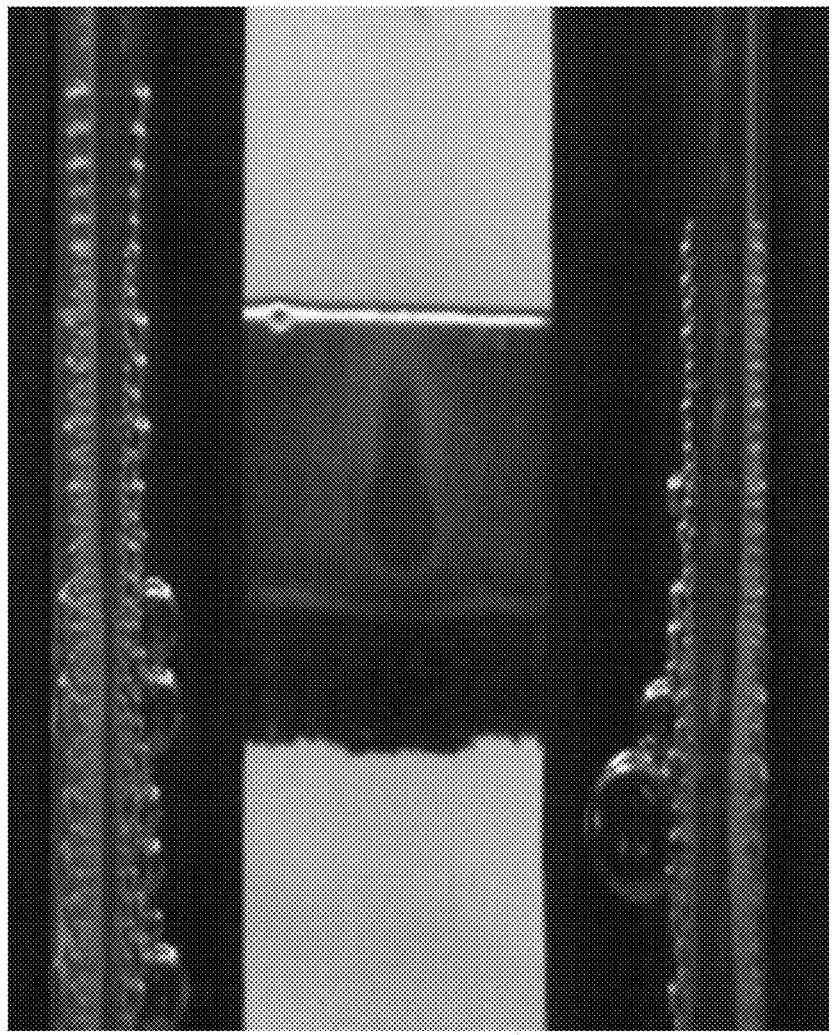
FIG. 57 illustrates an image of a SERS-magnetic bead precomplex (PC) in water after pelleting with a fixed magnet according to one embodiment.

FIG. 57 shows an image of PC in water after pelleting with a fixed magnet. PC in water was pelleted for 1.5 minutes by moving the tube over a fixed bar magnet at 0.5 Hz agitation frequency and 25 mm throw. Agitation was stopped and the magnet was allowed to persist for 30 seconds before moving the bar away from the tubes. As shown in FIG. 57, a single pellet was formed. This image highlights the ability to drag the magnetic complexes with the magnet through water.

Figure 58B:
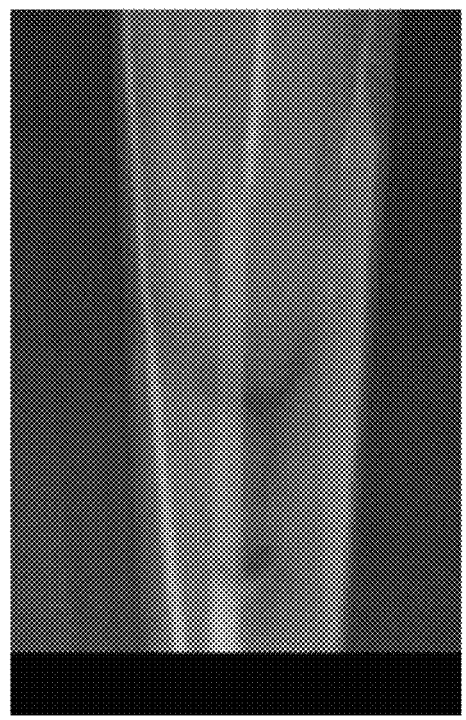
FIGS. 58A-58B are images of PC pellet formation in SDIX *Salmonella* secondary media using a fixed magnet and different agitation frequencies according to one embodiment.
Figure 58A:
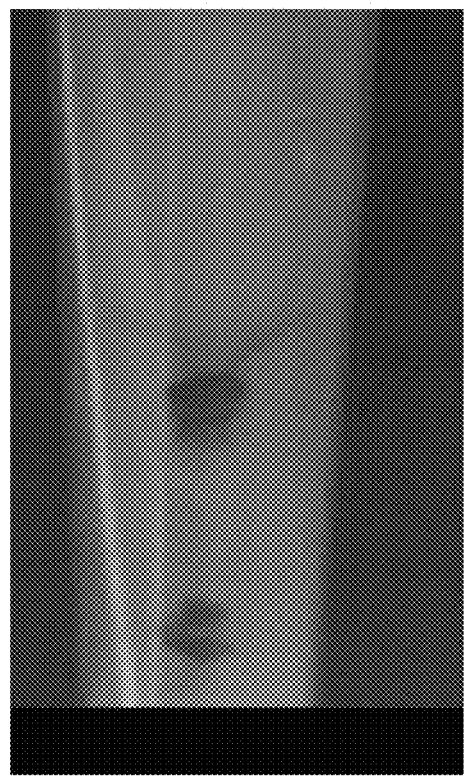

In contrast, FIGS. 58A and 58B show PC pellet formation in SDIX Salmonella secondary media using a fixed magnet and two different agitation frequencies. PC in SDIX secondary media was pelleted for 3 minutes by moving the tube over a fixed bar magnet at either 2 Hz (21A) or 0.5 Hz (21B) agitation frequency and 25 mm throw. Agitation was stopped and the magnet was allowed to persist for 30 seconds before moving the magnet bar away from the tubes. As shown in FIG. 58A, two pellets of magnetic complexes were pulled to the bottom of the tube, located at the limits of the relative motion between the tube and the magnet. For the slower agitation (FIG. 58B), two pellets were formed at the ends of the magnet travel along with an ill-defined line connecting the pellets. As reproducible SERS signal is best obtained with a dense, reproducibly placed pellet, FIGS. 58A and 58B highlight the disadvantages of the fixed magnet configuration, which appears unable to drag the magnetic beads through SDIX Salmonella secondary media, presumably due to the solid particulates present in this media.

Figure 59B:
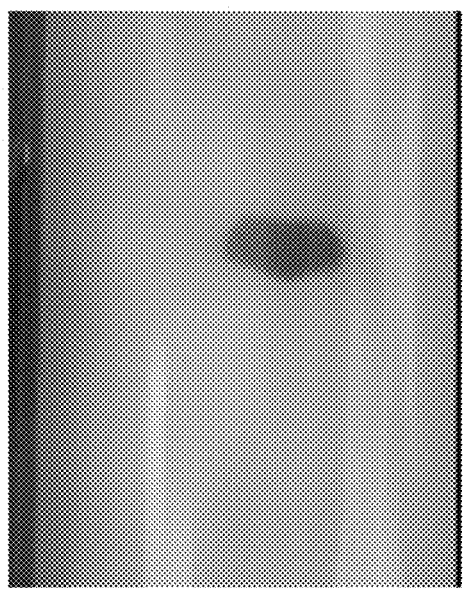
FIGS. 59A-59B are images of PC pellet formation in SDIX *Salmonella* secondary media using a coupled magnet and different agitation frequencies according to one embodiment.
Figure 59A:
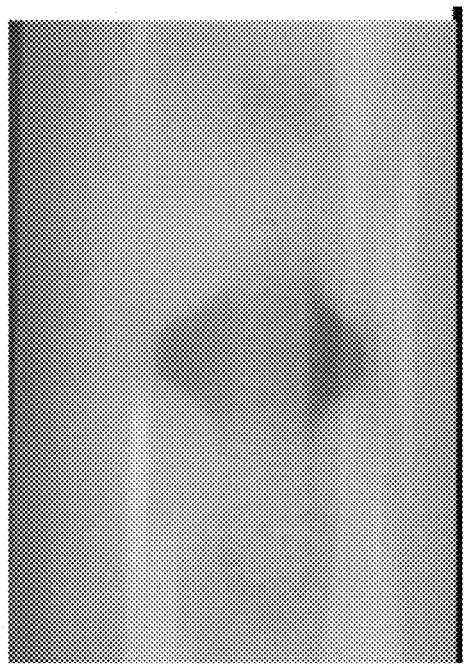

FIG. 59A shows a preferred embodiment using the coupled magnet configuration. PC in SDIX Salmonella secondary media was pelleted for 1.5 minutes by moving the tube coupled with a bar magnet at 1.5 Hz agitation frequency and 25 mm throw. Agitation was stopped and the magnet was allowed to persist for 30 seconds before moving the bar magnet away from the tubes. A single dense pellet was formed where the bar magnet contacts the sample tube. Compared to the pellets formed using the fixed magnet configuration, the pellet formed using coupled magnets is more compact and dense, as shown in FIG. 59A. FIG. 59B shows a similar experiment with a coupled magnet, only using a 0.8 Hz agitation frequency. Although a single pellet was formed, settled media interferes with the ability to pull a dense pellet, as evidenced by the diffuse particles in the center of the pellet.

The results illustrated in FIGS. 57-59 show that for a throw of 25 mm, the fixed magnet pelleting approach failed to form a single dense pellet in the presence of SDIX Salmonella secondary media using a variety of agitation frequencies. This media contains solid particulates that settle rapidly and interfere with the ability of the magnet to drag the magnetic complexes along the bottom of the tube. Although fast agitation will keep solid media from settling, two pellets are formed at the limits of the relative motion between the tube and the magnet. As agitation slows to a stop, these pellets cannot be dragged through the media to form a single pellet. Because the magnetic complexes can be dragged through water, the fixed magnet approach can be used to pellet PC in water.

The coupled magnet pelleting approach forms a single dense pellet in the presence of SDIX Salmonella secondary media at a variety of agitation frequencies. Coupling magnets to the tube for pelleting does not require magnetic complexes to drag along the bottom of the tube because they are pulled to a common point to form a single pellet.

Using coupled magnets, fast agitation forms a denser pellet compared to slow agitation. This is likely due to the solid media settling using slow agitation and interfering with pellet formation. Using fast agitation, the solid is suspended in solution and magnetic complexes can be pulled into a pellet with less interference from the media.

Example 5

Singleplex Detection of C. albicans in Human Blood

Figure 60:
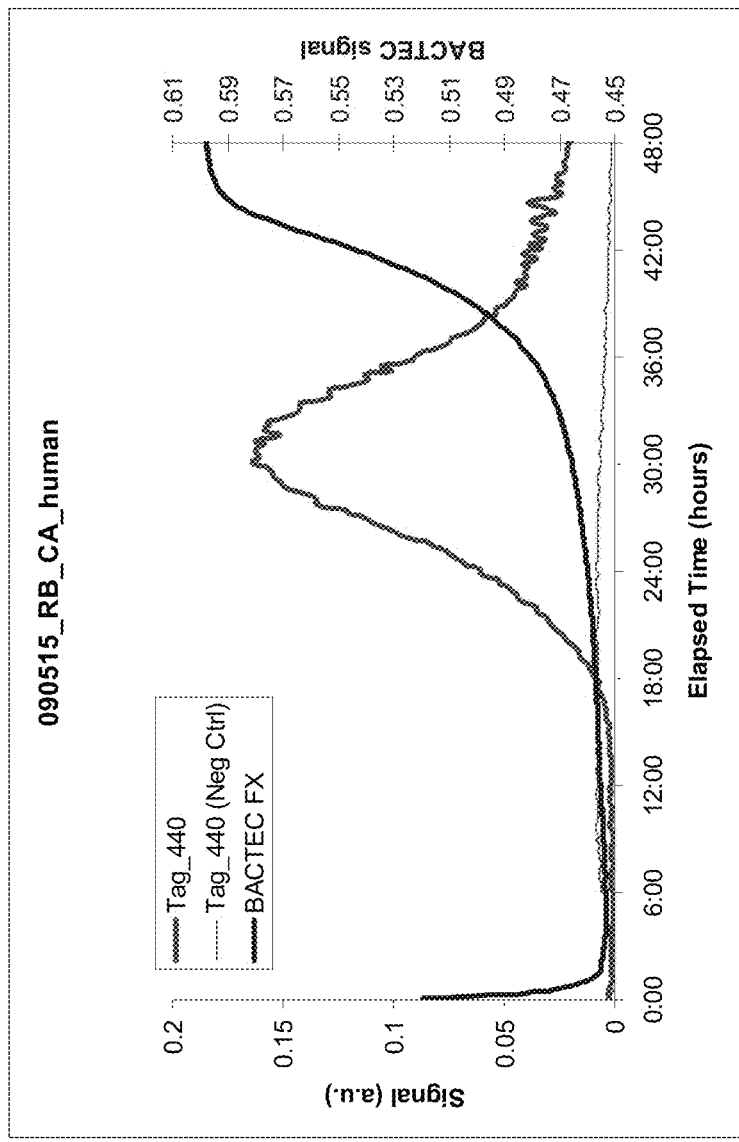
FIG. 60 shows a graph in which time to detection of *C. albicans* in blood was compared using a singleplex SERS detection according to an embodiment of the invention.

FIG. 60 shows an example of detection and identification of microorganisms within a blood culture sample (spiked blood) for a singleplex format. In this experiment, Candida albicans (ATCC 10231) was grown in an overnight culture in Sabouraud Dextrose Broth from a single colony at 30° C. in a shaking culture. The culture was diluted down and inoculated into human blood at 3 cfu/ml or 0 cfu/ml as a negative control. Positive and negative samples were inoculated into BACTEC™ Std 10 Aerobic/F bottles without detection reagents as well as into tubes containing BACTEC™ Std 10 Aerobic/F media and the detection reagents (SERS tags and magnetic particles conjugated with Virostat 6411 anti-Candida albicans antibody). The overall blood to media ratio was 1:8. The inocula were plated on BBL™ CHROMagar™ for enumeration. Detection tubes were inserted into the carousel system 150 (see FIG. 24) and BACTEC™ bottles were inserted into the BACTEC™ FX instrument for real time monitoring during growth at 35° C. The positive SERS tube was detected at 18 hours and the BACTEC™ bottle was positive at 30 hours. SERS signal provides detection and ID at least 12 hours before BACTEC™ FX for this singleplex assay in human blood.

Example 6

Detection of C. albicans in a 4-Pex Assay Format

Figure 61:
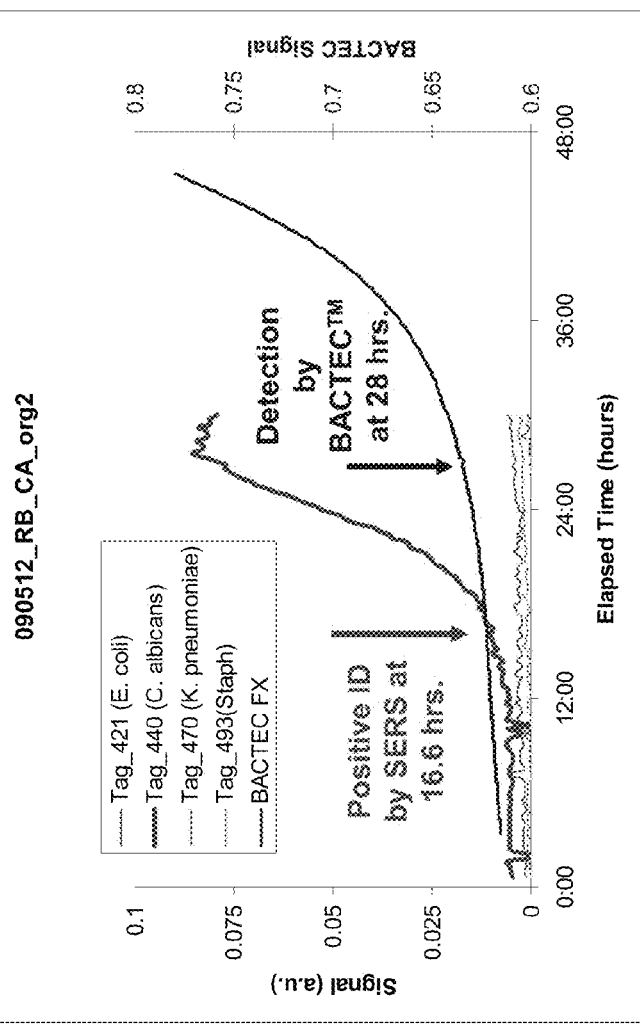
FIG. 61 shows a graph in which time to detection of *C. albicans* in blood was compared using a multiplex SERS method according to an embodiment of the invention.

FIG. 61 shows an example of detection and identification of microorganisms within a blood culture sample (spiked blood) for a multiplex format. In this 4-plex assay for the detection of *C. albicans, E. coli* O157, *K. pneumoniae*, and *S. aureus*, SERS tags with four distinct Raman reporters were each conjugated to antibodies for one of the four organisms. (Antibodies conjugated to SERS tags Virostat 6411 polyclonal anti-*C. albicans*, Biodesign MAV119-499 monoclonal anti-*E. coli* O157:H7, Biodesign C55573M monoclonal anti-Staphylococcus and Santa Cruz Biotechnology sc-80861 monoclonal anti-*K. pneumoniae*). All four SERS tag types were present in the assay mixture, along with magnetic beads conjugated with capture antibodies for the four microorganisms. The magnetic beads present in the assay were a pool of magnetic beads consisting of Dynal® anti-*E. coli* 0157 magnetic particles (Life Technologies catalog #710-03), Dynal® M280 beads conjugated to Virostat 6411 polyclonal anti-*C. albicans*, Dynal® M280 beads conjugated with Biodesign C55573M monoclonal anti-*Staphylococcus*, and Dynal® M280 bead conjugated with Affinity Bioreagents Pa.1-7226 polyclonal anti-*K. pneumoniae*.

In the experiment depicted in FIG. 61, *C. albicans* (ATCC 10231) was grown in an overnight culture in Sabouraud Dextrose Broth from a single colony at 30° C. in a shaking culture. The culture was diluted down and inoculated into human blood at 3 cfu/ml or 0 cfu/ml as a negative control. Positive and negative samples were inoculated into BACTEC™ Std 10 Aerobic/F bottles as well as sample tubes containing BACTEC™ Std 10 Aerobic/F media with the detection reagents. The blood to media ratio in the final sample was 1:8. The *C. albicans* inocula were plated on BBL™ CHROMagar™ for enumeration. The sample tubes containing the SERS reagents were inserted into a carousel system (see FIG. 24), while the BACTEC™ bottles without detection reagents were inserted into the BACTEC™ FX instrument for real time monitoring during growth at 35° C.

*C. albicans* was detected by SERS at 16.6 hours, while the BACTEC™ gas sensor gave positive detection at 28 hours. Furthermore, detection by SERS was accompanied by identification of the microorganism as *C. albicans*, whereas the BACTEC™ instrument provided no identification information. As can be seen in FIG. 61, the detection of *C. albicans* by SERS in a multiplexed format resulted in no significant SERS signal from the other (non-*C. albicans*) SERS tags.

Example 7

Detection of *E. coli* and *S. epidermis* Coninfection in Rabbit Blood

Figure 62:
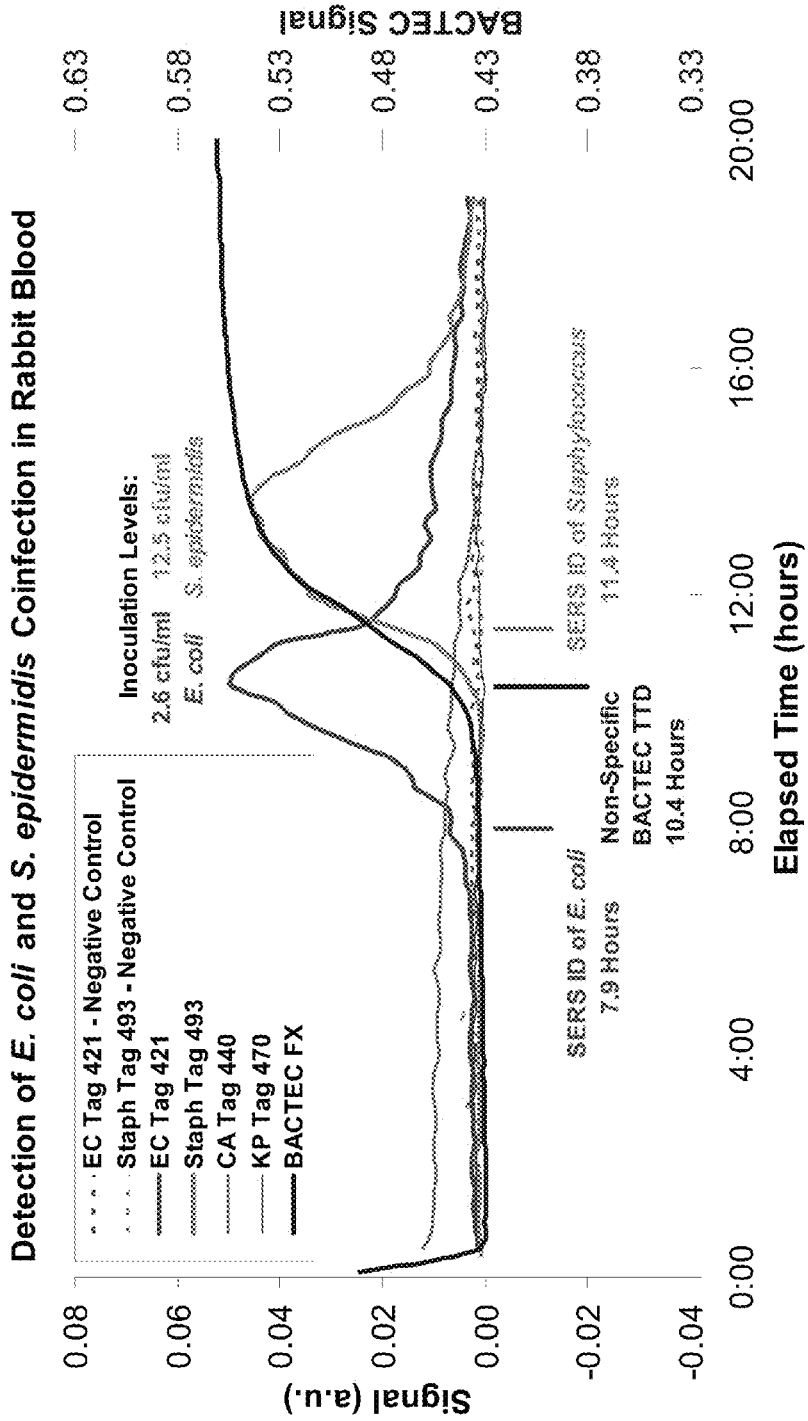
FIG. 62 shows a graph in which time to detection of *E. coli* and *S. epidermidis* in blood was compared using a multiplex SERS method according to an embodiment of the invention.

FIG. 62 shows an example of multiplexed detection and identification of microorganisms within a blood culture sample (spiked blood) for a model co-infection. *E. coli* O157:H7 (ATCC 700728) and *S. epidermidis* (ATCC 55133) were separately grown in overnight cultures in BD Nutrient Broth from a single colony at 37° C. in a shaking culture. The cultures were diluted down and co-inoculated into rabbit blood at 2.6 cfu/ml for *E. coli* O157:H7 and 12.5 cfu/ml for *S. epidermidis*. Positive and negative samples were inoculated into BACTEC™ Std 10 Aerobic/F bottles (no SERS reagents) as well as tubes containing BACTEC™ Std 10 Aerobic/F media and the detection reagents described in Example 6. (SERS tags conjugated to Virostat 6411, Biodesign MAV119-499, Biodesign C55573M and Santa Cruz Biotechnology sc-80861, as well as Dynal® anti-*E. coli* O157 magnetic particles and Dynal® M280 particles conjugated to Virostat 6411, Biodesign C55573M and Affinity Bioreagents PA1-7226.) The blood was diluted 1:8 in BACTEC™ media. The inocula were plated on BBL™ CHROMagar™ for enumeration. Detection tubes containing the SERS reagents were inserted into the carousel system 150 (see FIG. 24), while BACTEC™ bottles without SERS reagents were inserted into the BACTEC™ FX instrument for real time monitoring during growth at 35° C. *E. coli* O157:H7 was detected and identified by SERS at 7.9 hours, while *S. epidermidis* was detected and identified by SERS at 11.4 hours. The BACTEC™ bottle was positive at 10.4 hours, but provided no level of identification.

Example 8

Real-Time SERS Detection in Samples Containing Particulates

Figure 63:
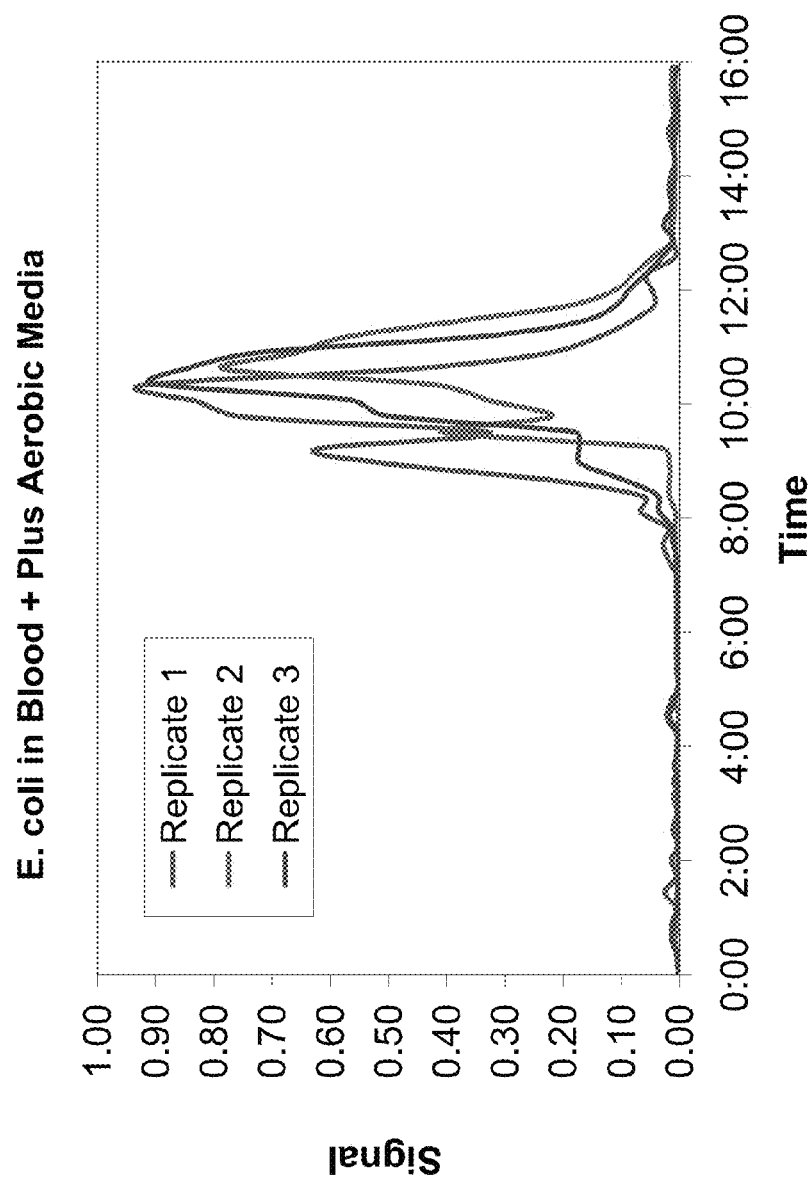
FIG. 63 illustrates a graph of real-time detection of *E. coli* in blood with aerobic media and antibiotic absorbing resins according to an embodiment of the present invention.

In this example, *E. coli* O157:H7 (ATCC 700728) was thawed from a glycerol stock and inoculated into rabbit blood diluted into BACTEC™ Plus Aerobic/F Media at a ratio of 1:8. BACTEC™ Plus Aerobic/F Media contains resin particles (17% w/v) to enhance the recovery of organisms without the need for special processing. The inoculated blood plus media was enumerated by plate counts to confirm an inoculation of 5 cfu/ml. The sample was placed in three replicate tubes containing SERS and magnetic bead conjugates (Biodesign MAV119-499 and G5V119-500 antibodies). Detection tubes were inserted into the carousel system 150 (see FIG. 24) for real time monitoring during growth at 35° C. Results are shown in FIG. 63. The carousel system was able to efficiently form and interrogate a pellet in the presence of the resin.

Example 9

Detection in Large Volumes

The agitation provided during pelleting allows magnetic beads to be captured efficiently, even in large sample volumes or at low magnetic bead concentrations.

In one example, assays were conducted with SERS and magnetic particle reagent volumes held constant, while varying sample volumes to achieve a range of reagent concentrations. Samples of 5, 10, 20, 30, 40, and 50 mL of a 1:10 dilution of rabbit blood in BD BACTEC™ Standard 10 Aerobic/F blood culture medium were tested in 50 mL Falcon™ tubes on a carousel-based assay system modified for large sample volumes (see e.g., FIG. 24). *E. coli* O157 was thawed from a frozen stock and spiked into each sample at $10^4$ cfu/mL. Over a course of six days, each volume was tested in triplicate, with only one sample of a given volume tested per day.

In each tube, a master mix typically used for 5 mL samples was created by combining 125 µL of SERS tags and 80 µL of magnetic particles in 795 µL of 1:10 blood and media. The resulting 1 mL master mix was added to each test sample. SERS tags conjugated with Biodesign MAV119-499 anti-*E. coli* antibodies, and Dynabeads® Anti-*E. coli* O157 (710-04) magnetic particles from Life Technologies™, were used.

Samples were placed in a carousel-based assay system (see e.g., FIG. 24) at 35° C., with pelleting for 60 sec, an incident laser power of 50 mW, a 5 sec CCD integration time, rocker operating at ~0.5 cycles/sec, and a read frequency of 5/hour.

Figure 64:
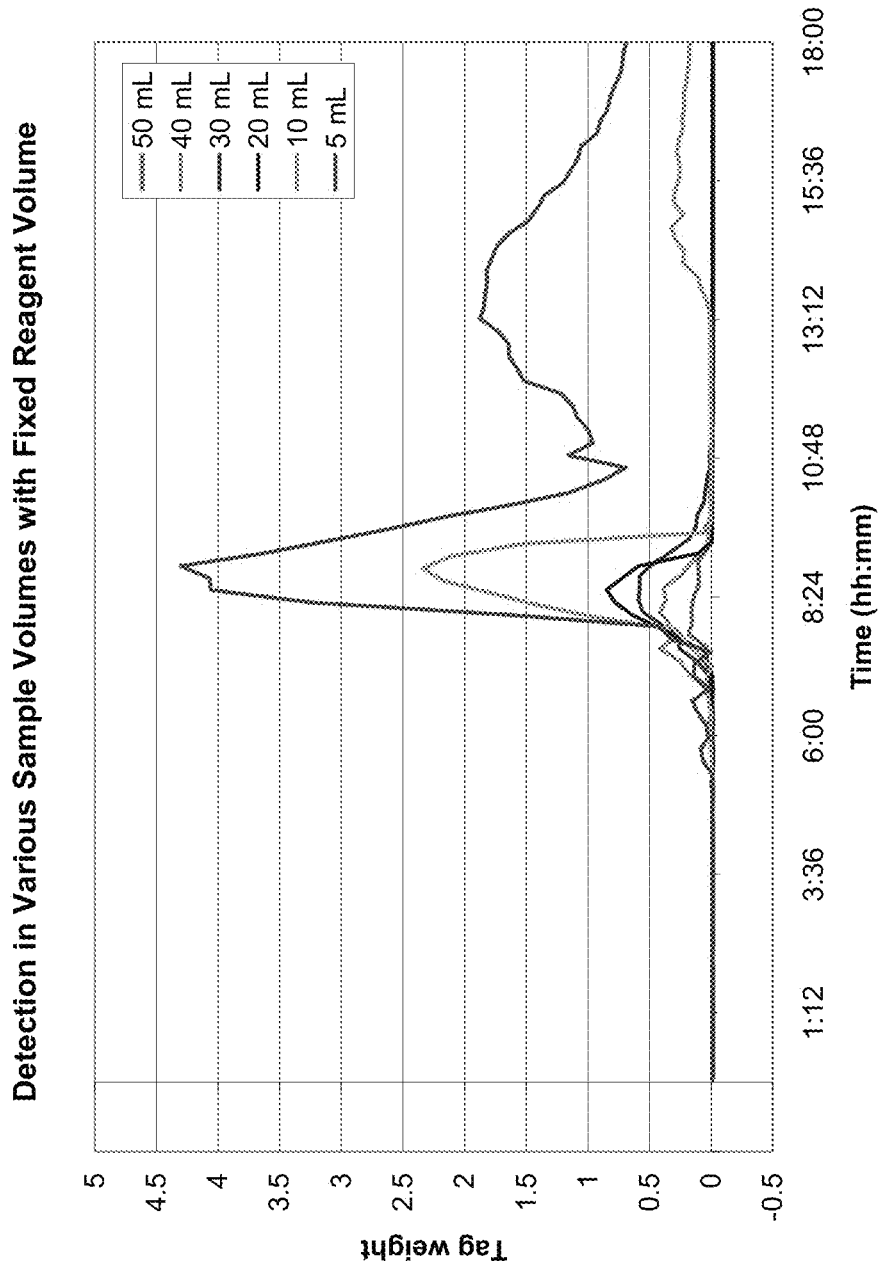
FIG. 64 shows a graph of the detection of *E. coli* in blood for different sample volumes according to an embodiment of the present invention.

Results for a representative sample of each volume are shown in FIG. 64. Although the signal strength is reduced with lower reagent concentrations, the system is able to effectively form pellets and detect growth even at a concentration 10× lower than the standard. As can be seen, the assay effectively detects growth for a variety of volumes.

Example 10

Failure to Pellet Using Fast Agitation in Carousel System

In the carousel system (see e.g., FIG. 24), the samples are agitated while the magnetic pellet is being formed to ensure that magnetic complexes from the full fluid volume pass through the localized magnetic field. A camera captures images of the pellet during laser interrogation to monitor pellet formation throughout the assay.

Figure 65A:
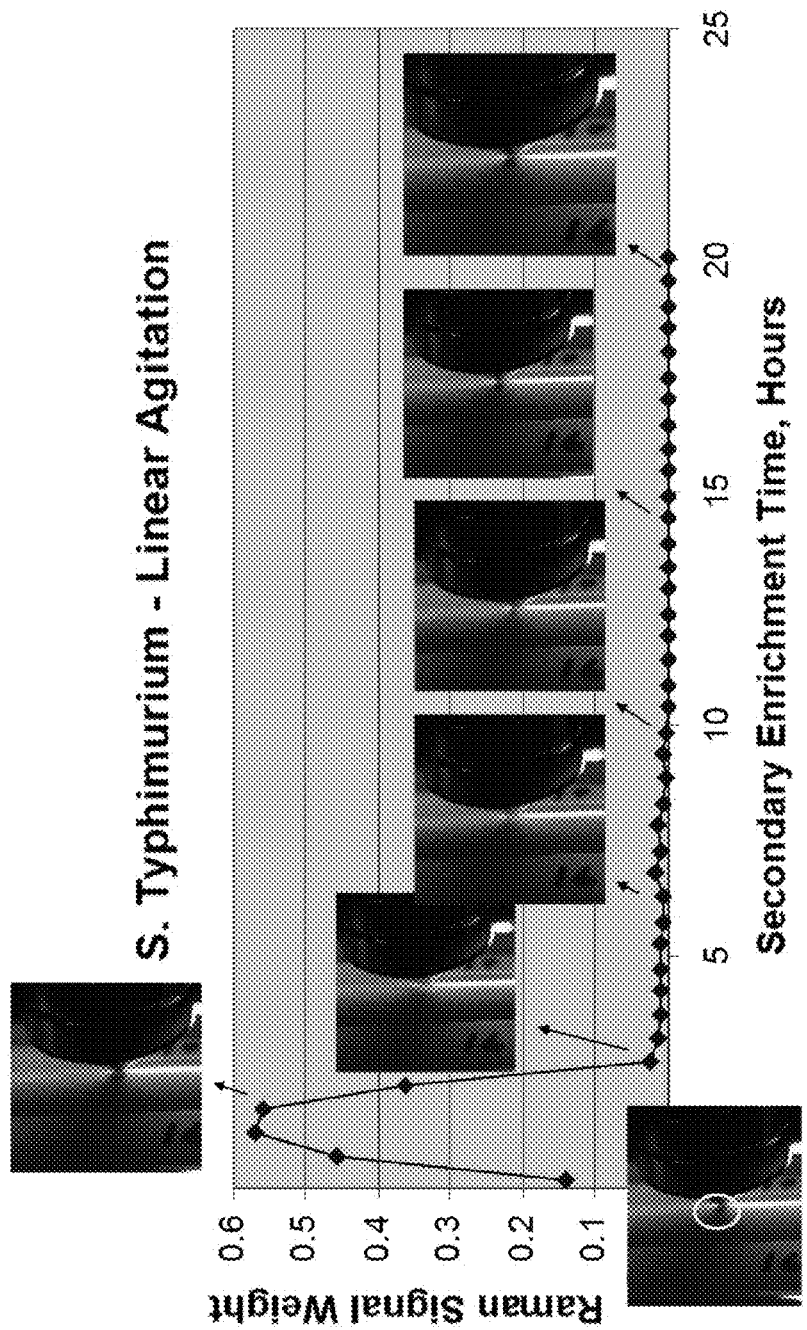
FIG. 65A shows a SERS curve with images captured at various times during secondary enrichment of *Salmonella* Typhimurium according to one embodiment.

FIG. 65A shows an example in which a pellet fails to form within a few hours of secondary enrichment of $10^7$ CFU/mL Salmonella Typhimurium (ATCC 14028) at fast agitation frequencies in the carousel system 150 (see FIG. 24). Salmonella Typhimurium (ATCC 14028) was cultured overnight in SDIX RapidChek® Salmonella SELECT™ Primary Media with supplement at 42° C. A 1:100 dilution of the culture with SDIX Salmonella Secondary Media was inoculated into a secondary container with conjugated magnetic particles and SERS tags and placed into the carousel system 150. The starting inoculation in secondary media was determined to be $1 \times 10^7$ CFU/mL by plate count on Nutrient agar plates. The instrument read 2 times per hour, pelleted for 30 seconds, and agitated at 2 Hz with 25 mm throw. FIG. 65A shows the resulting SERS curve with images captured at various times during secondary enrichment. The first pellet image contains a yellow circle to highlight the area where the pellet should form. This figure shows the pellet grows in size by 2 hours and fails to form near 3 hours of secondary enrichment time.

For very high loads of Salmonella, the pellet becomes particularly large because there is a lot of pathogen present in the pellet. When agitation is too fast, the magnetic field is unable to overcome the fluid dynamics, and the pellet fails to form.

Figure 65B:
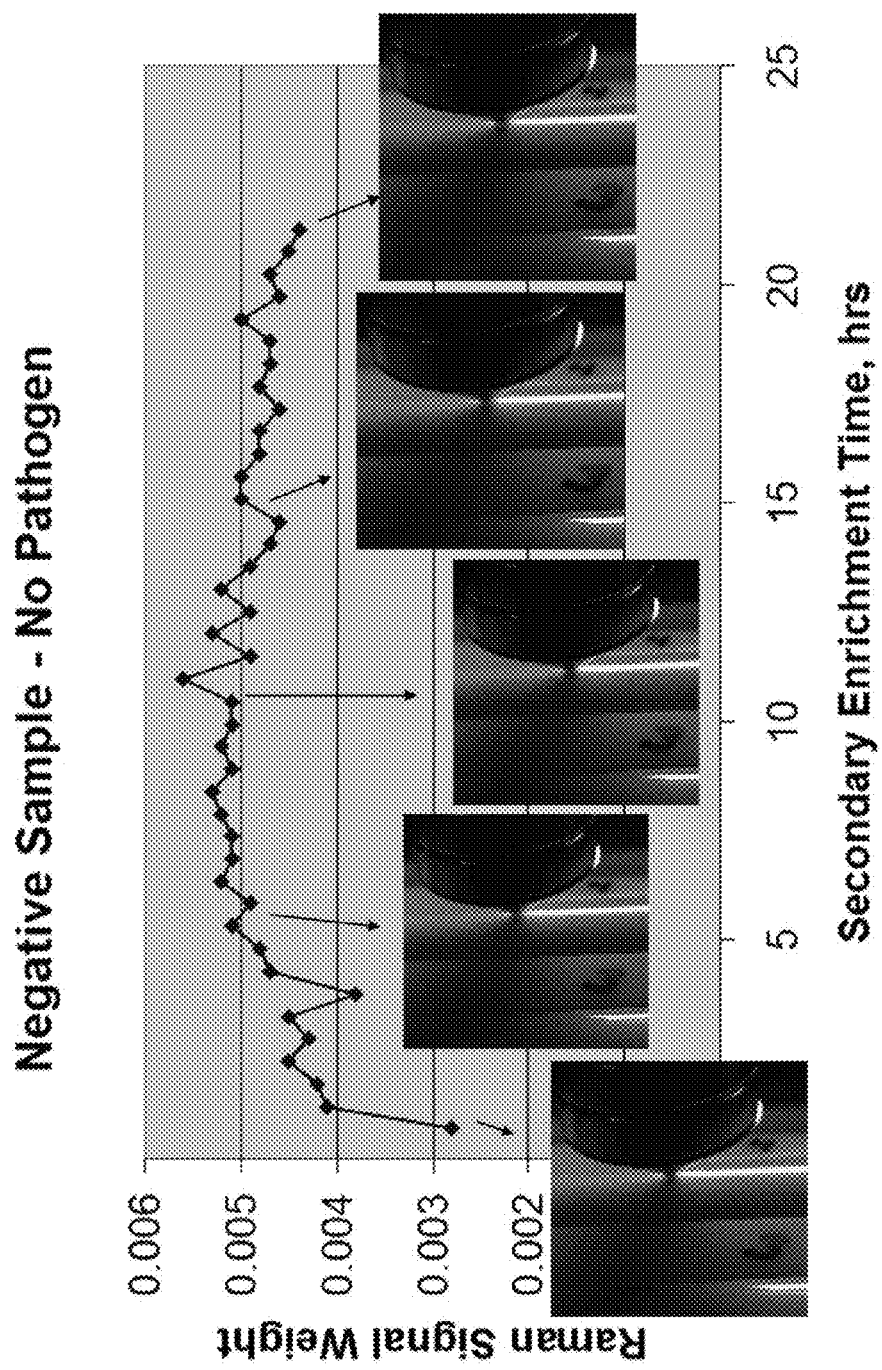
FIG. 65B shows a SERS curve with images captured at various times during secondary enrichment for a negative sample according to one embodiment.

FIG. 65B shows the SERS curve and corresponding images during secondary enrichment for a negative sample (conjugated magnetic beads and conjugated SERS tags in media). This data shows a consistently low Raman signal and consistent pellet size during the assay.

Figure 65C:
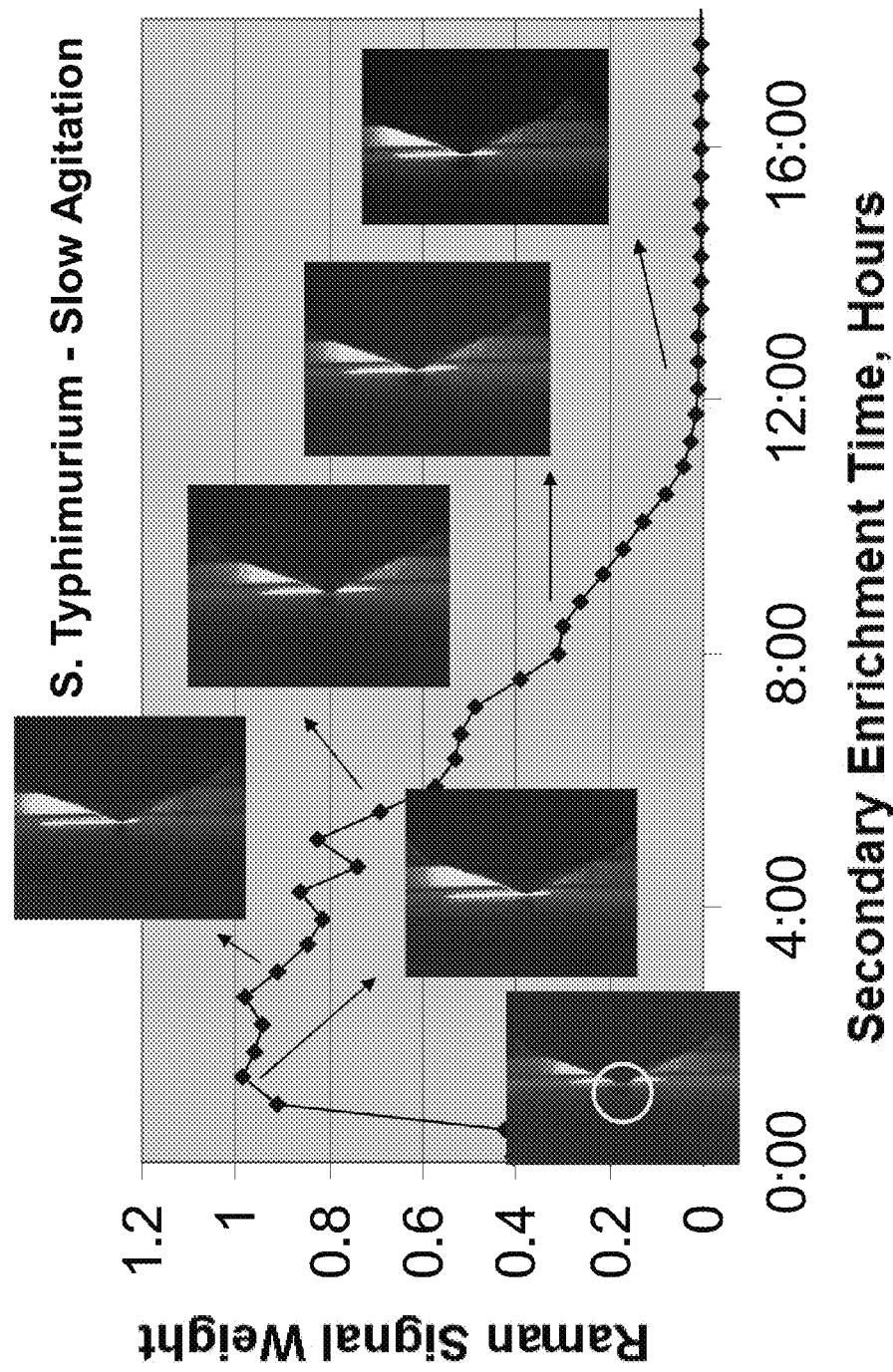
FIG. 65C shows a SERS curve with images captured at various times during secondary enrichment of *Salmonella* Typhimurium according to one embodiment.
Figure 66:
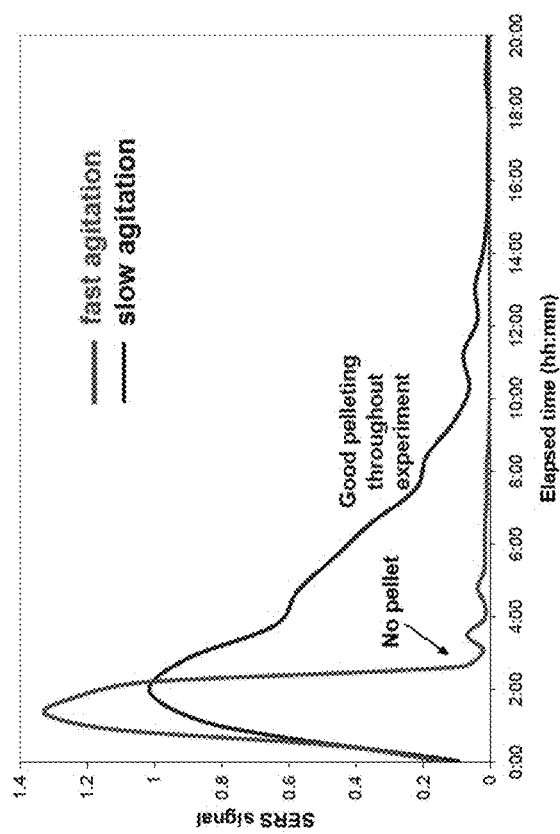
FIG. 66 shows overlaying SERS curves for different agitation rates during secondary enrichment of *Salmonella* Typhimurium according to one embodiment.

By slowing the agitation frequency to 1 Hz during secondary enrichment of $10^7$ CFU/mL of Salmonella Typhimurium (ATCC 14028), the pellet consistently formed throughout the assay. Salmonella Typhimurium (ATCC 14028) was cultured overnight in SDIX RapidChek® Salmonella SELECT™ Primary Media with supplement at 42° C. A 1:100 dilution of the culture with SDIX Salmonella Secondary Media was inoculated into a secondary container with conjugated magnetic particles and SERS tags and placed into the carousel system 150. The starting inoculation in secondary media was determined to be $1 \times 10^7$ CFU/mL by plate count on Nutrient agar plates. The instrument read 2 times per hour, pelleted for 30 seconds, and agitated at 1 Hz with 25 mm throw. FIG. 65C shows the resulting SERS curve with images captured at various times during secondary enrichment. The first pellet image contains a yellow circle to highlight the area where the pellet should form. FIG. 65C shows the pellet is retained throughout the experiment. FIG. 66 shows the impact of the agitation rate on pellet persistence by overlaying the SERS curves from the 2 Hz and 1 Hz agitation rates (FIGS. 65A and 65C, respectively). With slower agitation, the signal decay is much slower and the peak is much broader than when agitation is fast. Furthermore, real-time monitoring of the pellet through an in-line camera indicates that the loss of signal for fast agitation is due to the absence of the pellet, while for the slow agitation the pellet is always formed. The pellet fails to form near 3 hours at 2 Hz agitation, but is always present using 1 Hz agitation. Consistent formation of the pellet at high organism load leads to longer persistence of the SERS signal. This persistence in the SERS signal may be advantageous if, for example, there is a delay between when the sample is added to the detection reagents and when the sample is placed into the instrument.

Example 11

Determination of the Presence of a Targeted Pathogen Using Visual Inspection of the Pellet in Sandwich Immuno-Assays In this example a method for detection of microorganisms within a microbiological sample that can eliminate the need for laser, optics, and spectrometer according to an embodiment of the invention is described. This method involves the use of a camera to capture images during reads in order to monitor the formation of a pellet during the course of a SERS-HNW assay.

Figure 67:
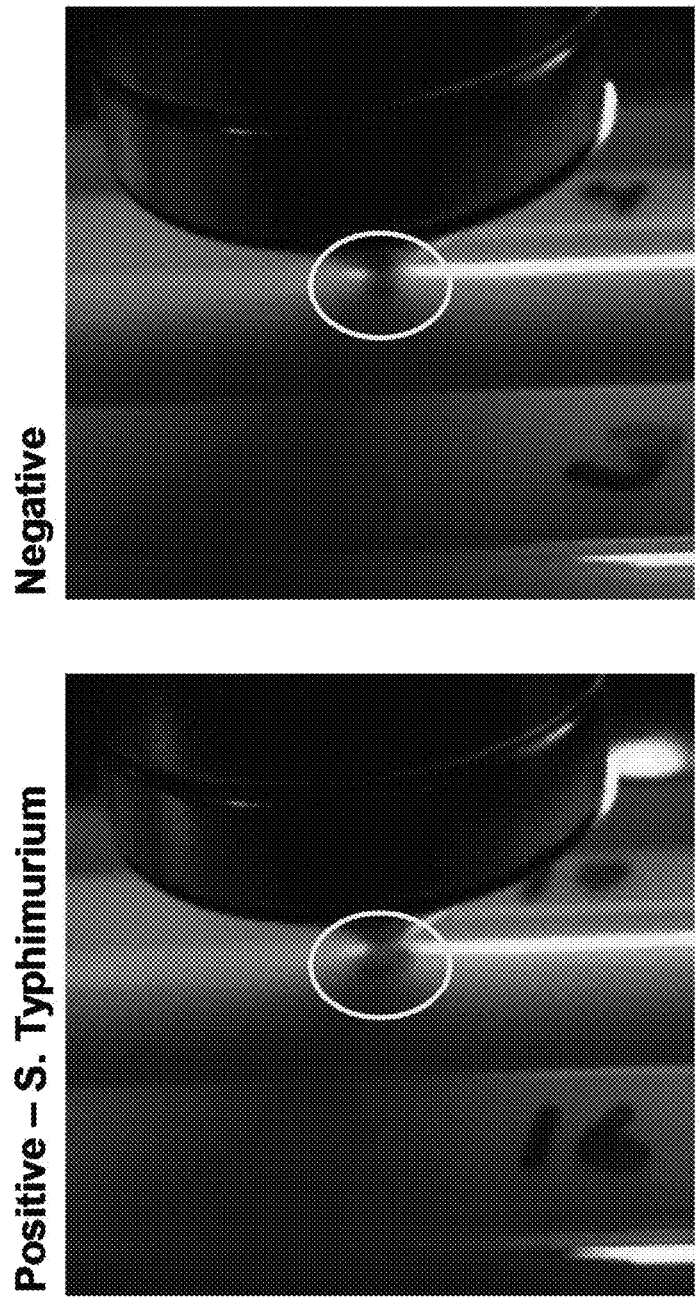
FIG. 67 shows images of pellets for a positive sample and a negative sample, respectively, according to an embodiment of the present invention.

In the experiment described in example 11 and shown in FIG. 65A, 65B, and 65C, the presence of the microorganism causes the pellet to grow in size (FIGS. 65A and 65C). In contrast, when the microorganism is absent, both the pellet size and the SERS signal remain stable. Without the presence of the targeted pathogen, no sandwiches can be formed, resulting in no Raman signal and no increase in pellet size. FIG. 67 shows the pellet size for a negative sample compared to the pellet size for a positive sample after 3 hours of secondary enrichment in a carousel system (see e.g., FIG. 24). This figure shows a larger pellet formed for the positive sample compared to the negative sample.

During secondary enrichment of a sample which contains conjugated SERS tags and magnetic beads and the targeted pathogen, images show that pellet size increases, and in some cases, fails to form as the assay progresses. The growth in pellet size and/or disappearance of the pellet is an indication of the presence of the targeted pathogen. Images captured during reads of samples that contain conjugated SERS tags and magnetic beads with no pathogen show no change in pellet size and no pellet disappearance. Using image analysis to monitor pellet size may present a method of detecting microorganisms in the assay. This method of detection can be used alone or in conjunction with another detection method.

Example 12

Real-Time Detection of E. coli O157:H7 During Culture in Food Samples

Figures 68A, 68B, 68C:
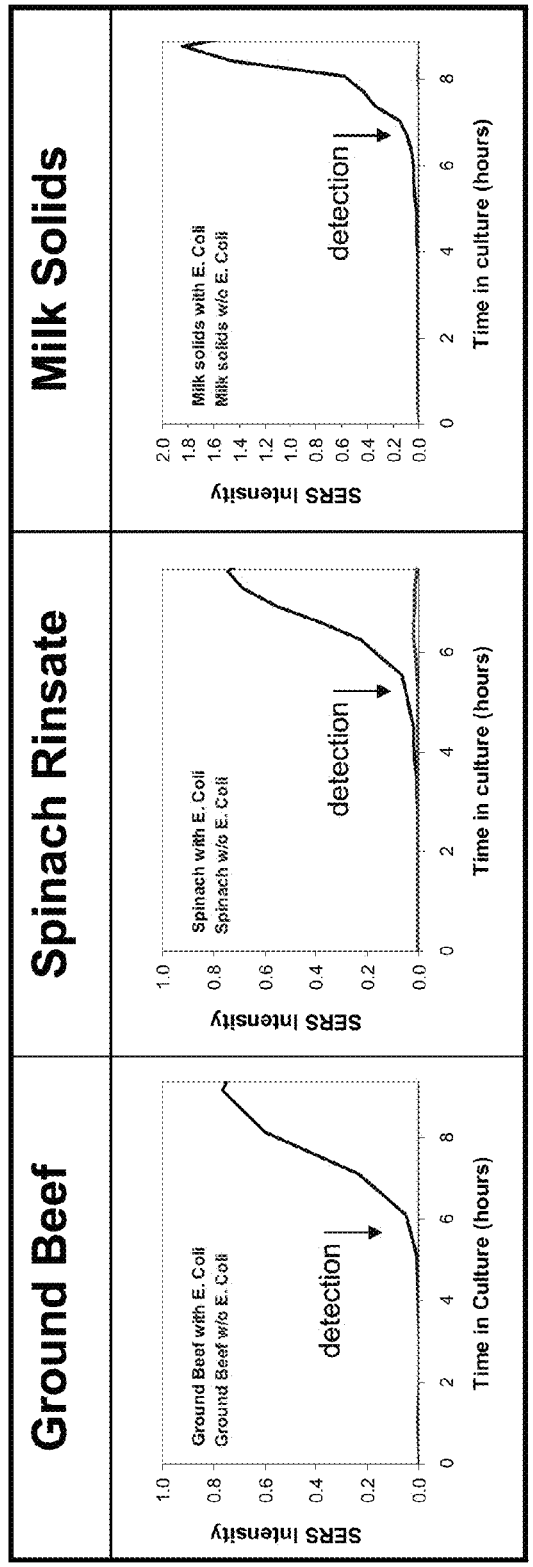
FIGS. 68A-68C illustrate SERS curves for the real-time detection of *E. coli* during culture in food samples according to embodiments of the present invention.

FIGS. 68A, 68B and 68C show representative data acquired with a carousel system (see e.g., FIG. 24) for the detection of E. coli 0157 in stomached ground beef, spinach rinsate, and milk solids.

Raw ground beef was prepared according to the USDA Microbiology Laboratory Guidebook (MLG Chapter 5). 25 g samples of ground beef were diluted with 225 ml mTSB with Novobiocin in a stomacher bags. Each stomacher bag was then stomached in a Seward Stomacher® 400 for 2 minutes. 5 ml aliquots of the stomached ground beef were transferred to tubes containing SERS tag and magnetic particle conjugates. *E. coli* O157:H7 (ATCC 43888) was grown in an overnight culture in Nutrient Broth from a single colony at 37° C. in a shaking culture. The culture was serially diluted down to approximately $10^2$-$10^4$ in Nutrient Broth. A 0.05 ml aliquot was added to each positive tube and a 0.05 ml aliquot of Nutrient Broth was added to negative control tubes.

The spinach rinsate sample was prepared according to the FDA Bacteriological Analytical Manual (BAM Chapter 4A). An equal weight of Butterfield's phosphate buffer was added to spinach leaves in a re-sealable plastic bag and agitated by hand for 5 minutes. The spinach rinsate was then added to an equal volume of double strength (×2) mBPWp. *E. coli* O157:H7 (ATCC 43888) was grown in an overnight culture in Nutrient Broth from a single colony at 37° C. in a shaking culture. The culture was serially diluted and inoculated into the spinach rinsate +(×2) mBPWp at a concentration of 103 or 0 cfu/ml. 5 ml aliquots of these samples were added to tubes containing SERS tag and magnetic particle conjugates.

The milk sample was prepared according to the FDA Bacteriological Analytical Manual (BAM Chapter 4A). Whole milk was centrifuged for 10 minutes at 10,000×g. The supernatant layer was poured off and the pellet was resuspended in mBPWp at 1.125 times the original milk volume. *E. coli* O157:H7 (ATCC 43888) was grown in an overnight culture in Nutrient Broth from a single colony at 37° C. in a shaking culture. The culture was diluted down to 5000 cfu/ml in Nutrient Broth. 50 ul aliquots of the diluted *E. coli* O157:H7 culture or Nutrient Broth (negative control) was added to 5 ml tubes of the resuspended milk culture plus assay reagents.

All inocula were plated for enumeration on BD BBL™ CHROMagar™ plates. Tubes were inserted into the carousel system for real time monitoring during growth at 35° C. for 8 hours.

Example 13

Real-Time Detection of *Salmonella* During Culture in Food Samples

Figure 69:
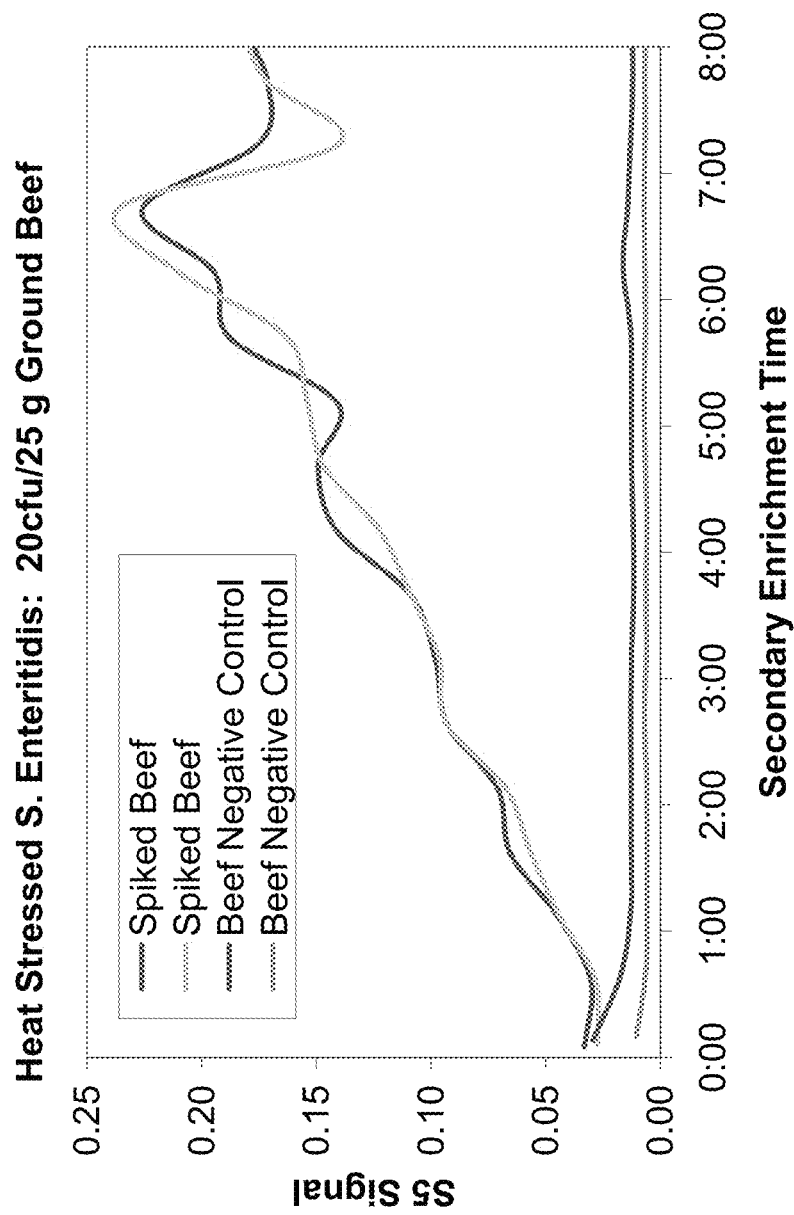
FIG. 69 illustrates SERS curves for the real-time detection of *Salmonella* Enteritidis during culture in food samples according to an embodiment of the present invention.

FIG. 69 shows an example in which heat stressed S. Enteritidis (ATCC 13076) was detected during real-time growth in ground beef plus culture media. *Salmonella* Enteritidis was grown in an overnight culture in Nutrient Broth from a single colony at 37° C. in a shaking culture. The culture was diluted down 1:100 in Nutrient Broth and heat stressed for 20 minutes at 54° C. The heat stressed sample was further diluted down to 200 cfu/ml in Nutrient Broth. Two 25 g samples of raw ground beef were inoculated with 1 ml aliquots of the diluted, heat stressed culture of S. Enteritidis. The inoculum was plated for enumeration on Nutrient Agar plates. The inoculated ground beef samples were hand massaged in a stomacher bag for 2 minutes to thoroughly mix the inoculum. 225 ml of SDIX RapidChek® *Salmonella* SELECT™ Primary Media with supplement were added to the inoculated samples in the stomacher bag. Negative control samples were prepared with 25 g of raw ground beef in 225 ml of SDIX RapidChek® *Salmonella* SELECT™ Primary Media with supplement. Each stomacher bag was then stomached in a Seward Stomacher® 400 for 2 minutes. The stomacher bags were then placed in a 42° C. incubator for approximately 22 hours. 100 ul samples of the enriched primary cultures were then added to tubes containing 4.5 ml SDIX *Salmonella* Secondary Media, 0.4 ml SDIX RapidChek® *Salmonella* SELECT™ Primary Media and assay reagents. The tubes were then inserted into the carousel system (see FIG. 24) for real time monitoring during growth at 42° C. for 8 hours. Positive samples were detected within approximately 2 hours, while negative samples resulted in flat detection curves.

Example 14

Detection of *Listeria* in an Environmental Sample

Figure 70:
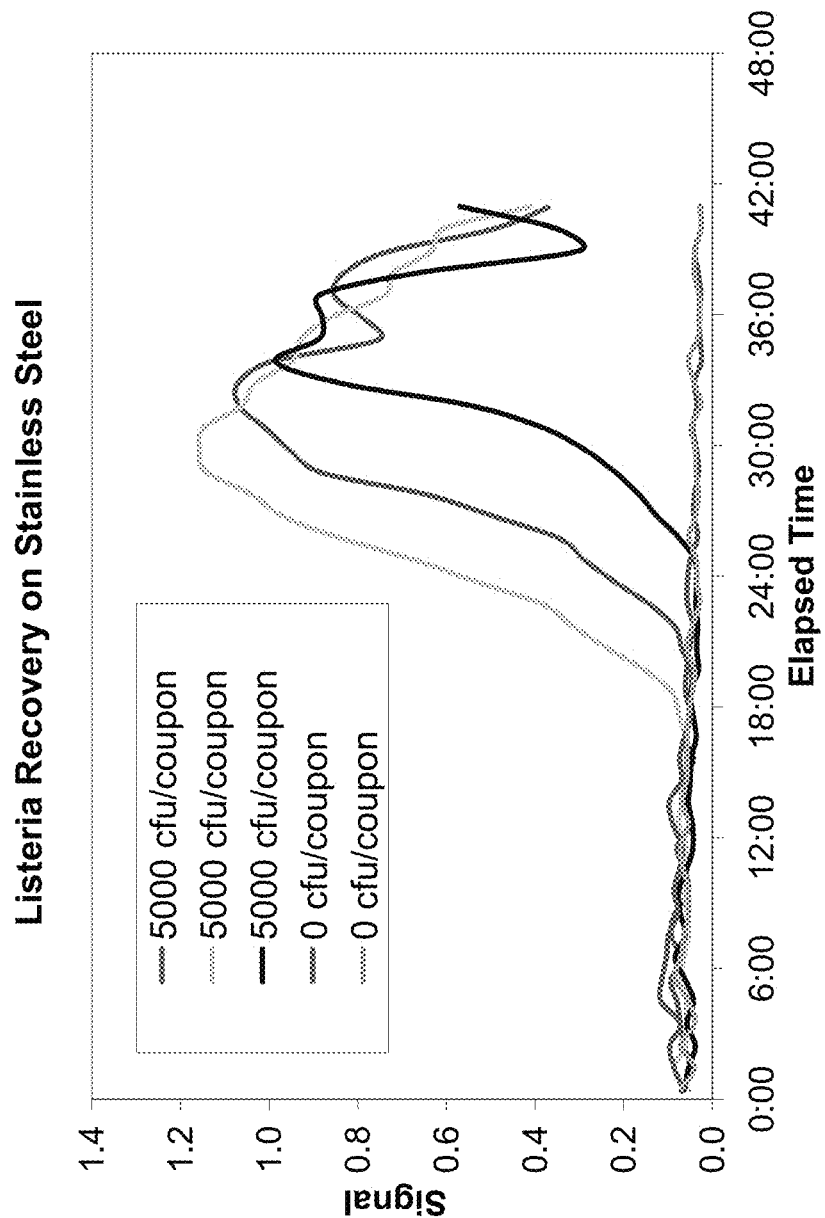
FIG. 70 illustrates SERS curves for the real-time detection of *Listeria* swabbed from stainless steel during culture according to an embodiment of the present invention.

FIG. 70 shows the detection of *Listeria monocytogenes* (ATCC 19115) on a stainless steel coupon. *L. monocytogenes* (ATCC 19115) was grown in an overnight culture in Brain Heart Infusion Broth from a single colony at 30° C. in a shaking culture. The culture was diluted down to 5×$10^4$ or 0 cfu/ml in PBS+5% milk. A 0.1 ml aliquot was placed on a 1"×1" stainless steel coupon and allowed to air dry overnight. The next day, cotton tipped swabs, wet with D/E neutralization broth, were swiped across the surface several times. The swabs were then added to 5 ml of SDIX *Listeria* media with supplement, SERS tags and magnetic particles in tubes. The tubes were then inserted into the carousel system (see FIG. 24) for real time monitoring during growth at 30° C. Positive samples were detected between approximately 19 and 27 hours, while negative samples resulted in flat detection curves.

Example 15

Detection of *Salmonella* Using Flat-Bed System

In this example *Salmonella* was detected using linear agitation and a flat-bed system (see e.g., FIG. 25). *Salmonella* Typhimurium (ATCC 14028) and *Salmonella* Enteritidis (ATCC 13076) were grown separately in overnight cultures in SDIX RapidChek® *Salmonella* SELECT™ Primary Media with supplement at 42° C. A 1:100 dilution of each strain was made into separate SDIX *Salmonella* Secondary Media lots. The starting inoculation for each strain in secondary media was determined to be 1×$10^7$ CFU/mL by plate count on Nutrient agar plates. Each strain was inoculated in duplicates into tubes containing SERS tags and magnetic particles conjugated with anti-Salmonella antibodies (Virostat 0701). These tubes, along with two negative samples (SDIX secondary media and conjugated SERS tags and magnetic particles with no *Salmonella*) were placed in the instrument for monitoring during secondary enrichment at 42° C.

Figure 71:
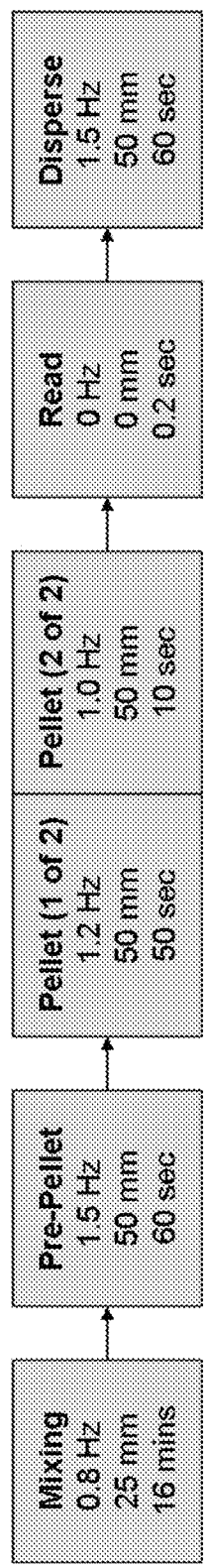
FIG. 71 shows a flowchart of phases for the detection of *Salmonella* Typhimurium using linear agitation according to an embodiment of the present invention.

The system used in this example was a flat-bed configuration (see e.g., FIG. 25). In this configuration, agitation is by linear reciprocation along the axis of the tubes, which may be programmed for different frequencies and profiles throughout the assay. Each cycle consists of the following phases: mixing, pre-pellet dispersion, pelleting, reading, and dispersing. The magnet configuration used in this example was a single bar magnet with N-pole facing the samples. Once a pellet was formed, the bar was moved away from the samples to allow reading. FIG. 71 shows the agitation frequency and throw used for each phase. The experiment was run for ~19 hours with a cycle repeating every ~20 minutes.

The pre-pellet dispersion phase is intended to re-suspend settled solid in the SDIX secondary media prior to pelleting. Settled solid from the media is known to interfere with pelleting of magnetic complexes. The single bar magnet is brought in contact with the tubes during agitation and the samples are pelleted for 60 seconds. Agitation is stopped for 5 seconds and the magnet is moved away from the sample tubes to allow the optics engine to interrogate each pellet. A camera also captures images of each pellet. The agitation resumes to disperse the pellet and the cycle repeats.

Figure 72:
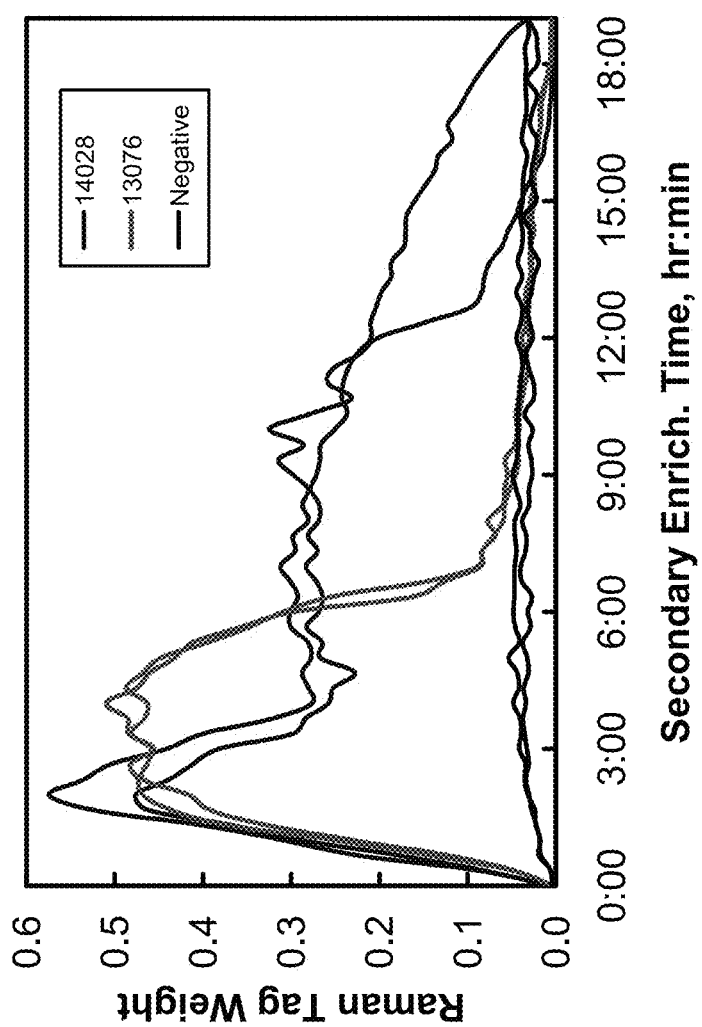
FIG. 72 illustrates overlaying SERS curves during secondary enrichment for *Salmonella* Typhimurium, *Salmonella* Enteritidis, and negative samples according to an embodiment of the present invention.
Figure 73:
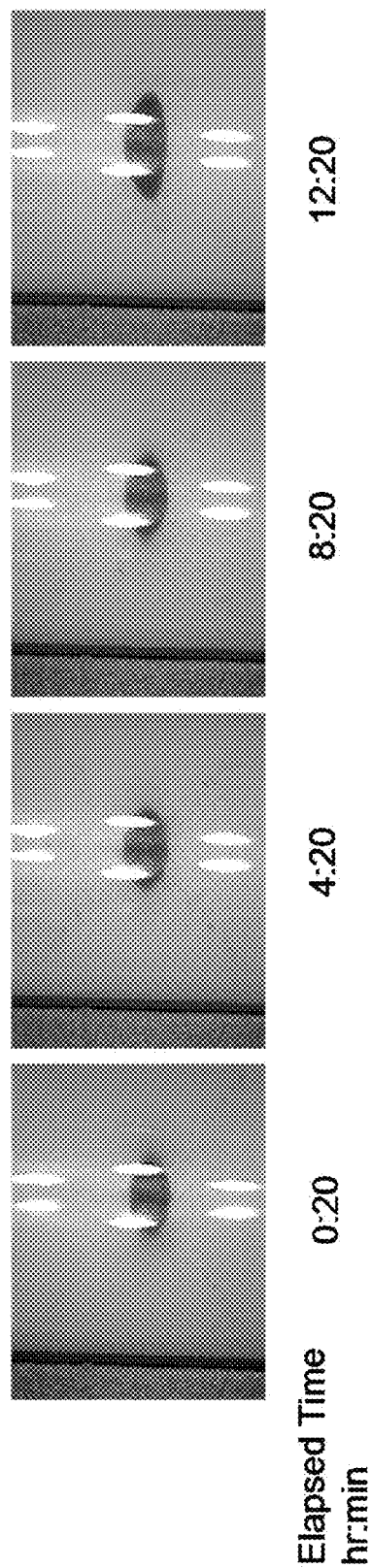
FIG. 73 shows images of pellets formed during secondary enrichment of *Salmonella* Typhimurium according to an embodiment of the present invention.

FIG. 72 shows the SERS curves during secondary enrichment of S. Typhimurium (ATCC 14028), S. Enteriditis (ATCC 13076), and negative samples. As can be seen, SERS curves are smooth and can easily be distinguished from the negatives. FIG. 73 shows images of the pellets formed at various times during secondary enrichment of S. Typhimurium. As can be seen, round, dense pellets are consistently formed throughout the assay using the flatbed instrument.

Example 16

Linear Versus Rocking Agitation

In this example, identical *Salmonella* assays were run on two carousel systems (see e.g., FIG. 24) using different agitation methods: a linear reciprocation along the axis of the tubes and a rocking oscillation. *Salmonella* Enteriditis (ATCC 13076) and *Salmonella* Kentucky (ATCC 9263) were grown separately in overnight cultures in SDIX Rapid-Chek® *Salmonella* SELECT™ Primary Media with supplement at 42° C. A 1:100 dilution of each strain was made into separate SDIX *Salmonella* Secondary Media lots. The starting inoculation for each strain in secondary media was determined to be $1 \times 10^7$ CFU/mL by plate count on Nutrient agar plates. Each strain was inoculated in duplicate into tubes containing SERS tags and magnetic particles conjugated with anti-*Salmonella*antibodies from Virostat (0701). These tubes were placed in the carousel systems for monitoring during secondary enrichment at 42° C. Each instrument read 2 times per hour, pelleted for 30 seconds, and agitated at 1 Hz.

Figure 74:
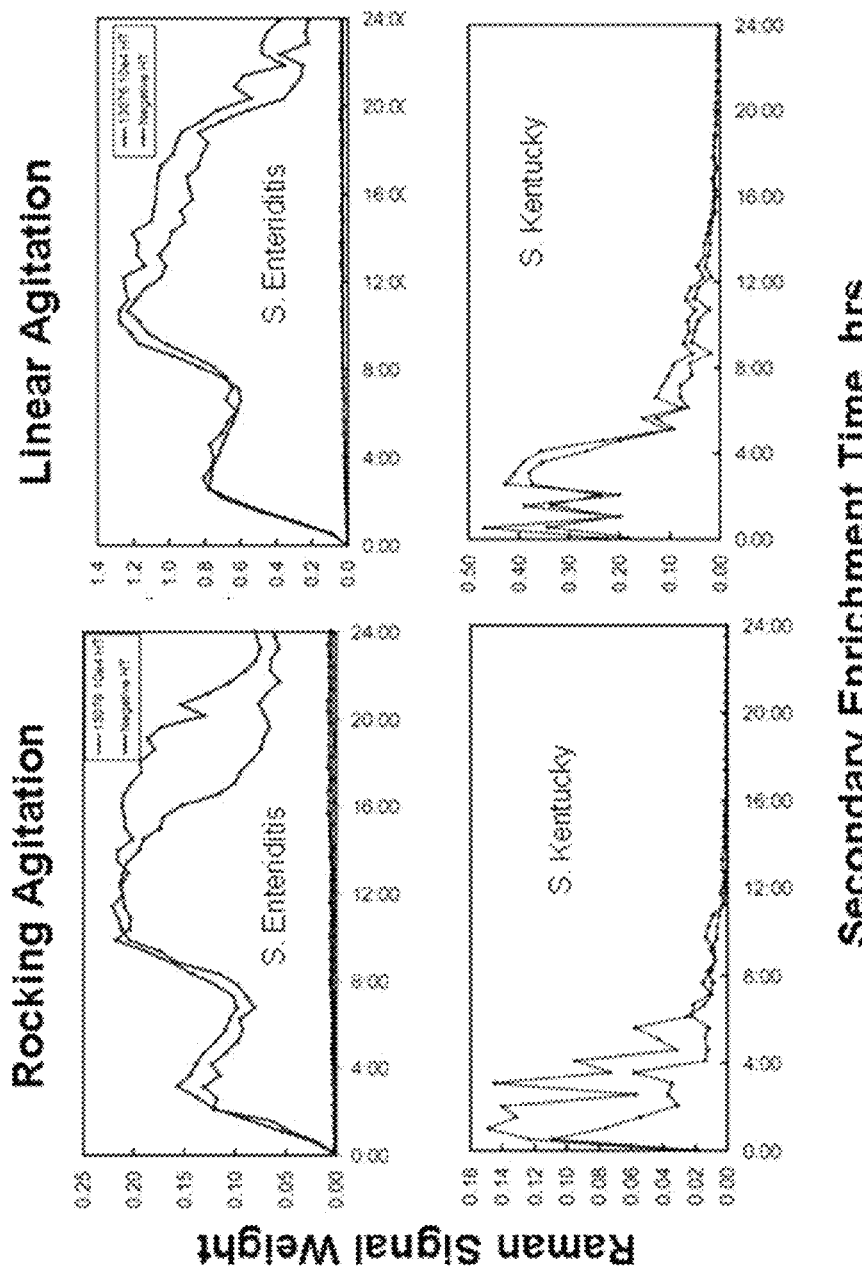
FIG. 74 shows SERS curves obtained from rocking agitation and linear agitation during secondary enrichment of *S.* Enteritidis and *S.* Kentucky according to one embodiment.

FIG. 74 shows SERS curves obtained from the rocking agitation and linear agitation carousel system during secondary enrichment of *S. Enteriditis* and *S. Kentucky*. It can be seen that good results are obtained with both methods.

In this example, linear agitation resulted in some advantages over the rocking motion. Pelleting performance was better using linear agitation compared to rocking because the pellet was always formed at the center of the read head using linear agitation. The rocking agitation system does not oscillate symmetrically about the rocker arm, causing the wheel of tubes to favor the forward motion. This asymmetric fluid motion causes the fluid force on the pellet to favor the front side of the tubes. Due to its mechanical simplicity compared to rocking agitation, linear agitation is a preferred method of agitation.

Example 17

Compatibility of Real Time No Wash Assay with Subsequent Sample Processing

In this example, the compatibility of the SERS-based real time assay with sample processing tests that are typically performed following detection of a positive blood culture sample by conventional gas sensors was tested. These tests may be used to provide organism identification out of a positive blood culture bottle. These tests include standard tube coagulase assays, latex agglutination assays, gram staining, chromogenic media development, manual antibiotic susceptibility testing and anti-fungal inhibition on plated cultures.

Figure 75:
FIG. 75 shows images of sample tubes containing *S. aureus* and *S. epidermidis* in EDTA rabbit plasma, with and without SERS reagents, according to one embodiment of the present invention.

The standard tube coagulase assays were performed by separately selecting several colonies of *S. aureus* or *S. epidermidis* from a streak plate and emulsifying them into BACTEC™ media. A 50 µl sample of emulsified bacteria with or without SERS reagents (at assay concentrations) was added to 500 µl of EDTA rabbit plasma and incubated at 37° C. The *S. aureus* samples with and without SERS reagents both coagulated the plasma within 4 hours (FIG. 75). The *S. epidermidis* samples did not coagulate the rabbit plasma within 4 hours. Therefore, the presence of SERS reagents does not impede the ability to distinguish *S. aureus* from *S. epidermidis* via coagulase activity, even at relatively high SERS reagent concentrations.

Figure 76:
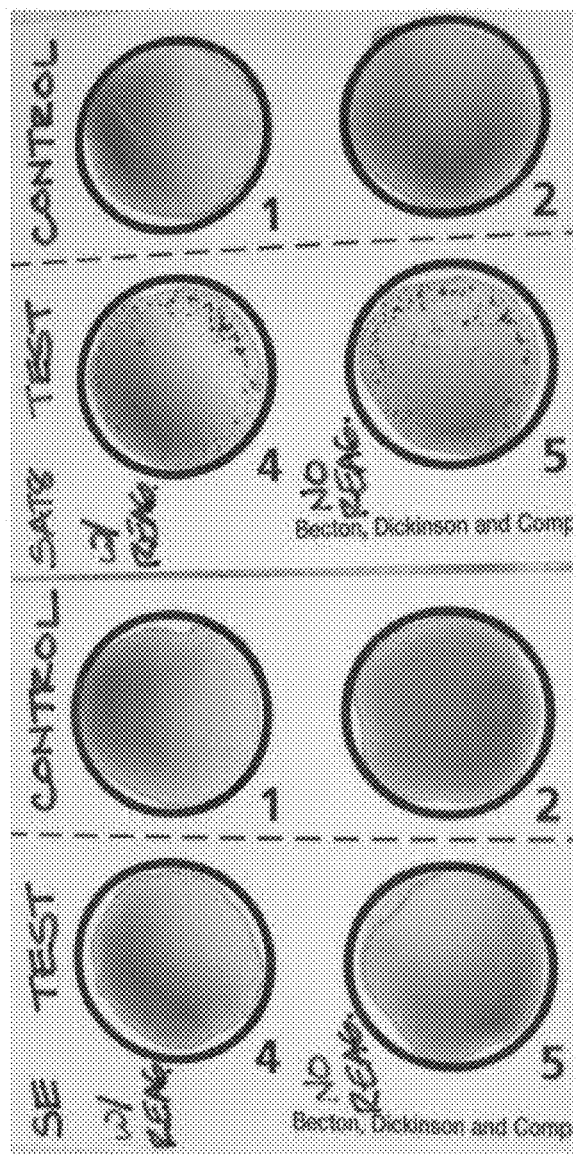
FIG. 76 shows images of latex agglutination assays with *S. aureus* and *S. epidermidis*, with and without SERS reagents, according to one embodiment of the present invention.

A latex agglutination test for *S. aureus* identification was also evaluated for any interference caused by the SERS assay particles. *S. aureus* and *S. epidermidis* samples with and without SERS reagents (at assay concentrations) were prepared as described above. One drop of BD BBL™ Staphyloslide™ test latex was then added to the assay card, as was one drop of control latex. To each type of latex, 10 µl samples of 1) *S. epidermidis* with SERS reagents, 2) *S. epidermidis* without SERS reagents, 3) *S. aureus* with SERS reagents, and 4) *S. aureus* without SERS reagents were added. The solutions were mixed and rocked for ~20 sec. FIG. 76 shows the cards with *S. epidermidis* (left card) and *S. aureus* type 8 (right card). Bacterial samples with SERS reagents were added to the top row, while samples without SERS reagents were added to the bottom row. The results are identical for samples with and without reagents, with only the *S. aureus* samples showing agglutination. The only samples to show agglutination were the *S. aureus* samples with and without SERS reagents, demonstrating the SERS reagents do not impede latex agglutination in the presence of *S. aureus*, do not falsely agglutinate control latex, and do not falsely agglutinate test latex in the presence of *S. epidermidis*.

Figure 77:
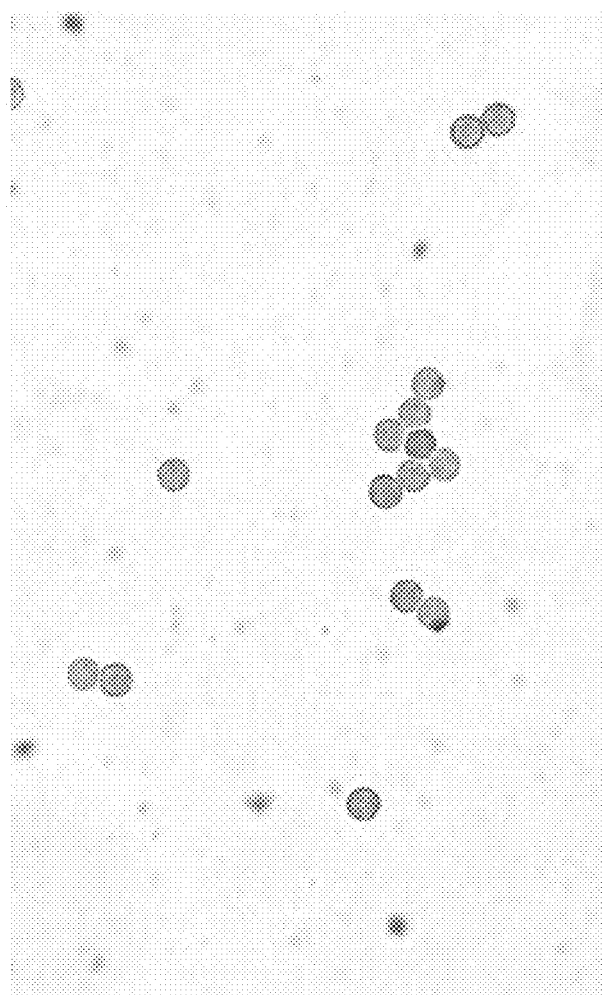
FIG. 77 is a magnified image of gram staining of a mixture of magnetic particles and SERS tags according to one embodiment of the present invention.
Figure 78:
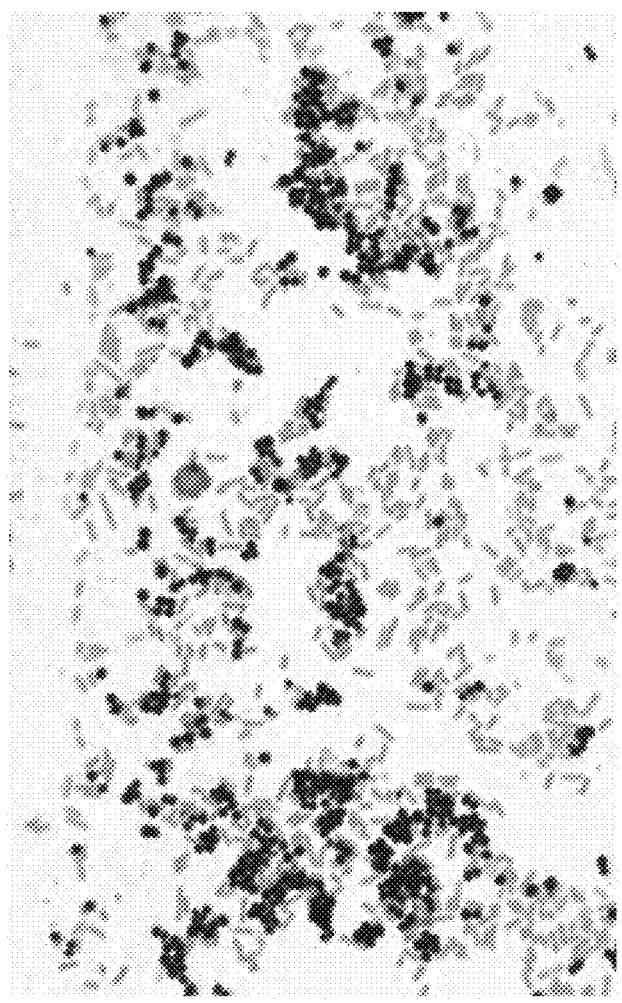
FIG. 78 is a magnified image of gram stained controls of *S. aureus* and *E. coli* with magnetic particles and SERS tags according to one embodiment of the present invention.

Gram staining with assay reagents was also performed as a test of downstream processing compatibility. SERS tags and magnetic particles in buffer were added to BD BBL Control Gram Slides containing *Staphylococcus aureus* ATCC 25923 (gram positive cocci) and *Escherichia coli* ATCC 25922 (gram negative rods) and imaged using a 100× oil immersion objective, as is typically used in the clinic. FIG. 77 shows the magnetic particles and SERS tags without the control organisms. The magnetic particles are clearly visible as large brown spheres. The magnetic particles are also uniform in color and size, effectively serving as an internal size standard (~3 µm) for microscopy. The SERS tags, which are 0.1-0.2 µm in diameter, are not visible. FIG. 78 shows a magnetic particle in the presence of a mixture of *S. aureus* (purple cocci) and *E. coli* (pink rods) imaged at 100×. Magnetic particles are clearly unstained and easily distinguishable from the microorganisms in this image.

CHROMagar™ chromogenic media allows identification, differentiation and separation of single pathogen by a single color developed in the solid media. Samples from overnight blood cultures of *S. aureus* type 8 and *S. epidermidis* containing SERS reagents were streaked onto CHROMagar™ plates. The results we obtained (FIG. 79) indicate that the SERS reagents do not impact the ability to obtain single colonies and do not impede the species-specific CHROMagar™ color development, wherein *S. aureus* is shown on the left and *S. epidermidis* is shown on the right. As expected, *S. aureus* colonies are mauve while *S. epidermidis* colonies are white when streaked on BD BBL™ CHROMagar™ Staph aureus plates.

Figure 80:
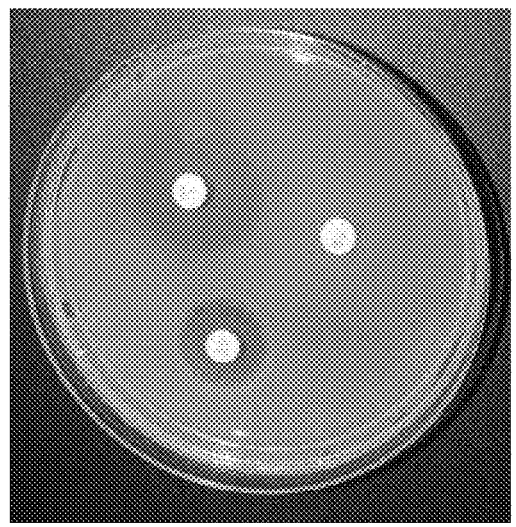
FIG. 80 is an image of an agar plate streaked with a blood culture of *E. coli* with Sensi-disc™ test discs according to an embodiment of the present invention.

Manual antibiotic testing using the agar disc diffusion method (BD Sensi-disc™) was also tested in the presence of SERS reagents. Overnight blood cultures of *E. coli* O157 with SERS reagents were streaked on BD BBL™ Mueller Hinton II Agar plates and three BD BBL™ Sensi-disc™ test discs were placed on top and the culture allowed to grow at 37° C. overnight. The next day, the zones of inhibition (FIG. 80) were measured (in mm) and compared to the Sensi-disc™ Zone Diameter Interpretive Chart for the determination of sensitive, inhibitory or resistant isolates. FIG. 80 shows Ampicillin-10 (top left), Levofloxacin-5 (top right), Vancomycin-30 (bottom)). The zone diameter measurements did not vary more than 1-2 mm between the *E. coli* culture with reagents and the culture without reagents (FIG. 81). This process was repeated with other blood culture bacteria and yeast (Table 82), which shows that the ability to determine the antibiotic susceptibility of a microorganism using the disc diffusion method is not impacted by the presence of SERS reagents.

For testing yeast, Nystatin Taxo™ discs were used. These discs are not used for susceptibility testing, but for differentiation and isolation of bacteria from specimens with both bacteria and yeast. Therefore, a slightly different method was tested. Mixed blood cultures of *E. coli* and *C. albicans* with and without SERS reagents were streaked onto TSA II plates. The Nystatin Taxo™ discs were placed on top and the cultures were grown at 37° C. overnight. In both samples with (left image of FIG. 83) and without (right image of FIG. 83) assay reagents, the Nystatin inhibition of *C. albicans* growth resulted in areas of isolated *E. coli* colonies.

Example 18

Effect of Agitation Frequency and Pelleting Time on Pellet Formation

This example pertains to pelleting using a configuration where the tube is coupled to the magnet (see e.g., FIG. 49) such that the magnet moves with the tube and is held in the same relative position to the tube throughout the agitation. In a series of experiments, SERS tags were covalently linked to tosyl-activated magnetic particles to form a SERS-magnetic bead precomplex (PC). Pre-complexed beads are prepared by covalent linkage of SERS particles to Dynabeads® M-280 Tosyl-activated magnetic particles through reaction of thiol(-SH) groups on the SERS surface with tosyl (Tos) groups on the surface of the magnetic particles PC acts as a model system for pellet formation testing where the pellet can be interrogated for SERS signal. In this example, pellet formation of PC in a commercial secondary media for *Salmonella* (SDIX RapidChek® *Salmonella* SELECT™) was compared using a variety of agitation frequencies and pelleting times. These tests were performed using a flat-bed system configuration (see e.g., FIG. 25) with a single bar magnet with the N-pole facing the tubes (see e.g., FIG. 52).

Figure 84:
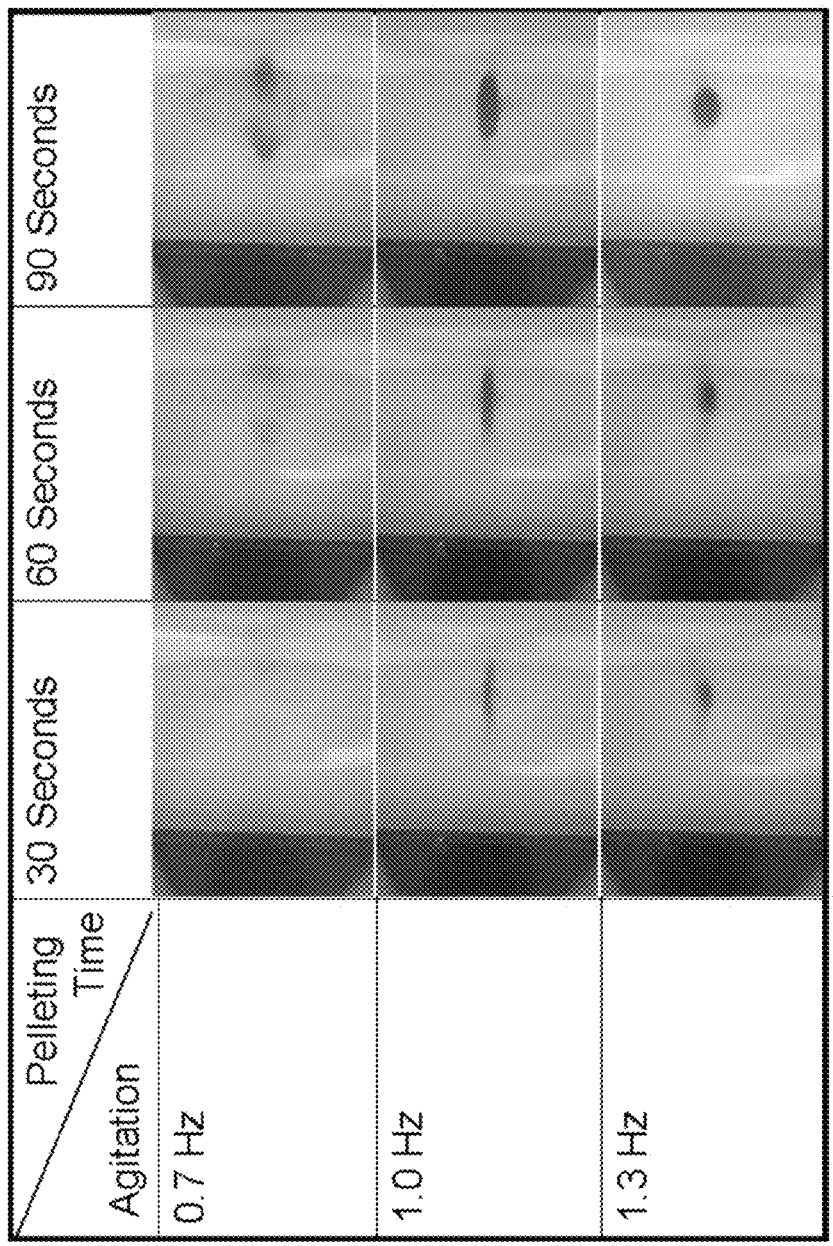
FIG. 84 is a table showing images of pellets formed in *Salmonella* secondary media using different agitation frequencies and pelleting times, according to an embodiment of the present invention.

FIG. 84 shows a table with images of pellets formed using PC in SDIX *Salmonella* secondary media using three different agitation frequencies and three different pelleting times. PC in SDIX secondary media was pelleted by agitating the tubes coupled with the bar magnet at varying agitation frequencies at 50 mm throw (amplitude). Agitation was stopped and the magnet was allowed to persist for 5 seconds before moving the bar magnet away from the tubes. Images of the pellets were captured once the bar magnet was moved away from the tubes.

As shown in FIG. 84, fast agitation forms a denser pellet compared to slow agitation. This is likely due to the solid media settling using slow agitation and interfering with pellet formation. Using fast agitation, the solid is suspended in solution and magnetic complexes can be pulled into a pellet with less interference from the media. It can be seen in the pellets formed using 0.7 Hz agitation frequency with 30, 60, and 90 second pelleting times that settled media interferes with the ability to pull a dense pellet, as evidenced by the diffuse pellet.

Example 19

Effect of Agitation Frequency on Pellet Dispersion

This example pertains to measuring the time required to fully disperse a pellet using a variety of agitation throws (amplitude) and frequencies. In each case, a pellet was formed using a configuration in which the tube is coupled to the magnet (see e.g., FIG. 49) such that the magnet moves with the tube and is held in the same relative position to the tube throughout the agitation. The magnet used in this example was a single bar magnet with the N-pole facing the sample tubes, such as shown in FIG. 52.

In this example, the tube was manually shaken before each test to thoroughly mix the media (SDIX RapidChek® *Salmonella* SELECT™) and PC. The sample was loaded into the flatbed instrument and a pellet was formed by agitating at 1.8 Hz and 25 mm throw for 90 seconds. Agitation was stopped and the magnet was allowed to persist for 5 seconds before moving the magnet bar away from the tubes. Various agitation frequencies and throws were used in separate tests to disperse the pellet. Pellet dispersal was monitored by visual inspection and the time required to fully disperse the pellet was measured. Data with an asterisk indicates that no settled media was observed.

As shown in FIG. 85, fast agitation disperses the pellet in less time compared to slow agitation. Also, for a given agitation frequency, the pellet disperses quicker with a longer agitation throw. Based on observations in this example, solid media in the secondary media remains suspended in solution at agitation frequencies above 2.5 Hz at 25 mm throw and above 1.5 Hz at 50 mm throw.

Example 20

Fluorescence HNW Assay Feasibility Testing in the Presence of Food

Figure 97:
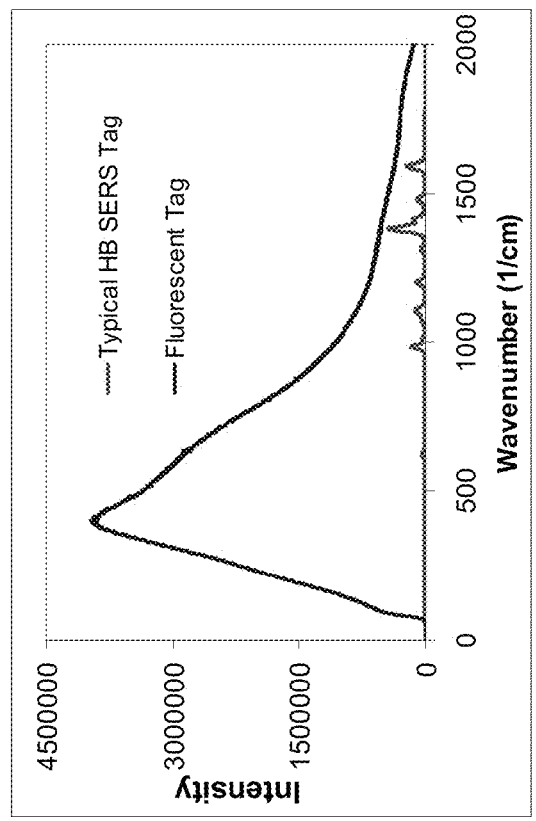
FIG. 97 shows a graph depicting the signal intensity of fabricated fluorescent silica nanoparticles and conventional SERS tags according to one embodiment of the present invention.
Figure 96:
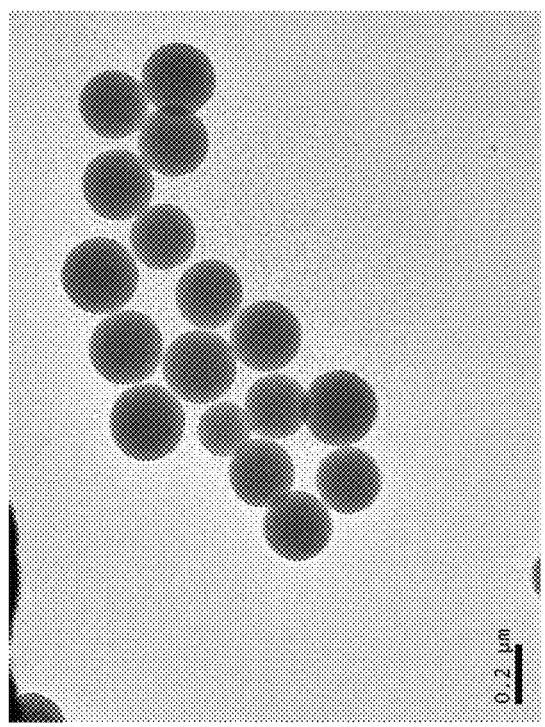
FIG. 96 is an image of fabricated fluorescent silica nanoparticles according to one embodiment of the present invention.
Figure 99:
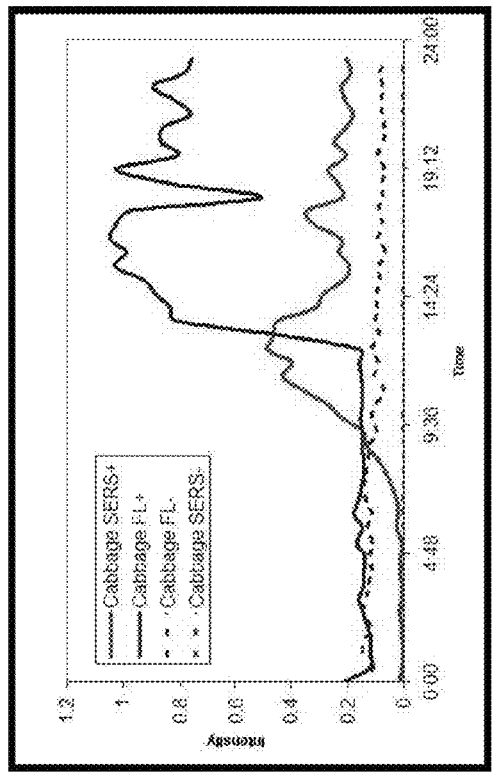
FIG. 99 shows a graph depicting the signal intensity over time of fabricated fluorescent silica nanoparticles and conventional SERS tags for detecting the presence *Listeria* in cabbage according to one embodiment of the present invention.
Figure 98:
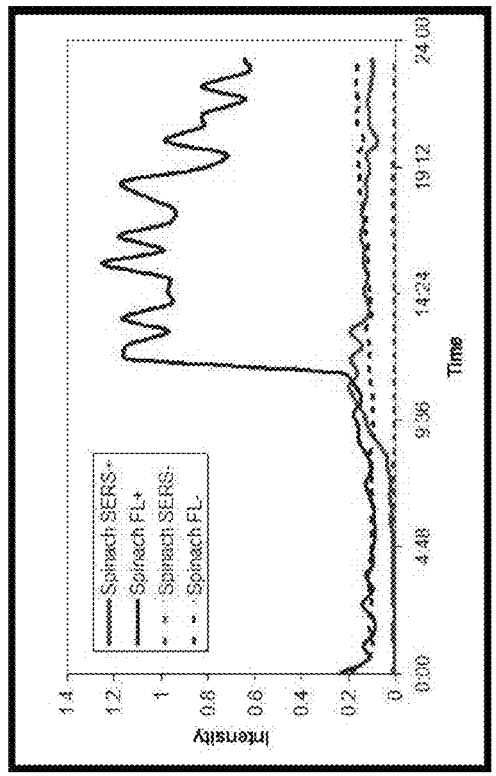
FIG. 98 shows a graph depicting the signal intensity over time of fabricated fluorescent silica nanoparticles and conventional SERS tags for detecting the presence of *Listeria* in spinach according to one embodiment of the present invention.

This example demonstrates the feasibility of conducting a homogeneous no wash assay in conjunction with culture using near infrared ("NIR") fluorescent particles instead of SERS tags. In this example, fluorescent silica nanoparticles were fabricated using a modified Stober growth technique incorporating both a silane-NIR dye conjugate (to provide the fluorescent signal) and a thiolated silane (to provide a chemical handle for antibody conjugation). Particles were characterized by transmission electron microscopy ("TEM"), UV/Vis extinction spectroscopy, and fluorescence spectroscopy, and found to be relatively monodisperse and bright. FIG. 96 illustrates a TEM image of NIR fluorescent silica nanoparticles (scale bar is 200 nm), while FIG. 97 illustrates a fluorescence spectrum of NIR fluorescent nanoparticles (OD 0.5) and Raman spectrum of standard ES/HB SERS tags (OD 1.2). Fluorescent nanoparticles were conjugated with *Listeria* Ab using a standard conjugation protocol which was modified to account for differences in fluorescent nanoparticle concentration, surface area, and mass relative to SERS tags. Conjugated fluorescent silica nanoparticles were tested in a *Listeria* HNW assay on a carousel system 150 (See FIG. 24) using 10% w/v blended samples of spinach and cabbage. Control tests were performed using SERS tags with both spinach and cabbage samples.

Fluorescent tags were able to successfully detect *Listeria* in both food samples. FIG. 98 depicts the spinach data collected using NIR fluorescent nanoparticle tags and SERS tags, while FIG. 99 depicts the cabbage data collected using NIR fluorescent nanoparticle tags and SERS tags. Both signal and background were found to be higher for fluorescent tags than for SERS tags, however, detection was successful with relatively high signal to background ratios of ~4:1.

Although the foregoing subject matter has been described in some detail by way of illustration and example for purposes of clarity of understanding, it will be understood by those skilled in the art that certain changes and modifications can be practiced within the scope of the appended claims and equivalents thereof.

All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

The foregoing description is intended to be exemplary of various embodiments of the invention. It will be understood by those skilled in the art that various changes and modifications to the disclosed embodiments can be made without departing from the purview and spirit of the invention as defined in the appended claims.

The invention claimed is:

1. A method for detecting growth of one or more microorganisms in a sample, the method comprising:

(a) providing the sample suspected of containing the one or more microorganisms;

(b) disposing said sample in an assay vial, wherein said assay vial has disposed therein a culture medium capable of supporting microorganism growth to form a culture sample and a reagent comprising one or more indicator particles having associated therewith at least one specific binding member having an affinity for said one or more microorganisms; and one or more magnetic capture particles having associated therewith at least one specific binding member having an affinity for said one or more microorganisms, wherein the binding member associated with the indicator particles can be the same or different than the binding member associated with the magnetic capture particles;

(c) incubating the culture sample for a predetermined period of time to form a magnetic capture particle-microorganism-indicator particle complex if said one or more microorganisms are present in said sample, wherein incubating the culture sample promotes growth of said one or more microorganisms;

(d) agitating the assay vial;

(e) exposing said magnetic capture particle-microorganism-indicator particle complex to a magnetic field to induce said magnetic capture particle-microorganism-indicator particle complex to migrate to a localized area of said assay vial;

(f) optically interrogating said localized area of said assay vial to induce said capture particle-microorganism-indicator particle complex to produce a detectable signal indicating an amount of said one or more microorganisms in said sample;

(g) dispersing said magnetic capture particle-microorganism-indicator particle complex;

(h) repeating steps (c)-(g) one or more times; and (i) determining whether said one or more microorganisms are present in said sample by comparing two or more of the detectable signals obtained in steps (c)-(h).

2. The method according to claim 1, wherein steps (c)-(g) are repeated more than once, and wherein each repeating of steps (c)-(g) occurs in regular time intervals.

3. The method according to claim 1, wherein steps (c) and (d) occur concurrently.

4. The method according to claim 1, wherein step (e) forms a pellet comprising magnetic capture particle-microorganism-indicator particle complexes.

5. The method according to claim 4, wherein the pellet is detectable using visual or optical means.

6. The method according to claim 1, wherein the sample comprises a blood sample.

7. The method according to claim 1, wherein the sample comprises a food sample.

8. The method according to claim 1, wherein the sample comprises an environmental sample.

9. The method according to claim 1, wherein the sample comprises an agricultural sample.

10. The method according to claim 1, wherein disposing said sample in the assay vial comprises transferring a desired amount of said sample, along with optional culture media, from a vessel, wherein the vessel comprises: a container for receiving a culture sample therein, the container having an open end and a closed end; a lid configured to engage the open end of the container in a fluid-tight connection; a basket coupled to the lid and including at least one reservoir, the basket being disposed between the open end and the closed end of the container, the reservoir configured to hold a volume of the culture sample therein; and at least one needle assembly engaged with the lid, the needle assembly including a needle extending within the reservoir, wherein the needle is configured to selectively withdraw the culture sample contained in the reservoir, and wherein the needle is further configured to engage the assay vial for a biocontained transfer of the culture sample from the reservoir to the assay vial.

11. The method according to claim 1, wherein disposing said sample in an assay vial comprises extracting the sample, along with culture media, in a biocontained fashion from a vessel in which the magnetic capture particles and indicator particles are not present.

* * * * *